(12) United States Patent
Bishop et al.

(10) Patent No.: US 7,837,651 B2
(45) Date of Patent: Nov. 23, 2010

(54) INFUSION PUMP

(75) Inventors: Gregory D. Bishop, Hamilton, OH (US); DeWayne A. Davis, Lebanon, IN (US); Anil K. Nalagatla, Mason, OH (US); Jeffery J. Wuennemann, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 899 days.

(21) Appl. No.: 11/158,148

(22) Filed: Jun. 21, 2005

(65) Prior Publication Data

US 2006/0042633 A1   Mar. 2, 2006

Related U.S. Application Data

(60) Provisional application No. 60/629,137, filed on Nov. 18, 2004, provisional application No. 60/605,717, filed on Aug. 31, 2004.

(51) Int. Cl.
*A61M 1/00* (2006.01)
*A61M 37/00* (2006.01)
*A61M 15/08* (2006.01)

(52) U.S. Cl. .................. 604/122; 604/131; 128/207.18

(58) Field of Classification Search .................. 604/65, 604/131, 122, 45, 94.01; 128/207.18
See application file for complete search history.

(56) References Cited

U.S. PATENT DOCUMENTS

| | | | |
|---|---|---|---|
| 5,335,656 A | 8/1994 | Bowe et al. | |
| 5,400,781 A | 3/1995 | Davenport | |
| 5,490,490 A | 2/1996 | Weber et al. | |
| 5,513,634 A | 5/1996 | Jackson | |
| 6,712,753 B2 | 3/2004 | Manne | |
| 6,745,764 B2 | 6/2004 | Hickle | |
| 6,938,619 B1 | 9/2005 | Hickle et al. | |
| 7,007,694 B2 | 3/2006 | Aylsworth et al. | |
| 7,013,898 B2 | 3/2006 | Rashad et al. | |
| 7,152,604 B2 | 12/2006 | Hickle et al. | |
| 7,198,605 B2 | 4/2007 | Donofrio et al. | |
| 7,222,624 B2 | 5/2007 | Rashad et al. | |
| 7,261,106 B2 | 8/2007 | Donofrio | |
| 2001/0031929 A1 | 10/2001 | O'Toole | |
| 2002/0017300 A1 | 2/2002 | Hickle et al. | |
| 2003/0040700 A1 | 2/2003 | Hickle et al. | |

(Continued)

FOREIGN PATENT DOCUMENTS

WO   WO 03/059422 A1   7/2003

OTHER PUBLICATIONS

International Search Report dated Jun. 11, 2008 for corresponding application PCT/US2005/030201.

(Continued)

*Primary Examiner*—Nicholas D Lucchesi
*Assistant Examiner*—Victoria P Campbell
(74) *Attorney, Agent, or Firm*—Verne E. Kreger, Jr.

(57) ABSTRACT

Disclosed is a drug delivery infusion pump assembly containing a drug delivery pump, a drug delivery cassette, a pump door, and a housing adapted to receive a drug vial. A drug vial centering mechanism ensures varieties of drug vial sizes are compatible with this device. The drug delivery cassette is capable of being positioned on the drug delivery infusion pump assembly so the drug delivery pump will interface with a drug delivery tube located on the drug delivery cassette.

7 Claims, 65 Drawing Sheets

U.S. PATENT DOCUMENTS

| | | |
|---|---|---|
| 2003/0060766 A1* | 3/2003 | Kamen et al. .............. 604/131 |
| 2004/0103897 A1 | 6/2004 | Hickle et al. |
| 2004/0107965 A1 | 6/2004 | Hickle et al. |
| 2004/0119341 A1 | 6/2004 | Hickle |
| 2004/0129272 A1 | 7/2004 | Ganesh et al. |
| 2004/0133172 A1* | 7/2004 | Wilkinson ................ 604/263 |
| 2004/0149282 A1 | 8/2004 | Hickle |
| 2004/0230108 A1 | 11/2004 | Melker et al. |
| 2005/0059924 A1 | 3/2005 | Katz et al. |
| 2005/0066970 A1 | 3/2005 | Donofrio |
| 2005/0066971 A1 | 3/2005 | Donofrio |
| 2005/0070812 A1 | 3/2005 | Donofrio |
| 2005/0070813 A1 | 3/2005 | Donofrio |
| 2005/0070814 A1 | 3/2005 | Donofrio et al. |
| 2005/0070815 A1 | 3/2005 | Shahrestani et al. |
| 2005/0070822 A1 | 3/2005 | Donofrio et al. |
| 2005/0070823 A1 | 3/2005 | Donofrio et al. |
| 2005/0070824 A1 | 3/2005 | Rhad et al. |
| 2005/0092322 A1 | 5/2005 | Collins, Jr. |
| 2005/0096583 A1* | 5/2005 | Demers et al. .............. 604/15 |
| 2005/0124929 A1 | 6/2005 | Katz |
| 2006/0009733 A1 | 1/2006 | Martin |
| 2006/0009734 A1 | 1/2006 | Martin |
| 2007/0095347 A1 | 5/2007 | Lampotang et al. |

OTHER PUBLICATIONS

European Search Report dated Oct. 27, 2009, EP05789936.

* cited by examiner

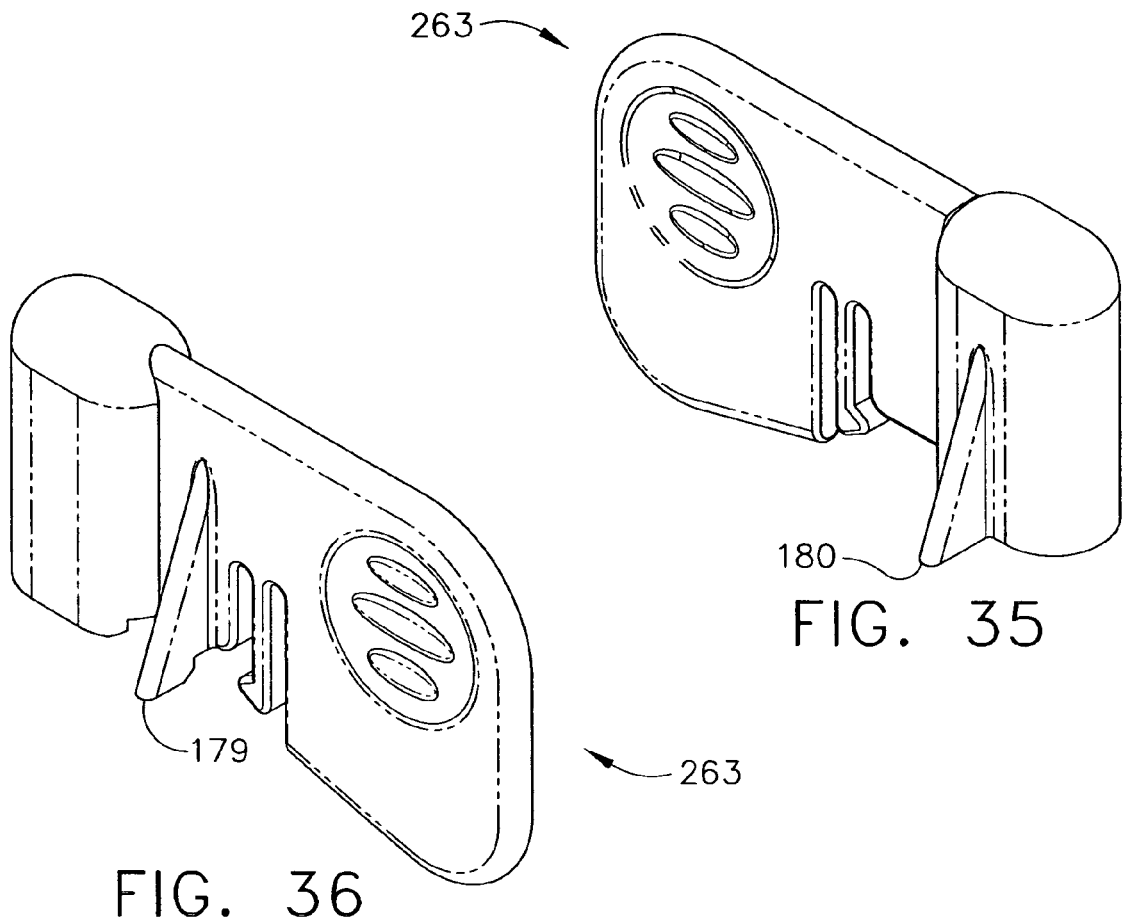
FIG. 35
FIG. 36
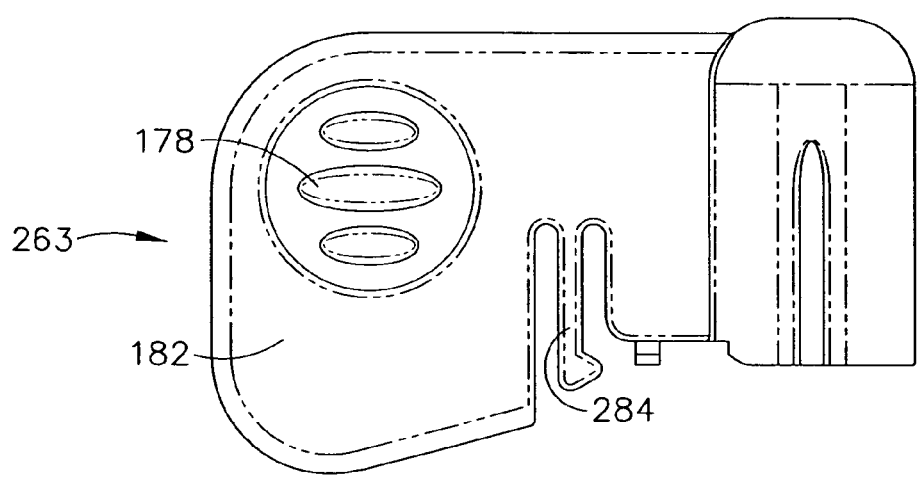
FIG. 37

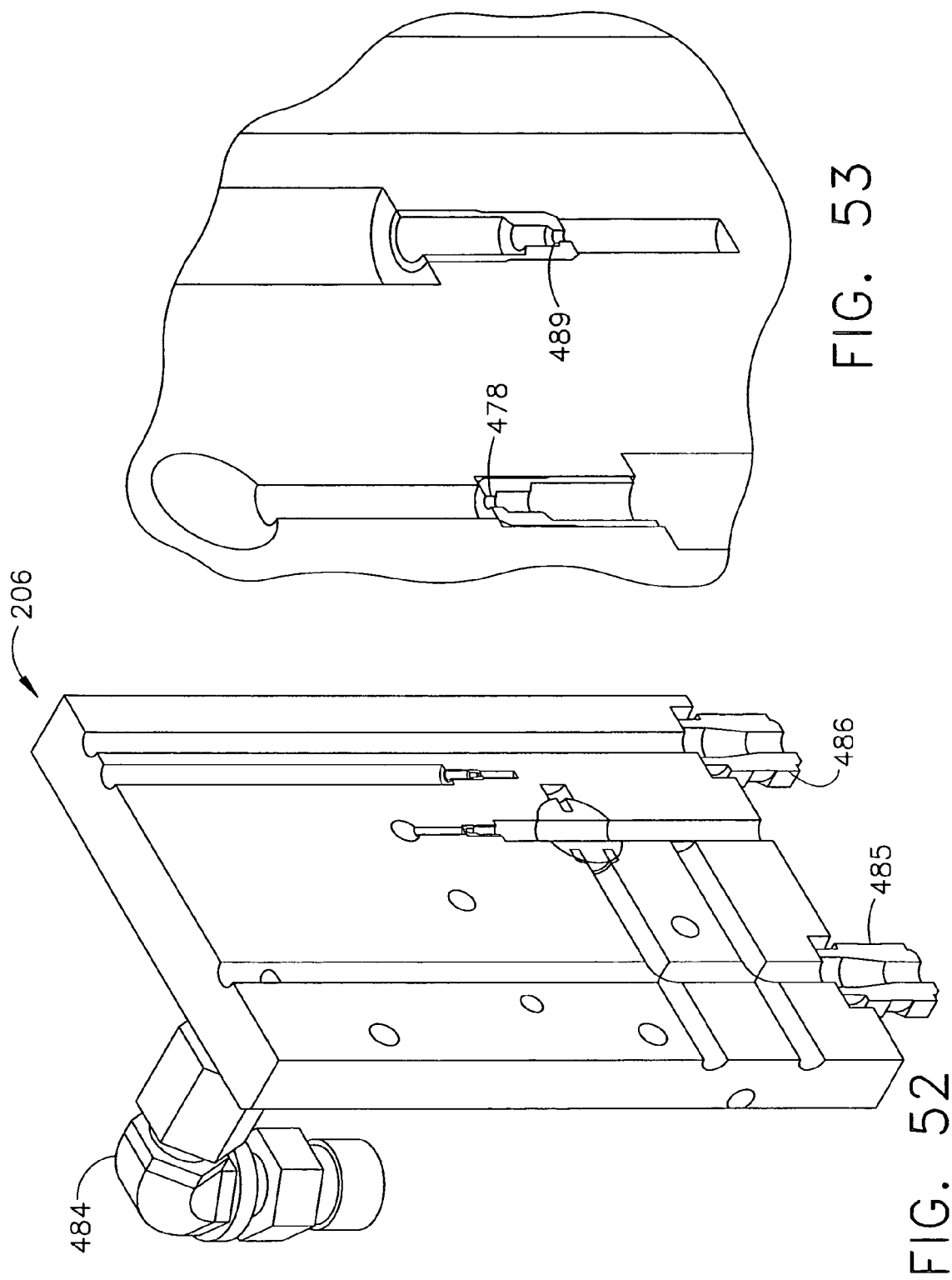

INFUSION PUMP

CROSS REFERENCE TO RELATED APPLICATIONS

This application claims the benefit of earlier filed provisional applications entitled "Medical Effector System Such As a Sedation Delivery System (SDS) and Components Which Can Be Used Therein", Ser. No. 60/629,137, filed on Nov. 18, 2004 and "Medical Effector System Such As a Sedation Delivery System (SDS) and Components Which Can Be Used Therein", Ser. No. 60/605,717, filed on Aug. 31, 2004, both of which are incorporated by reference herein.

RELATED APPLICATIONS

The present application relates to the following commonly assigned patent applications "Bite Block Assembly", Ser. No. 11/158,253; "Apparatus For Monitoring A Patient During Drug Delivery", Ser. No. 11/158,106; "Drug Delivery Cassette", Ser. No. 11/157,750; "Medical Effector System", Ser. No. 11/158,161; "Infusion Pump", Ser. No. 11/158,148; "Capnometry System For Use With A Medical Effector System", Ser. No. 11/158,162; "Device For Connecting A Cannula To A Medical Effector System", Ser. No. 11/158,159; "Apparatus To Deliver Oxygen To A Patient", Ser. No. 11/157,459; "Single Use Drug Delivery Components", Ser. No. 11/157,436; "Drug Delivery Cassette And A Medical Effector System", Ser. No. 11/158,262; "Oral Nasal Cannula", Ser. No. 11/158,213; all filed concurrently herewith; and Dose Rate Control, Ser. No. 10/886,255, filed on Jul. 7, 2004; BIS Closed Loop Anesthetic Delivery, Ser. No. 10/886,322, filed on Jul. 7, 2004; Patient Monitoring Systems and Method of Use, Ser. No. 10/791,959, filed on Mar. 3, 2004; Air-Bubble-Monitoring Medication Assembly, Medical System and Method, Ser. No. 10/726,845, filed on Dec. 3, 2003; Cannula Assembly and Medical System Employing a Known $CO_2$ Gas Concentration, Ser. No. 10/701,737, filed on Nov. 5, 2003; Automated Audio Calibration for Conscious Sedation, Ser. No. 10/674,244, filed on Sep. 29, 2003; Response Testing for Conscious Sedation Using Finger Movement Response Assembly, Ser. No. 10/674,184, filed on Sep. 29, 2003; Personalized Audio Requests for Conscious Sedation, Ser. No. 10/674,185, filed on Sep. 29, 2003; Response Testing for Conscious Sedation Utilizing a Non-Ear-Canal-Contacting Speaker, Ser. No. 10/674,183, filed on Sep. 29, 2003; Response Testing for Conscious Sedation Involving Hand Grip Dynamics, Ser. No. 10/674,160, filed on Sep. 29, 2003; Response Testing for Conscious Sedation Utilizing a Hand Motion Response, Ser. No. 10/673,660, filed on Sep. 29, 2003; Response Testing for Conscious Sedation Utilizing a Cannula for Support/Response, Ser. No. 10/670,453, filed on Sep. 25, 2003; Time Variant Vibration Stimulus Response for a Conscious Sedation System, Ser. No. 10/670,489, filed on Sep. 25, 2003; Response Testing for Conscious Sedation using Cableless Communication, Ser. No. 10/671,183, filed on Sep. 25, 2003; System and Method for Monitoring Gas Supply and Delivering Gas to a Patient, Ser. No. 10/660,286, filed on Sep. 11, 2003; Drug Delivery System and Method, Ser. No. 10/660,201, filed Sep. 11, 2003; and Battery Backup Method and System, Ser. No. 10/660,285, filed Sep. 11, 2003, all of which are incorporated herein by reference in their entirety.

FIELD OF THE INVENTION

The present invention is related generally to medical systems and components, which can be used in medical systems, and more particularly to a medical effector system, such as a sedation delivery system, and components, which can be used therein.

BACKGROUND OF THE INVENTION

A conscious sedation system is known and described in U.S. Pat. No. 6,745,764 entitled "Apparatus and method for providing a conscious patient relief from pain and anxiety associated with medical or surgical procedures". In that system, a procedure room unit included a controller, which generated a request for a predetermined response from a patient. The request was in the form of an auditory command, which was received by a patient through an earphone in the ear of the patient or was in the form of a vibration signal, which was received by the patient through a vibrator in a handpiece, which was attached to the hand of the patient. The predetermined response to the request was the pushing of a button on the handpiece by the patient, which closed a switch sending a signal to the controller. The controller analyzed medical information from the patient. Such medical information included, for example, blood pressure from a blood pressure cuff attached to the procedure room unit and placed on the arm of the patient and respiratory carbon dioxide levels obtained from a cannula (which also delivered oxygen to the patient) attached to the procedure room unit and placed on the face of the patient. The controller also analyzed the time delay between the request and the response. Based on the medical information and the time delay between the request and the response, the controller determined the level of sedation of the patient and decreased the flow of a gaseous or IV (intravenous) conscious sedation drug to the patient if the controller determined the patient was in a deeper level of conscious sedation than desired.

It is known to deliver IV sedation drugs to a patient from a drug-delivery cassette assembly using a peristaltic pump wherein the cassette assembly and pump are attached to the procedure room unit.

Still, scientists and engineers continue to seek improved medical effector systems, such as sedation delivery systems, and components, which can be used therein.

SUMMARY OF THE INVENTION

Various embodiments of the invention include a cannula assembly, a bite block, a drug-delivery cassette assembly (which is used in a drug-delivery infusion pump assembly which is a type of drug-delivery flow control assembly which is an example of a drug-delivery medical effector), an energy-delivery medical effector, a procedure room unit, an interface between a procedure room unit and a bedside monitoring unit, a bedside monitoring unit, and components thereof, which can be used separately and in various combinations including in a medical effector system such as a sedation delivery system.

This invention is directed toward use in a minimal sedation, moderate "conscious" sedation or deep sedation procedure, but not to an anesthesia or "general anesthesia" application as defined by the American Society of Anesthesiologists (ASA) in the document "Continuum of Depth of Sedation: Definition of General Anesthesia and Levels of Sedation/Analgesia, approved by the ASA house of delegates on Oct. 13, 1999, and amended on Oct. 27, 2004. The ASA defines general anesthesia as a drug-induced loss of consciousness during which patients are not arousable, even by painful stimulation. Further, patients often require assistance in maintaining a patient airway, and positive pressure ventilation may be required because of depressed spontaneous ventilation or drug-induced depression of neuromuscular function, cardiovascular function may be impaired.

In short, this invention provides a means for a procedural physician outside the practice of anesthesiology to provide sedation and/or pain relief to patients. The automation provided by the invention compensates for lack of clear standards of practice for non-anesthetists to guide the relief of pain and anxiety for conscious patients. Moreover, the invention will subsidize the limited training available to procedural physicians in the diagnosis and treatment of complications that may arise or result from the provision of sedation and analgesia to conscious patients.

BRIEF DESCRIPTION OF THE FIGURES

FIGS. 35 and 36 are a right-side and left-side perspective views of the spike cap of the drug-delivery cassette assembly of FIG. 26 showing details of the cap handle and latching system;

FIG. 37 is a side elevational view of the spike cap of the drug-delivery cassette assembly of FIG. 26;

FIG. 52 is a cross-sectional view of the oxygen-delivery manifold of FIG. 51 taken along arrows 52-52 in FIG. 51;

FIG. 53 is an enlarged view of a portion of the oxygen-delivery manifold of FIG. 52;

DETAILED DESCRIPTION OF THE INVENTION

Figure 1:
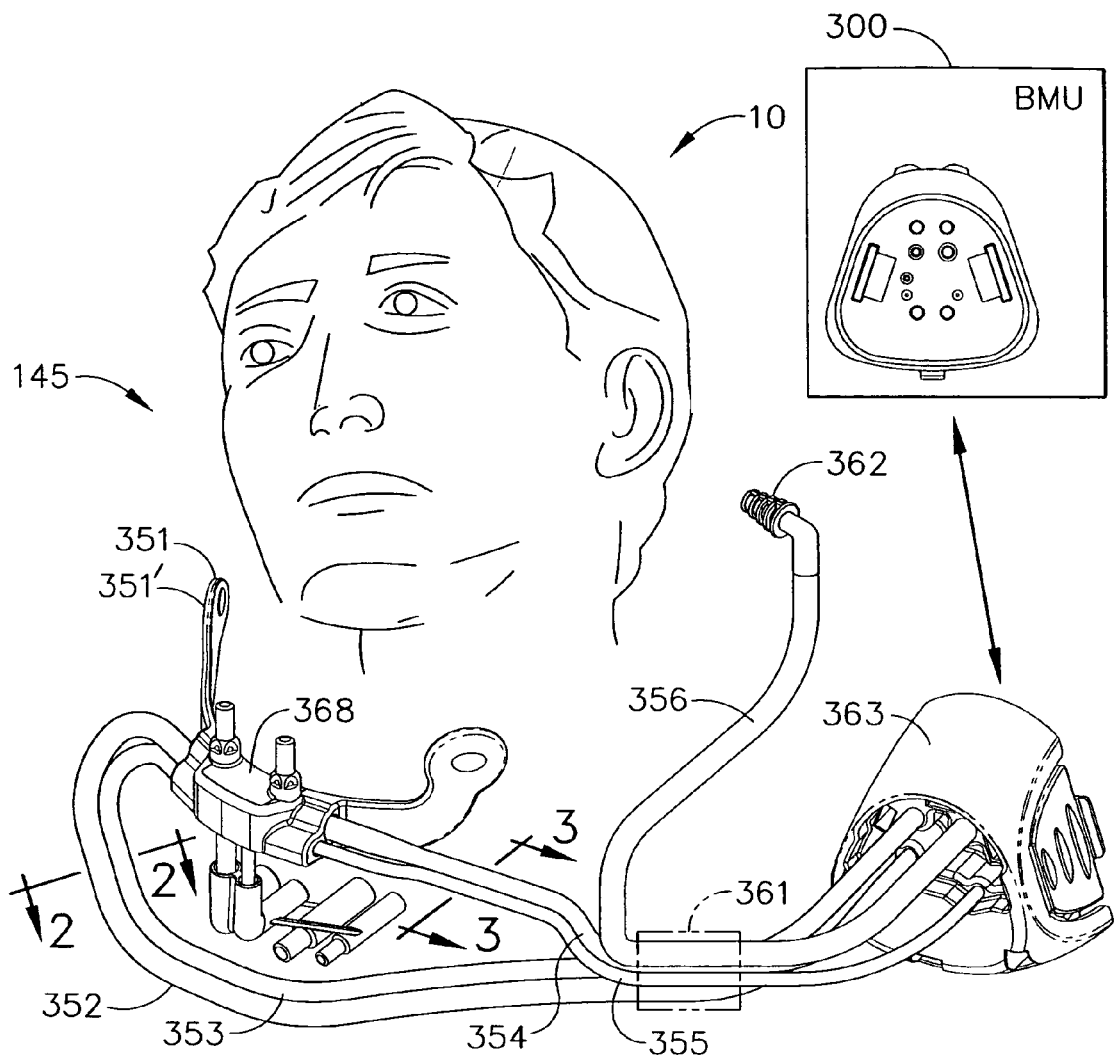
FIG. 1 is a perspective view of an embodiment of a cannula assembly of the invention, including the cannula, BMU-connector and tubes and of an embodiment of an earpiece and an audio tube.

Before explaining the present invention in detail, it should be noted that the invention is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

A medical effector is a device adapted to deliver at least one medical substance and/or at least one type of medical energy locally and/or generally to a patient during a medical procedure. A medical procedure includes, without limitation, a medical diagnostic procedure, a medical therapy procedure, and/or a surgical procedure. A medical substance is at least one gas, liquid, and/or solid having alone and/or together a medical effect on a patient, and an example is a pharmaceutical drug. Medical energy is energy having a medical effect on a patient. An example, without limitation, of a medical effect is a sedative effect. The terminology "sedative effect" includes conscious sedation and unconscious (anesthetic) sedation depending on the type and/or amount of the medical substance and/or medical energy being used. For purposes of describing the embodiments of the invention, an analgesic effect is considered to be a sedative effect, and an amnestic effect is considered to be a sedative effect. An example, without limitation, of a medical substance having a sedative effect is the sedation drug Propofol. An example, without limitation, of a medical effector for delivering Propofol to a patient is a drug-delivery flow control assembly such as a drug-delivery infusion pump assembly. An example, without limitation, of a type of medical energy having a sedative effect is a time-varying magnetic field as described in U.S. Pat. No. 6,712,753. An example, without limitation, of a medical effector for delivering a time-varying magnetic field to a patient is at least one magnetic flux generator as described in U.S. Pat. No. 6,712,753. Thus, a sedation delivery system employing a sedation-drug-delivery flow control assembly and a sedation delivery system employing at least one magnetic flux generator are examples of sedation medical effector systems. Other examples of medical effector systems, medical effectors, medical substances, drugs, types of medical energy, medical effects, and medical procedures are left to the artisan. It is noted that the hereinafter-used terms "attachable", "attached", "connectable", and "connected" include, respectively, directly or indirectly attachable, directly or indirectly attached, directly or indirectly connectable, and directly or indirectly connected. It is further noted that describing an apparatus as having a particular component means that the apparatus has at least one such particular component. Likewise, describing a component as having a particular feature means that the component has at least one such particular feature.

Various aspects and embodiments of the invention are hereinafter described, for ease of understanding, with reference to a sedation delivery system 100 and a sedation drug-delivery flow control assembly 220', but it is understood that such aspects and embodiments have equal application with reference to other examples of medical effector systems 100' than a sedation delivery system 100 and/or to other examples of medical effectors 220" than a drug-delivery flow control assembly 220'. Such other examples include, without limitation, a medical effector system including a non-sedation drug-delivery flow control assembly and a medical effector system including at least one magnetic flux generator.

It is further understood that any one or more of the following-described aspects, embodiments, expressions of embodiments, examples, etc. can be combined with any one or more of the other following-described aspects, embodiments, expressions of embodiments, examples, etc.

Cannula Assembly

A first aspect of the invention is directed to, or a component of, or can be used by, a cannula assembly 145, an embodiment of which is shown in FIGS. 1-18. A first expression of the embodiment of FIGS. 1-18 is for a cannula assembly 145 including an oral-nasal cannula 351 and a slidable tube 371'. The oral-nasal cannula 351 is disposable on the face of a patient 10 and includes a respiratory-gas-sampling nasal prong 364 or 365 and a respiratory-gas-sampling oral prong 369'. The slidable tube 371' is slidably connected to one of the respiratory-gas-sampling nasal and oral prongs 364, 365 or 369' to accommodate different distances between the nose and mouth of different patients 10. In one example, the slidable tube 371' is slidably connected to the respiratory-gas-sampling oral prong 369', wherein the slidable tube 371' has a substantially right-angle bend and a distal end 14, and wherein, when the oral-nasal cannula 351 is disposed on the face of the patient 10, the distal end 14 of the slidable tube 371' extends distally toward or into the mouth of the patient 10. Other examples are left to the artisan.

A second expression of the embodiment of FIGS. 1-18 is for a cannula assembly 145 including a cannula 351' (such as, but not limited to, an oral-nasal cannula 351) and a user-detachable oral prong extension 370' or 370". The cannula 351' is disposable on the face of a patient 10 and includes a respiratory-gas-sampling or respiratory-gas-delivery oral prong 369'/371' or 369"/371" having an opening. The user-detachable oral prong extension 370' or 370" comes removably attached to the oral prong 369'/371' or 369"/371" and is user-connectable to the opening of the oral prong 369'/371' or 369"/371". In one example of the second expression of the embodiment of FIGS. 1-18, the oral prong 369' or 369" lacks the slidable prong 371' or 371", and in another example it does not. In one implementation of the second expression, the oral prong extension 370' or 370" is connected to the opening of the oral prong when the user is employing a bite block (not shown) with the patient such as during esophageal procedures requiring an endoscope. In one illustration, the user-detachable oral prong extension 370' or 370" is manually detached by the user without the use of any tool. In one construction, the oral prong extension 370' or 370" comes removably attached to the oral prong 369'/371' or 369"/371" by a manually-breakable tether 12. Alternate constructions include removable attachment by use of score lines or perforations. Other examples, implementations, and constructions are left to the artisan.

A third expression of the embodiment of FIGS. 1-18 is for a cannula assembly 145 comprising a cannula 351' which is disposable on the face of a patient 10 and which includes a respiratory-gas-sampling oral prong 369'/371' having a distal end 14 and a respiratory-gas-delivery oral prong 369"/371" having a distal end 16 wherein, when the cannula 351' is disposed on the face of the patient 10, the distal end 14 of the respiratory-gas-sampling oral prong 369'/371' extends distally further toward or into the mouth of the patient 10 than the distal end 16 of the respiratory-gas-delivery oral prong 369"/371". In one example of the third expression of the embodiment of FIGS. 1-18, the respiratory-gas-sampling oral prong 369'/371' is a carbon-dioxide respiratory-gas-sampling oral prong, and the respiratory-gas-delivery oral prong 369"/371" is used to deliver air with an enriched oxygen content (sometimes just referred to as "oxygen") to the patient 10. In this example, such staggering of the distal ends 14 and 16 of the two prongs 369'/371' and 369"/371" reduces oxygen dilution of the carbon-dioxide sample, as can be appreciated by those skilled in the art. Other examples are left to the artisan.

A fourth expression of the embodiment of FIGS. 1-18 is for a cannula assembly 145 comprising a cannula 351' which is disposable on the face of a patient, 10 and which includes left and right cannula support wings 367' and 367" each having a wing tip portion with an adhesive pad 366 removably adhesively attachable to a side of the face of the patient 10. In one example, no other attachment is used to secure the cannula 351' to the face of the patient 10. In this example, the adhesive pad 366 provides for a more convenient cannula attachment for the patient than a conventional headband, etc. Other examples are left to the artisan.

A fifth expression of the embodiment of FIGS. 1-18 is for a cannula assembly 145 comprising a cannula 351' which is disposable on the face of a patient 10, which includes a cannula body 18 having a respiratory-gas-sampling nasal prong 364 or 365, and which includes a cannula cap 368 having a respiratory-gas-delivery nasal prong 422 with a tube-receiving hole 26. The cannula cap 368 is attached to the cannula body 18 with the respiratory-gas-sampling nasal prong 364 or 365 passing through and extending beyond the tube-receiving hole 26. The tube-receiving hole 26 is disposed to bend the respiratory-gas-sampling nasal prong 364 or 365 toward the nose of the patient 10 when the cannula 351' is disposed on the face of the patient 10. This arrangement allows for better respiratory gas sample acquisition as can be appreciated by those skilled in the art. In one example of the fifth expression of the embodiment of FIGS. 1-18, the nasal prong 364 or 365 is substantially straight before the cannula cap 368 is attached to the cannula body 18.

A sixth expression of the embodiment of FIGS. 1-18 is for a cannula assembly 145 comprising a cannula 351' which is disposable on the face of a patient 10 and which includes a respiratory-gas-sampling nasal prong 364 or 365 having a distal end 20 and a respiratory-gas-delivery nasal prong 422' or 422" having a distal end 22, wherein, when the cannula 351' is disposed on the face of the patient 10, the distal end 20 of the respiratory-gas-sampling nasal prong 364 or 365 extends distally further toward or into one of the nostrils of the patient 10 than the distal end 22 of the respiratory-gas-delivery nasal prong 422' or 422". Such staggering of the distal ends 20 and 22 of the two prongs 364 or 365 and 422' or 422" reduces respiratory delivered gas dilution of the respiratory gas sample, as can be appreciated by those skilled in the art. In one example of the sixth expression of the embodiment of FIGS. 1-18, the respiratory-gas-sampling nasal prong 364 or 365 is circumferentially surrounded by the respiratory-gas-delivery nasal prong 422' or 422". Other examples are left to the artisan.

A seventh expression of the embodiment of FIGS. 1-18 is for a cannula assembly 145 including an oral-nasal cannula 351 and a connector 363. The oral-nasal cannula 351 is disposable on the face of a patient 10 and includes a left-nostril respiratory-gas-sampling tube 354, a right-nostril respiratory-gas-sampling tube 352, and an oral respiratory-gas-sampling tube 355. The connector 363 includes a cover 394 and a back plate 423 attached to the cover 394. The cover 394 includes an interior nasal moisture trap chamber 412 and an interior oral moisture trap chamber 411 isolated from the interior nasal moisture trap chamber 412. The back plate 423 includes a nasal capnometry port 402 and an oral capnometry port 400. The left and right nostril respiratory-gas-sampling tubes 354 and 352 are connected to the cover 394 and are in fluid communication with the interior nasal moisture trap chamber 412. The oral respiratory-gas-sampling tube 355 is connected to the cover 394 and is in fluid communication with the interior oral moisture trap chamber 411. The nasal capnometry port 402 is in fluid communication with the interior nasal moisture trap chamber 412. The oral capnometry port 400 is in fluid communication with the interior oral moisture trap chamber 411.

In one example of the seventh expression of the embodiment of FIGS. 1-18, the connector 363 also includes a hydrophobic filter 395' disposed between the interior nasal moisture trap chamber 412 and the nasal capnometry port 402 and a hydrophobic filter 395" disposed between the interior oral moisture trap chamber 411 and the oral capnometry port 400. In another example, not shown, a desiccant is disposed in the nasal and oral moisture trap chambers 412 and 411. Other examples are left to the artisan.

In one variation of the seventh expression of the embodiment of FIGS. 1-18, the connector 363 also includes an inter-flow-path-sealing gasket 396 disposed between the interior nasal and oral moisture trap chambers 412 and 411 and the nasal capnometry and oral capnometry ports 402 and 400. The gasket 396 includes annular towers 24 which extend into the nasal capnometry and oral capnometry ports 402 and 400 and provide, at least in part, the fluid communication between the interior nasal moisture trap chamber 412 and the nasal capnometry port 402 and between the oral moisture trap chamber 411 and the oral capnometry port 400.

An eighth expression of the embodiment of FIGS. 1-18 is for a cannula assembly 145 including a cannula 351' and a connector 363. The cannula 351' is disposable on the face of a patient 10 and includes a respiratory-gas-sampling tube 354, 352 or 355. The connector 363 includes a cover 394, a back plate 423, and a gasket 396. The back plate 423 is attached to the cover 394. The cover 394 includes an interior moisture trap chamber 412 or 411. The back plate 423 includes a capnometry port 402 or 400. The respiratory-gas-sampling tube 354, 352 or 355 is connected to the cover 394 and is in fluid communication with the interior moisture trap chamber 412 or 411, and the capnometry port 402 or 400 is in fluid communication with the interior moisture trap chamber 412 or 411. The gasket 396 is disposed between the interior moisture trap chamber 412 or 411 and the capnometry port 402 or 400. The gasket 396 includes an annular tower 24 which extends into the capnometry port 402 or 400 and provides, at least in part, the fluid communication between the interior moisture trap chamber 412 or 411 and the capnometry port 402 or 400.

A ninth expression of the embodiment of FIGS. 1-18 is for a cannula-assembly connector 363. The cannula-assembly connector 363 includes at least one cannula-assembly connector member together having a nasal capnometry port 402, an oral capnometry port 400, a nasal pressure port 401, and a respiratory-gas-delivery port 399. Each of the ports 402, 400, 401 and 399 is fluidly-connectable to a bedside monitoring unit (BMU) 300 (an embodiment of which is seen in FIGS. 6 and 60-62) of a sedation delivery system (SDS) 100 (or other type of medical effector system 100'). The terminology "fluidly-connectable" includes directly fluidly-connectable and indirectly fluidly-connectable.

Figure 15:
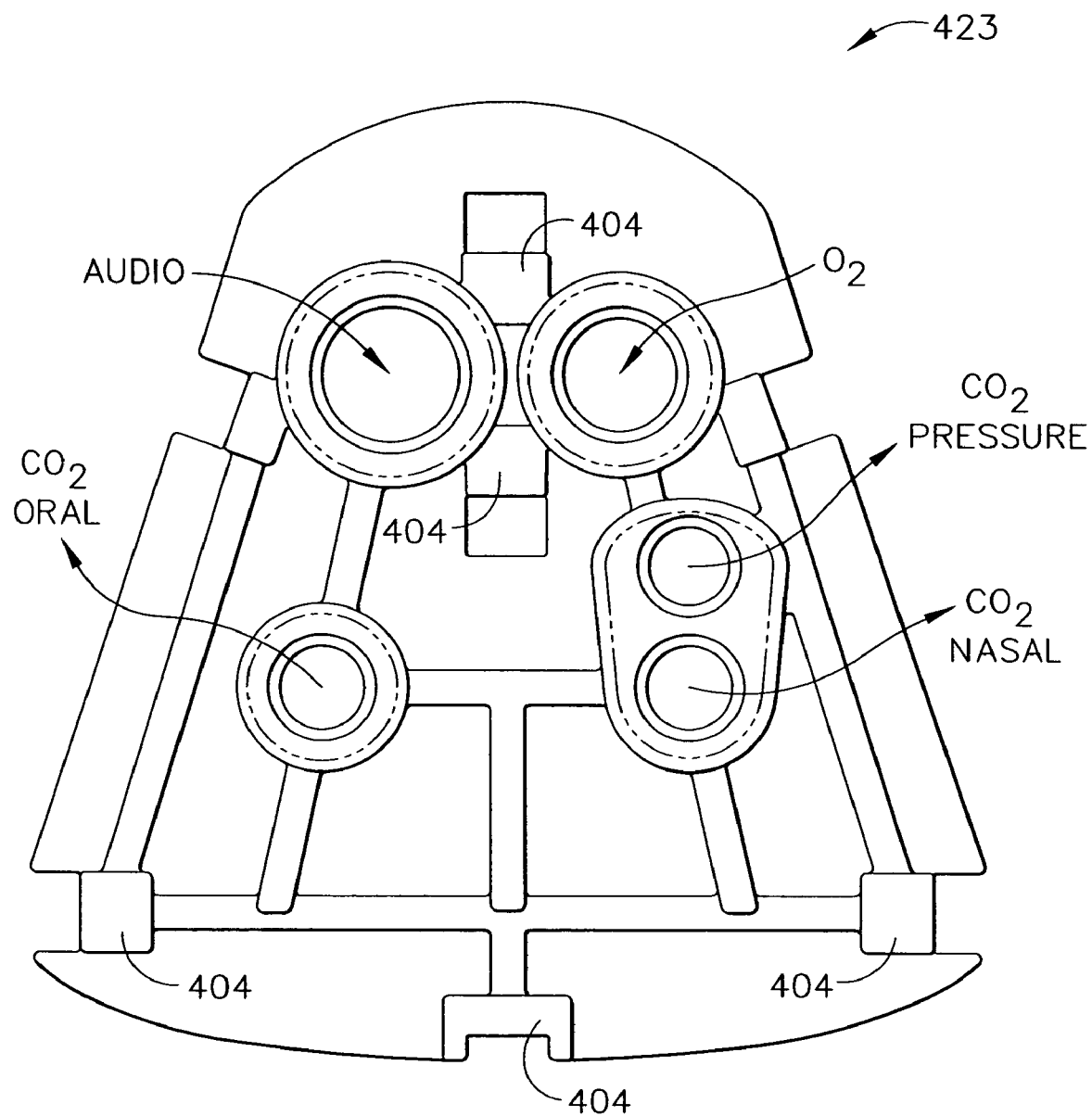
FIG. 15 is proximal connecting-end view of the back plate of the oral/nasal cannula connector of FIG. 13 identifying individual ports.
Figure 16:
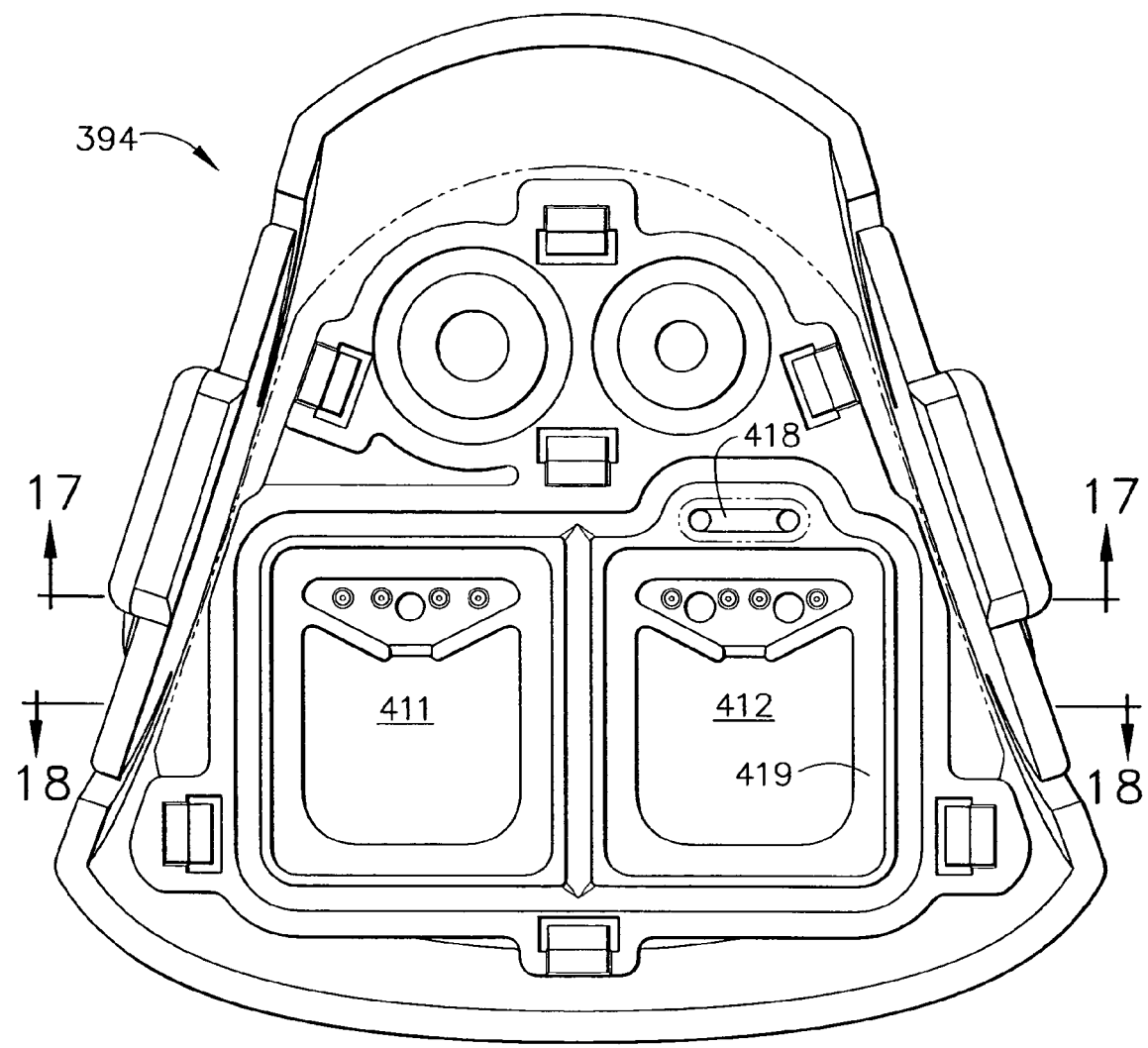
FIG. 16 is a proximal end view of the outlet cover of the oral/nasal cannula of FIG. 13.
Figure 17:
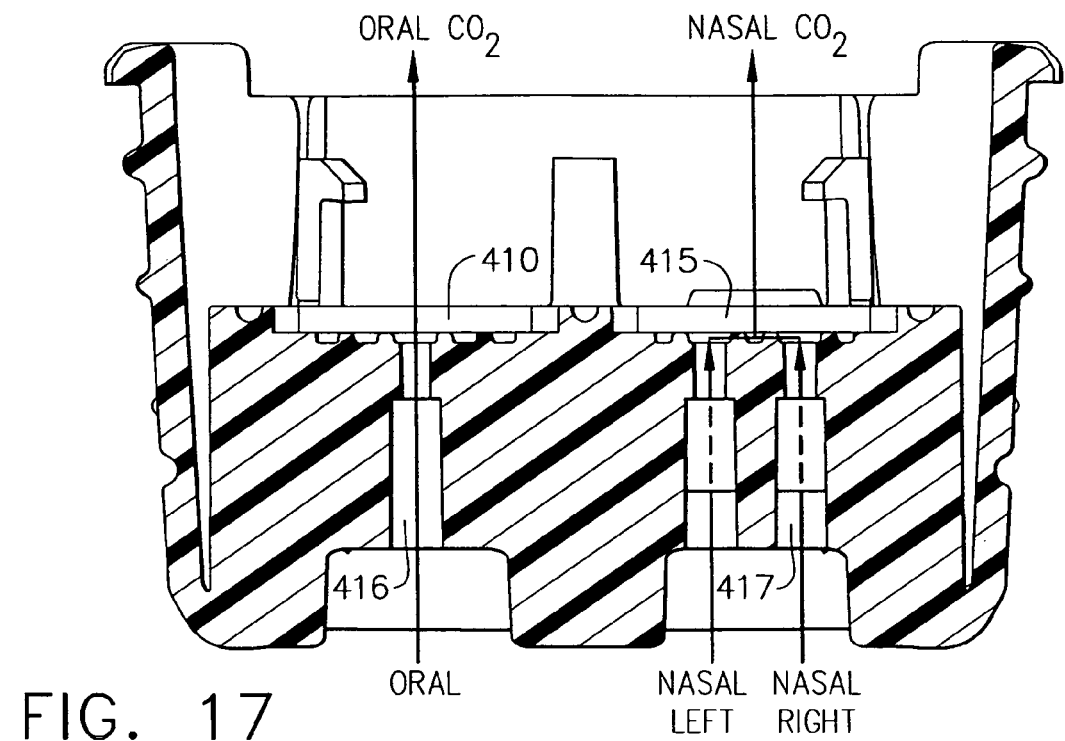
FIGS. 17 and 18 are cross-sectional views of the outlet cover of FIG. 16, taken along lines 17-17 and 18-18 of FIG. 16, indicating paths for gases and moisture chamber details.
Figure 18:
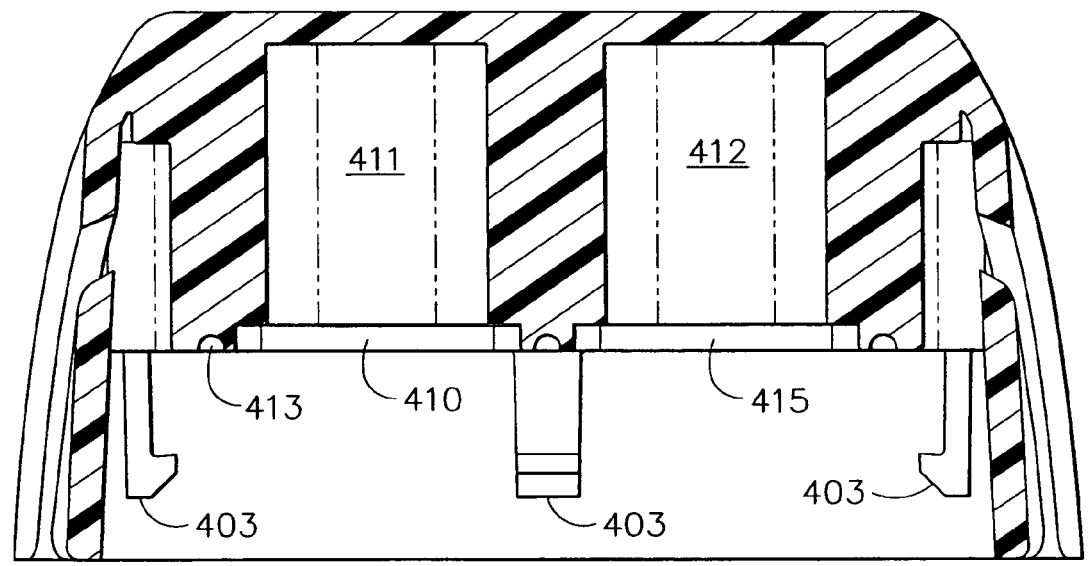

In one example of the ninth expression of the embodiment of FIGS. 1-18, the at-least-one cannula-assembly connector member consists of a plate (e.g., back plate 423). In the same or a different example, each of the ports 402, 400, 401 and 399 has a center and the distance between the centers of any two ports 402, 400, 401 and 399 is shortest for the nasal capnometry and nasal pressure ports 402 and 401. In one extension of the ninth expression, the at-least-one cannula-assembly connector member together have an audio port 398. In one construction, the connector 363 includes a back plate 423, wherein one or more or all of the ports 402, 400, 401 and 399 (and, when present, 398) are ports of the back plate 423. In one variation, the back plate 423 includes adapter pins 397 for aligning and/or assisting in connecting the ports 402, 400, 401 and 399 (and, when present, 398) to the BMU 300. In one modification, the back plate 423 is configured as shown in FIGS. 13 and 15. In another construction, not shown, the connector 363 lacks a plate or a back plate. In one arrangement, the BMU 300 has ports, which enter the ports 402, 400, 401 and 399 (and, when present, 398) of the connector 363 to provide the fluid connection. In another arrangement, the ports 402, 400, 401 and 399 (and, when present, 398) of the connector 363 enter ports on the BMU 300 to provide the fluid connection. Other arrangements (including connector ports which are flush with the back plate, not shown) providing the fluid connection of the connector ports and the BMU are left to the artisan.

Figure 54:
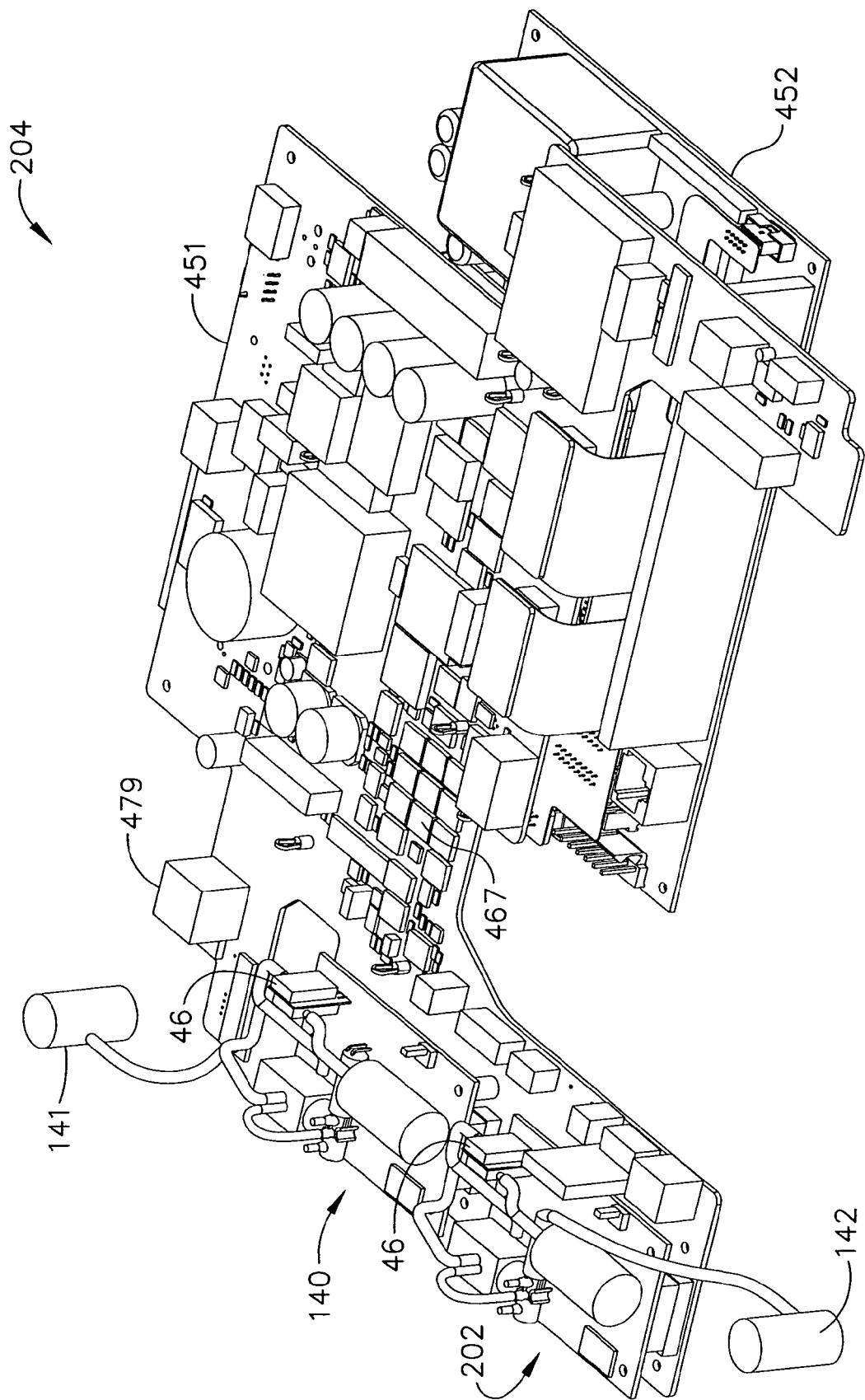
FIG. 54 is a top perspective view of the PRU host controller of the PRU of FIG. 43.
Figure 55:
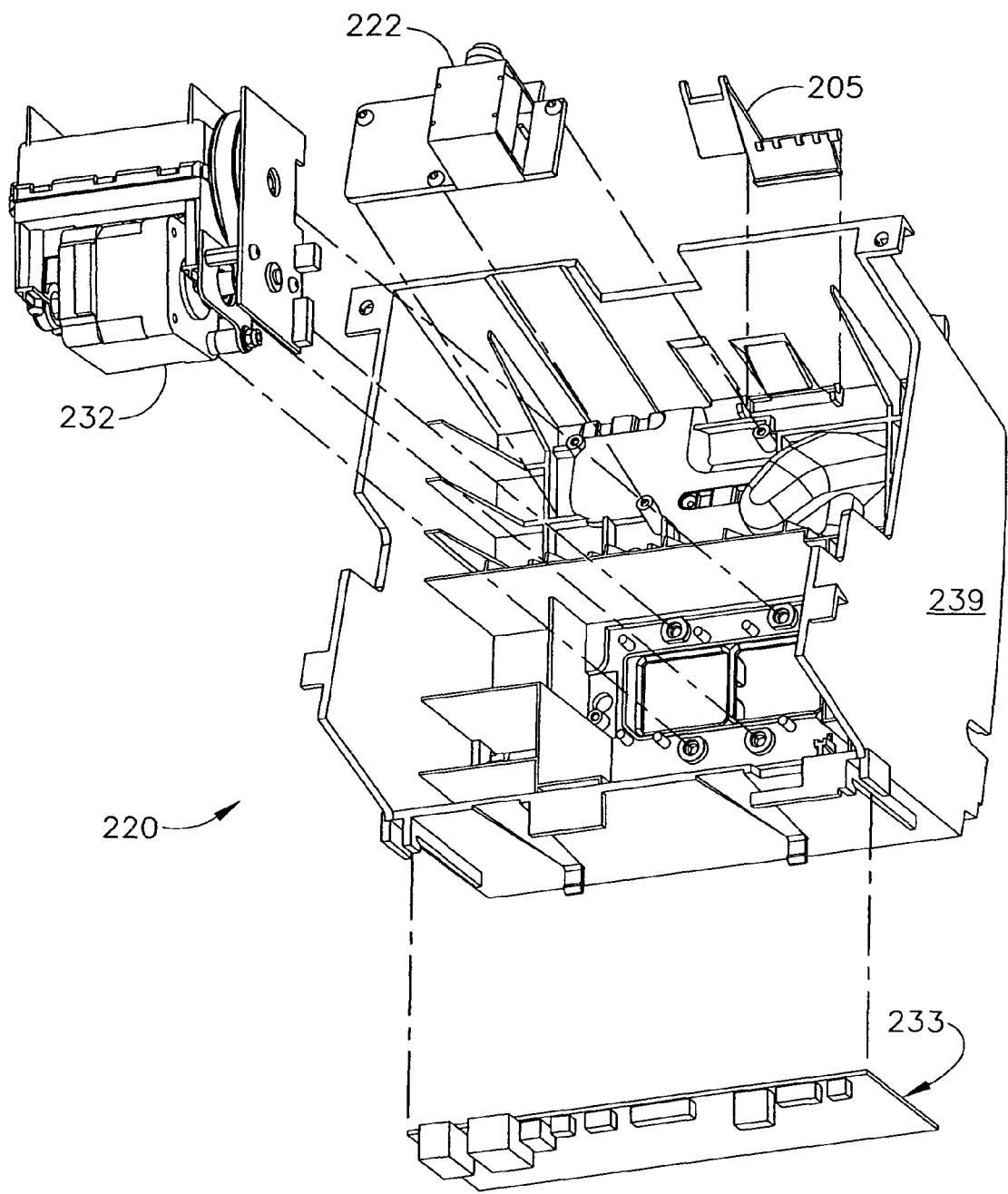
FIG. 55 is an exploded view of the drug-delivery infusion pump assembly of the PRU of FIG. 43.
Figure 56:
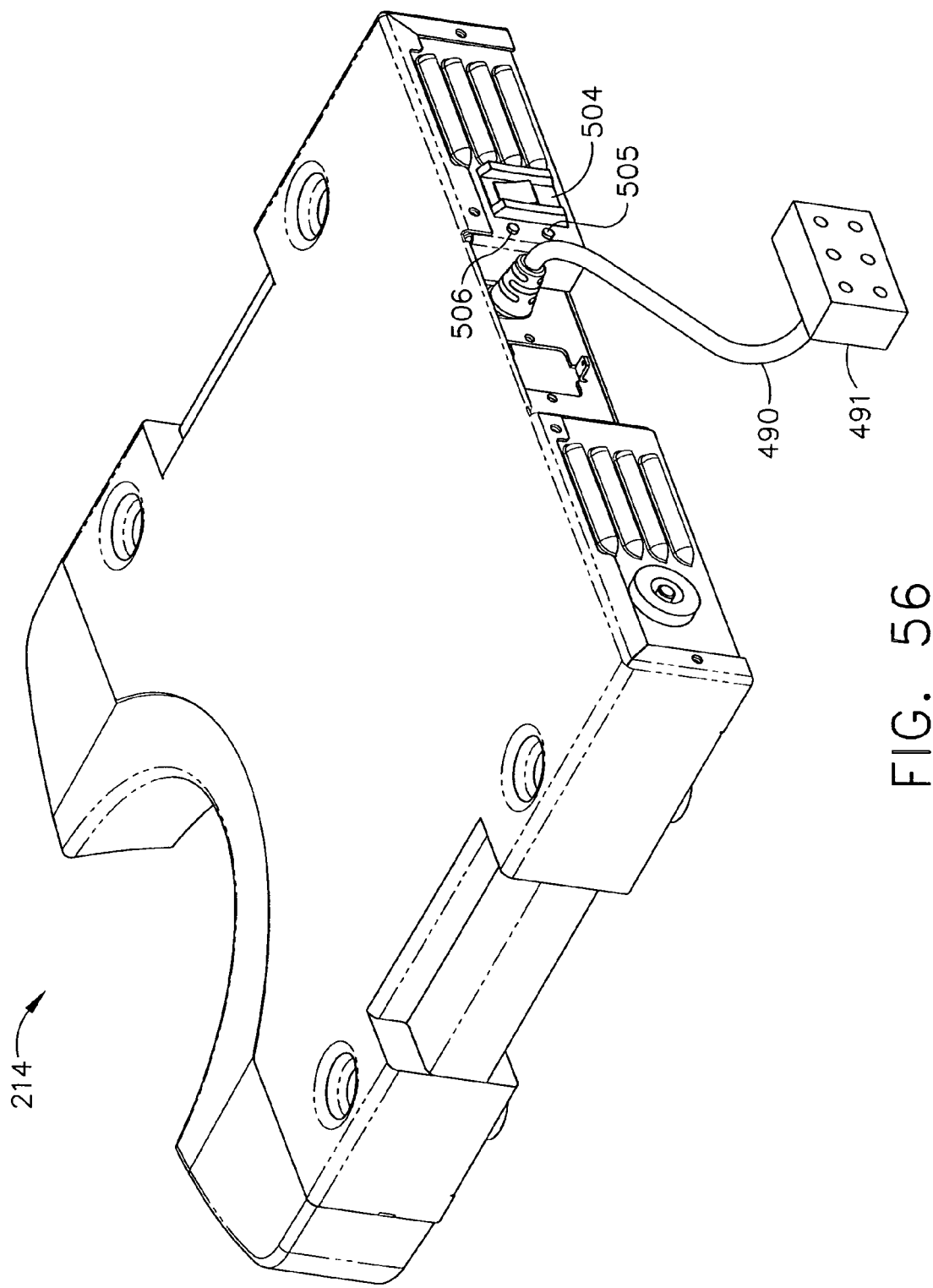
FIG. 56 is a rear perspective view of the UPS of FIG. 42.
Figure 57:
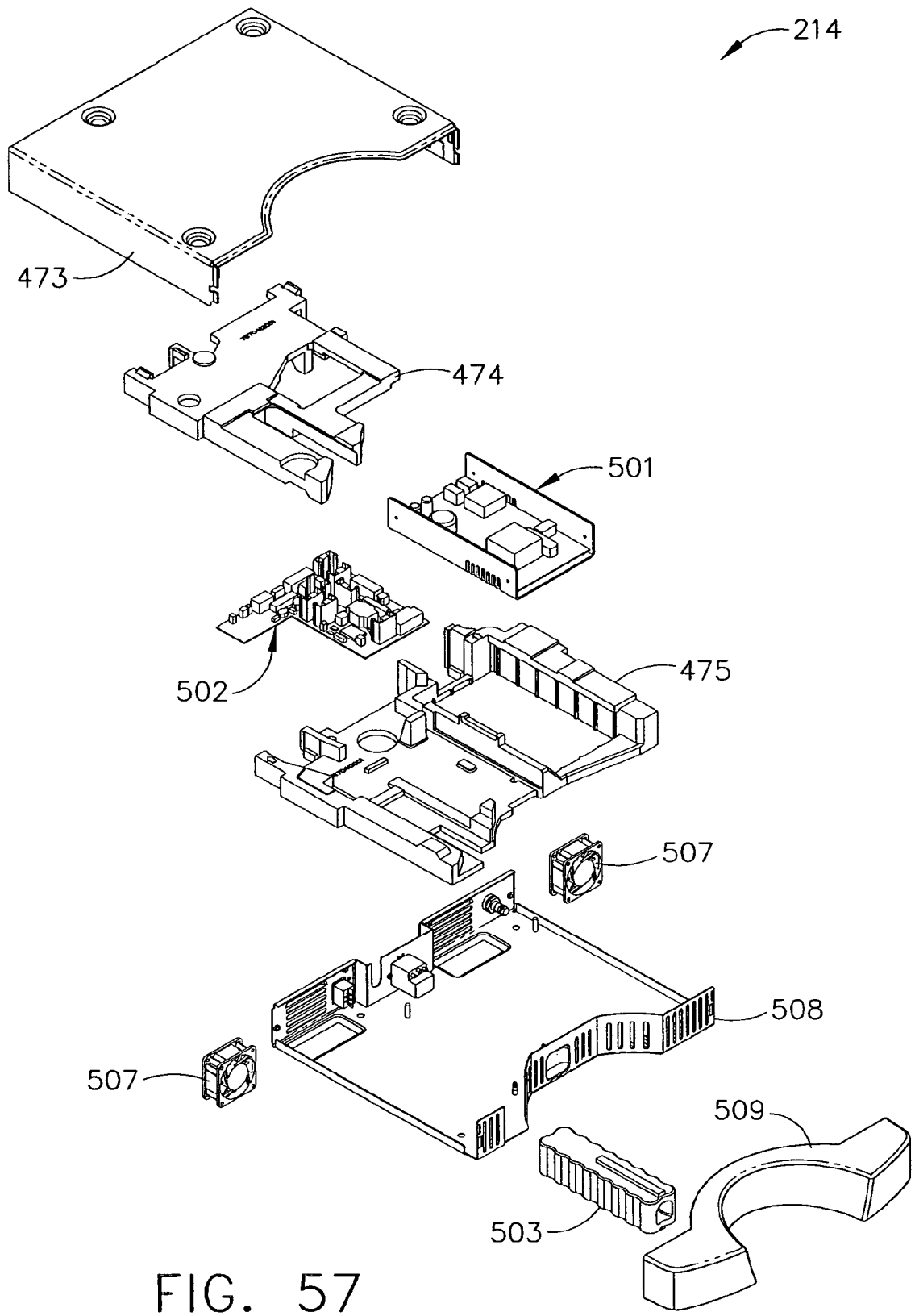
FIG. 57 is an exploded view of the UPS of FIG. 42.

In one implementation of the ninth expression of the embodiment of FIGS. 1-18, the bedside monitoring unit (BMU) 300 is fluidly-connectable to a procedure room unit (PRU) 200 (an embodiment of which is shown in FIGS. 6 and 41-57) of the sedation delivery system (SDS) 100 (or other type of medical effector system 100'). The procedure room unit 200 includes an oral capnometer 202 and a nasal capnometer 140 (see FIG. 54). When the oral and nasal capnometry ports 400 and 402 of the connector 363 are fluidly connected to the bedside monitoring unit 300 and the bedside monitoring unit 300 is fluidly connected to the procedure room unit 200, the oral capnometer 202 is in fluid communication with the oral capnometry port 400 and the nasal capnometer 140 is in fluid communication with the nasal capnometry port 402. The terminology "fluidly connected" includes directly fluidly connected and indirectly fluidly connected.

A tenth expression of the embodiment of FIGS. 1-18 is for a cannula water-trap subassembly 28 including a cannula water-trap housing 30 and a hydrophobic filter 395. The cannula water-trap housing 30 includes a moisture trap chamber 411 or 412 having a moisture-collection cavity 32 and a sampled-respiratory-gas pass-through cavity 34. The sampled-respiratory-gas pass-through cavity 34 is disposed higher than, and in fluid communication with, the moisture-collection cavity 32. The sampled-respiratory-gas pass-through cavity 34 has a smaller volume than the moisture-collection cavity 32. The sampled-respiratory-gas pass-through cavity 34 has a sampled-respiratory-gas entrance and a sampled-respiratory-gas exit. The hydrophobic filter 395 is disposed to cover the exit of the sampled-respiratory-gas pass-through cavity 34. All sampled respiratory gas 36 entering the sampled-respiratory-gas pass-through cavity 34 must pass through the hydrophobic filter 395 to exit the sampled-respiratory-gas pass-through cavity 34. Moisture in the sampled respiratory gas 36 collects in the moisture-collection cavity 32.

An eleventh expression of the embodiment of FIGS. 1-18 is for a cannula assembly 145 including a cannula 351', a connector 363, and an audio earpiece 362. The cannula 351' is disposable on the face of a patient 10 and includes a respiratory-gas-sampling tube 354, 352 or 355. The respiratory-gas-sampling tube 354, 352 or 355 is fluidly-connected to the connector 363, and the connector 363 is connectable to a bedside monitoring unit 300 of a sedation delivery system 100 (or other type of medical effector system 100'). The audio earpiece 362 is disposable proximate an ear of the patient 10 and is operatively-connected to the connector 363 to give sound to the patient 10 at least at the direction of the bedside monitoring unit 300 when the connector 363 is connected to the bedside monitoring unit 300 and the audio earpiece 362 is disposed proximate the ear of the patient 10. The term "proximate" includes, without limitation, "in" and "on".

In one example of the eleventh expression of the embodiment of FIGS. 1-18, the audio earpiece 362 is disposable in the ear of the patient 10, and the cannula assembly 145 includes an audio (i.e., sound) tube 356 which is operatively-connected to the audio earpiece 362 and to the connector 363 and which acoustically transmits sound from a speaker in the bedside monitoring unit (BMU) 300 to the audio earpiece 362 when the connector 363 is connected to the BMU 300. In one employment, the BMU 300 uses the audio earpiece 362 to provide the patient 10, while in the pre-procedure room, with training commands to squeeze an automated response monitor (e.g., a handpiece) to establish a patient response time while conscious. In one-variation, a training computer program in the BMU 300 controls the speaker during such training. Thereafter, the patient 10, while in the procedure room undergoing sedation, is provided operational commands to squeeze the automated response monitor at the request of a procedure room unit (PRU) 200 of the sedation delivery system 100 (or other type of medical effector system 100'). The PRU 200 uses at least the patient response time to determine a level of consciousness of the patient 10 undergoing sedation (or other type of medical procedure). In one variation, a computer program in the PRU 200 controls the speaker during patient sedation. In another employment, soothing sounds, such as music, are given to the patient in the pre-procedure room by the audio earpiece 362. In a different example, the audio earpiece 362 is a speaker on a headset and the audio tube 356 is replaced by electric wiring. Other examples are left to the artisan.

In one application of any of the above-described expressions of FIGS. 1-18, including examples, etc. thereof, the cannula assembly 145 is directly connectable to the Bedside Monitoring Unit (BMU) 300. For example, in one application of the seventh expression of the embodiment of FIGS. 1-18, the connector 363 is directly connectable to the Bedside Monitoring Unit (BMU) 300, wherein inlet ports of the BMU 300 enter the annular towers 24 of the gasket 396 and compress the annular towers 24 against the corresponding nasal capnometry and oral capnometry ports 402 and 400 to provide a leak-free seal. In a different application of any of the above-described expressions of FIGS. 1-18, including examples, etc. thereof, the cannula assembly 145 is directly connectable to a unit (not shown) that stays in the procedure room. For example, in a different application of the seventh expression of the embodiment of FIGS. 1-18, the connector 363 is directly connectable to a unit (not shown) that stays in the procedure room. In one variation, the unit (not shown) includes delivery of a sedation drug(s) to the patient 10, and in another variation, the unit (not shown) does not include delivery of a sedation drug(s) to the patient. Other applications are left to the artisan.

Any one or more of the above-described expressions of the embodiment of FIGS. 1-18, including examples, etc. thereof can be combined with any other one or more of the above-described expressions of the embodiment of FIGS. 1-18, including examples, etc. thereof, as can be appreciated by those skilled in the art.

Figure 19:
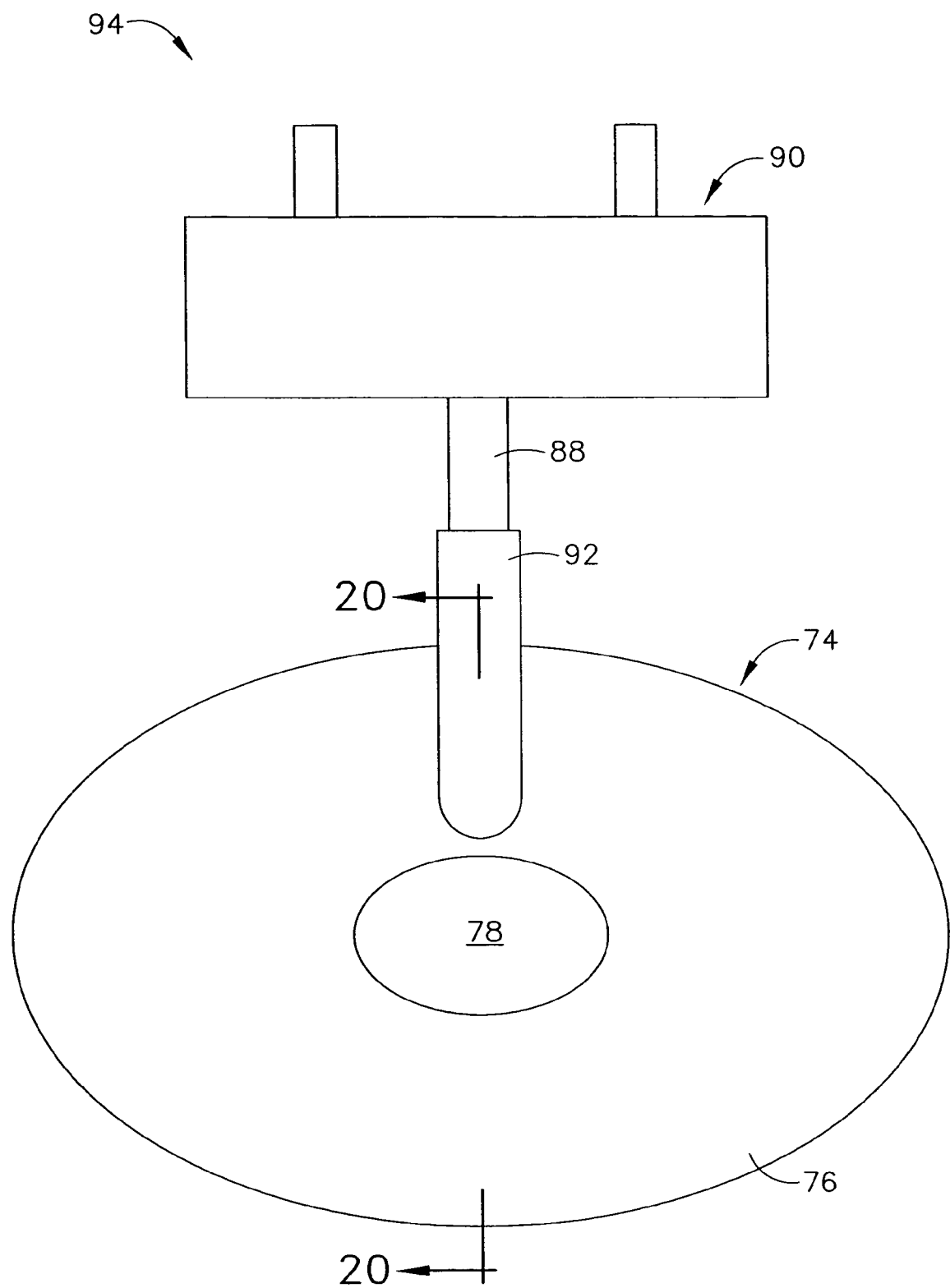
FIG. 19 is a front elevational view of a first embodiment of a bite block and a portion of a first alternate embodiment of a cannula.
Figure 20:
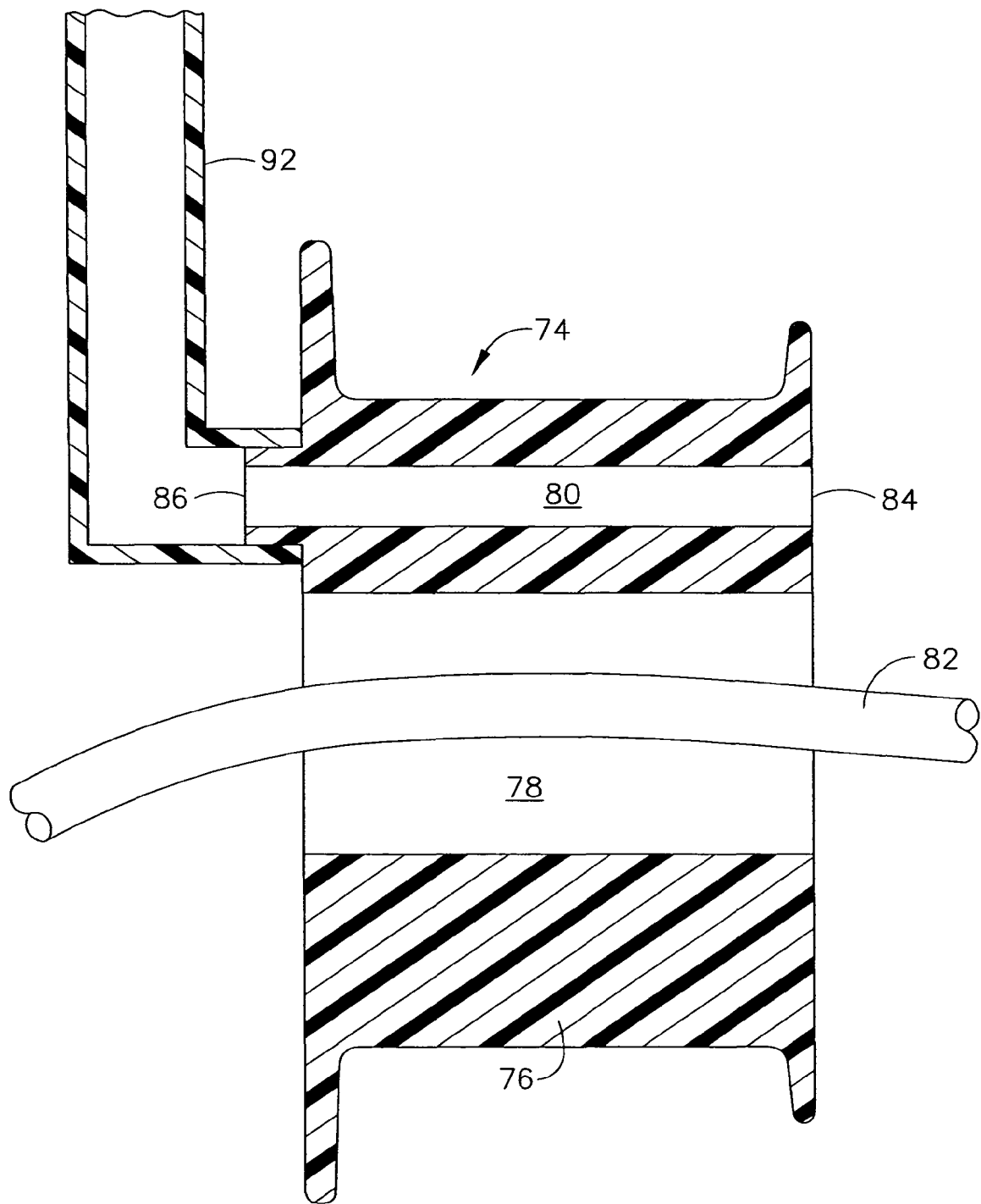
FIG. 20 is a cross-sectional view of the bite block of FIG. 19 taken along the lines 20-20 of FIG. 19 with the addition of a medical instrument inserted in the through passageway of the bite block.

FIGS. 19 and 20 show a first embodiment of a bite block 74, which, in one example, is used with the cannula assembly 145 of FIGS. 1-18. A bite block, in one example, is used on a patient during an upper-gastrointestinal endoscopic medical procedure. The bite block has a bite-block body, which is inserted into the mouth of the patient. The bite-block body has a through passageway for insertion of an endoscope therethrough. The patient bites down on the bite-block body instead of on the endoscope.

A first expression of the embodiment of FIGS. 19 and 20 is for a bite block 74 including a bite-block body 76 adapted for insertion into the mouth of a patient. The bite-block body 76 includes a through passageway 78 and includes an air sampling passageway 80 spaced apart from the through passageway 78. The through passageway 78 is adapted for receiving therethrough a medical instrument 82 (only an unhatched portion of which is shown in FIG. 20). The air sampling passageway 80 has an inlet 84 disposed to receive exhaled air from the patient when the bite-block body 76 is inserted into the mouth of the patient. The air sampling passageway 80 has an outlet 86 adapted for coupling to a respiratory gas sampling port 88 of a cannula 90 (only the body/cap portion of an embodiment of an oral/nasal cannula without respiratory-gas-delivery prongs is shown). In one variation, the outlet 86 of the air sampling passageway 80 is adapted for indirectly coupling to the respiratory gas sampling port 88 of the cannula 90 through a connector tube 92.

A second expression of the embodiment of FIGS. 19 and 20 is for a cannula assembly 94 including a cannula 90, a bite block 74, and a connector tube 92. The cannula 90 is disposable on the face of a patient and includes a respiratory gas sampling port 88. The bite block 74 has a bite-block body 76 adapted for insertion into the mouth of a patient. The bite-block body 76 includes a through passageway 78 and includes an air sampling passageway 80 spaced apart from the through passageway 78. The through passageway 78 is adapted for receiving therethrough a medical instrument 82. The air sampling passageway 80 has an inlet 84 disposed to receive exhaled air from the patient when the bite-block body 76 is inserted into the mouth of the patient and has an outlet 86. The connector tube 92 having a first end attached or attachable to the respiratory gas sampling port 88 of the cannula 90 and has a second end attached or attachable to the bite-block body 76 at the outlet 86 of the air sampling passageway 80 of the bite-block body 76.

Figure 21:
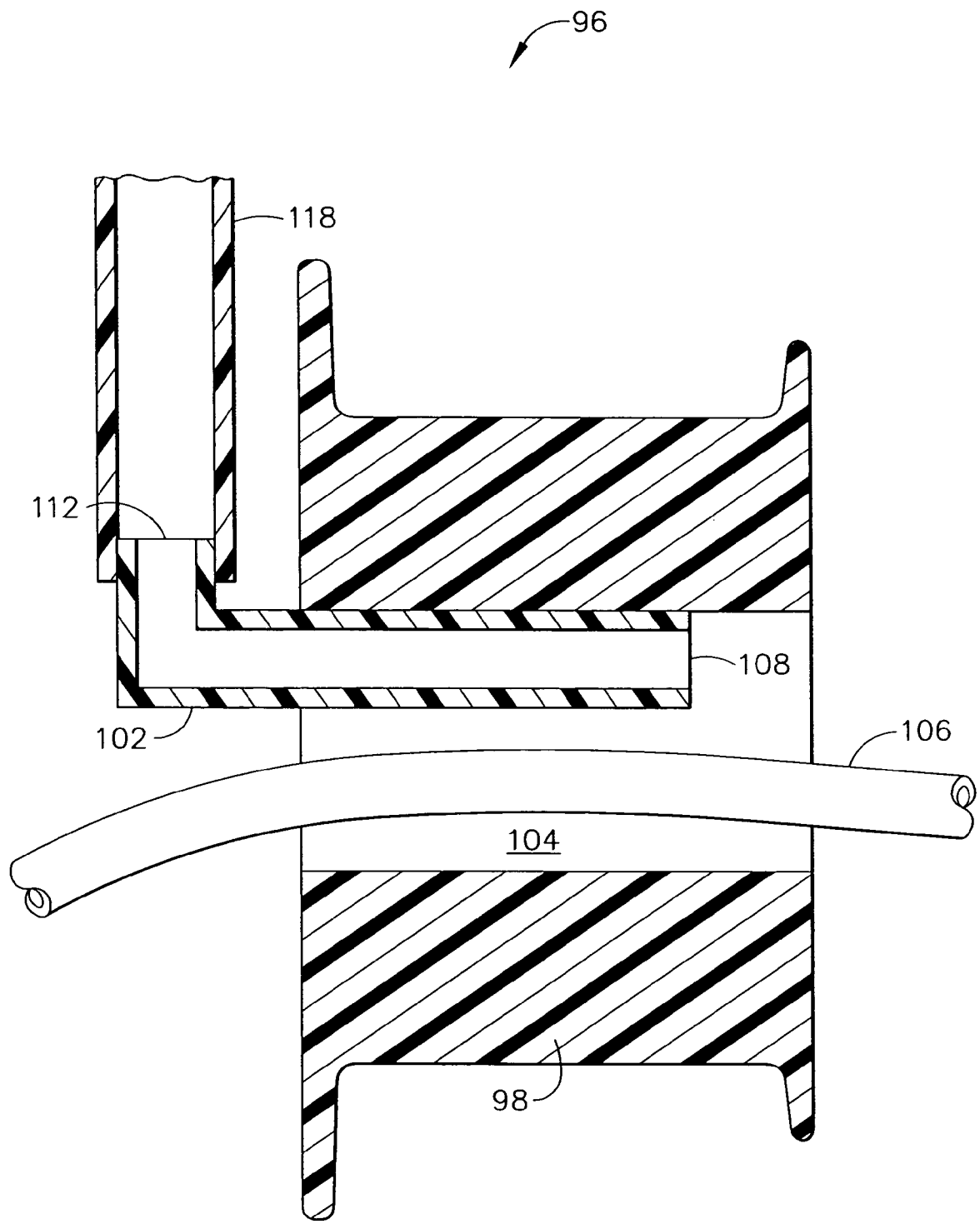
FIG. 21 is a view, as in FIG. 20 but of a second embodiment of a bite block.

FIG. 21 shows a second embodiment of a bite block. An expression of the embodiment of FIG. 21 is for a bite block assembly 96 including a bite-block body 98 and an air sampling tube 102. The bite-block body 98 is adapted for insertion into the mouth of a patient and includes a through passageway 104 adapted for receiving therethrough a medical instrument 106 (only a portion of which is shown). The air sampling tube 102 is attached to the bite-block body 98, has an inlet 108 disposed to receive exhaled air from the patient when the bite-block body 98 is inserted into the mouth of the patient and has an outlet 112 attached or attachable to a respiratory gas sampling port of a cannula.

In one variation of the embodiment of FIG. 21, the air sampling tube 102 is at least partially disposed within the through passageway 104. In one construction, the air sampling tube 102 is adhesively attached to the bite-block body 98. In one employment, the outlet 112 of the air sampling tube 102 is adapted for indirect attachment to the respiratory gas sampling port of the cannula through a connector tube 118.

Figure 22:
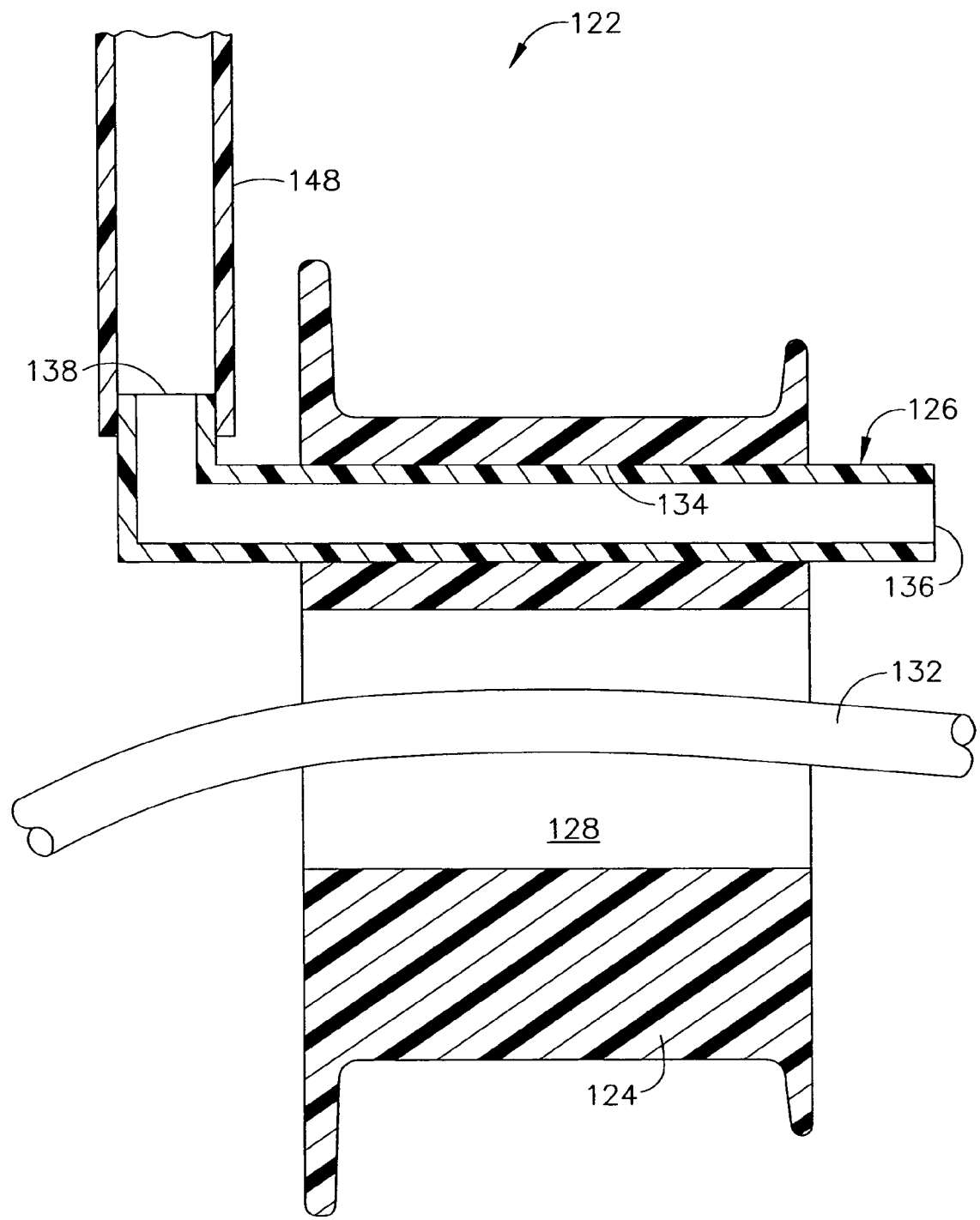
FIG. 22 is a view, as in FIG. 20 but of a third embodiment of a bite block.

FIG. 22 shows a third embodiment of a bite block. An expression of the embodiment of FIG. 22 is for a bite block assembly 122 including a bite-block body 124 and an air sampling tube 126. The bite-block body 124 is adapted for insertion into the mouth of a patient. The bite-block body 124 includes a through passageway 128 adapted for receiving therethrough a medical instrument 132 (only a portion of which is shown) and includes an air sampling passageway 134. The air sampling tube 126 is at least partially disposed within the air sampling passageway 134, has an inlet 136 disposed to receive exhaled air from the patient when the bite-block body 124 is inserted into the mouth of the patient, and has an outlet 138 attached or attachable to a respiratory gas sampling port of a cannula. In one variation, the outlet 138 of the air sampling tube 126 is adapted for indirect attachment to the respiratory gas sampling port of the cannula through a connector tube 148.

Examples of the embodiments of FIGS. 19 and 20, 21, and 22 have the advantage of maintaining the air sampling passageway/tube in proper air-sampling position despite movement of the instrument in the through passageway during a medical procedure. This results in more accurate carbon dioxide gas concentration measurements of the exhaled air of the patient than is achieved with conventional bite block and cannula arrangements which employ a cannula having an air sampling tube which does not stay in position relative to the bite block.

Figure 23:
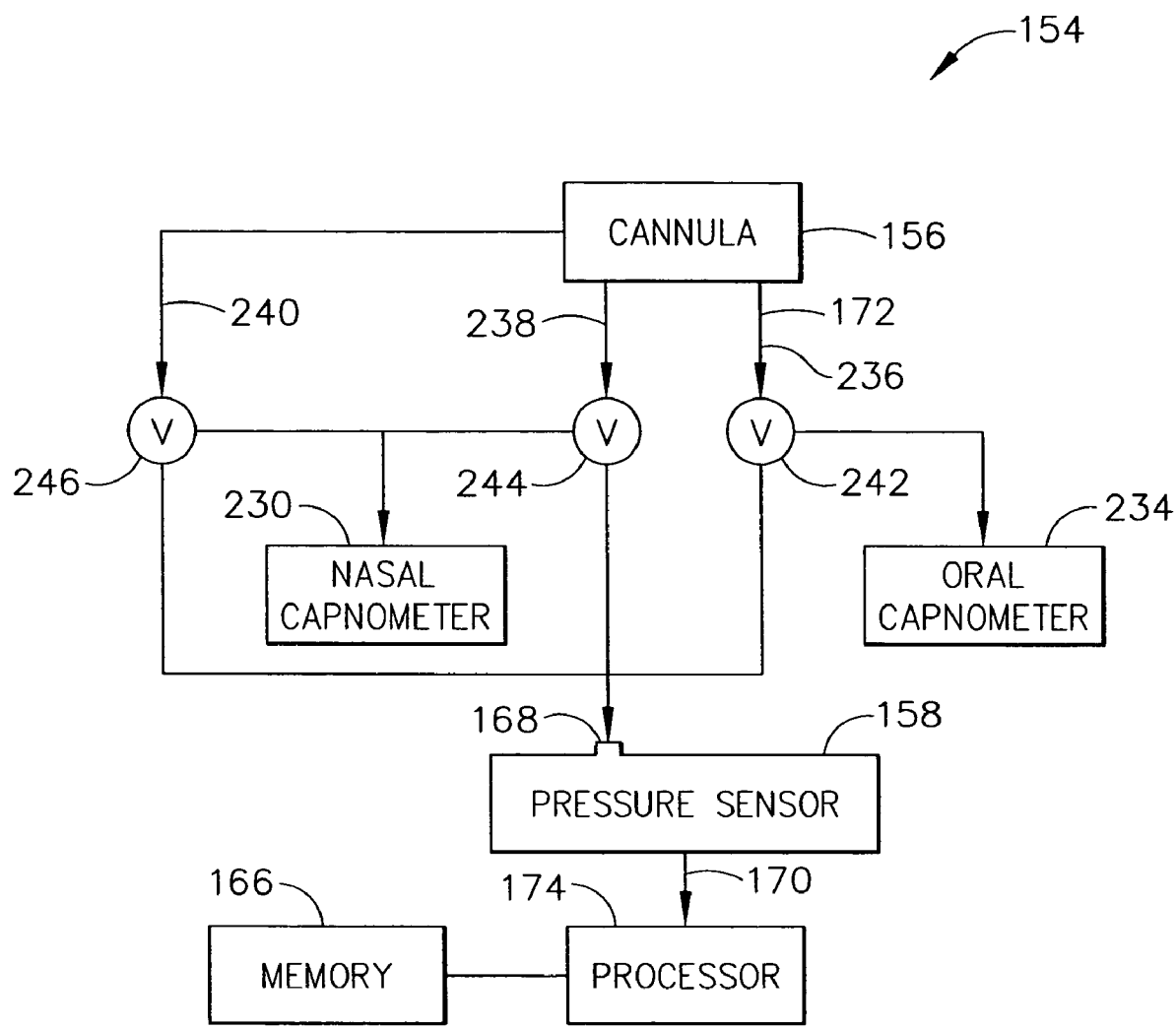
FIG. 23 is a schematic diagram of a further embodiment of a medical effector system having a cannula, wherein the medical effector system alerts a user of a possible problem with the cannula.

FIG. 23 shows a further embodiment of a medical effector system 154, wherein the medical effector system 154 alerts a user of a possible problem with a cannula 156 of the medical effector system 154. An expression of the embodiment of FIG. 23 is for a medical effector system 154 including a pressure sensor 158, a cannula 156, and a memory 166. The pressure sensor 158 includes an input 168 and has an output signal 170. The cannula 156 is disposable on the face of a patient and includes a respiratory-gas-sampling tube 172 operatively connectable to the input 168 of the pressure sensor 158. The memory 166 contains a cannula program which when running on a processor 174 is operatively connected to the output signal 170 of the pressure sensor 158. The cannula program alerts a user of a possible problem with the cannula 156 based at least in part (and in one example based entirely) on the output signal 170 of the pressure sensor 158. It is noted that, in one example, the input 168 of the pressure sensor 158 is for receiving a pneumatic signal in the form of respiratory gas from the patient.

In one deployment of the embodiment of FIG. 23, when the cannula 156 is disposed on the face of the patient and when the respiratory-gas-sampling tube 172 is operatively connected to the input 168 of the pressure sensor 158, the output signal 170 of the pressure sensor 158 corresponds to the pressure generated by the patient's breathing which is a time varying signal corresponding to the breath rate of the patient. If no cannula 156 is disposed on the face of the patient and/or if the respiratory-gas-sampling tube 172 of the cannula 156 is not operatively connected to the input 168 of the pressure sensor 158, then the output signal 170 (which typically is an electrical signal) of the pressure sensor 158 would substantially equal that of atmospheric pressure.

In one construction of the embodiment of FIG. 23, the respiratory-gas-sampling tube 172 is adapted to sample respiratory gas from at least one of the mouth, left nostril and right nostril of the patient. In one variation, not shown, the respiratory-gas-sampling tube is adapted to sample respiratory gas from the mouth and both nostrils of the patient. In another variation, not shown, the respiratory-gas-sampling tube is adapted to sample respiratory gas from just both nostrils of the patient. In an additional variation, the respiratory-gas-sampling tube 172 is adapted to sample respiratory gas from just one of the left nostril, right nostril, and mouth of the patient.

In one employment of the embodiment of FIG. 23, the possible cannula problem includes the cannula 156 not being disposed (or not being disposed properly) on the face of the patient when the cannula program is running on the processor 174. In the same or a different employment, the possible cannula problem includes the cannula 156 not being operatively connected to the input 168 of the pressure sensor 158 when the cannula program is running on the processor 174.

Figure 6:
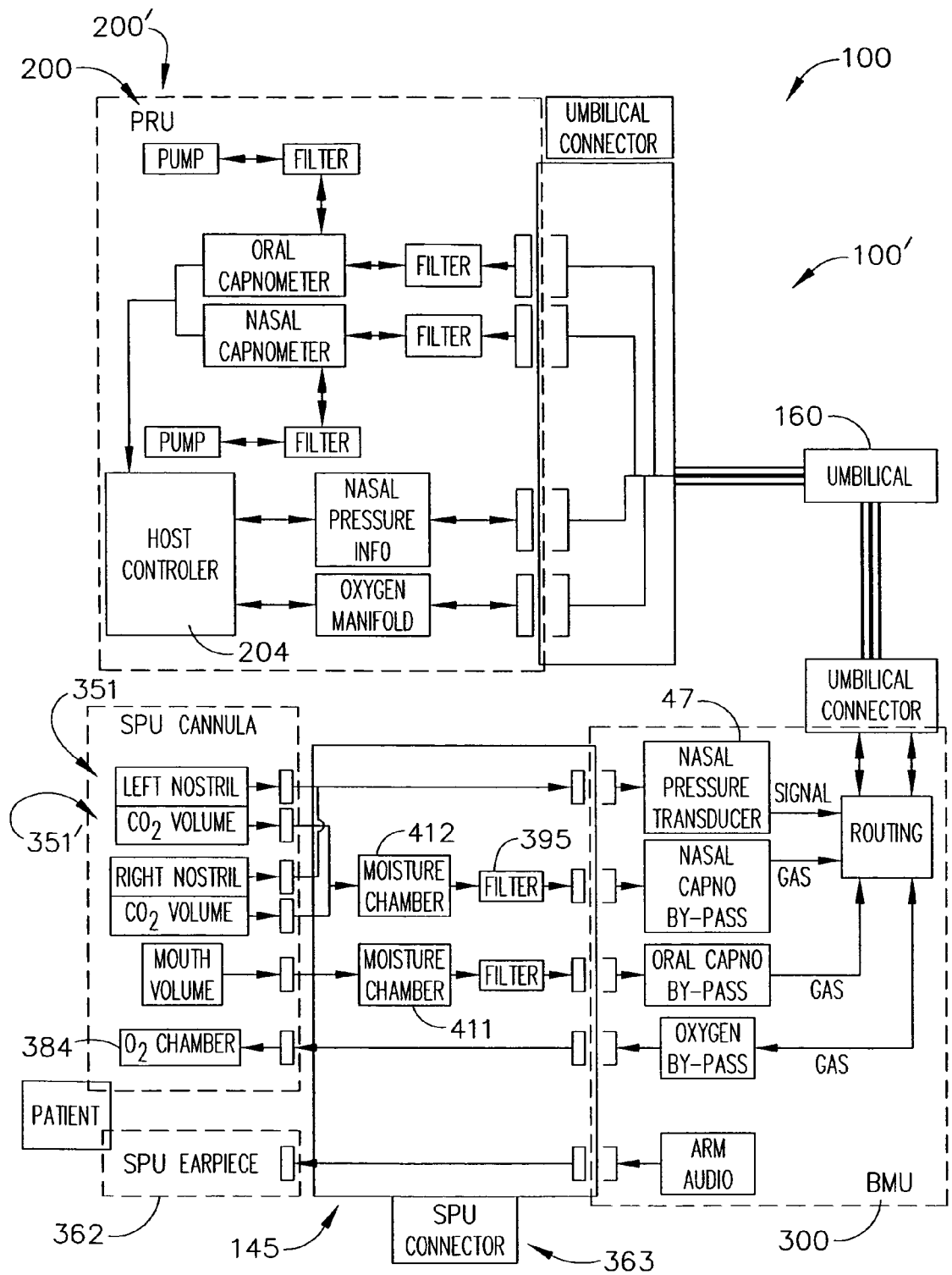
FIG. 6 is a block diagram identifying elements of an embodiment of an oral/nasal cannula assembly, including the oral/nasal cannula of FIG. 1, and identifying elements of an embodiment of a medical gas analysis/delivery system of an embodiment of an SDS (sedation delivery system), which is an example of a medical effector system, including an embodiment of a PRU (procedure room unit) and an embodiment of a BMU (bedside monitoring unit)

In one application of the embodiment of FIG. 23, the pressure sensor 158 is a component of a bedside monitoring unit (e.g., the bedside monitoring unit 300 of FIG. 6 wherein pressure sensor 158 would replace nasal pressure transducer 47). In the same or a different application, the memory 166 and the processor 174 are components of a host controller of a procedure room unit (such as host controller 204 of the procedure room unit 200 of FIG. 6). In one variation, the medical effector system 154 also includes an umbilical cable (such as the umbilical cable 160 of FIG. 6). In this variation, the cannula program automatically starts running after the bedside monitoring unit and the procedure room unit are operatively connected together with the umbilical cable when at least one of the bedside monitoring unit and the procedure room unit has been turned on. In one employment, the possible problem with the cannula includes the umbilical cable not being connected (or not being properly connected) to the bedside monitoring unit and the procedure room unit. In one modification, the procedure room unit includes a capnometer 230 and 234 operatively connectable to the cannula 156, and the cannula program starts the capnometer 230 and 234 if the cannula program does not alert the user of the possible problem with the cannula 156. In another application, the pressure sensor 158, the memory 166, the processor 174, and the capnometer 230 and 234 are components of a single unit.

In one arrangement of the embodiment of FIG. 23, the respiratory-gas-sampling tube 172 is an oral respiratory-gas sampling tube 236, the cannula 156 also includes a left-nostril respiratory-gas-sampling tube 238 operatively connectable to the input 168 of the pressure sensor 158, and the cannula 156 additionally includes a right-nostril respiratory-gas-sampling tube 240 operatively connectable to the input 168 of the pressure sensor 158. In one variation, at least one valve 242, 244 and 246 is controllable by the cannula program to selectively operatively connect to the pressure sensor 158, one at a time, the oral, left-nostril and right-nostril respiratory-gas-sampling tubes 236, 238 and 240. Other configurations using a different number of valves, different valve design, and/or different valve connections than that shown in FIG. 23 are left to the artisan. In one modification, the medical effector system 154 also includes at least one capnometer 230 and 234, wherein the at-least-one valve 242, 244 and 246 is controllable by the cannula program to operatively connect the oral, left-nostril and right-nostril respiratory-gas-sampling tubes 236, 238 and 240 to the at-least-one capnometer 230 and 234.

In one application, the at least one capnometer 230 and 234 includes a nasal capnometer 230 which receives respiratory-gas-sampling input from both nostrils of the patient and an oral capnometer 234 which receives respiratory-gas-sampling input from the mouth of the patient. In one implementation, the nasal capnometer 230 and the oral capnometer 234 are components of a procedure room unit (such as the previously-discussed procedure room unit 200). It is noted that the connections between the processor 174 and the capnometers 230 and 234 and between the processor 174 and the at-least-one valve 242, 244 and 246 have been omitted from FIG. 23 for clarity. In other arrangements, not shown, two or three pressure sensors are employed.

In other configurations, not shown, of a medical effector system which alerts a user of a possible problem with a cannula, each valve 242, 244 and 246 (which in one example also has an off position blocking any flow from exiting the valve) of FIG. 23 is replaced with a splitter which divides the associated respiratory-gas-sampling tube into one branch connected to the associated capnometer and another branch connected to the pressure sensor. In one variation, one, two or three pressure sensors and/or one, two or three capnometers are employed. It is noted that, in one deployment, the strongest pressure signal from a breathing site identifies the best breathing site for use in capnometer measurements of carbon dioxide in the exhaled breath of the patient.

In one example, benefits of the medical effector system 154 include automatically alerting the user of a possible problem with the cannula 156 without employing less reliable mechanical switches and include providing baseline pressure measurements for a patient's oral breathing and nasal breathing. Such baseline pressure measurements, in one application, are used to later determine if a patient's preferred breathing orifice has changed whereupon the flow rate of oxygen to the patient undergoing a medical procedure is raised or lowered.

The following paragraphs present a detailed description of one particular enablement of the embodiment of FIGS. 1-18. It is noted that any feature(s) of this particular enablement can be added to any of the previously-described expressions (including examples, etc. thereof) of the embodiment of FIGS. 1-18. In this particular enablement, the cannula assembly 145 is an oxygen (the term "oxygen" includes air with an enriched oxygen content) delivery cannula assembly, more specifically a cannula assembly 145 (shown in FIG. 1) that supplies oxygen to a patient 10 and collects oral and nasal exhaled breath samples for analysis. The oral/nasal cannula 351 allows for measurement of end-tidal $CO_2$ gas (the term "$CO_2$ gas" means gas containing $CO_2$) from both oral and nasal cavities, as well as measurement of $CO_2$ gas pressure from combined nasal cavities.

Oral/nasal cannula 351 provides a stream of oxygen directed into the oral and nasal cavities, unlike prior art cannulas, which provide oxygen as a cloud to the exterior of the oral or nasal cavities. Cannula assembly 145 includes a nasal pressure sensor line that provides a signal to an oxygen controller to decrease oxygen flow rates during exhalation thus preventing dilution of the end-tidal gas sample, increasing measurement accuracy. Cannula 145 allows for independent oral and nasal capnometry measurement, different from prior art capnometry cannulas, which combine the sampling to come up with an average measurement. The invention also includes a connector 363 as an integral part of the cannula system to facilitate easy attachment and removal from Bedside Monitoring Unit (BMU) 300. Cannula 145 also provides for the delivery of audible commands to a patient 10 requesting a response for an Automated Responsiveness Monitor (ARM).

In one construction, oral nasal cannula 351 is made of a soft pliable material that is easily deformable and will fit comfortably on a patient's 10 face. This ensures patient 10 comfort and minimize irritation.

Cannula assembly 145 (shown in FIG. 1) is part of an integrated monitoring and sedation delivery system (SDS) intended to provide a safe means to administer sedation drug in surgical procedures. The system uses a drug delivery algorithm and an intravenous infusion peristaltic pump to deliver drug(s) with variable rate infusion that achieves and maintains a desired sedation effect. All drug delivery is performed by a Procedure Room Unit (PRU) 200, which together with a Bedside Monitoring Unit (BMU) 300 enables the care team to make necessary drug dosing changes possible from any location.

As used herein, the term "proximal" refers to a location on the oral/nasal cannula assembly closest to the device using the cannula assembly and thus furthest from the patient 10 on which the cannula assembly is used. Conversely, the term "distal" refers to a location farthest from the device using the cannula assembly and closest to the patient 10.

Figure 2:
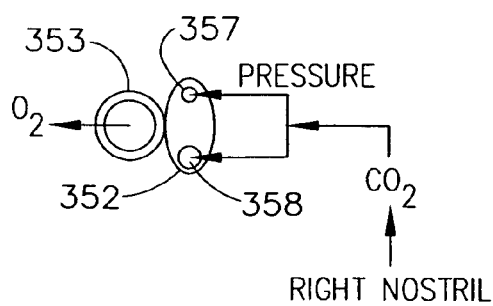
FIGS. 2 and 3 are cross-sectional views of tubing, taken along lines 2-2 and 3-3 of FIG. 1, showing separate lumens that conduct gases to/from the oral/nasal cannula.
Figure 3:
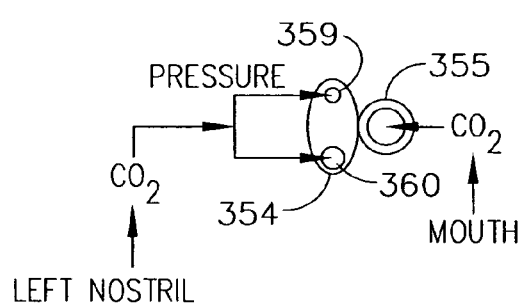

As illustrated on FIGS. 1-3, oral/nasal cannula 351 is designed to fit comfortably upon the upper lip of a patient 10 between the nose and mouth. Oral/nasal cannula 351 functions as a mask-free delivery apparatus for supplying oxygen gas to a patient 10 while also providing for the monitoring of patient 10 breathing. Oral/nasal cannula 351 is connected to a set of tubing for gas sample collection, audio and oxygen delivery, and includes cinch 361 to help secure to the patient 10, an earpiece 362 to allow audio messages to be sent to the patient 10, and BMU connector 363 for secure connection to the bedside monitoring unit (BMU) 300.

Referring to FIGS. 1 and 6, the cannula assembly 145 includes distal oral-nasal cannula 351 earpiece 362 and proximal connector 363. Exhalation samples from the patient 10 are collected by oral-nasal cannula 351 and flow through independent channels and lumens to connector 363. Connector 363 is removably attached to bedside monitoring unit (BMU) 300. Gases (oxygen and $CO_2$) are then routed via the umbilical to/from procedure room unit (PRU) 200. The capnometry system includes two capnometers in PRU 200. A particle and hydrophobic filter are located inside cannula connector 363. Oral chamber 411 and nasal chamber 412 are designed to trap condensation from the patient's 10 exhaled breath to avoid moisture damage to the capnometers. A nasal pressure transducer 47 is located in the bedside monitoring unit (BMU) 300. The pressure transducer 47 provides patient 10 breathing information to procedure room unit (PRU) 200 through the umbilical cable.

Figure 4:
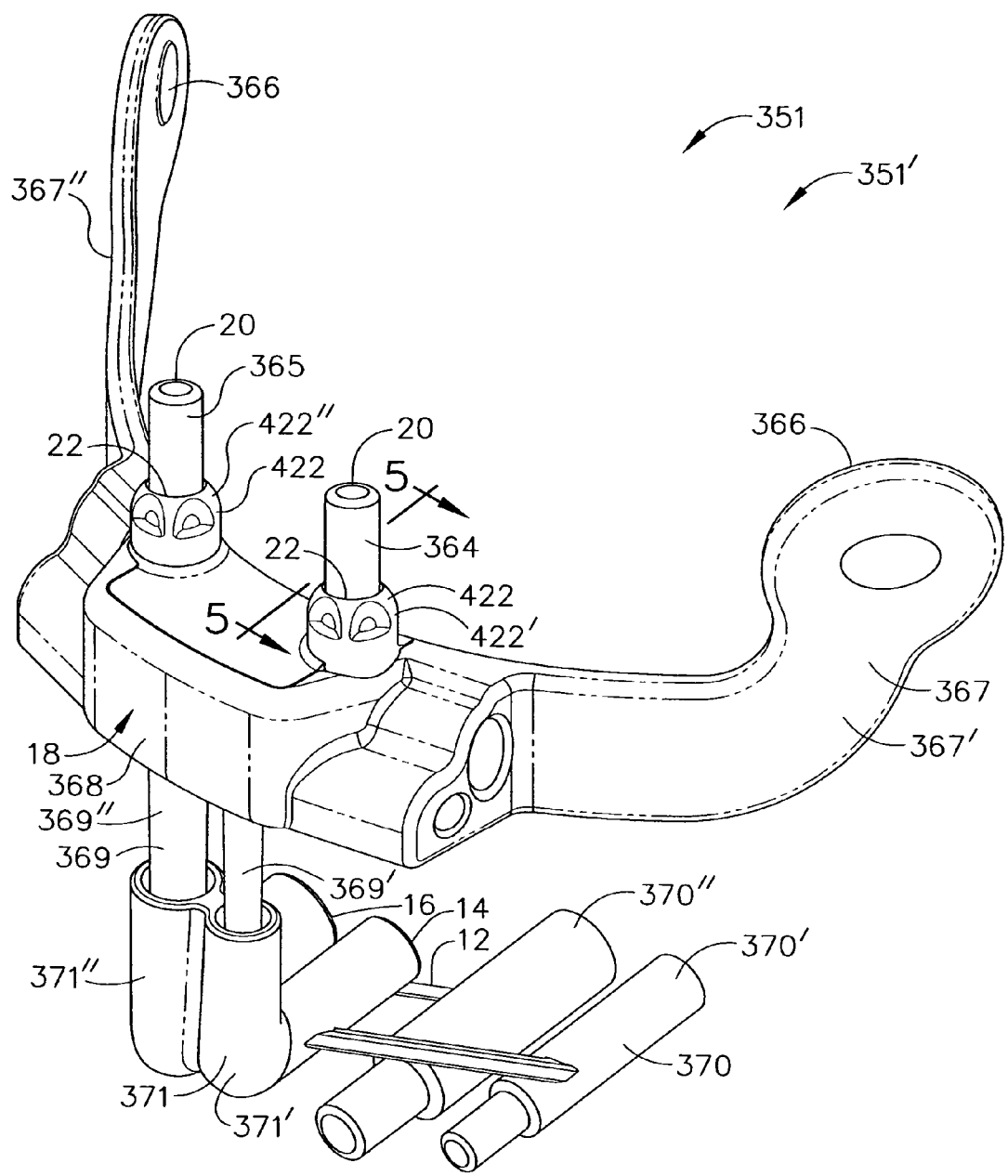
FIG. 4 is a perspective view of the oral/nasal cannula of FIG. 1 without any connecting tubes.
Figure 5:
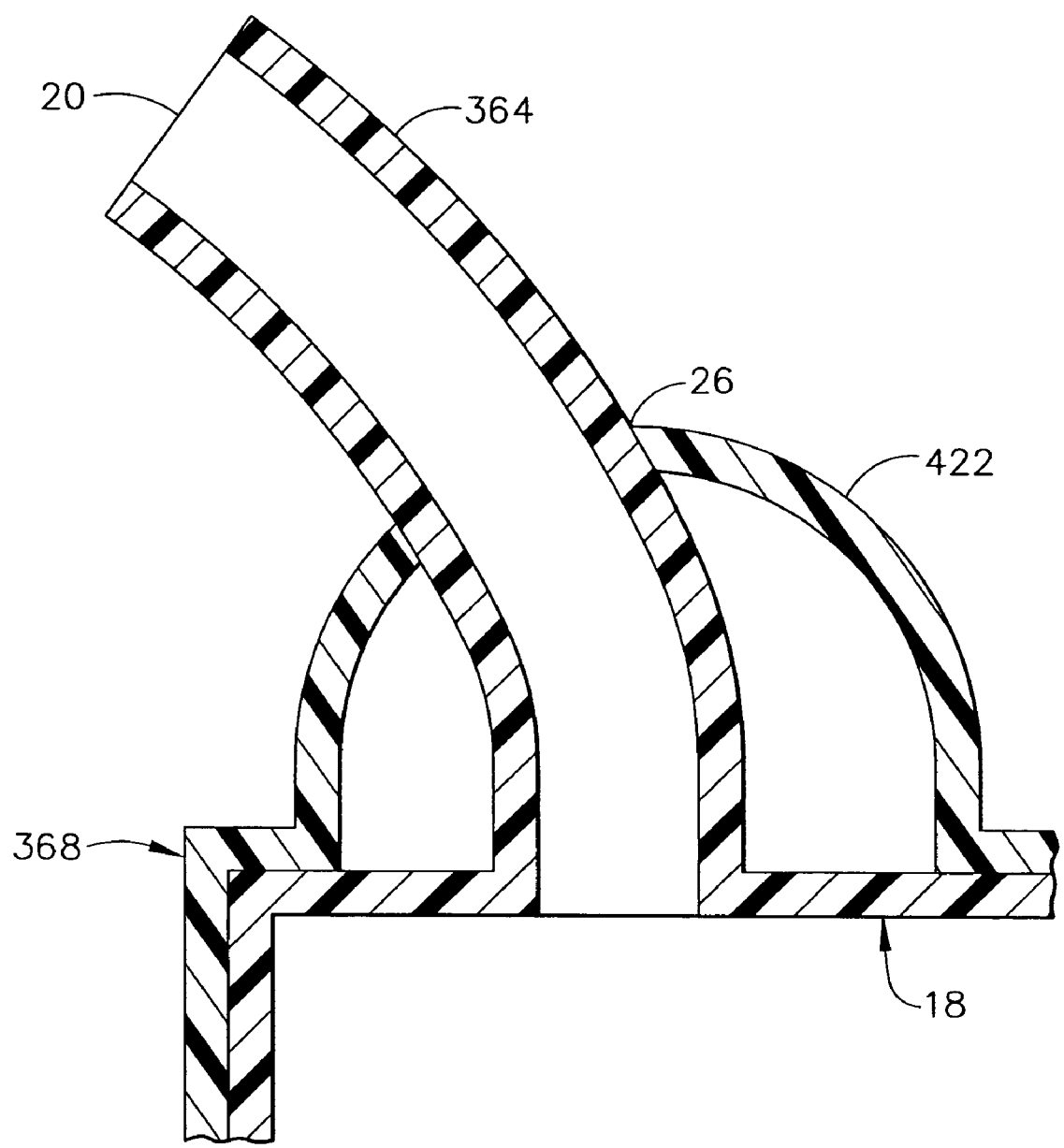
FIG. 5 is a cross-sectional view taken along lines 5-5 in FIG. 4 of a portion of the cannula cap and cannula body showing the bending of a respiratory-gas-sampling nasal prong of the cannula body because of the location of the tube-receiving hole of a respiratory-gas-delivery nasal prong of the cannula cap when the cannula cap is attached to the cannula body.

As shown in FIG. 4, oral-nasal piece 351 is made of soft and flexible material, such as polyurethane, silicon or some other elastomer, and is generally constructed by either injection-molding or liquid injection molding techniques. Cannula cap 368 is generally a hollow cube and is the platform for supporting other features. Oral-nasal piece 351 profile is designed to easily adapt to patient 10 anatomy. Oral-nasal cannula 351 includes adhesive pads 366 located on the patient 10 side of cannula wings 367 and are intended to adhere to and secure comfortably oral-nasal piece 351 in place on the patient 10's face. Cannula cap 368 includes nasal prong 422 and oral prong 369. Cannula body 18 includes nasal prongs 364 and 365 and oral prongs 370 and 371.

Figure 7:
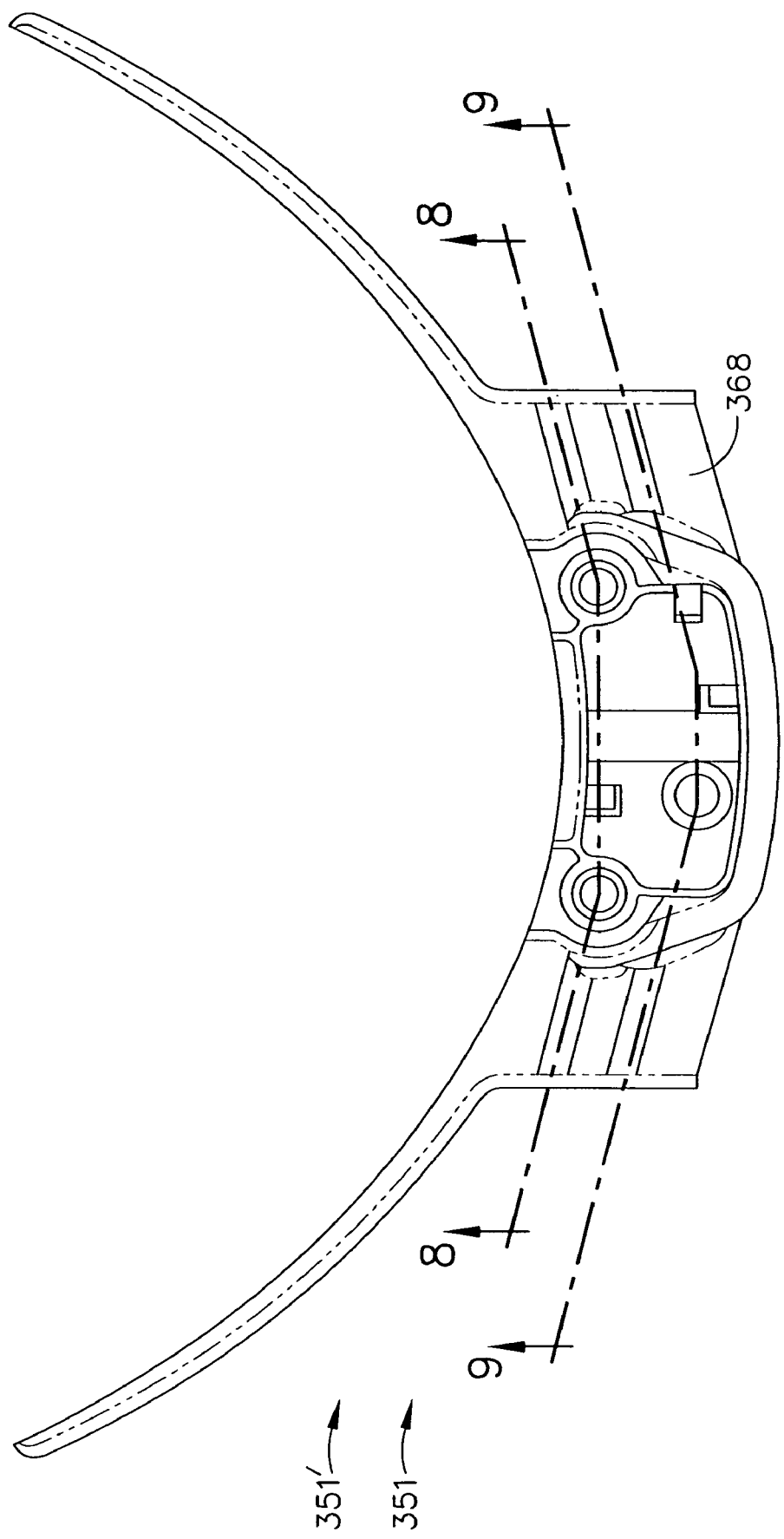
FIG. 7 is a top planar view of the oral/nasal cannula of FIG. 4 with the cannula cap removed.
Figure 8:
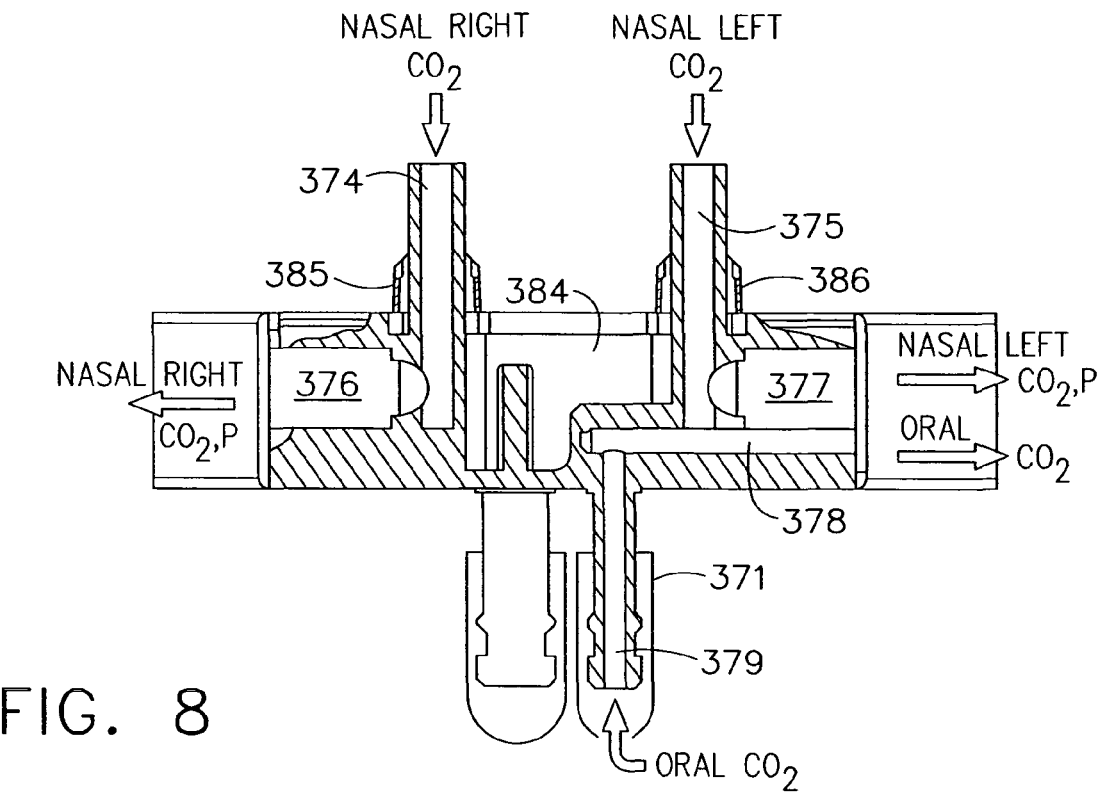
FIGS. 8 and 9 are cross-sectional views of the oral/nasal cannula of FIG. 7, taken along lines 8-8 and 9-9 of FIG. 7, indicating paths for oxygen and $CO_2$ gases.

FIGS. 4 and 6-9 illustrate that cannula cap 368 includes two independent gas circuits, one for collecting oral and nasal exhaled $CO_2$ for capnometry and pressure analysis, and a second for supplying oxygen into the patient's 10 nose and mouth. FIG. 8 shows a cross-section view of the oral/nasal cannula 351 $CO_2$ sampling circuit. The $CO_2$ sampling circuit comprises a left and right nostril circuit and oral sample circuit, which are internally molded and interconnected inside cannula cap 368. $CO_2$ left circuit is comprised of left prong channel 375 and left channel 377, interconnected at right angles, and functioning to collect $CO_2$ samples from the patient's 10 left nostril. Left sample tube 354 (FIG. 1) is inserted into and fixedly attached to left channel 377, which divides the $CO_2$ sampling volume into two lumens (shown on FIGS. 2-3 and 6): left pressure lumen 359 and left sample lumen 360. In addition, $CO_2$ right circuit is comprised of right prong channel 374 and right channel 376, interconnected at right angles, and functioning to collect $CO_2$ samples from the patient 10's right nostril. Right sample tube 352 (FIG. 1) is inserted into and fixedly attached to right channel 376, which divides the $CO_2$ sampling volume into two lumens (shown on FIGS. 2-3 and 6): right pressure lumen 357 and right sample lumen 358. The arrangement is essentially the same for an oral circuit which comprises an oral prong channel 379 within oral prongs 369, 371 and 370; and an oral channel 378 inside cannula cap 368. Oral prong channel 379 and oral channel 378 are interconnected and collect $CO_2$ samples from the patient 10's mouth.

Figure 9:
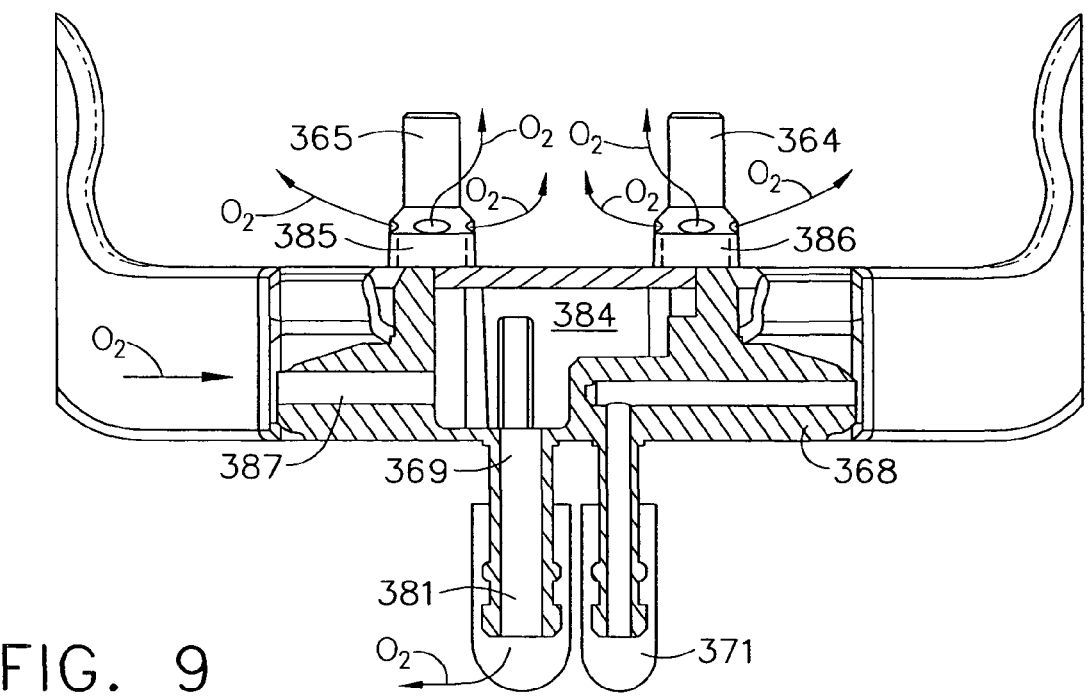
Figure 10:
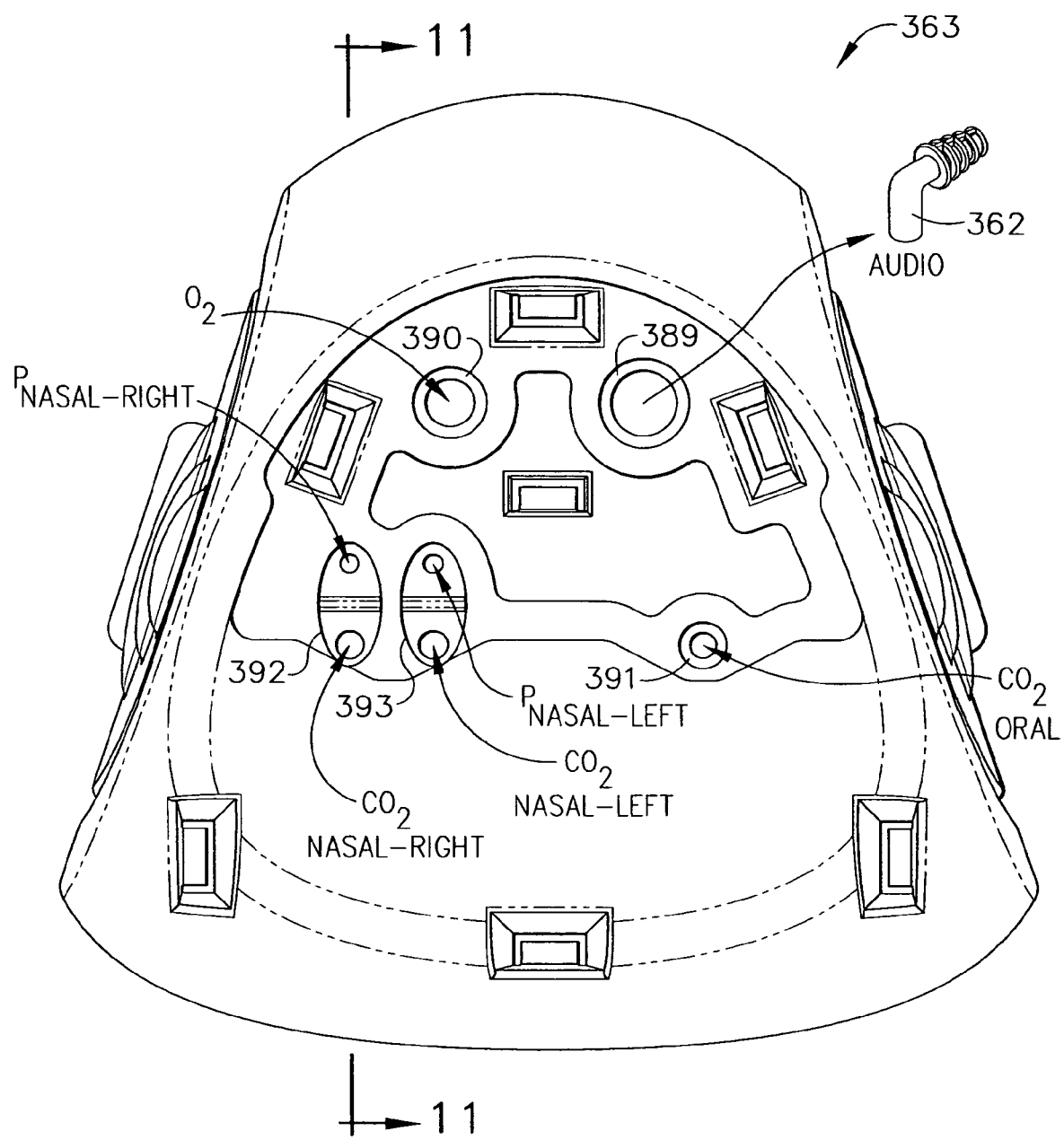
FIG. 10 is a distal end view of the oral/nasal cannula BMU connector of FIG. 1 without any connecting tubes.
Figure 11:
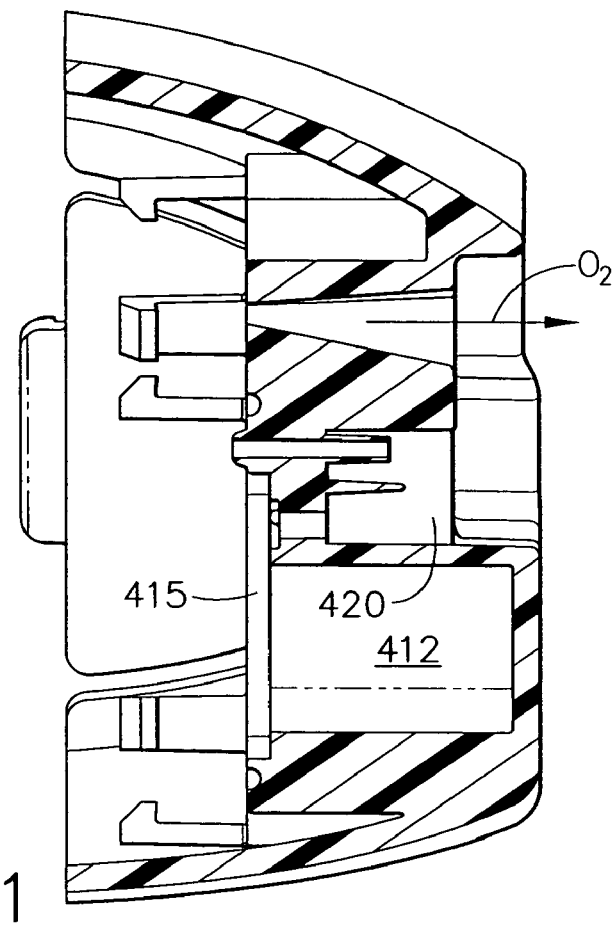
FIG. 11 is a cross-sectional view of the oral/nasal cannula BMU connector of FIG. 10, taken along lines 11-11 in FIG. 10, showing the recess for the nasal moisture chamber.

As illustrated in FIGS. 7-9, a second gas circuit delivers oxygen in the proximity of the patient's 10 nose and mouth. FIG. 9 shows a cross-section view of oral/nasal cannula 351. Oxygen channel 387 is in fluid communication with chamber 384 within cannula cap 368. Oxygen chamber 384 has three openings: a first opening connecting to oxygen prong channel 381, which delivers oxygen in the vicinity of the mouth; a second opening which communicates with right channel 385 that delivers oxygen into the right nostril; and a third opening which delivers oxygen to the left nostril through channel 386.

As shown on FIG. 4, nasal oxygen prongs 422 are mounted over prongs 364 and 365. Prongs 422 have a tapered shape and fit co-axial around nasal prongs 364 and 365. Prongs 422 include a number of holes to permit oxygen passage from within cannula cap 368 to the vicinity of the patient's 10 nostrils.

The oral system is comprised of oral prongs 369 which are an integral part of oral-nasal cannula 351, sliding prongs 371 which are slidably mounted over prongs 369, and EGD (esophageo-gastro-duodenoscopy) prong extension 370. The oral prong system consists of two independent channels: oxygen prong channel 381 for oxygen supply; and oral prong channel 379 for $CO_2$ sample collection. Sliding prongs 371 are slidably mounted over prongs 369 forming an "L" shape and allow for flexibility in adapting to different patients 10. Prongs 369 are extendable and retractable to be easily positioned in front of the mouth. A third piece comprising the oral prong system are detachable/attachable prong extension EGD (esophageo-gastro-duodenoscopy) prongs 370, which are designed to mount slidably on sliding prongs 371 to reach inside the patient's 10 mouth. EGD prong extension 370 is manufactured tethered to prongs 371 but is easily detached by the user. EGD extension 370 improves the delivery and collection of gases into the mouth, but can be easily removed and discarded if not used.

As shown on FIG. 1, the tubing set is comprised of two extruded tubes 352 and 354 for transporting $CO_2$ nasal samples, each tube set containing two small lumens, tube 355 for transporting the $CO_2$ oral sample, audio tube 356, and oxygen tube 353 to transport oxygen into chamber 384 (shown in FIGS. 7-9). The tubes are commercially available and preferably constructed of pliable plastic material such as extruded polyvinyl chloride. Each extruded tube 352 and 354 transports $CO_2$ samples from right and left nostrils, respectively. Sample tube 352 is connected to cannula cap 368 adjacent oxygen tube 353 on the right side. In a similar arrangement sample tube 354 is connected to cannula cap 368 adjacent oral sample tube 355 on the left side.

Now referring to FIGS. 2 and 3, right pressure lumen 357 and right sample lumen 358 are located within tube 352 and transport $CO_2$ gas samples from the right nostril for pneumatic and capnometry analysis. In the same form, left pressure lumen 359 and left sample lumen 360 are located within tube 354 to transport $CO_2$ gas samples from the left nostril. In one arrangement, tube 352 is adhered to oxygen tube 353, and in the same manner, tube 354 is adhered to oral sample tube 355. The connection between tubes is designed such that the tubes can be easily separated as needed. A separate audio tube 356 is attached to earpiece 362 and is used to transport sound to the patient 10's ear.

As illustrated on FIG. 13, oral/nasal cannula connector 363 is comprised of four components which when assembled together form internal chambers and channels. The components are outlet cover 394, hydrophobic filter 395, gasket 396, and back plate 423. The components are held together by internal latches 403 which are snapped and locked onto internal notches 404.

Figure 12:
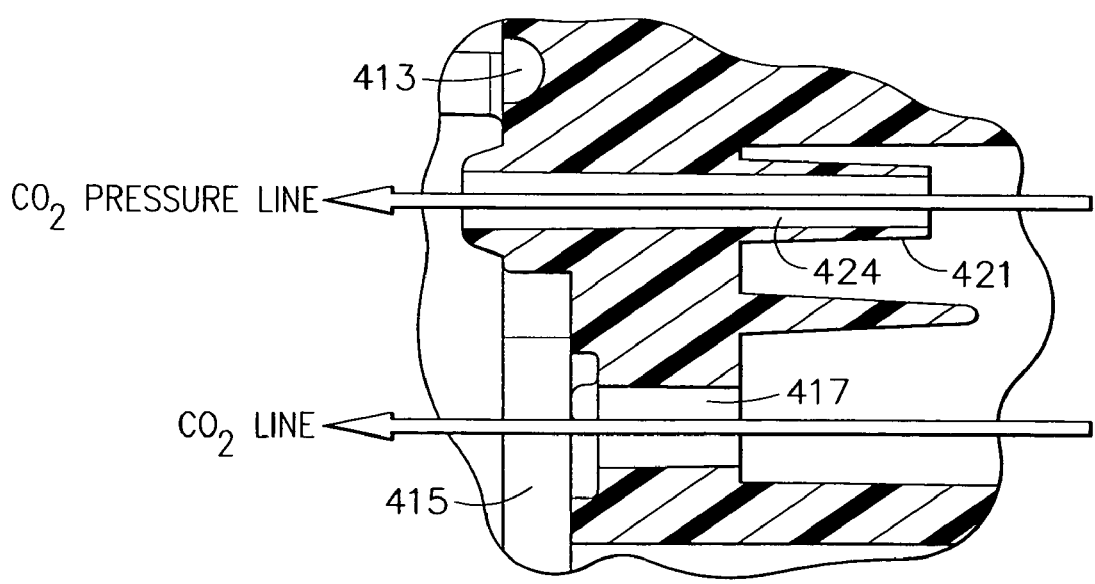
FIG. 12 is an enlarged view of a portion of the oral/nasal cannula BMU connector of FIG. 11 showing details of $CO_2$ gas lines.
Figure 13:
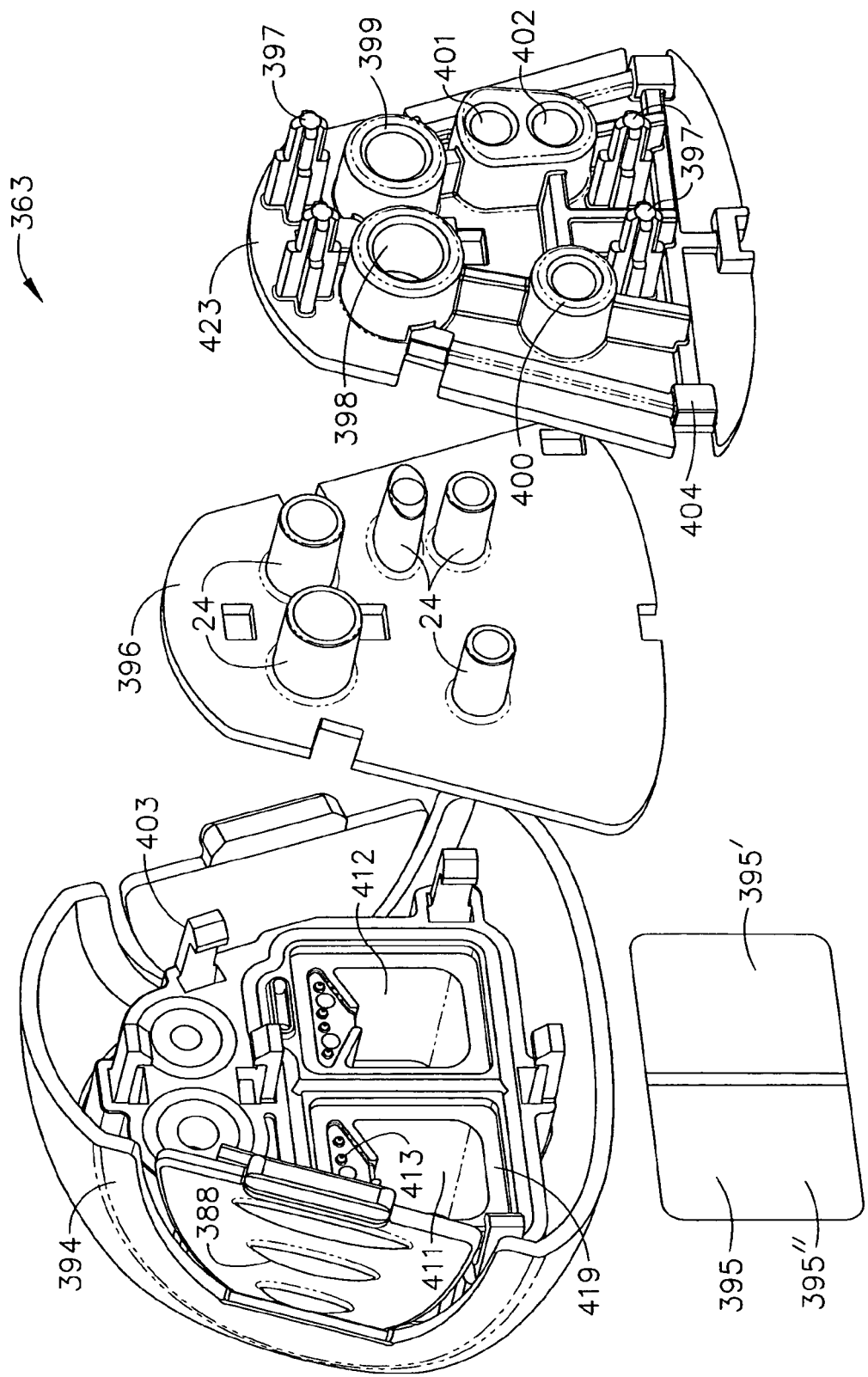
FIG. 13 is an exploded view of the oral/nasal cannula connector of FIG. 10 showing the outlet cover, gasket and back plate.
Figure 14:
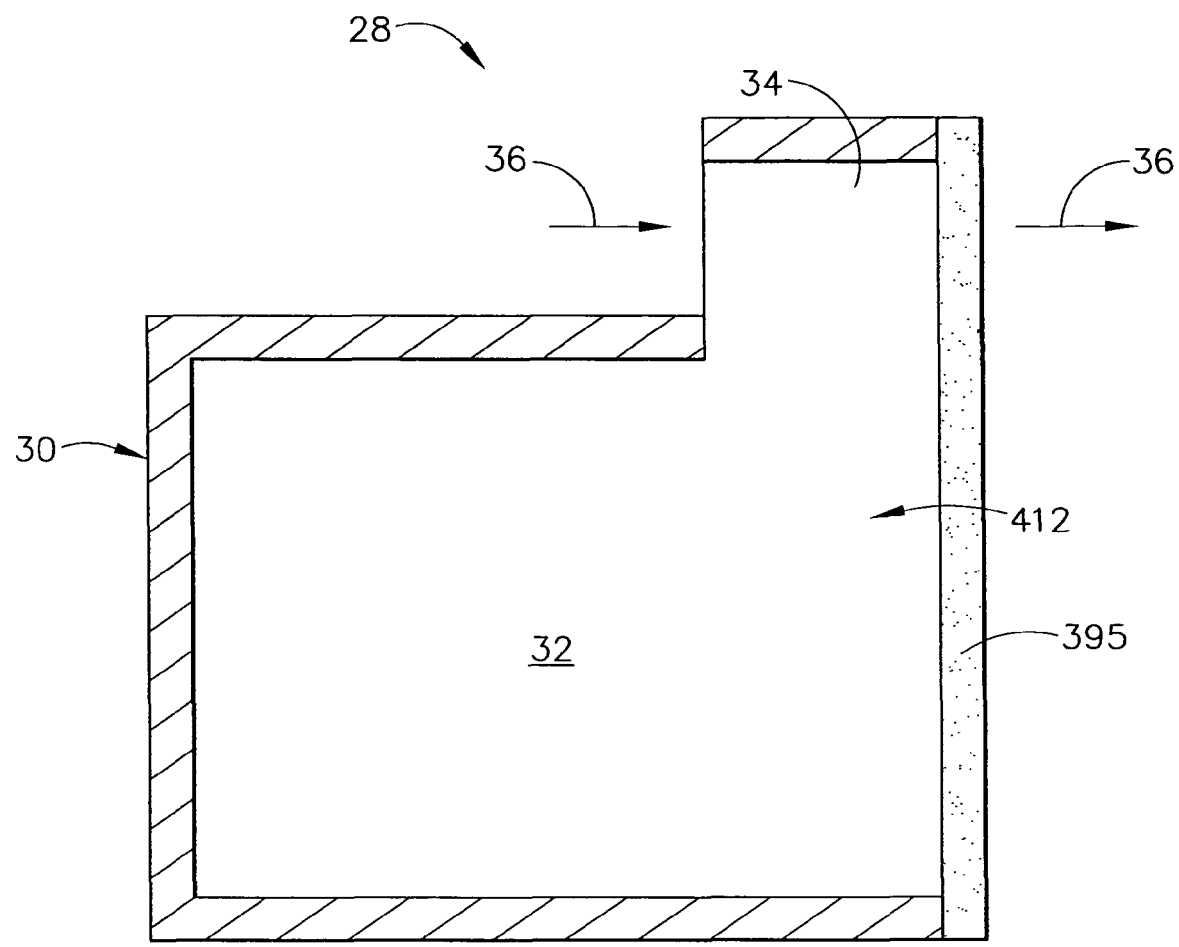
FIG. 14 is a schematic, side-elevational, cross-sectional view of the nasal moisture trap chamber of FIG. 13.

Referring to FIGS. 10-13 and 15-18, outlet cover 394 and back plate 423 are made of molded rigid thermoplastic, while gasket 396 is made of an elastic, flexible material. Included in outlet cover 394 are moisture chambers 411 and 412 used for trapping moisture from oral and nasal $CO_2$ sampling gases. Outlet cover 394 includes gripper snaps 388 to facilitate the user securely attaching the connector assembly to the BMU interface connector (shown on FIG. 1). Left and right nasal $CO_2$ gases are combined in recess 415 after passing through capnometry outlet channels 417 (shown on FIGS. 16-18). The nasal capnometry analysis is performed on the combined gas sample in PRU 200 (see FIG. 6). Pressure analysis is also made on a combined gas sample after $CO_2$ gases pass through pressure lines 424 (FIG. 12).

Oral capnometry analysis is performed on a $CO_2$ gas sample, which is taken after gas has passed through oral outlet channel 416 and into oral recess 410 and moisture chamber 411 (see FIG. 6). Recesses 410 and 415 hold hydrophobic filter 395 which traps moisture and allows it to drain into moisture chambers 411 and 412, preventing moisture damage to other sensitive parts of the capnometry system.

Referring to FIGS. 1 and 10-13, the distal face of outlet cover 394 provides connectors for all cannula tubing. The distal face of cover 394 includes oxygen tube opening 390, which is the connection point for tube 353, audio tube opening 389 which is the connection point for tube 356, right tube opening 392 which receives sample tube 352, left tube opening 393 connecting to sample tube 354, and oral tube opening 391 which receives oral sample tube 355. All connection points are designed to create a leak tight seal with the mating tubing. Both right and left nasal $CO_2$ pressure lines 418 (see FIG. 16) connect to pressure lumen ports 421 located in recess 420.

As best illustrated on FIGS. 13 and 15, gasket 396 is sandwiched between outlet cover 394 and back plate 423. Its function is to create internal channels and to isolate individual flow paths. It also secures hydrophobic filter 395. Hydrophobic filter 395 is also held by filter notch 419 and bumps 413 located on outlet cover 394 proximal face. Hydrophobic filter 395 is commercially available and has the properties of being particle-blocking and hydrophobic. Back plate 423 includes a number of ports that interface with the connector on BMU 300 (FIG. 1) including audio port 398, oxygen port 399, oral port 400, and pressure port 401. Adaptor pins 397 function to guide the connection between cannula connector 363 and the connector on BMU 300.

It is noted that in the detailed description of the one particular enablement of the embodiment of FIGS. 1-18, the cannula 351', the connector 363, and the earpiece 362 are single-patient-use (SPU) items.

Drug-Delivery Cassette Assembly

A second aspect of the invention is directed to, or a component of, or can be used by, a drug-delivery cassette assembly 251, an embodiment of which is shown in FIGS. 24-40 and which, in one enablement is used in an embodiment of a procedure room unit (PRU) 200 shown in FIGS. 41-57. A first expression of the embodiment of FIGS. 24-40 is for a drug-delivery cassette assembly 251 including a luer 269, tubing 277 and 259 and a drug-delivery-cassette main board 253. The tubing 277 and 259 has a drug-receiving end, which is fluidly-connectable to a drug vial 250 containing a drug, and has a drug-delivery end, which is fluidly-connected to the luer 269. The terminology "fluidly-connectable" includes directly fluidly-connectable and indirectly fluidly-connectable, and the terminology "fluidly-connected" includes directly fluidly-connected and indirectly fluidly-connected. The cassette main board 253 has a luer-site base portion 271. The luer 269 is attachable to and detachable from the luer-site base portion 271. The luer-site base portion 271 has a deflectable luer-site sensor beam 275 which is disposed to be deflected by the luer 269 when the luer 269 is attached to the luer-site base portion 271 and to be undeflected when the luer 259 is detached from the luer-site base portion 271. The luer-site base portion 271 is also referred to, in one construction, as a T-site base 271, and the luer-site sensor beam 275 is also referred to, in that one construction, as a T-site sensor beam 275. Other constructions are left to the artisan.

In one example of the first expression of the embodiment of FIGS. 24-40, the cassette main board 253 is attachable to and detachable from a procedure room unit (PRU) 200 (shown in FIGS. 41-57) having a luer-in-place optical sensor 226 (see FIG. 44) disposed to sense only one of the deflected luer-site sensor beam 275 and the undeflected luer-site sensor beam 275. In one variation, the procedure room unit 200 controls flow of the drug in the tubing 277 and 259 to air purge the tubing 277 and 259 and to deliver the drug through the tubing to a patient based at least in part on the luer-in-place optical sensor 226 sensing or not sensing the luer-site sensor beam 275. Other examples are left to the artisan.

Figure 41:
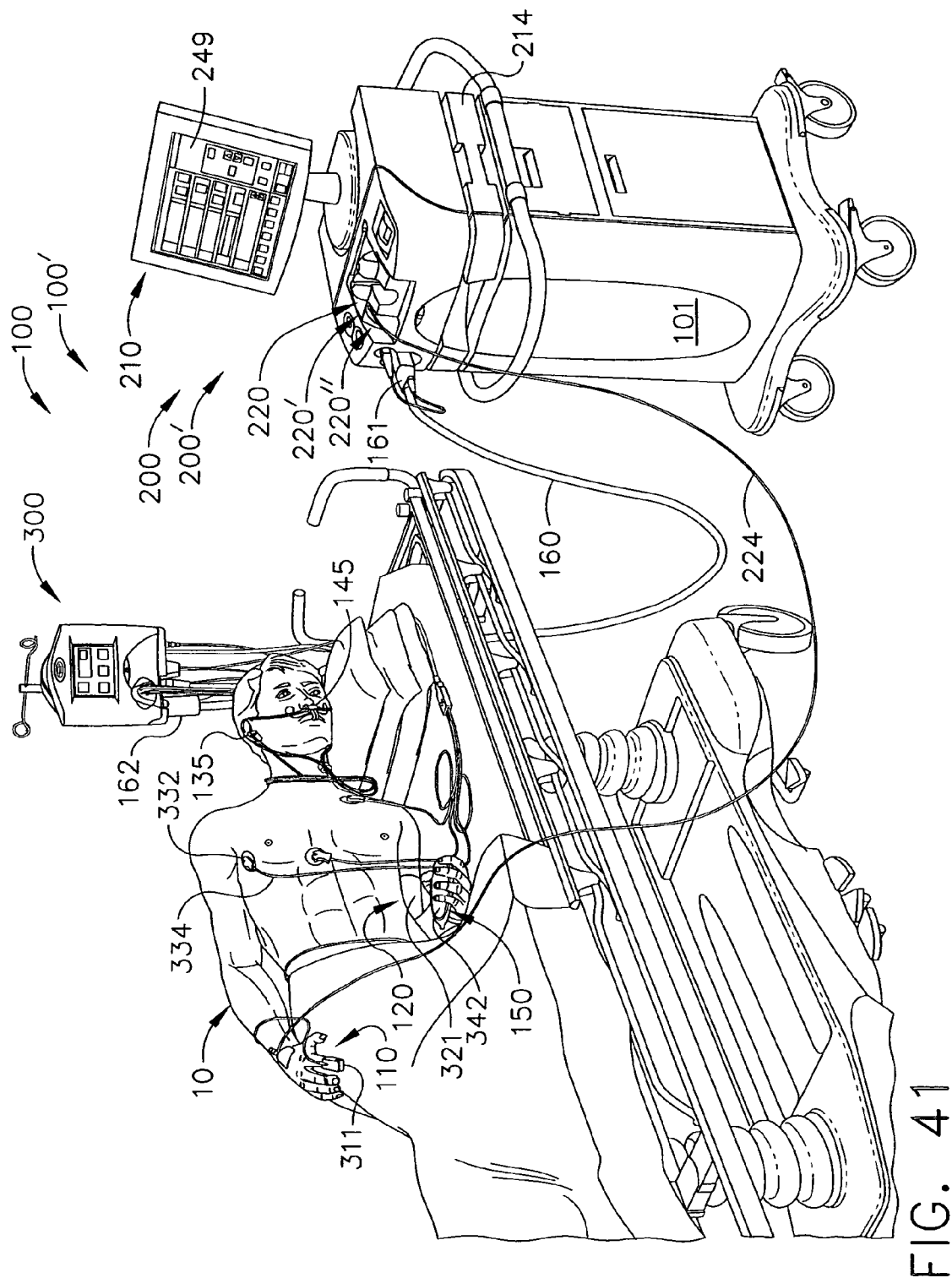
FIG. 41 is a perspective view of the sedation delivery system (SDS) of FIG. 6, which is an example of a medical effector system, including the procedure room unit (PRU), the bedside monitoring unit (BMU), and the umbilical cable.

A broad description of a combination of the second aspect of the invention (a drug-delivery cassette assembly embodiment of which is shown in FIGS. 24-40) and a later-discussed third aspect of the invention (a procedure room unit embodiment of which is shown in FIGS. 41-57) is for a drug-delivery assembly (e.g., drug-delivery cassette assembly 251 and procedure room unit 200). In one expression of the combination, the drug-delivery assembly (e.g., 251 and 200) includes tubing (e.g., 277 and 259), a storage site (e.g., luer-site base portion 271), a pump (e.g., 220 as seen in FIG. 41), and a sensor (e.g., luer-in-place optical sensor 226, as seen in FIG. 44). The tubing (e.g., 277 and 259) has a drug-receiving end that is fluidly-connectable to a drug vial (e.g., 250) containing a drug and has a drug-delivery end portion (e.g., luer 269). The storage site (e.g., 271) is adapted for releasably storing the drug-delivery end portion (e.g., 269) of the tubing (e.g., 277 and 259) when the drug-delivery end portion of the tubing is not in drug-delivering communication with a patient. The pump (e.g., 220) controls flow of the drug in the tubing (e.g., 277 and 259), when the tubing (e.g., 277 and 259) is operatively connected to the pump (e.g., 220), to air purge the tubing (e.g., 277 and 259) and to deliver the drug through the tubing (e.g., 277 and 259) to the patient. The sensor (e.g., 226) has an output and is disposed to sense the presence and/or absence of the drug-delivery end portion (e.g., 269) of the tubing (e.g., 277 and 259) in the storage site (e.g., 271).

It is noted that, in one example of the broadly-described combination, the drug-delivery end portion of the tubing has a length of substantially one to four inches and includes any end fitting (e.g., luer 269) attached to the drug-delivery end portion of the tubing (e.g., 277 and 259) itself. In one application, the sensor directly senses the presence and/or absence of the drug-delivery end portion (e.g., 269) of the tubing (e.g., 277 and 259) in the storage site (e.g., 271). In another application, the sensor (e.g., 226) indirectly senses the presence and/or absence of the drug-delivery end portion (e.g., 269) of the tubing (e.g., 277 and 259) by sensing the presence and/or absence of another component (e.g., the luer-site sensor beam 275) which changes position between the presence and absence of the drug-delivery end portion (e.g., 269) of the tubing (e.g., 277 and 259) in the storage site (e.g., 271). It is understood that the recited components are not limited to the particular component examples found in parentheses following the components. Thus, other examples of a sensor can be used such as, without limitation, another optical sensor, an ultrasonic sensor, a proximity sensor, or an electromagnetic sensor. Likewise, other examples of a storage site, etc. can be used, and the drug-delivery system is not limited to requiring a drug-delivery cassette assembly and/or a procedure room unit, as can be appreciated by the artisan.

In one implementation of the drug-delivery assembly (e.g., 251 and 200), the pump (e.g., 220) air purges the tubing (e.g., 277 and 259) only when the drug-delivery end portion (e.g., 269) of the tubing (e.g., 277 and 259) is stored in the storage site (e.g., 271) as determined from the output of the sensor (e.g., 226). This helps prevent inadvertent priming (i.e., air purging) of the tubing (e.g., 277 and 259) when the drug-delivery end portion (e.g., 269) of the tubing (e.g., 277 and 259) is in fluid communication with the patient.

In the same or a different implementation of the drug-delivery assembly (e.g., 251 and 200), the tubing (e.g., 277 and 259) is operatively disconnectable from the pump (e.g., 220) only when the drug-delivery end portion (e.g., 269) of the tubing (e.g., 277 and 259) is stored in the storage site (e.g., 271) as determined from the output of the sensor (e.g., 226). This helps prevent free flow of the drug into the patient or the environment. In one variation, a pump-housing door (e.g., 201) pinches the operatively connected tubing (e.g., 277 and 259) against the pump (e.g., 220) so that pump action is required for drug flow and drug flow is shut off (i.e., there is no free flow) when the pump (e.g., 220) is not pumping. In this variation, the pump-housing door (e.g., 201) is locked and cannot be opened to remove the pinched tubing (e.g., 277 and 259) unless the drug-delivery end portion (e.g., 269) of the tubing (e.g., 277 and 259) is stored in the storage site (e.g., 271) as determined from the output of the sensor (e.g., 226).

A second expression of the embodiment of FIGS. 24-40 is for a drug-delivery cassette assembly 251 including a drug-delivery-cassette main board 253. A drug vial 250 is attachable to the cassette main board 253. The cassette main board 253 has a deflectable drug-vial-site sensor beam 267 which is disposed to be deflected by the drug vial 250 when the drug vial 250 is attached to the cassette main board 253 and to be undeflected when the drug vial 250 is unattached to the cassette main board 253. The drug-vial-site sensor beam 267 is also referred to, in one construction, as a spike sensor beam 267. Other constructions are left to the artisan.

In one example of the second expression of the embodiment of FIGS. 24-40, the cassette main board 253 is attachable to and detachable from a procedure room unit (PRU) 200 (shown in FIGS. 41-57) having a drug-vial-in-place optical sensor 228 (see FIG. 44) disposed to sense only one of the deflected drug-vial-site sensor beam 267 and the undeflected drug-vial-site sensor beam 267. In one variation, the procedure room unit 200 controls flow of the drug from the drug vial 250 based at least in part on the drug-vial-in-place optical sensor 228 sensing or not sensing the drug-vial-site sensor beam 267.

In the same or a different example of the second expression of the embodiment of FIGS. 24-40, the drug vial 250 includes a drug-vial seal 42, and the drug-delivery cassette assembly 251 also includes a spike 261 having a spike tip 296 and a spike barb 184. When the drug vial 250 is attached to the cassette main board 253, the drug-vial seal 42 is perforated by the spike tip 296 and held by the spike barb 184 and the drug-vial-site sensor beam 267 pushes the drug vial 250 up against the spike barb 184. Such pushing up reduces drug wastage, as can be appreciated by those skilled in the art. Other examples are left to the artisan.

A third expression of the embodiment of FIGS. 24-40 is for a drug-delivery cassette assembly 251 including a drug-delivery-cassette spike 261. A drug vial 250 is attachable to the spike 261. The drug vial 250 includes a drug-vial seal 42. The spike 261 has a spike tip 296 and a spike barb 184. When the drug vial 250 is attached to the spike 261, the drug-vial seal 42 is perforated by the spike tip 296 and held by the spike barb 184.

A fourth expression of the embodiment of FIGS. 24-40 is for a drug-delivery cassette assembly 251 including a luer 269, a drug-delivery-cassette spike 261, tubing 277 and 259, and a drug-delivery-cassette main board 253. The spike 261 includes a drug-vial-seal-perforating spike tip 296. The tubing 277 and 259 has a drug-receiving end, which is fluidly-connectable to and fluidly-disconnectable from the spike 261 and has a drug-delivery end, which is fluidly-connected to the luer 269. The spike 261 is attachable to and detachable from the cassette main board 253. This allows just the spike 261 to be disposed in a sharps container reducing overall sharps-waste volume and disposal fees, as can be appreciated by those skilled in the art.

A fifth expression of the embodiment of FIGS. 24-40 is for a drug-delivery cassette assembly 251 including a luer 269, tubing 277 and 259, and a drug-delivery-cassette main board 253. The tubing 277 and 259 has a drug-receiving end, which is fluidly-connectable to a drug vial 250 containing a drug, and has a drug-delivery end, which is fluidly-connected to the luer 269. The cassette main board 253 has a luer-site base portion 271. The luer 269 is attachable to and detachable from the luer-site base portion 271. The luer-site base portion 271 has a drip chamber 273 disposed to collect any of the drug, which exits the luer 269 when the luer 269 is attached to the luer-site base portion 271. The luer-site base portion 271 is also referred to, in one construction, as a T-site base 271. Other constructions are left to the artisan. In one example of the fifth expression of the embodiment of FIGS. 24-40, the drug-delivery cassette assembly 251 also includes a drug-absorbent pad 273' disposed in the drip chamber 273. Other examples are left to the artisan.

A sixth expression of the embodiment of FIGS. 24-40 is for a drug-delivery cassette assembly 251 including a luer 269 and tubing 277 and 259. The tubing 277 and 259 includes a coiled tube 259 and a flexible tube 277 fluidly-connected together. The flexible tube 277 has a drug-receiving end, which is fluidly-connectable to a drug vial 250 containing a drug, and the coiled tube 259 has a drug-delivery end, which is fluidly-connected to the luer 269. The coiled tube 259 is extendible by the user. In one example of the sixth expression of the embodiment of FIGS. 24-40, the coiled tube 250 includes a plurality of coils wherein adjacent coils are releasably adhered together. This arrangement allows the user to pull out only the length of coiled tube 259 needed for use with a patient thus providing for improved tubing management. In one variation, adjacent coils are thermally tacked together. In another variation, irradiation during sterilization releasably adheres together adjacent coils of the coiled tube 259. In the same or a different example, the coiled tube 259 has a smaller inside diameter than the flexible tube 277. This reduces drug wastage remaining in the tubing 277 and 259 after its use and expedites removal of air during an initial purge. Other examples are left to the artisan.

A seventh expression of the embodiment of FIGS. 24-40 is for a drug-delivery cassette assembly 251 including a drug-delivery-cassette main board 253, which is removably attachable to a procedure room unit 200 of a sedation delivery system 100 (or other type of medical effector system 100') and which includes a peristaltic pump cutout 254. In one example, of the seventh expression of the embodiment of FIGS. 24-40, the drug-delivery cassette assembly 251 also includes a drug-delivery flexible tube 277 having a substantially linear portion attached to the main board 253 and spanning the peristaltic pump cutout 254, wherein, when the main board 253 is attached to the procedure room unit 200, the portion of the flexible tube 277 is operatively connected to pump fingers of a drug-delivery peristaltic pump of the procedure room unit 200.

An eighth expression of the embodiment of FIGS. 24-40 is for a drug-delivery cassette assembly 251 including a drug-delivery-cassette main board 253. The main board 253 has a top-left portion, a top-right portion, a bottom-right portion and a bottom-left portion. The cassette main board 253 is removably attachable to a procedure room unit 200 of a sedation delivery system 100 (or other type of medical effector system 100'). The main board 253 has a peristaltic pump cutout 254 disposed between the top-left and top-right portions. The main board 253 has an air-in-line sensor cutout 255 disposed between the top-right portion and the bottom-right portion.

In one example of the eighth expression of the embodiment of FIGS. 24-40, the drug-delivery cassette assembly 251 also includes a drug-delivery flexible tube 277 having a substantially linear first portion attached to the top-left portion and the top-right portion of the main board 253 and spanning the peristaltic pump cutout 254 and having a substantially linear second portion attached to the top-right portion and the bottom-right portion of the main board 253 and spanning the air-in-line sensor cutout 255. When the main board 253 is attached to the procedure room unit 200, the first portion of the flexible tube 277 is operatively connected to pump fingers of a drug-delivery peristaltic pump of the procedure room unit 200 and the second portion of the flexible tube 277 is operatively connected to an air-in-line sensor of the procedure room unit 200.

In the same or a different example of the eighth expression of the embodiment of FIGS. 24-40, the lower-left portion of the main board 253 extends below the lower-right portion of the main board 253 defining a pump-door-latch cutout extending to the right of the lower-left portion and below the lower-right portion of the main board 253.

In one application of any of the above-described expressions of FIGS. 24-40, including examples, etc. thereof, the cassette main board 253 is directly attachable to a procedure room unit (PRU) 200 (shown in FIGS. 41-57). Other applications are left to the artisan.

Any one or more of the above-described expressions of the embodiment of FIGS. 24-40, including examples, etc. thereof can be combined with any other one or more of the above-described expressions of the embodiment of FIGS. 24-40, including examples, etc. thereof, as can be appreciated by those skilled in the art.

The following paragraphs present a detailed description of one particular enablement of the embodiment of FIGS. 24-40. It is noted that any feature(s) of this particular enablement can be added to any of the previously-described expressions (including examples, etc. thereof) of the embodiment of FIGS. 24-40. In this enablement, the drug-delivery cassette assembly 251 is used in conjunction with a drug-delivery infusion pump assembly 220. In this enablement, drug-delivery cassette assembly 251 is part of an integrated patient monitoring and sedation delivery system (SDS) 100 (shown in FIG. 41) intended to administer sedation drug(s) during brief procedures. The system uses a drug delivery algorithm and an intravenous infusion peristaltic (or other type) pump 220 (see FIG. 41), together with the drug-delivery cassette assembly 251, to deliver drug(s) with variable rate infusion that achieves and maintains a desired sedation effect.

As used herein, the term "proximal" refers to a location on the drug-delivery cassette assembly 251 closest to the device using the drug-delivery cassette assembly 251 and thus furthest from the patient on which the drug-delivery cassette assembly 251 is used. Conversely, the term "distal" refers to a location farthest from the device using the drug-delivery cassette assembly 251 and closest to the patient.

Figure 24:
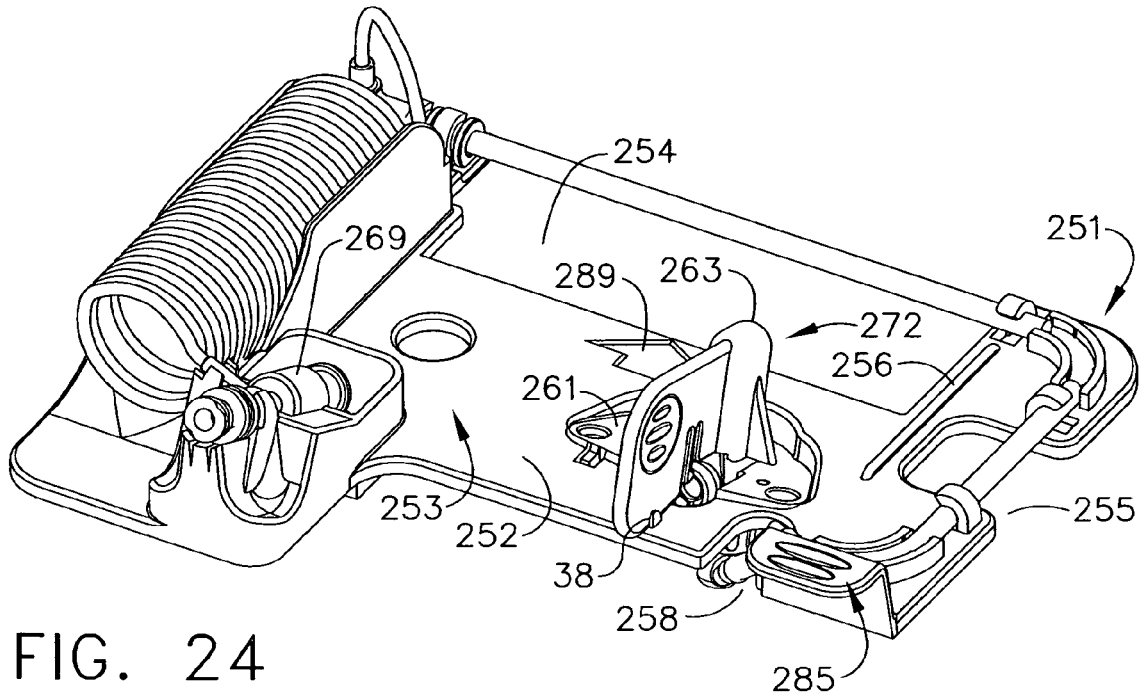
FIG. 24 is a top perspective view of an embodiment of a drug-delivery cassette assembly of the invention.
Figure 25:
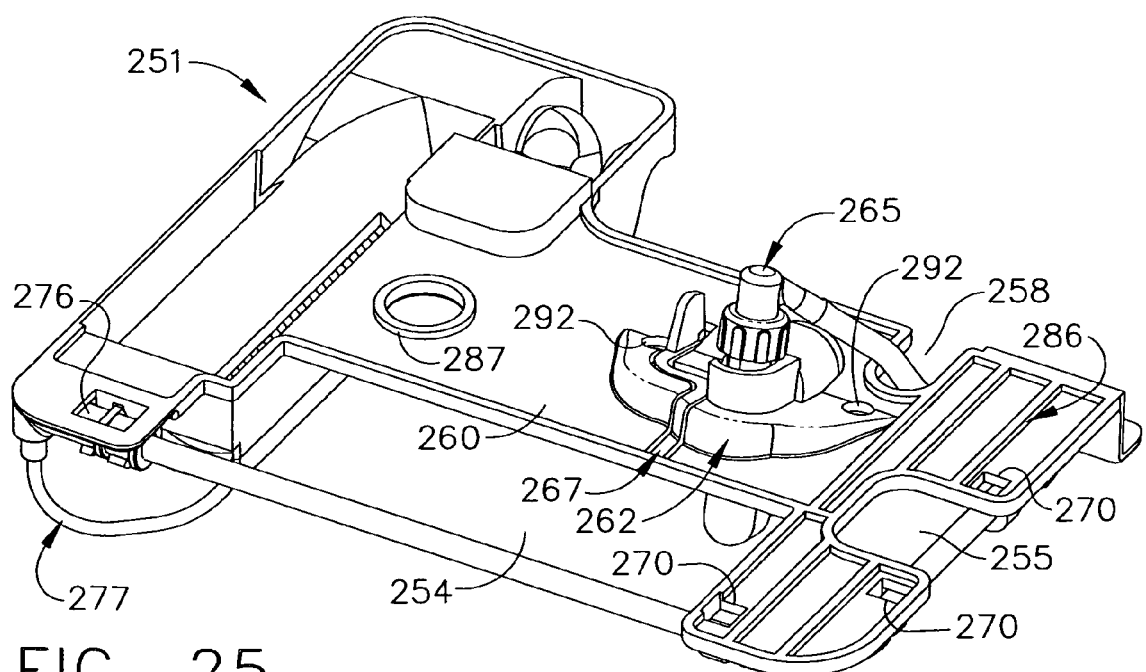
FIG. 25 is a bottom perspective view of the drug-delivery cassette assembly of FIG. 24.
Figure 26:
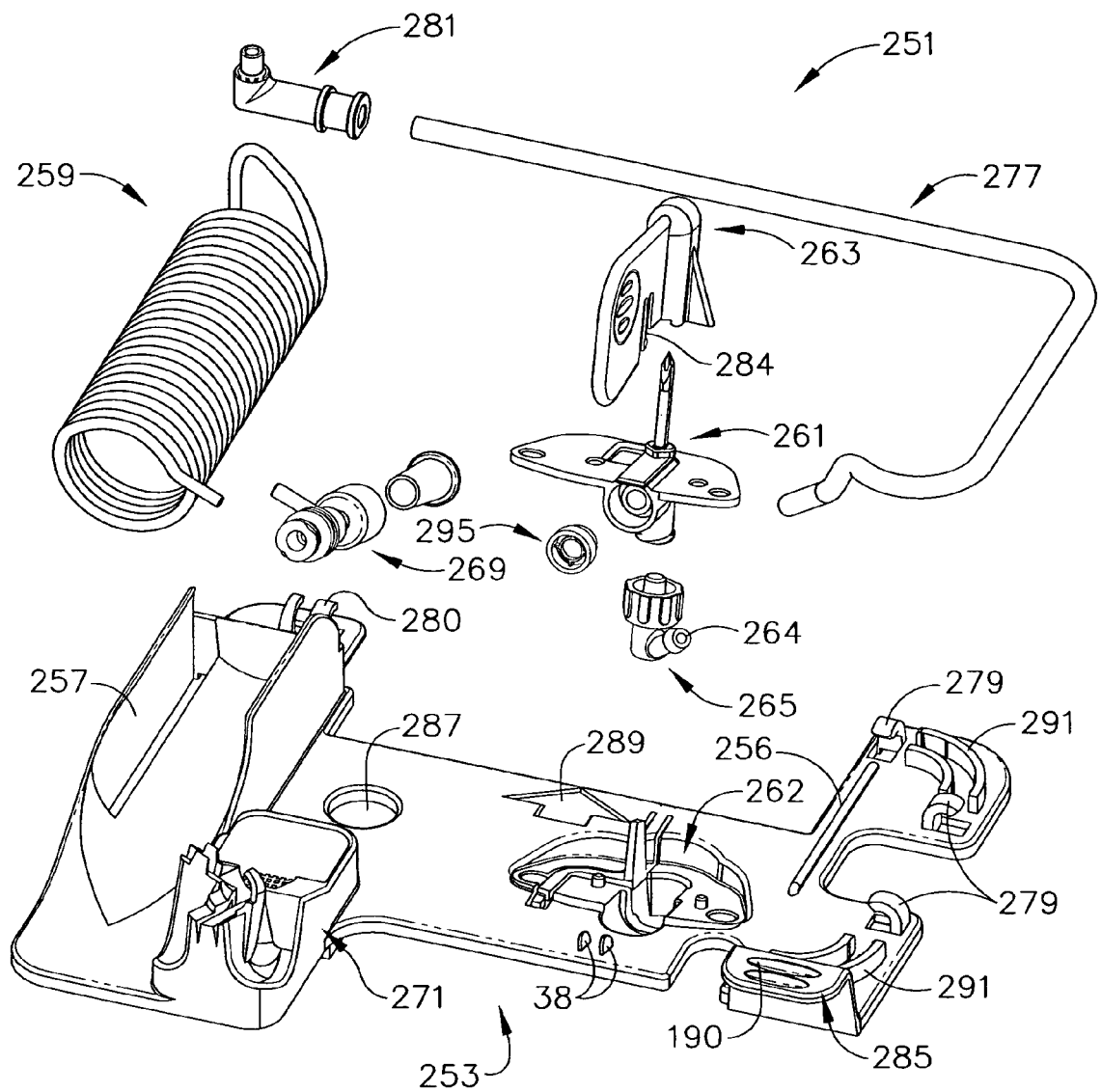
FIG. 26 is an exploded view of the drug-delivery cassette assembly of FIG. 24 showing individual components.

As shown in FIGS. 24-26, cassette 251 is comprised of a cassette main board 253 which in one example is molded of rigid thermoplastic having a generally flat rectangular shape, with smooth rounded corners, and rectangular cutouts 254 and 255 designed to permit interface with a peristaltic pump 220 (see FIG. 41) and its sensor components (e.g., 226 and 228 as shown in FIG. 44). In one employment, cassette 251, including main board 253 and components are single-patient-use components and are disposable. Cassette main board 253 is comprised of a generally flat thin base designed with molded features to support fluid communication tubes 277 and 259, reducer 281, spike system 272, and commercial luer 269. Spike system 272 includes spike cap 263, spike 261, air vent filter 295, and spike elbow 265.

Again referring to FIGS. 24-26, cassette main board 253 has a top face 252 and a bottom face 260, which hold secure components assembled to cassette 251. Cassette main board 253 has a peristaltic pump cutout 254 on the proximal side. Air-in-line sensor cutout 255 and a tube passage 258 are apertures generally located on the sides of main board 253. A visible arrow sign 289 is relief molded generally on the center of main board 253, and the arrow tip indicates the insert direction of cassette 251 to the user. Alignment hole 287 is a round aperture through main board 253 used to help the user position and align cassette 251 in the pump 220 (see FIG. 41).

As illustrated in FIGS. 24-26, in one construction cassette main board 253 is comprised of one reinforcement rib 256 on top face 252 and parallel reinforcement grooves 286 on bottom face 260 to increase stiffness of plastic molded structure 253 adjacent to pump cutout 254 and air-in-line sensor cutout 255. Reinforcement rib 256 and reinforcement grooves 286 help to make main board 253 rigid for handling and use purposes. Reinforcement rib 256 and reinforcement grooves 286 are integrally molded as part of cassette main board 253.

As shown in FIGS. 24 and 26, cassette main board 253 has: (a) a coiled tube base 257 designed to hold coiled tube 259; (b) a T-site base 271 to hold luer 269; and (c) a spike bed 262 to accommodate spike system 272. Cassette main board 253 also includes gripper handle 285.

As illustrated on FIG. 26, gripper handle 285 is an integral part of cassette main board 253, extending from the distal side to facilitate user handling. Gripper handle 285 is shaped with smooth rounded corners to make it easy and comfortable to hold. Parallel ribs 190 are molded on the top surface of gripper handle 285, which function to give a firm non-slip surface for gripping firmly while inserting or removing cassette 251 from the pump 220 (see FIG. 41).

As illustrated on FIGS. 24 and 26, the drug delivery system mounted on cassette 251 is comprised of a set of flexible tubes assembled in fluid communication. The tubing set includes (a) a coiled tube 259 and (b) a flexible tube 277. The drug system also is comprised of: (c) a reducer 281; (d) a spike system 272 mounted to spike bed 262; and (e) a commercial luer 269 mounted on a T-site base 271. In one construction, all pieces are removably mounted in place for handling and transportation purposes.

As shown on FIGS. 25 and 26, tube 277 is made of transparent flexible plastic, such as commercially available pvc, with constant internal and external diameter cross section. Tube 277 is made of a flexible resilient material to permit bending through passage 258 and to fit into clips 279. Tube 277 is generally assembled to follow the cassette external contour. Cassette 251 utilizes clips 279 and track wall retainers 291 to guide and route tube 277, generally keeping its cross-sectional diameter constant around the corners of cassette 251 and through passage 258. In one construction, not shown, the track wall retainers 291 are replaced by one or more additional clips 279.

As illustrated on FIGS. 25 and 26, tube 277 is part of the drug fluid communication system and connects at one end to (a) spike elbow 265 and at the other end to (b) reducer 281. Tube 277 connects into spike elbow 265 on the bottom side of cassette 251. Then tube 277 makes a turn into the transversal direction of cassette 251, extending from cassette bottom side 260 through tube passage 258. The opposite end of tube 277 is connected into reducer 281 on the top side of cassette 251. Tube 277 extends freely across cutouts 254 and 255. Tube 277 crosses air-in-line cutout 255 and peristaltic pump cutout 254.

Figure 29:
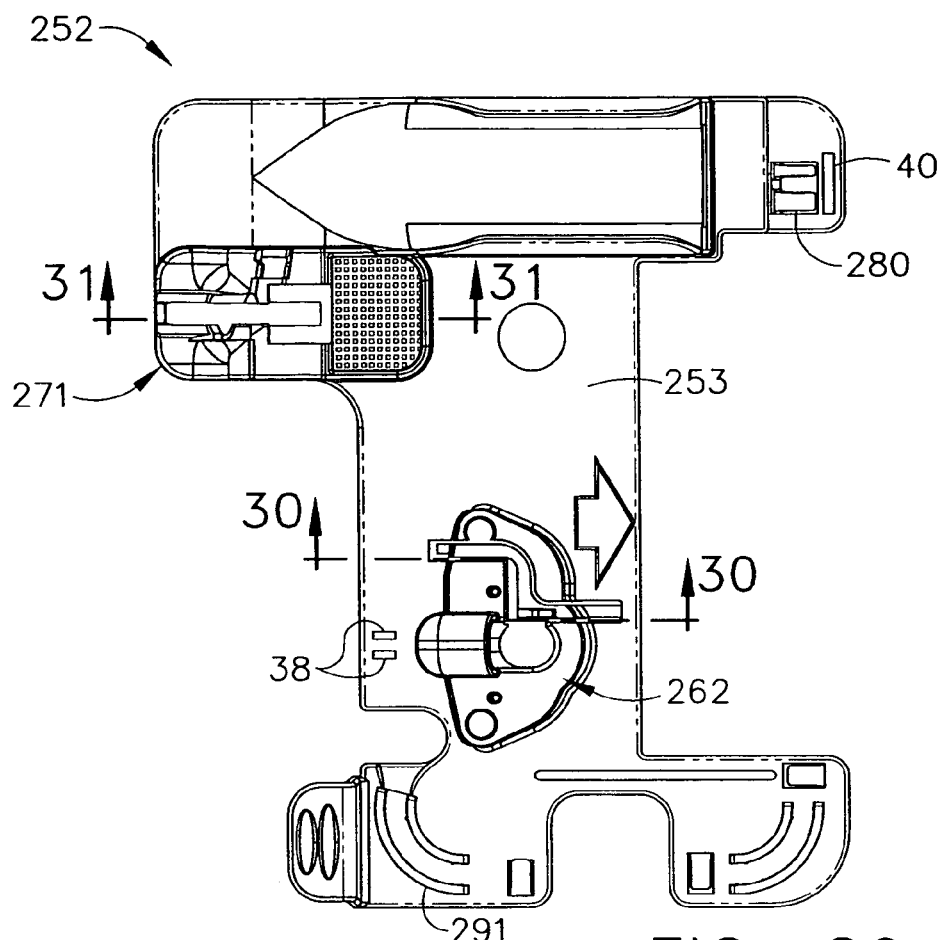
FIG. 29 is a top planar view of the drug-delivery-cassette main board of the drug-delivery cassette assembly of FIG. 26.
Figure 30:
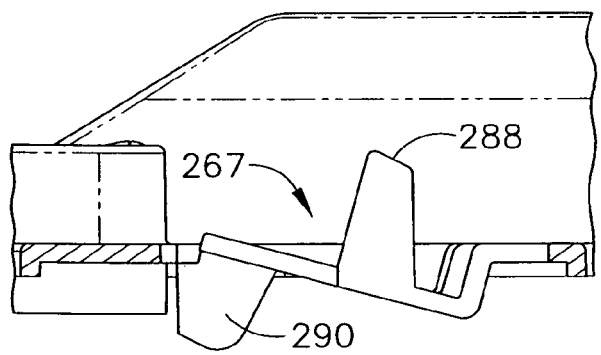
FIGS. 30 and 31 are cross-sectional views of the drug-delivery-cassette main board of FIG. 29, taken along lines 30-30 and 31-31 in FIG. 29, showing the vial sensor beam and the T-site sensor beam.
Figure 31:
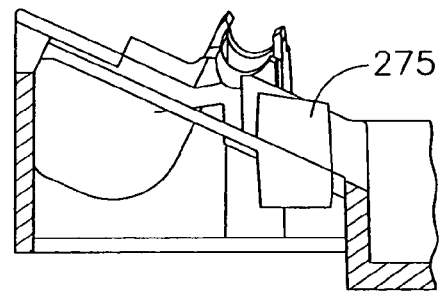

As shown on FIGS. 24, 26 and 29, flexible tube 277 is held in place by molded clips 279 located on cassette top face 252. Clips 279 have alternating openings to keep tube 277 aligned and secured in place without distortion. Clips 279 are generally curved to match the outside diameter of tube 277. Clip openings 270 and 276 are the result of the manufacturing process that creates the clips. Double clips 280 secure reducer 281 on cassette main board 253. In one construction, double clips 280 are built with only a small clearance between them (as shown on FIG. 29) to attach firmly to reducer 281 and anchor the tubing system. Clips 280 also have a curved shape to match the outside contour of reducer 281 body. Double clips 280 keep the two rings on the body of reducer 281 restrained in a fixed position, preventing sliding during handling or use. The reducer 281 has a flat bottom, and the cassette main board 253 has a reducer-positioning rib 40 (seen in FIG. 29 but omitted from FIG. 26 for clarity), which also helps the reducer 281 stay in position when the reducer 281 is secured by double clips 280. In one example, tube 277 is kept firm and straight after connection to a peristaltic pump 220, which is accomplished by clips 280.

As illustrated on FIGS. 26 and 29, track wall retainers 291 are molded on cassette top face 252 to trap and keep constrained tube 277 as it is routed around corners. The distance between walls is such that it creates a slight interference with tube 277 helping to retain tube 277. As previously mentioned, in one construction, not shown, the track wall retainers 291 are replaced by one or more additional clips 279.

As shown on FIG. 26, reducer 281 is part of the fluid communication system, and is mounted onto the proximal part of cassette 251. In one construction, it is made of transparent thermoplastic material and comprises an inlet and outlet in fluid communication, with the inlet and outlet at approximately right angles to each other. The inlet end of reducer 281 is larger than the outlet. The outlet end is adapted to be connected to IV (intravenous) coiled tube 259 while the inlet end is adapted to connect to flexible tube 277. Reducer 281 main body is generally cylindrical shaped with two molded rings to mount onto clips 280 to keep it fixed in place. Reducer 281 also helps secure smaller diameter tubing assembly coiled tube 259 and larger diameter flexible tube 277 in place.

Figure 27:
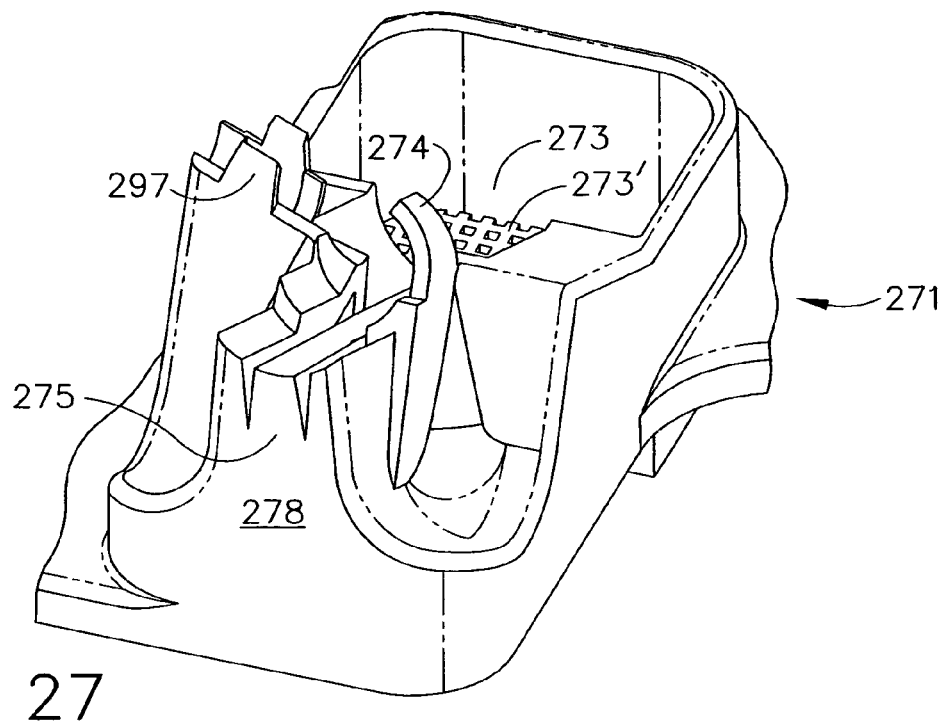
FIG. 27 is a perspective view of the luer-site base portion (also called a T-site base area when the luer is "T"-shaped) of the drug-delivery cassette assembly of FIG. 26.
Figure 28:
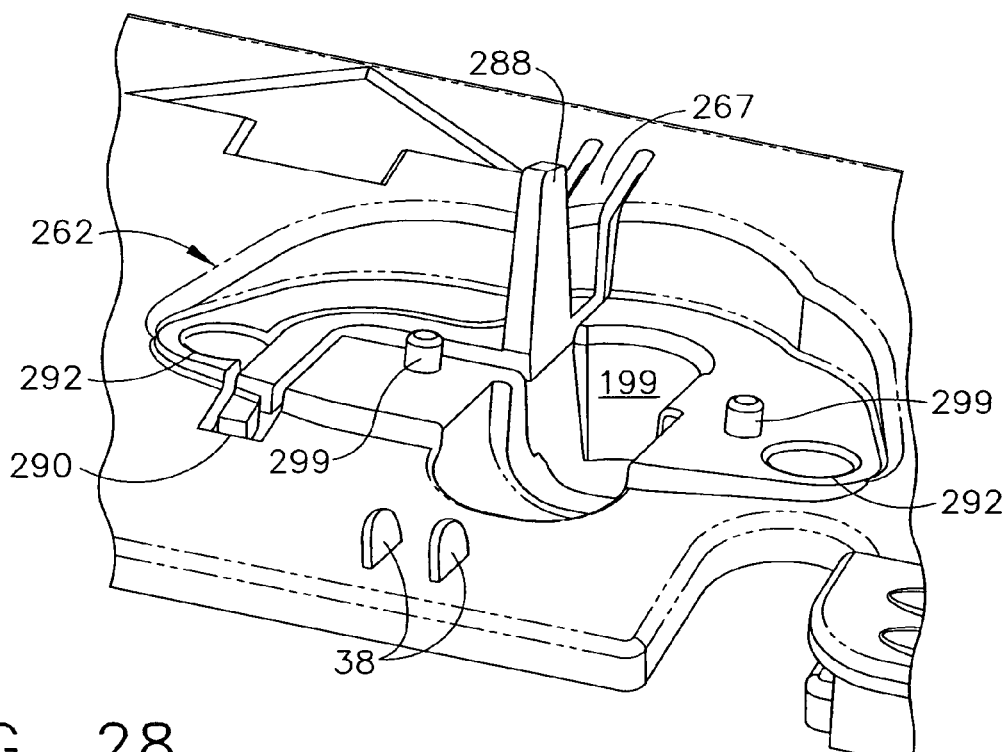
FIG. 28 is a perspective view of the spike bed area of the drug-delivery cassette assembly of FIG. 26.

As illustrated on FIGS. 26 and 27, coiled tube 259 is made of transparent IV tubing, for example commercially available pvc, manufactured and assembled to be biased into a generally cylindrical spiral as a way to minimize overall size and to facilitate handling and management by the user. In one construction, coiled tube 259, when uncoiled and extended to its maximum length, would total approximately 8 feet. This would be a sufficient length for the user to extend coiled tube 259 between cassette 251 and the patient. In one construction, coiled tube 259 is stored on cassette 251 in a half-cylindrical shape base 257 designed to prevent movement during cassette 251 shipping and installation into the pump 220. One end of coiled tube 259 is affixed to reducer 281 while the other end is connected to luer 269. In use, the clinician removes luer 269 from T-site bed 271, disconnecting luer 269 from first luer clip 274 and second luer clip 297, and pulls and uncoils tube 259 as far as necessary to reach the patient. It should be noted that the inside fluid path of tube 259 is minimized as compared with flexible tube 277 so as to minimize wasted drug(s) remaining in the tubing after its use and to expedite removal of air during an initial purge.

As shown on FIGS. 24, 27 and 29-31, T-site base 271 is designed to removably capture luer 269. T-site base 271 also includes a deflective built-in beam 275, which contacts luer 269 when luer 269 is fixed in place, causing beam 275 to deflect and interface with an optical sensor 226 on the Procedure Room Unit (PRU) 200 (shown in FIGS. 41-57). T-site base 271 further includes open drip chamber 273 used as a reservoir to capture and contain drug spillage during drug line purge. T-site base 271 has built-in walls to create a sloped bed (as shown on FIG. 35) on cassette top face 252. T-site base 271 has two molded-in clips. First luer clip 274 and second luer clip 297 firmly secure luer 269. T-site base 271 includes a thin tower 278. Luer 269 lays on top of T-site tower 278 at an inclined angle to direct excess drug spillage into chamber 273.

As illustrated on FIGS. 27 and 29, drip chamber 273 is integrally part of T-site base 271 and in one example is a molded part of cassette main board 253. Drip chamber 273 is generally located in a central area of cassette main board 253. Drip chamber 273 has a generally rectangular shape with one wall congruent to T-site tower 278 and is sized to contain a specific volume of the total drug vial 250 (see FIG. 32) content. Drip chamber 273 functions to prevent spillage during drug line purge and to capture any residual drug after cassette use. In one variation, drip chamber 273 contains an absorbent pad 273' to absorb all drained drug(s).

As shown on FIGS. 25-27 and 29-31, T-site sensor beam 275 is molded as an integral part of cassette main board 253 and acts as a cantilever beam. The pivot point of beam 275 is built in the distal side of cassette 251 on the top face of T-site tower 278. In one construction, the free hanging end of beam 275 extends through cassette bottom face 260 into a central longitudinal opening of T-site base 262 (as shown on FIG. 31), which interfaces with T-site-in-place optical sensor 226 located on the PRU 200. The free hanging end of beam 275 is generally designed as a "T". One tip of the "T" touches luer 269. When luer 269 is secured in base 271, beam 275 deflects and the other T tip breaks the light beam of the optical T-site-in-place sensor 226. This indicates to the PRU 200 (shown in FIGS. 41-57) that luer 269 is in place so that drug line purge can be performed.

As illustrated on FIGS. 26 and 27, luer 269 is commercially available and well known in the medical arts. It is made of rigid plastic. In one construction, luer 269 is "T" shaped with an internal lumen in fluid communication with all three legs of the "T". One T-leg connects to coiled tube 259. Another "T" leg contains a needleless port that can be attached to IV luer fitting. The last "T" leg has a removable dust cap.

As shown on FIGS. 26, 28 and 32-34, spike bed 262 is a recessed area molded into cassette main board 253 at a slight angle so that when spike 261 is assembled to main board 253, spike 261 is substantially vertically oriented when cassette 251 is placed into the pump 220 in the PRU 200 (shown in FIGS. 41-57). The vertical position of spike 261 helps the drug vial 250, when placed on spike 261, to drain properly and completely. Spike bed 262 has upright walls to accommodate spike wing 197. Spike bed 262 bottom includes two guiding pins 299 extending upwards and two apertures 292 to help in aligning spike assembly 261. The center area of spike bed 262 has a half-cylindrical base 199 to accommodate air-vent boss 177. The air-vent boss base 199 generally creates a step on the round contour to hold hollow spike 261 in place. In the center of spike bed 262 bottom there is a round aperture for inserting spike drug boss 185. In the longitudinal direction, in the middle of spike bed 262, is the cutout of spike sensor beam 267, which has a flat curved shape. Spike sensor beam 267 is fixed at the proximal side of spike bed 262, and is a cantilever beam.

As shown on FIGS. 29-34, cantilever spike sensor beam 267 (shown on FIG. 30), is an integral part of cassette main board 253. At the extreme end of spike beam 267 is lower spike tab 290, which is positioned to interface with an optical vial-in-place sensor 228 located on the PRU 200 pump 220 (shown in FIG. 41). Upper spike tab 288 is a second tab located in an intermediate position along beam 267 and is positioned to interface with a drug vial 250 when a drug vial 250 is placed on spike 261. Upper spike tab 288 extends through aperture 198 on spike wing 197 when spike 261 is properly assembled to cassette main board 253. When cassette assembly 251 is in place in the pump 220 on the PRU 200 (shown in FIGS. 41-57) and when a drug vial 250 is placed on spike 261, the vial makes contact with upper spike tab 288 causing spike sensor beam 267 to deflect sufficiently to cause lower spike tab 290 to interface with optical vial-in-place sensor 228 located on the PRU 200. This indicates to the PRU 200 that a drug vial 250 is properly in place so that drug line purge can be performed and so that the PRU 200 pump 220 can deliver drug(s) to the patient.

As shown on FIGS. 24, 26 and 32-34, spike system 272 is comprised of spike cap 263, spike 261, and spike elbow 265. Spike cap 263 helps protect clinicians from inadvertent sticks by spike tip 296. Spike cap 263 is removably attached on top of spike tip 296 by a latching mechanism. Spike elbow 265 is removably threaded (with a luer lock) onto drug boss 185. Spike elbow 265 securely attaches spike 261 to cassette main board 253. Unthreading spike elbow 265 from drug boss 185 allows spike 261 to be easily removed from cassette main board 253 so that spike 261 can be properly disposed in a sharps container, minimizing overall waste volume, and saving disposal fees for the user.

Figure 32:
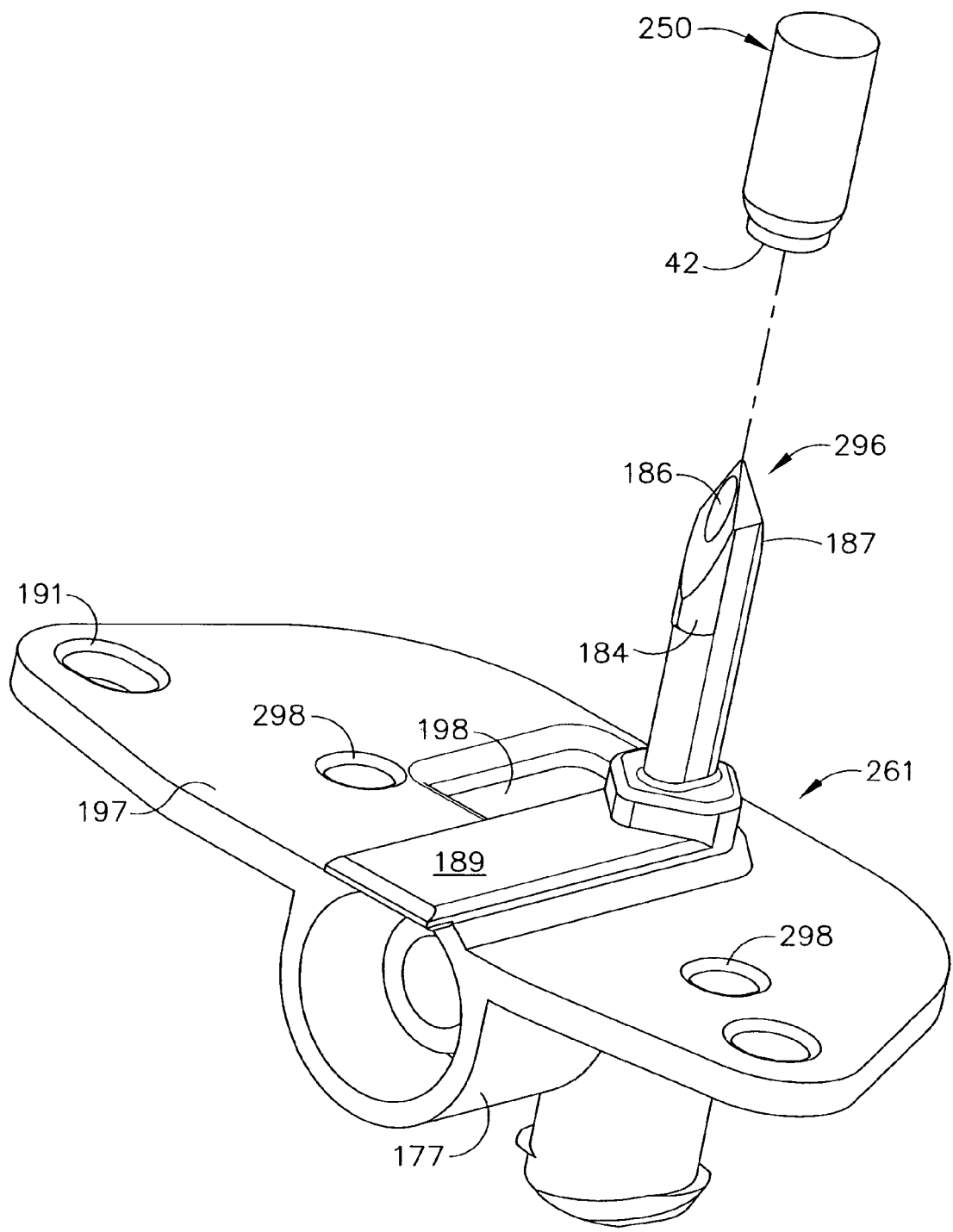
FIG. 32 is a perspective view of the spike of the drug-delivery cassette assembly of FIG. 26.
Figure 33:
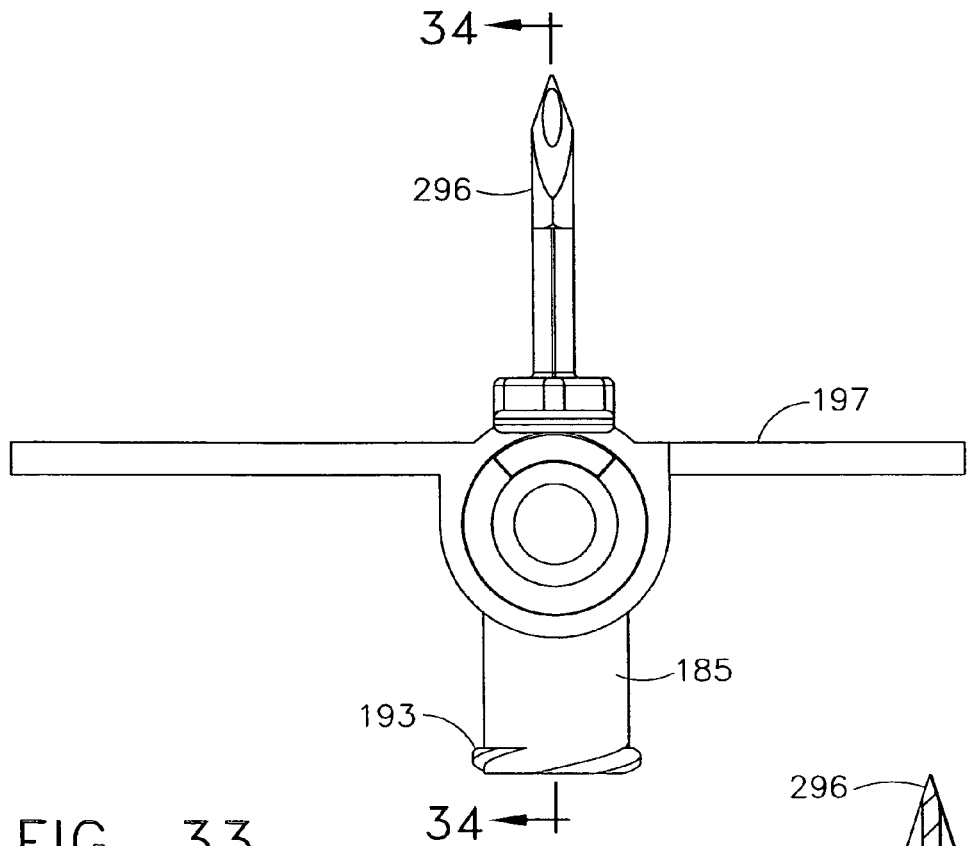
FIG. 33 is an end view of the spike of FIG. 32.
Figure 34:
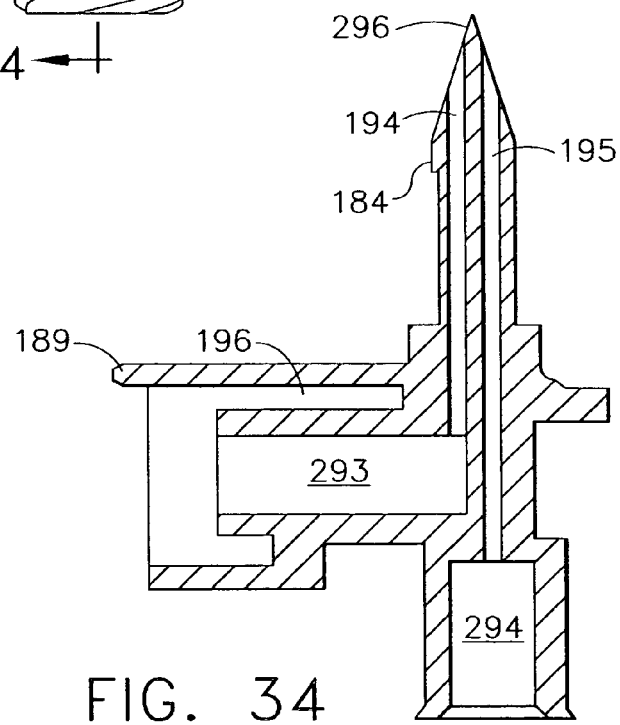
FIG. 34 is a cross-sectional view (which has been rotated ninety degrees counterclockwise) of the spike of FIG. 33 taken along lines 34-34 of FIG. 33.
Figure 38:
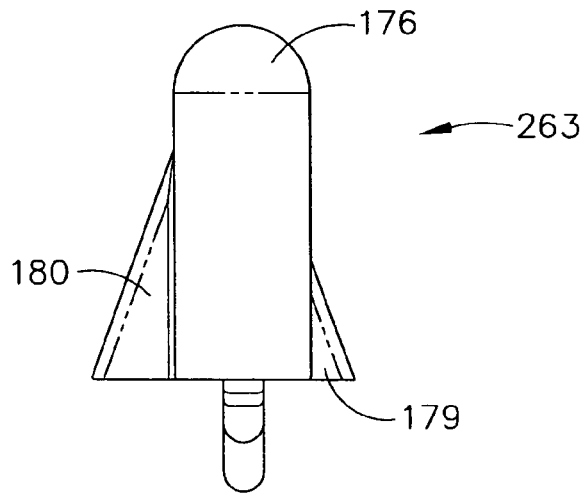
FIG. 38 is an end elevational view of the spike cap of the drug-delivery cassette assembly of FIG. 26.
Figure 39:
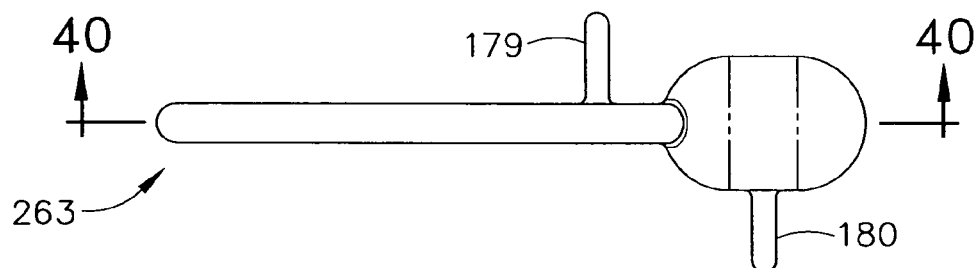
FIG. 39 is a top planar view of the spike cap of the drug-delivery cassette assembly of FIG. 26.
Figure 40:
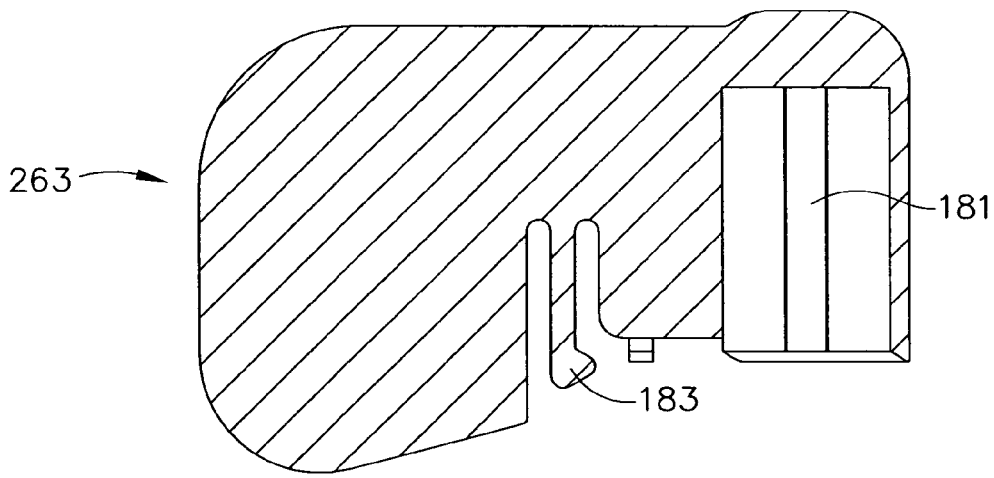
FIG. 40 is a cross-sectional view of the spike cap of FIG. 39, taken along lines 40-40 in FIG. 39, showing the spike hollow.

As illustrated on FIGS. 32-34, spike 261 is molded of rigid thermoplastic material and contains two internal lumens running generally parallel the length of spike 261. Spike 261 is generally cylindrical, having a perforating tip 296 and a spike wing 197 that serves as a base to spike tip 296. Spike 261 includes spike barb 184 that will prevent a drug vial 250 from slipping off of spike tip 296. Spike tip 296 includes a first bevel 186 and a second bevel 187. First bevel 186 includes a drug opening, which is in fluid communication with drug line lumen 195. Similarly, second bevel 187 includes an air-vial opening, which is in airway communication with air-vent lumen 196. In use, a drug vial bottle seal 42 is perforated by spike tip 296 and held by spike barb 184.

As shown on FIGS. 26 and 32-34, drug line lumen 195 is in fluid communication between spike tip 296 and drug channel 294. External to drug channel 294 is drug boss 185. On the outside of drug boss 185 is thread 193 for attaching spike elbow 265. Air-vent lumen 194 is in fluid communication with air-vent channel 293. External to air-vent channel 293 is air-vent boss 177. Air-vent lumen 194 is used to equalize the air pressure inside the drug vial 250, permitting fluid to flow by gravity from the drug vial 250 through drug line lumen 195 into the drug tubing line. In one construction, there is an air-vent filter 295 (as shown on FIG. 26), commercially available, that snaps into air-vent boss 177. Generally air-vent filter 295 has a cylindrical shape with a fine mesh feature on one side. Air-vent filter 295 is permeable to passage of gases, including air, in either direction though the air-vent channel 293, but precludes passage of liquid and solid materials in either direction through air-vent channel 293.

As shown on FIGS. 26, 28, 32-40, spike 261 has a flat wing 197 base designed as a generally trapezoidal thin plate, with smooth round corners. The flat thin shape of spike wing 197 facilitates user handling and creates support for spike cap 263. Two spike apertures 191 are coincident with spike base apertures 292 and serve to align the spike 261 to the vial centering mechanism in the PRU 200. Spike alignment apertures 298 are used for alignment when inserting spike 261 on cassette 251 and engages through spike pins 299, to align spike 261 on spike bed 262.

As shown on FIGS. 32-40, spike 261 includes snap lock 189 on top of spike wing 197. Snap lock 189 is integrally formed from spike wing 197. Snap lock 189 interfaces with spike latch 284 located on spike cap 263 to retain spike cap 263 on spike 261.

As illustrated on FIGS. 24 and 32-40, spike cap 263 is made of rigid thermoplastic and is a safety protection device for spike system 272. Spike cap 263 includes covering head 176, which is a hollow body, used to cover spike tip 296. Spike hollow 181 has a generally oblong shape and facilitates the assembly of spike cap 263 over spike tip 296. Spike cap 263 includes cap handle 182 to facilitate easy handling by the user. On each side of cap handle 182 are located gripper ribs 178. A latching mechanism includes spike latch 284 and two supporting arms, first arm 179 and second arm 180, molded integrally on both sides of covering head 176. Spike latch 284 has a spring-like property and is capable of deflecting normal to the axis of covering head 176. When spike cap 263 is assembled over spike tip 296, latch 284 is deflected by snap lock 189 located on spike 296, causing lip 183 to lock onto the edge of snap lock 189. First arm 179 and second arm 180 prevent spike cap 263 from tilting. As shown in FIGS. 24, 26, 28-31, the cassette main board 253 includes two cap-attaching ribs 38 which provide for a removable snap-fit attachment therebetween of the cap handle 182 of the spike cap 263 to the cassette main board 253. A brisk, quick upward force on cap handle 182 will cause spike cap 263 to release from spike 261 and from cap-attaching ribs 38.

As shown on FIGS. 25 and 26, spike elbow 265 is made of a rigid thermoplastic and is generally cylindrical in shape with two openings connected by internal fluid channel 264. One opening of fluid channel 264 connects to tube 277. The other opening of channel 264 is in fluid communication with drug channel 294 located in spike 261, and permits drug(s) to flow by gravity from a spiked vial through drug lumen 195, and through to tube 277. Spike elbow 265 includes an internally threaded ring to permit spike elbow 265 to be removably attached to spike boss 185 (See FIG. 33). When spike 261 is properly assembled to cassette main board 253, spike elbow retains spike 261.

Drug delivery cassette 251 is for single patient use (SPU) and is manually loaded in a pump cassette deck 219 on a Procedure Room Unit (PRU) 200 (shown in FIGS. 41-57). The pump cassette deck 219 has a hinged door that serves to press cassette 251 against the peristaltic pump 220. Cassette 251 contains intravenous tubing that is connected to a patient's catheter.

Procedure Room Unit

A third aspect of the invention is directed to, or a component of, or can be used by, a procedure room unit 200, an embodiment of which is shown in FIGS. 41-57. A first expression of the embodiment of FIGS. 41-57 is for a drug-delivery infusion pump assembly 220 including a drug-delivery infusion pump housing 239, a drug-delivery cassette assembly 251 (an embodiment of which has been previously discussed and shown in greater detail in FIGS. 24-40), and a pump-housing door 201. The drug-delivery cassette assembly 251 is attachable to the infusion pump housing 239 and has a drug-vial spike 261 (See FIG. 32). The pump-housing door 201 is attached to the infusion pump housing 239, has door-open and door-closed positions, and has drug-vial-aligning fingers 44. The drug-vial-aligning fingers 44 center and align different diameter drug vials 250 when: the cassette assembly 251 is attached to the infusion pump housing 239; the pump-housing door 201 is in the door-closed position; and a drug vial 250 is inserted between the drug-vial-aligning fingers 44 for engagement with the spike 261.

In one construction of the first expression of the embodiment of FIGS. 41-57, the drug-vial-aligning fingers 44 center and align ten and twenty cubic-centimeter drug vials 250 having different outside diameters and having the same or different lengths. In one variation, the drug-vial-centering fingers 44 consist essentially of two resilient, concave and opposing fingers. In the same or a different construction, the pump-housing door 201 is rotatably attached to the infusion pump housing 239 and is rotatable between the door-open and door-closed positions. Other constructions and variations are left to the artisan.

In one example of the first expression of the embodiment of FIGS. 41-57, the cassette assembly 251 is attachable to, and removable from, the infusion pump housing 239 when the pump-housing door 201 is in the door-open position. In the same or a different example, the drug-delivery infusion pump assembly 220 also includes a drug-delivery peristaltic pump 232 disposed in the infusion pump housing 239 and having pump fingers 229. In this example, the cassette assembly 251 is operatively connectable to the pump fingers 229 when the cassette assembly 251 is attached to the infusion pump housing 239 and the pump-housing door 201 is in the door-open position.

In one application of the first expression of the embodiment of FIGS. 41-57, the drug-delivery infusion pump assembly 220 is a part of a procedure room unit (PRU) 200 of a sedation delivery system (SDS) 100 (or other type of medical effector system 100') wherein the SDS 100 (or other type of medical effector system 100') also has a bedside monitoring unit (BMU) 300 and an umbilical cable 160. In this application, the BMU 300 has a first series of connection points for receiving input signals from patient monitoring connections and a second series of connection points for outputting patient parameters and has a display screen for displaying patient parameters. In this application, the PRU 200 is used during a medical procedure and for receiving patient parameters from the BMU 300 and has a display screen for displaying patient parameters. In this application, the umbilical cable 160 is used for communicating patient parameters from the BMU 300 to the PRU 200.

A second expression of the embodiment of FIGS. 41-57 is for a drug-delivery infusion pump assembly 220 and drug-delivery cassette assembly 251 combination including a drug-delivery infusion pump housing 239, a drug-delivery cassette assembly 251, a pump-housing door 201, and a pump-housing door lock 205/222. The cassette assembly 251 is attachable to the infusion pump housing 239, has a luer 269, and has a drug-delivery-cassette main board 253 including a luer-site base portion 271. The luer 269 is attachable to and detachable from the luer-site base portion 271. The pump-housing door 201 is attached to the infusion pump housing 239 and has door-open and door-closed positions. The pump-housing door lock 205/222, when the cassette assembly 251 is attached to the infusion pump housing 239, unlocks the pump-housing door 201 when the luer 269 is attached to the luer-site base portion 271.

In one enablement of the second expression of the embodiment of FIGS. 41-57, the lock 205/222 includes a pump-door latch 205 and a door latch solenoid 222 operatively connected to the pump-door latch 205. Other enablements are left to the artisan. It is noted that the pump-housing door 201 can be opened to remove the cassette assembly 251 when the luer 269 is returned to the luer-site base portion 271 at the end of a medical procedure.

A third expression of the embodiment of FIGS. 41-57 is for a sedation-delivery-system procedure room unit 200 (or other type of medical-effector-system procedure room unit 200') including a capnometer 140 and 202 and a barcode reader assembly 455. The capnometer 140 and 202 is adapted to receive directly or indirectly respiratory gas obtained from a single-patient-use cannula 351' which is disposable on the face of a patient. The barcode reader assembly 455 is adapted to read a barcode of a package containing the cannula 351' and/or a barcode of the cannula 351'.

An additional third expression of the embodiment of FIGS. 41-57 is for a sedation-delivery-system procedure room unit 200 (or other type of medical-effector-system procedure room unit 200') including a drug-delivery infusion pump housing 239 and a barcode reader assembly 455. The drug-delivery infusion pump housing 239 is adapted to receive a single-patient-use drug-delivery cassette assembly 251. The barcode reader assembly 455 is adapted to read a barcode of a package containing the drug-delivery cassette assembly 251 and/or a barcode of the drug-delivery cassette assembly 251.

In a further third expression of the embodiment of FIGS. 41-57, the cassette assembly 251 is adapted to receive a single-patient-use drug vial 250 containing a drug (such as, but not limited to, a sedation drug), and the barcode reader assembly 455 is adapted to read a barcode of the drug vial 250 and/or a barcode of a package containing the drug vial 250.

In one employment of the third expression, the additional third expression and/or the further third expression of the embodiment of FIGS. 41-57, the procedure room unit 200 uses the barcode reader assembly 455 to prevent multiple use of a single-patient-use item such as the drug-delivery cassette assembly 251, the cannula 351', and the drug vial 250 in the procedure room unit 200. In another employment, the procedure room unit 200 uses the barcode reader assembly 455 to match single-patient-use items to a particular patient. Other employments are left to the artisan.

A fourth expression of the embodiment of FIGS. 41-57 is for a sedation delivery system 100 (or other type of medical effector system 100') including a microprocessor-based bedside monitoring unit 300, a microprocessor-based procedure room unit 200, and an umbilical cable 160. The bedside monitoring unit 300 has a first series of connection points for receiving patient inputs from patient monitoring connections, has a second series of connection points for outputting patient outputs based on the received inputs, and has a display screen for displaying at least some of the patient outputs. The procedure room unit 200 has a drug-delivery flow control assembly 220' (or other type of medical effector 220"), and has a host controller 204 with a memory containing a patient-monitoring and drug-delivery-scheduling program (or other type of patient-monitoring and medical-effector scheduling program). The program is operatively connected to program inputs based at least in part on at least some of the patient outputs, and the program controls, and/or advises a user to control, the drug-delivery flow control assembly 220' (or other type of medical effector 220") based at least in part on the program inputs. The umbilical cable 160 has a first end attached or attachable to the second series of connection points of the bedside monitoring unit 300 and has a second end attached or attachable to the procedure room unit 200. At least one of the first and second ends of the umbilical cable 160 is detachable from the corresponding bedside monitoring unit 300 or the procedure room unit 200. The procedure room unit 200 includes an Ethernet and/or a modem connector 471/470 operatively connected to the host controller 204.

In one arrangement of the fourth expression of the embodiment of FIGS. 41-57, the drug-delivery flow control assembly 220' includes a drug-delivery infusion pump assembly 220 such as a peristaltic pump assembly. In one variation of this arrangement, the drug(s) is delivered to the patient through an IV. In another arrangement, not shown, the drug-delivery flow control assembly includes a gaseous-drug gas flow controller. In one variation of this arrangement, the gaseous drug(s) is oxygen and/or a non-oxygen gas and is delivered to the patient through a cannula assembly.

In one employment of the fourth expression of the embodiment of FIGS. 41-57, the Ethernet and/or modem connector 471/470 is used for remote software updates of programs residing in the memory of the host controller 204 of the procedure room unit 200, such as the patient-monitoring and drug-delivery-scheduling program (or other type of patient-monitoring and medical-effector-scheduling program). The term "memory" includes all memory of the host controller 204 including, in one example, all memory of the system input/output board 451 of the host controller and all memory of the processor board 452 of the host controller. In the same or a different employment, the host controller 204 of the procedure room unit 200 uses the Ethernet and/or modem connector 471/470 to send patient data to a remote computer for data management purposes. Other employments are left to the artisan. In one construction, the procedure room unit 200 has only an Ethernet connector 471 and not a modem connector 470. In a different construction, only a modem interface 470 and not an Ethernet interface 471 is present. In another construction, both an Ethernet and a modem interface 471 and 470 are present. In one enablement of the fourth expression of the embodiment of FIGS. 41-57, the procedure room unit 200 includes a monitor display 442 for displaying at least some of the program inputs and the status of the drug-delivery flow control assembly 220' (or other type of medical effector 220').

A fifth expression of the embodiment of FIGS. 41-57 is for a sedation delivery system 100 (or other type of medical effector system 100') including a microprocessor-based bedside monitoring unit 300, a microprocessor-based procedure room unit 200, and an umbilical cable 160. The bedside monitoring unit 300 has a first series of connection points for receiving patient inputs from patient monitoring connections, has a second series of connection points for outputting patient outputs based on the received inputs, and has a display screen for displaying at least some of the patient outputs. The procedure room unit 200 has a drug-delivery flow control assembly 220' (or other type of medical effector 220"), and has a host controller 204 with a memory containing a patient-monitoring and drug-delivery-scheduling program (or other type of patient-monitoring and medical-effector-scheduling program). The program is operatively connected to program inputs based at least in part on at least some of the patient outputs. The program controls, and/or advises a user to control, the drug-delivery flow control assembly 220' (or other type of medical effector 220") based at least in part on the program inputs. The umbilical cable 160 has a first end attached or attachable to the second series of connection points of the bedside monitoring unit 300 and has a second end attached or attachable to the procedure room unit 200. At least one of the first and second ends of the umbilical cable 160 is detachable from the corresponding bedside monitoring unit 300 or the procedure room unit 200. The host controller 204 of the procedure room unit 200 includes Health Level Seven application protocol to electronically send and/or receive communications to and/or from a remote computer.

In one employment of the fifth expression of the embodiment of FIGS. 41-57, the Health Level Seven application protocol is used to electronically send patient data to a remote computer for data management purposes. In the same or a different employment, the Health Level Seven application protocol is used to electronically receive remote servicing of (such as running remote diagnostic programs on) the procedure room unit 200. Other applications are left to the artisan.

A sixth expression of the embodiment of FIGS. 41-57 is for a sedation delivery system 100 (or other type of medical effector system 100') including a microprocessor-based bedside monitoring unit 300, a microprocessor-based procedure room unit 200, and an umbilical cable 160. The bedside monitoring unit 300 has a first series of connection points for receiving patient inputs from patient monitoring connections, has a second series of connection points for outputting patient outputs based on the received inputs, and has a display screen for displaying at least some of the patient outputs. The procedure room unit 200 has a drug-delivery flow control assembly 220' (or other type of medical effector 220"), and has a host controller 204 with a memory containing a patient-monitoring and drug-delivery-scheduling program (or other type of patient monitoring and medical-effector-scheduling program). The program is operatively connected to program inputs based at least in part on at least some of the patient outputs. The program controls, and/or advises a user to control, the drug-delivery flow control assembly 220' (or other type of end effector 220") based at least in part on the program inputs. The umbilical cable 160 has a first end attached or attachable to the second series of connection points of the bedside monitoring unit 300 and has a second end attached or attachable to the procedure room unit 200. At least one of the first and second ends of the umbilical cable 160 is detachable from the corresponding bedside monitoring unit 300 or the procedure room unit 200. The procedure room unit 200 includes a printer 454 operatively connected to the host controller 204.

In one employment of the sixth expression of the embodiment of FIGS. 41-57, the printer 454 is used to create a printed patient record of the role of the sedation delivery system 100 (or other type of medical effector system 100') during the medical procedure undergone by the patient. In one example of the sixth expression of the embodiment of FIGS. 36-52, the procedure room unit 200 includes a procedure-room-unit console 444, wherein the console 444 contains the drug-delivery flow control assembly 220' (or other type of medical effector 220"), the host controller 204, and the printer 454. In one construction, the printer 454 is a thermal printer.

A seventh expression of the embodiment of FIGS. 41-57 is for a sedation delivery system 100 comprising a microprocessor-based bedside monitoring unit 300, a microprocessor-based procedure room unit 200, and an umbilical cable 160. The bedside monitoring unit 300 has a bedside-monitoring-unit host controller 301 (See FIG. 62), which contains a first program. The first program performs the steps of: issuing a request to a non-sedated patient for a non-sedated patient response; receiving a signal based on the non-sedated patient response; and calculating a non-sedated response time for the patient based at least in part on a time difference between issuing the request and receiving the signal. The procedure room unit 200 has a procedure-room-unit host controller 204, which contains a second program. The second program performs the steps of: issuing requests through the bedside monitoring unit 300 to a sedated patient for a sedated patient response; receiving a signal through the bedside monitoring unit 300 based on the sedated patient response; calculating a sedated response time for the sedated patient, and calculating a response time difference between the non-sedated and sedated response times. The umbilical cable 160 has a first end attached or attachable to the bedside monitoring unit 300 and has a second end attached or attachable to the procedure room unit 200. At least one of the first and second ends is detachable from the corresponding bedside monitoring unit 300 or the procedure room unit 200.

In one example of the seventh expression of the embodiment of FIGS. 41-57, the procedure room unit 200 has a drug-delivery infusion pump assembly 220. The drug-delivery infusion pump assembly 220 is controlled by the procedure-room-unit host controller 204 based at least in part on the response time difference. In the same or a different example, the sedation delivery system 100 includes a cannula assembly 145 disposable on the face of a patient and having a respiratory gas sampling tube 354, 352 and 355 (See FIG. 1). The respiratory gas sampling tube 354, 352 and 355 (See FIG. 1) is connectable to the bedside monitoring unit 300. The procedure room unit 200 includes a capnometer 202 and 140 having a capnometer output signal, and the umbilical cable 160 is operatively connectable to the respiratory gas sampling tube 354, 352 and 355 and the capnometer 202 and 140. The drug-delivery infusion pump assembly 220 is controlled at least in part by the capnometer output signal.

In one employment of the seventh expression of the embodiment of FIGS. 41-57, the bedside monitoring unit 300 uses an audio earpiece 362 (See FIG. 1) to provide the patient 10 with requests to squeeze an automated-responsiveness-monitor (ARM) handset 342 (e.g., a handpiece which, in one illustration includes a vibrator to also request a response from the patient) to calculate patient response times. The requests are issued by the bedside monitoring unit 300 in a pre-procedure room to train the non-sedated patient to use the ARM handset 342 and to calculate the non-sedated response time. The requests are issued by the procedure room unit 200 (and transmitted to the bedside monitoring unit 300 through the umbilical cable 160) when the patient undergoes sedation in the procedure room to calculate sedated response times throughout the procedure. The requests are issued by the bedside monitoring unit 300 in a post-procedure room to present YES/NO questions, multiple choice questions, time-based responsiveness queries or other such prompt/reply interactions and combine the responses with other monitored parameters to conduct patient assessment. An example would be a series of questions/activities to show cognitive and motor functions prior to patient discharge. A further example would be to monitor the level of responsiveness and alerting the appropriate medical staff if the patient does not reach certain defined thresholds within an appropriate period of time.

A still further example would be to utilize the ARM handset 342 in place of a call button. While patients are in the pre-procedure or post-procedure room, a long squeeze or rapid squeezes on ARM handset 342 would be detected by BMU 300 as a request for assistance. BMU 300 would then log the request, post it on the BMU GUI 212 (See FIG. 60) and illuminate the light bar 208 (See FIG. 60) in an appropriate color or flashing scheme.

A further example is BMU 300 detecting a low respiration rate, apnea condition, or low $SpO_2$ and communicating this status to the patient. BMU 300 would send an audio request, such as "TAKE A DEEP BREATH" to the patient by way of audio earpiece 362, instructing the patient to take a deep breath. The command may be repeated at a predetermined time interval if the patient's respiration rate does not increase. Furthermore, the command may be initially provided at a first nominal volume level, and subsequent commands are provided at a second volume level, higher than said first volume level. If the patient does not respond to the request for respiration, an alarm will alert the care team of the patient's condition. Other similar type of audio commands may be given to the patient as other conditions warrant a specific patient response.

An eighth expression of the embodiment of FIGS. 41-57 is for a sedation-delivery-system procedure room unit 200 (or other type of medical-effector-system procedure room unit 200') comprising a procedure-room-unit host controller 204 which contains an oxygen delivery program which performs the steps of: receiving a pulse-oximeter signal from a patient undergoing sedation and calculating an oxygen flow rate based at least in part on the received pulse-oximeter signal, wherein the procedure-room-host controller 204 controls a flow of oxygen to the patient based on the calculated oxygen flow rate.

In the eighth expression of the embodiment of FIGS. 41-57, the oxygen flow rate to the patient is variable and is based at least in part on patient blood oxygen levels from the received pulse-oximeter signal. It is noted that the term "oxygen", when describing oxygen delivery, includes air with an enriched oxygen content.

A first extension of the eighth expression of the embodiment of FIGS. 41-57 is for a sedation delivery system 100 (or other type of medical-effector system 100') including the sedation-delivery-system procedure room unit 200 (or other type of medical-effector-system procedure room unit 200') as described in the previous paragraph, including a bedside monitoring unit 300, and including an umbilical cable 160. The umbilical cable 160 has a first end attached or attachable to the bedside monitoring unit 300 and has a second end attached or attachable to the procedure room unit 200. At least one of the first and second ends is detachable from the corresponding bedside monitoring unit 300 or the procedure room unit 200. When the umbilical cable 160 is attached to the procedure room unit 200 and the bedside monitoring unit 300, the pulse-oximeter signal flows from the patient through the bedside monitoring unit 300 and through the umbilical cable 160 to the procedure room unit 200 and the flow of oxygen flows through the umbilical cable 160 and the bedside monitoring unit 300 to the patient.

A ninth expression of the embodiment of FIGS. 41-57 is for medical oxygen-delivery apparatus including an oxygen-delivery manifold 206 having an oxygen-delivery flow path, a fixed-size-orifice flow restrictor 489, and a variable-size-orifice flow restrictor 480. The oxygen-delivery flow path includes a flow-path inlet fluidly-connectable to a source of pressurized oxygen and a flow-path outlet fluidly-connectable to a cannula 351' disposable on the face of a patient. The fixed-size-orifice flow restrictor 489 is disposed in the flow path downstream of the flow-path inlet, and the variable-size-orifice flow restrictor 480 is disposed in the flow path downstream of the fixed-size-orifice flow restrictor 489.

In one example of the ninth expression of the embodiment of FIGS. 41-57, the medical oxygen-delivery apparatus also includes a high side pressure sensor 487 in fluid communication with the flow path at a first location disposed between the flow-path inlet and the fixed-size-orifice flow restrictor 489 and includes a differential pressure sensor 479 in fluid communication with the flow path at an entrance location disposed between the first location and the fixed-size-orifice flow restrictor 489 and at an exit location disposed between the fixed-size-orifice flow restrictor 489 and the variable-size-orifice flow restrictor 480. The orifice size of the variable-size-orifice flow restrictor 480 is related to the measured pressure and pressure difference and is used to control the flow rate as is within the routine capabilities of those skilled in the art. In the same or a different example, the variable-size-orifice flow restrictor 480 is a variable-size-orifice solenoid. In one application, the oxygen-delivery manifold 206 is a subassembly of a procedure room unit 200 of a sedation delivery system 100 (or other type of medical effector system 100').

A tenth expression of the embodiment of FIGS. 41-57 is for a sedation-delivery-system procedure room unit 200 (or other medical-effector-system procedure room unit 200') including a procedure-room-unit host controller 204, which contains an oxygen delivery program. The program performs the steps of: controlling the delivery of oxygen at a predetermined first rate to at least one respiratory-gas-delivery oral prong 369"/371" of a cannula assembly 145 operatively connected to a patient, when the patient is determined to be inhaling and exhaling through the mouth; controlling the delivery of oxygen at a predetermined second rate to at least one respiratory-gas-delivery nasal prong 422' and 422" of the cannula assembly 145 when the patient is determined to be breathing through the nose and when the patient is determined to be inhaling; and controlling the delivery of oxygen at a predetermined third rate to the at-least-one respiratory-gas-delivery nasal prong 422' or 422" when the patient is determined to be breathing through the nose and when the patient is determined to be exhaling. The second rate is higher than the third rate.

In one example of the tenth expression of the embodiment of FIGS. 41-57, when oxygen flows, oxygen always flows to all respiratory-gas-delivery oral and nasal prongs when the rate of oxygen delivery is being controlled to either the respiratory-gas-delivery oral or nasal prongs.

In one enablement of the tenth expression of the embodiment of FIGS. 41-57, the oxygen delivery program also performs the steps of determining that the patient is breathing through the nose or the mouth and, if through the nose, that the patient is inhaling or exhaling based at least in part on nasal pressure readings from sampled respiratory gas taken from at least one respiratory-gas-sampling nasal prong 364 and 365 of the cannula assembly 145.

A first alternate tenth expression of the embodiment of FIGS. 41-57 is for a medical-effector-system procedure room unit 200' (such as a sedation-delivery-system procedure room unit 200') including a procedure-room-unit host controller 204 which contains an oxygen delivery program. The program performs the steps of: controlling the delivery of oxygen at a variable first rate to at least one respiratory-gas-delivery oral prong 369"/371" of a cannula assembly 145 operatively connected to a patient, when the patient is determined to be inhaling and exhaling through the mouth; controlling the delivery of oxygen at a variable second rate to at least one respiratory-gas-delivery nasal prong 422' and 422" of the cannula assembly 145 when the patient is determined to be breathing through the nose and when the patient is determined to be inhaling; and controlling the delivery of oxygen at a variable third rate to the at-least-one respiratory-gas-delivery nasal prong 422' and 422" when the patient is determined to be breathing through the nose and when the patient is determined to be exhaling. The patient has a variable percentage of blood oxygen saturation, and the first, second and third rates depend on the percentage of blood oxygen saturation.

In one enablement of the first alternate tenth expression of the embodiment of FIGS. 41-57, the second rate is a fixed low rate for percentages of blood oxygen saturation above a predetermined high percentage and is a fixed high rate for percentages of blood oxygen saturation below a predetermined low percentage. In one variation, the second rate steps up a plurality of times from the fixed low rate to the fixed high rate as the percentage of blood oxygen saturation decreases from the predetermined high percentage to the predetermined low percentage. In one modification, the second rate is higher than the third rate for the same percentage of blood oxygen saturation. In one implementation, the third rate is zero at the predetermined high percentage. In the same or a different enablement, the first rate corresponding to a particular percentage of blood oxygen saturation is the arithmetic mean of the second and third rates corresponding to the particular percentage of blood oxygen saturation. In the same or a different enablement, the oxygen delivery program accepts a user input to raise, but never lower, the second rate above the fixed low rate when the percentage of blood oxygen saturation is above, but never below, the predetermined high percentage. In one variation, the oxygen delivery program accepts a user input to raise, but never lower, the third rate when the percentage of blood oxygen saturation is above, but never below, the predetermined high percentage.

In one example of the first alternate tenth expression of the embodiment of FIGS. 41-57, the second rate is substantially 2 liters per minute and the third rate is 0 liters per minute for a predetermined high percentage of substantially 96%, and the second rate is substantially 15 liters per minute and the third rate is substantially 2 liters per minute for a predetermined low percentage of substantially 84%. In this example, the second rate is substantially 8 liters per minute and the third rate is substantially 2 liters per minute when the percentage of blood oxygen saturation is between substantially 88% and 96%, and the second rate is substantially 12 liters per minute and the third rate is substantially 2 liters per minute when the percentage of blood oxygen saturation is between substantially 84% and 88%. Benefits and advantages of this example include basing the oxygen delivery rate on the patient's oxygen saturation level, which provides a higher oxygen delivery rate for a patient having low blood oxygen saturation while providing a lower oxygen delivery rate for a patient having high blood oxygen saturation, which conserves oxygen use. In this example, the flow rates may be associated with a patient that is predominantly nasal breathing. If the patient is predominantly oral breathing (indicated by the absence of a nasal pressure signal) the flow rate may be the arithmetic means of the inhalation and exhalation rates for each blood oxygen segment.

A second alternate tenth expression of the embodiment of FIGS. 41-57 is for a medical-effector-system procedure room unit 200' (such as a sedation-delivery-system procedure room unit 200) including a procedure-room-unit host controller 204 which contains an oxygen delivery program. The program performs the steps of: controlling the delivery of oxygen at a variable nasal-inhale oxygen-delivery flow rate to at least one respiratory-gas-delivery nasal prong 422' and 422" of a cannula assembly 145 operatively connected to a patient, when the patient is determined to be breathing through the nose and when the patient is determined to be inhaling; and controlling the delivery of oxygen at a nasal-exhale oxygen-delivery flow rate to the at-least-one respiratory-gas-delivery nasal prong 422' and 422" when the patient is determined to be breathing through the nose and when the patient is determined to be exhaling. The patient has a variable percentage of blood oxygen saturation, and the nasal-inhale oxygen-delivery flow rate is a variable rate, which depends on the percentage of blood oxygen saturation.

In one enablement of the second alternate tenth expression of the embodiment of FIGS. 41-57, the nasal-exhale oxygen-delivery flow rate is a variable rate, which depends on the percentage of blood oxygen saturation, and the nasal-inhale oxygen-delivery rate is greater than the nasal-exhale oxygen-delivery rate for the same percentage of blood oxygen saturation.

An eleventh expression of the embodiment of FIGS. 41-57 is for medical oxygen-delivery apparatus including an oxygen-delivery manifold 206. The oxygen-delivery manifold 206 has an oxygen-delivery flow path and an oxygen-sampling flow path fluidly-connectable to the oxygen-delivery flow path. The oxygen-delivery flow path includes a flow-path inlet fluidly-connectable to a source of pressurized oxygen and a flow-path outlet fluidly-connectable to a cannula 351' disposable on the face of a patient. The oxygen-sampling flow path includes an oxygen sensor 482, which detects hypoxic gas.

In one example of the eleventh expression of the embodiment of FIGS. 41-57, an oxygen sample solenoid 481 fluidly connects the oxygen-sampling flow path to the oxygen-delivery flow path. In one implementation, a detection of hypoxic (low oxygen) gas by the oxygen sensor 482 is used to issue a user alert to check the source of oxygen. In one employment, the oxygen-delivery manifold 206 is a subassembly of a procedure room unit 200 of a sedation delivery system 100 (or other type of medical-effector system 100').

A twelfth expression of the embodiment of FIGS. 41-57 is for a sedation-delivery-system procedure room unit 200 (or other type of medical-effector-system procedure room unit 200') including a procedure-room-unit host controller 204 and a capnometer 140 and 202. The capnometer 140 and 202 has a capnometer gas input which receives directly or indirectly respiratory gas obtained from a cannula 351' which is disposable on the face of a patient. The capnometer 140 and 202 also has a capnometer signal output operatively connected to the procedure-room-unit host controller 204. The procedure-room-unit host controller 204 issues a user alert that the capnometer 140 and 202 is fluidly connected and/or not fluidly connected to the cannula 351' based at least in part on the capnometer signal output of the capnometer 140 and 202.

In one example of the twelfth expression of the embodiment of FIGS. 41-57, the capnometer input receives indirectly respiratory gas obtained from the cannula 351' through an intervening bedside monitoring unit 300. The bedside monitoring unit 300 is attachable to the cannula 351' and is attached or attachable to a first end of an umbilical cable 160. The umbilical cable 160 has a second end attached or attachable to the procedure room unit 200. At least one of the first and second ends is detachable from the corresponding bedside monitoring unit 300 or the procedure room unit 200. Typically, in this example, a detached umbilical cable 160 would be responsible for most user alerts from the procedure-room-unit host controller 204 that the capnometer 140 and 202 is not fluidly connected to the cannula 351'. In one enablement, the procedure-room-unit host controller 204 determines that the capnometer 140 and 202 is fluidly connected to the cannula 351' if the capnometer output indicates a valid respiratory rate of the patient based on a rise and fall of the capnometer output (i.e., a rise and fall of the carbon dioxide level measured by the capnometer 140 and 202).

A thirteenth expression of the embodiment of FIGS. 41-57 is for a sedation-delivery-system procedure room unit 200 (or other type of medical-effector-system procedure room unit 200') including a sedation-delivery-system procedure-room-unit console 444 (or other type of medical-effector-system procedure-room-unit console 444') having a console fan 456 and a capnometer subassembly 140/202 and 141/142. The console fan 456 moves air into, through, and out of the procedure-room-unit console 444 (or 444'). The capnometer subassembly 140/202 and 141/142 has a capnometer-subassembly gas inlet and a capnometer-subassembly gas outlet. The capnometer-subassembly gas outlet is disposed to enable gas leaving the capnometer-subassembly gas outlet to be entrained with air moved by the console fan 456.

In one example of the thirteenth expression of the embodiment of FIGS. 41-57, the capnometer subassembly 140/202 and 141/142 has a capnometer 140 and 202 and a capnometer pump 141 and 142 operatively connected to the capnometer 140 and 202. In one construction of this example, gas flows from the capnometer-subassembly gas inlet to the capnometer to the capnometer pump and to the capnometer-subassembly gas outlet. In another construction of this example, gas flows from the capnometer-subassembly gas inlet to the capnometer pump to the capnometer and to the capnometer-subassembly gas outlet. One benefit of having gas from the capnometer-subassembly gas outlet be fan-vented outside the console by the console fan is that such outlet gas is less likely to contaminate the capnometer calibration. In one arrangement, calibration gas and console fan air are drawn in the front of the console and exhausted from the back of the console.

In one extension of the thirteenth expression of the embodiment of FIGS. 41-57, a sedation delivery system 100 (or other type of medical-effector system 100') includes the sedation-delivery-system procedure room unit 200 (or other type of medical-effector-system procedure room unit 200') described in the second previous paragraph, includes a bedside monitoring unit 300, and includes an umbilical cable 160. The umbilical cable 160 has a first end attached or attachable to the bedside monitoring unit 300 and has a second end attached or attachable to the procedure room unit 200. At least one of the first and second ends is detachable from the corresponding bedside monitoring unit 300 or the procedure room unit 200.

A fourteenth expression of the embodiment of FIGS. 41-57 is for a sedation-delivery-system procedure room unit 200 (or other type of medical-effector-system procedure room unit 200') including a procedure-room-unit host controller 204, a capnometer 140 and 202, an oxygen manifold 206, and a low side pressure sensor 488. The capnometer 140 and 202 has a capnometer gas input which receives directly or indirectly respiratory gas obtained from a cannula 351' which is disposable on the face of a patient and has a capnometer signal output operatively connected to the procedure-room-unit host controller 204. The oxygen manifold 206 has an oxygen-delivery flow path including in series a flow-path inlet fluidly-connectable to a source of pressurized oxygen, a flow restrictor 489 and 480, and a flow-path outlet fluidly-connectable to the cannula 351'. The low side pressure sensor 488 is in fluid communication with the flow-path outlet, is disposed downstream of any oxygen-manifold flow restrictor 489 and 480, and has a low-side pressure signal output operatively connected to the procedure-room-unit host controller 204. The procedure-room-unit host controller 204 issues a user alert that the capnometer 140 and 202 is fluidly connected and/or not fluidly connected to the cannula 351' based at least in part on the capnometer signal output of the capnometer 140 and 202 and the low-side pressure signal output of the low side pressure sensor 488.

In one example of the fourteenth expression of the embodiment of FIGS. 41-57, the capnometer input receives indirectly respiratory gas obtained from the cannula 351' through an intervening bedside monitoring unit 300 which is attachable to the cannula 351' and attached or attachable to a first end of an umbilical cable 160 having a second end attached or attachable to the procedure room unit 200. The flow-path outlet of the oxygen manifold 206 is indirectly fluidly-connected to the cannula 351' through the bedside monitoring unit 300 and the umbilical cable 160. At least one of the first and second ends is detachable from the corresponding bedside monitoring unit 300 or the procedure room unit 200.

A fifteenth expression of the embodiment of FIGS. 41-57 is for a sedation-delivery-system procedure room unit 200 (or other type of medical-effector-system procedure room unit 200') including a procedure-room-unit host controller 204, a capnometer 140 and 202 and a capnometer pump 141 and 142. The capnometer 140 and 202 has a capnometer gas input which receives directly or indirectly respiratory gas obtained from a cannula 351' which is disposable on the face of a patient. The capnometer 140 and 202 also has a capnometer signal output operatively connected to the procedure-room-unit host controller 204. The capnometer pump 141 and 142 is operatively connected to the capnometer 140 and 202 and is controlled by the procedure-room-unit host controller 204. The procedure-room-unit host controller 204 determines that the capnometer 140 and 202 is fluidly connected and/or not fluidly connected to the cannula 351' based at least in part on the capnometer signal output of the capnometer 140 and 202.

The procedure-room-unit host controller 204 shuts off, with or without a time delay, the capnometer pump 141 and 142 when the capnometer 140 and 202 is not fluidly connected to the cannula 351'. In one employment, shutting off the capnometer pump 141 and 142 during times when the cannula 351' is not in use avoids pollutants, impurities, etc. in the air from contaminating the capnometer 140 and 202 during such times.

In one example of the fifteenth expression of the embodiment of FIGS. 41-57, the capnometer input receives indirectly respiratory gas obtained from the cannula 351' through an intervening bedside monitoring unit 300. The bedside monitoring unit 300 is attachable to the cannula 351' and is attached or attachable to a first end of an umbilical cable 160. The umbilical cable 160 has a second end attached or attachable to the procedure room unit 200. At least one of the first and second ends is detachable from the corresponding bedside monitoring unit 300 or the procedure room unit 200.

A sixteenth expression of the embodiment of FIGS. 41-57 is for a sedation-delivery-system procedure room unit 200 (or other type of medical-effector-system procedure room unit 200') including a procedure-room-unit host controller 204, a capnometer 140 and 202, and an ambient-air pressure sensor 46. The capnometer 140 and 202 has a capnometer gas input which receives directly or indirectly respiratory gas obtained from a cannula 351' which is disposable on the face of a patient. The capnometer 140 and 202 has a capnometer signal output operatively connected to the procedure-room-unit host controller 204. The ambient-air pressure sensor 46 has an ambient-air-pressure-sensor signal output operatively connected to the procedure-room-unit host controller 204. The procedure-room-unit host controller 204 determines if the sedation-delivery-system procedure room unit 200 (or other type of medical-effector-system procedure room unit 200') has been moved to a new location having an altitude difference greater than a predetermined altitude difference using at least the ambient-air-pressure-sensor signal output of the ambient-air pressure sensor 46. The procedure-room-unit host controller 204 issues a capnometer-calibration user alert when the sedation-delivery-system procedure room unit 200 (or other type of medical-effector-system procedure room unit 200') has been moved to a new location having an altitude difference greater than the predetermined altitude difference.

In one example of the sixteenth expression of the embodiment of FIGS. 41-57, the capnometer input receives indirectly respiratory gas obtained from the cannula 351' through an intervening bedside monitoring unit 300. The bedside monitoring unit 300 is attachable to the cannula 351' and is attached or attachable to a first end of an umbilical cable 160. The umbilical cable 160 has a second end attached or attachable to the procedure room unit 200. At least one of the first and second ends is detachable from the corresponding bedside monitoring unit 300 or the procedure room unit 200.

A seventeenth expression of the embodiment of FIGS. 41-57 is for a sedation-delivery-system procedure room unit 200 (or other type of medical-effector-system procedure room unit 200') including a procedure-room-unit host controller 204, a cannula 351', and an oxygen manifold 206. The cannula 351' is disposable on the face of a patient and has a respiratory-gas-sample output operatively connectable to the procedure-room-unit host controller 204. The oxygen manifold 206 has a flow-path outlet fluidly-connectable to the cannula 351' and has a variable-size-orifice flow restrictor 480 operatively connected to, and disposed upstream of, the flow-path outlet. The procedure-room-unit host controller 204 determines when the patient is first breathing with a disposed cannula 351' based at least on the respiratory-gas-sample output of the cannula 351' and opens the variable-size-orifice flow restrictor 480 when the patient is first determined to be breathing with a disposed cannula 351'.

In one enablement of the seventeenth expression of the embodiment of FIGS. 41-57, the respiratory-gas-sample output of the cannula 351' is operatively connected to the procedure-room-unit host controller 204 via a pressure transducer (such as nasal pressure transducer 47) and/or through a capnometer 140 and 202. In the same or a different enablement, the variable-size-orifice flow restrictor 480 is a variable-size-orifice solenoid.

In one application of any of the above-described expressions of FIGS. 41-57, including examples, etc. thereof, the procedure room unit 200 is directly attachable to a bedside monitoring unit 300. Other applications are left to the artisan.

Any one or more of the above-described expressions of the embodiment of FIGS. 41-57, including examples, etc. thereof can be combined with any other one or more of the above-described expressions of the embodiment of FIGS. 41-57, including examples, etc. thereof, as can be appreciated by those skilled in the art.

Figure 58:
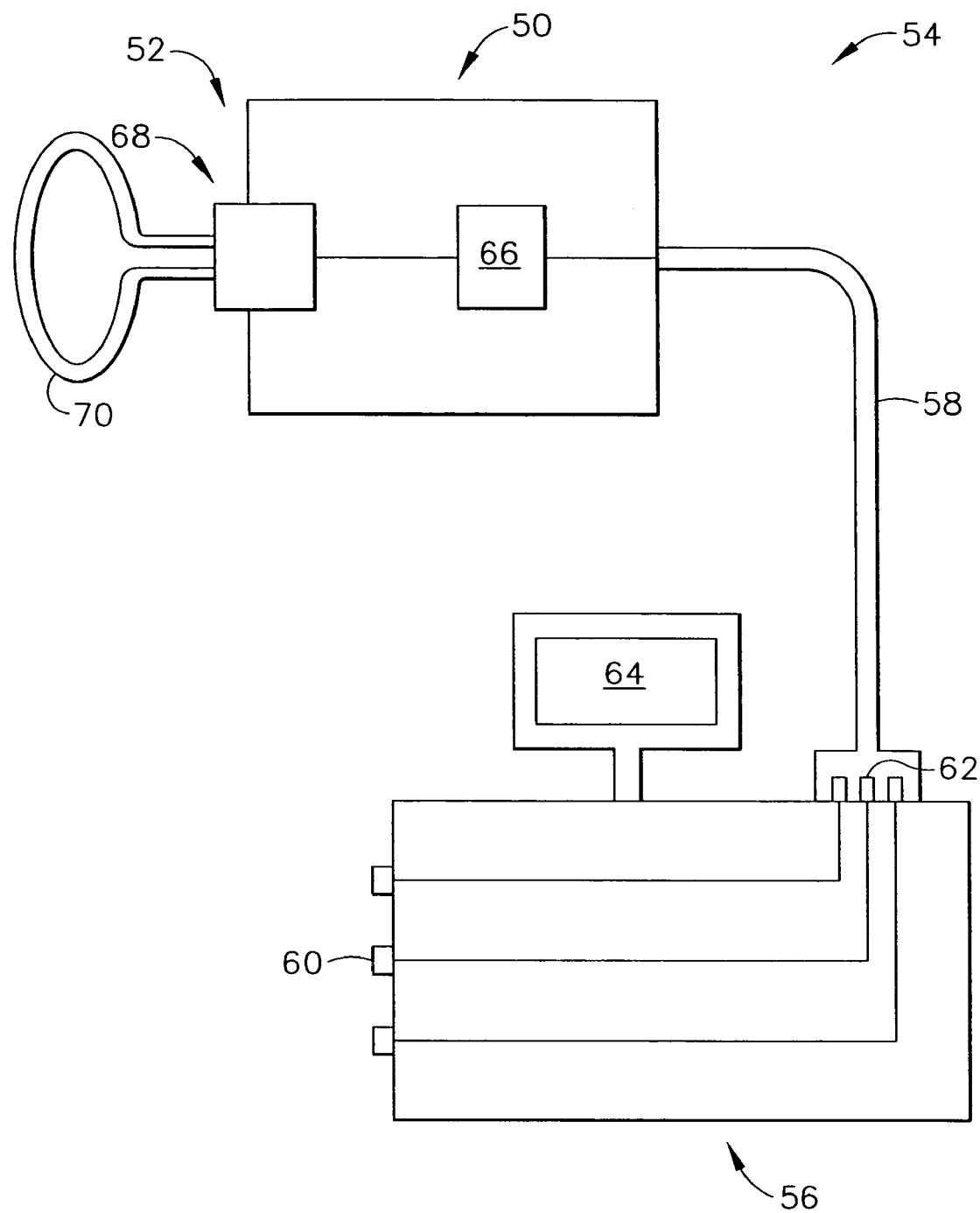
FIG. 58 is a schematic view of an alternate embodiment of a medical effector system of the invention including an energy-delivery medical effector.

In an alternate embodiment, as shown in FIG. 58, a procedure room unit 50 includes an energy-delivery medical effector 52. An expression of the embodiment of FIG. 58 is for a medical effector system 54 including a microprocessor-based bedside monitoring unit 56, a microprocessor-based procedure room unit 50, and an umbilical cable 58. The bedside monitoring unit 56 has a first series of connection points 60 for receiving patient inputs from patient monitoring connections, has a second series of connection points 62 for outputting patient outputs based on the received inputs, and has a display screen 64 for displaying at least some of the patient outputs. The procedure room unit 50 has an energy-delivery medical effector 52, and has a host controller 66 with a memory containing a patient-monitoring and medical-effector-scheduling program which is operatively connected to program inputs based at least in part on at least some of the patient outputs and which controls, and/or advises a user to control, the energy-delivery medical effector 52 based at least in part on the program inputs. The umbilical cable 58 has a first end attached or attachable to the second series of connection points 62 of the bedside monitoring unit 56 and has a second end attached or attachable to the procedure room unit 50. At least one of the first and second ends is detachable from the corresponding bedside monitoring unit 56 or the procedure room unit 50. In one example, the energy-delivery medical effector 52 includes at least one magnetic flux generator 68 adapted to deliver a time varying magnetic field to a patient to have a sedative effect on the patient. In one variation, the at-least-one magnetic flux generator 68 includes a coil 70.

Figure 59:
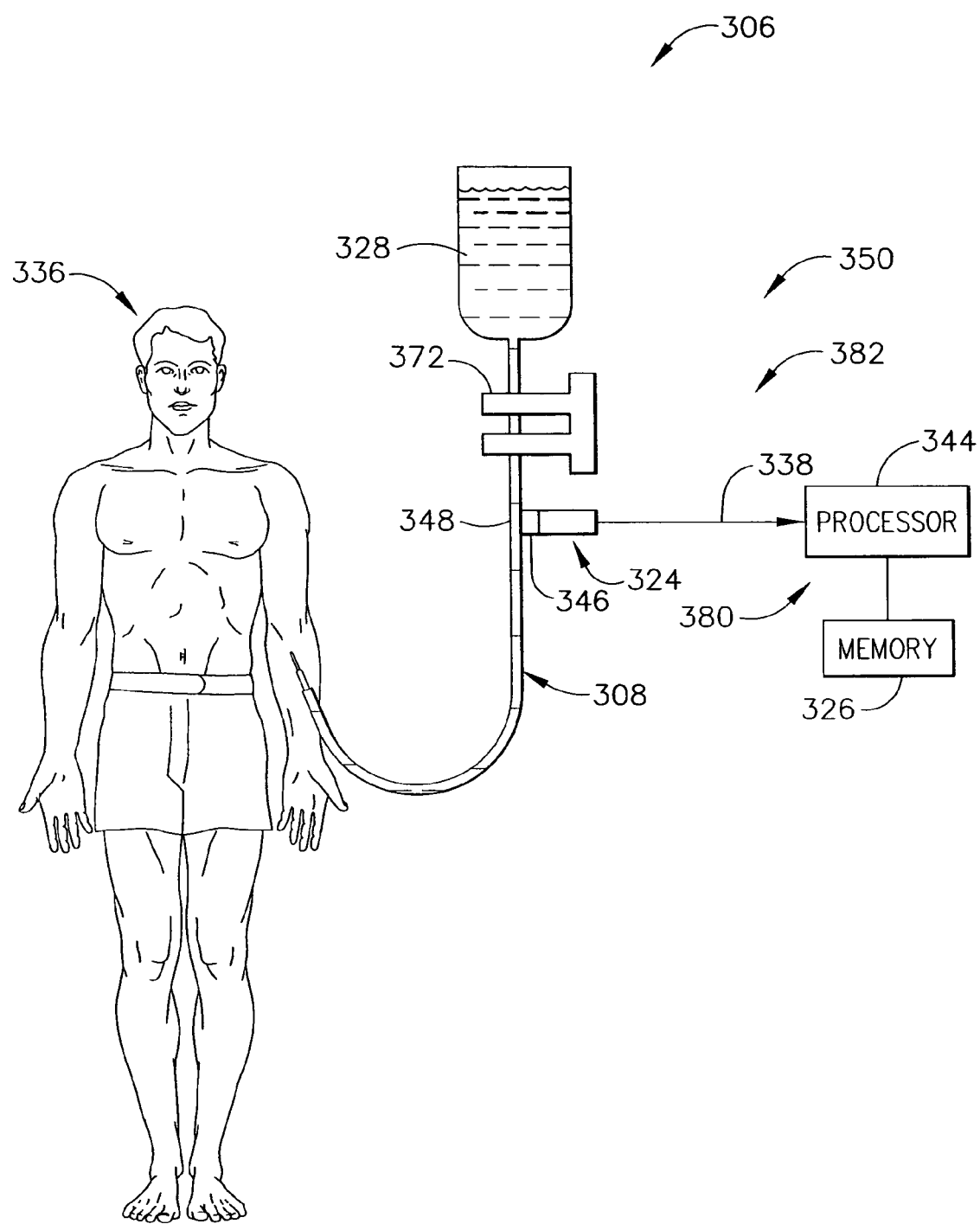
FIG. 59 is a schematic diagram of an embodiment of a medical effector subsystem having a drug-delivery infusion pump subassembly, wherein the medical effector subsystem alerts a user of an occluded drug-delivery tube.
Figure 60:
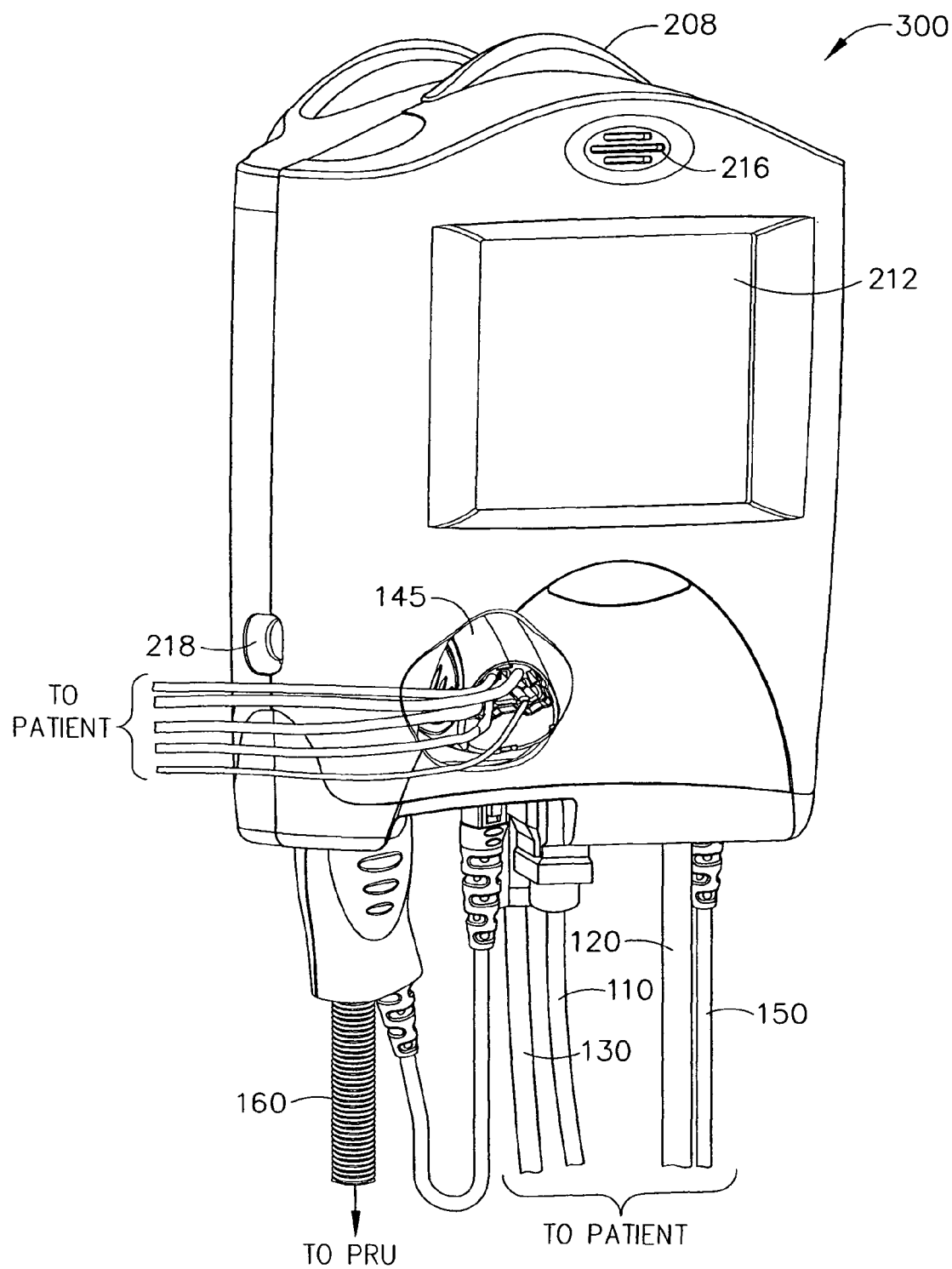
FIG. 60 is a front perspective view of the BMU of FIG. 41 with connecting lines attached.
Figure 61:
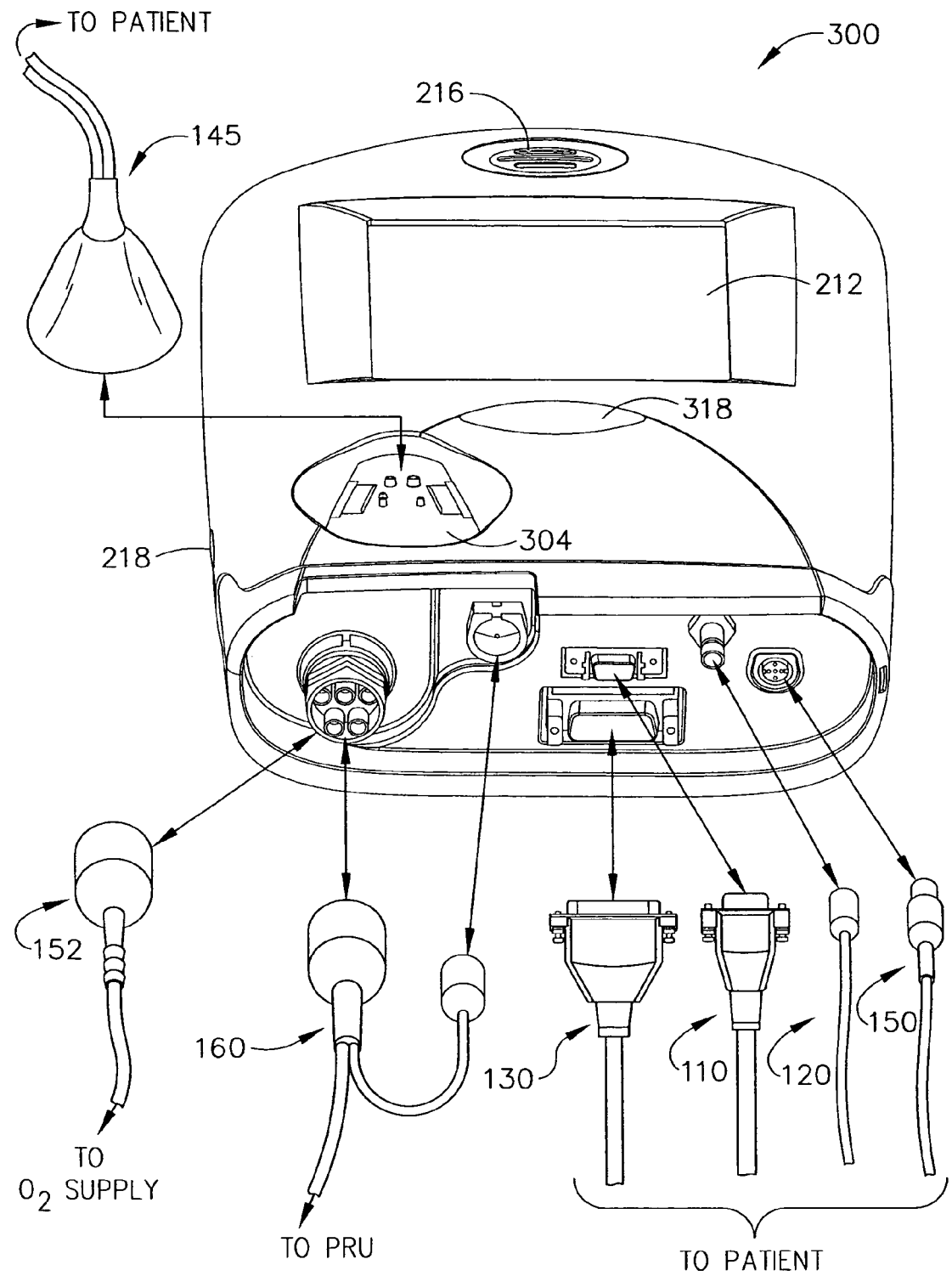
FIG. 61 is a bottom perspective view of the BMU of FIG. 41 with connecting lines detached.

FIG. 59 shows an embodiment of a medical effector subsystem 306. A first expression of the embodiment of FIG. 59 is for a medical effector subsystem 306 including a drug-delivery tube 308, a pressure sensor 324, and a memory 326. The drug-delivery tube 308 is adapted to contain therein a drug 328 having a variable commanded flow rate and is disposable to deliver the drug to a patient 336. The pressure sensor 324 has an output signal 338 and is adapted to sense internal pressure of the drug-delivery tube 308. The memory 326 contains an occlusion program which when running on a processor 344 is operatively connected to the output signal 338 of the pressure sensor 324. The occlusion program has a variable pressure alarm setting and alerts a user of an occluded drug-delivery tube 308 when the output signal 338 of the pressure sensor 324 exceeds the variable pressure alarm setting. The occlusion program changes the variable pressure alarm setting based at least in part, and directly or indirectly, on the variable commanded flow rate of the drug 328.

The term "occluded" includes partially occluded and completely occluded. Causes of an occluded drug-delivery tube 308 include, without limitation, a bent, twisted, squeezed, and/or blocked tube. In one operation of the first expression of the embodiment of FIG. 59, the drug 328 is a pumped drug, which is pumped at the variable commanded flow rate. In this operation, when the drug-delivery tube 308 is occluded, the continued pumping of the drug 328 increases the internal pressure of the drug-delivery tube 308. It is noted that changing the variable pressure alarm setting based on commanded or actual pump speed is changing the variable pressure alarm setting based indirectly on the variable commanded flow rate of the drug, as is understood by the artisan. In one arrangement, since increasing the drug flow rate increases the internal pressure of a non-occluded tube, the variable pressure alarm setting is set to always be higher (by a predetermined amount in one example) than the non-occluded tube internal pressure corresponding to the present commanded flow rate (or corresponding to the present commanded or actual pump speed).

In one implementation of the first expression of the embodiment of FIG. 59, the occlusion program sets the variable pressure alarm setting to a fixed low setting when the variable commanded flow rate is below a predetermined value and sets the variable pressure alarm setting to a fixed high setting when the variable commanded flow rate is at or above the predetermined value. In a different implementation, the occlusion program changes the variable pressure alarm setting whenever there is a change in the variable commanded flow rate. Other implementations are left to the artisan.

In one employment of the first expression of the embodiment of FIG. 59, the drug-delivery tube 308 is an intravenous drug-delivery tube. In a different employment, not shown, the drug-delivery tube is a pneumatic tube, wherein the drug is a gaseous drug. As previously mentioned, oxygen (i.e., air having an enriched oxygen content) is an example, without limitation, of a gaseous drug.

In one construction of the first expression of the embodiment of FIG. 59, the pressure sensor 324 includes a pressure-sensitive input portion 346 and the drug-delivery tube 308 has an imperforate outside surface portion 348. In this construction, the input portion 346 of the pressure sensor 324 is disposed in contact with the imperforate outside surface portion 348 of the drug-delivery tube 308. Other pressure sensor and/or drug-delivery tube types and constructions are left to the artisan including, without limitation, a pressure sensor input which is in fluid communication with the drug inside the drug-delivery tube.

In one enablement of the first expression of the embodiment of FIG. 59, the memory 326 and the processor 344 are components of a host controller of a procedure room unit (such as host controller 204 of the previously-described procedure room unit 200). In one variation, the memory 326 also contains a drug delivery algorithm, such as the previously mentioned Dosage Controller (DC) algorithm, which when running on the processor 344 determines the variable commanded flow rate. In one modification, the variable commanded flow rate includes a zero flow rate, a fixed maintenance flow rate, and a much larger fixed bolus flow rate. Other modifications, variations, and enablements are left to the artisan.

In one application of the first expression of the embodiment of FIG. 59, the medical effector subsystem 306 also includes an infusion pump 350, which is adapted to receive the variable commanded flow rate. The infusion pump 350 has peristaltic pump fingers 372. The peristaltic pump fingers 372 are disposed to interact with the drug-delivery tube 308 and are controllable to pump the drug 328 at the variable commanded flow rate.

A second expression of the embodiment of FIG. 59 is for a medical effector subsystem 306 including a drug-delivery tube 308, a pressure sensor 324, and a memory 326. The drug-delivery tube 308 is adapted to contain therein a drug 328 having a variable commanded flow rate, is disposable to deliver the drug 328 to a patient 336, and includes an imperforate outside surface portion 348. The pressure sensor 324 has an output signal 338 and includes a pressure-sensitive input portion 346 disposed in contact with the imperforate outside surface portion 348 of the drug-delivery tube 308. The memory 326 contains an occlusion program which when running on a processor 344 is operatively connected to the output signal 338 of the pressure sensor 324. The occlusion program has a variable pressure alarm setting and alerts a user of an occluded drug-delivery tube 308 when the output signal 338 of the pressure sensor 324 exceeds the variable pressure alarm setting. The occlusion program changes the variable pressure alarm setting based entirely, and directly, on the variable commanded flow rate of the drug 328.

Figure 48:
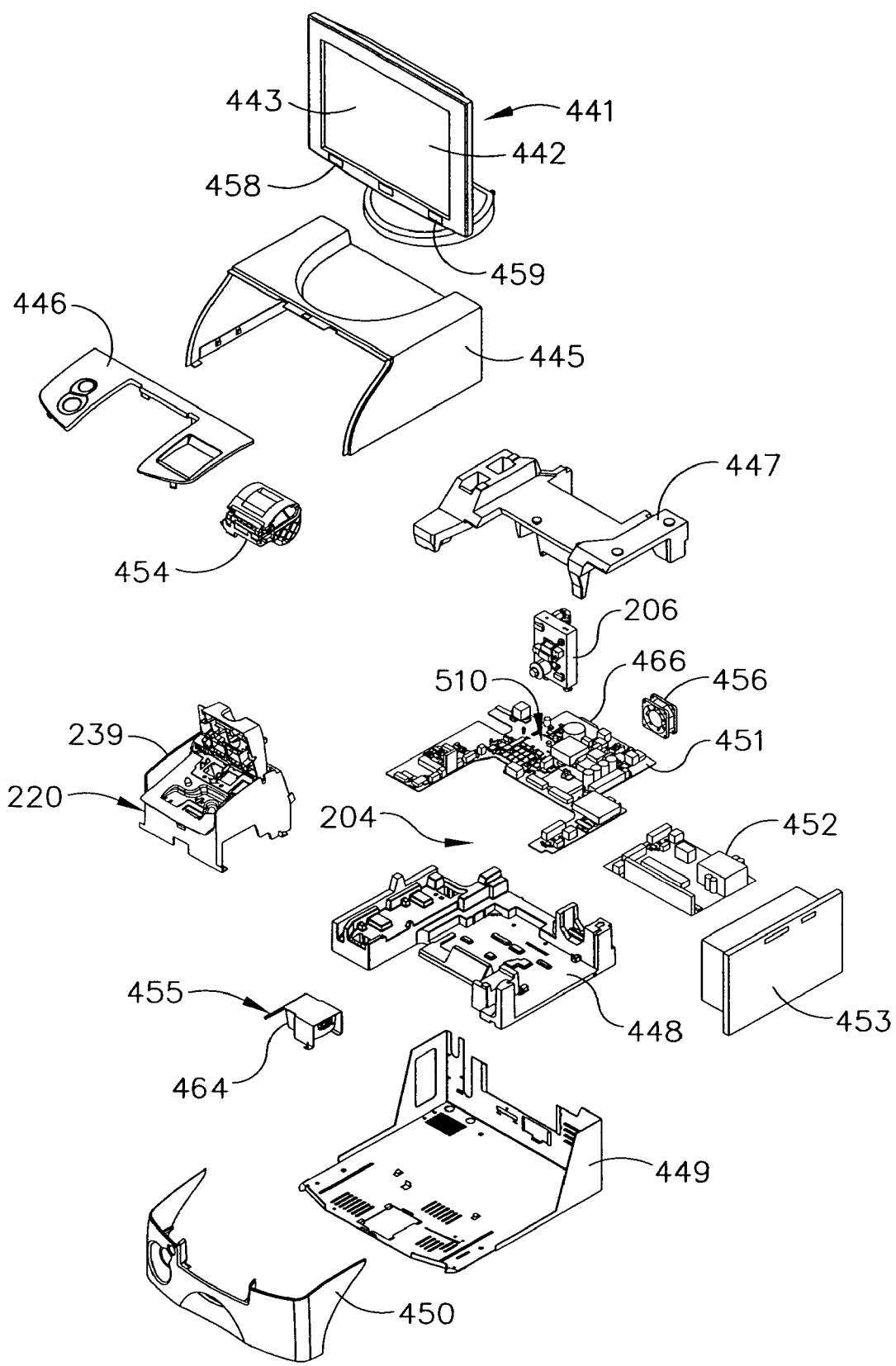
FIG. 48 is an exploded view of the PRU of FIG. 43.
Figure 49:
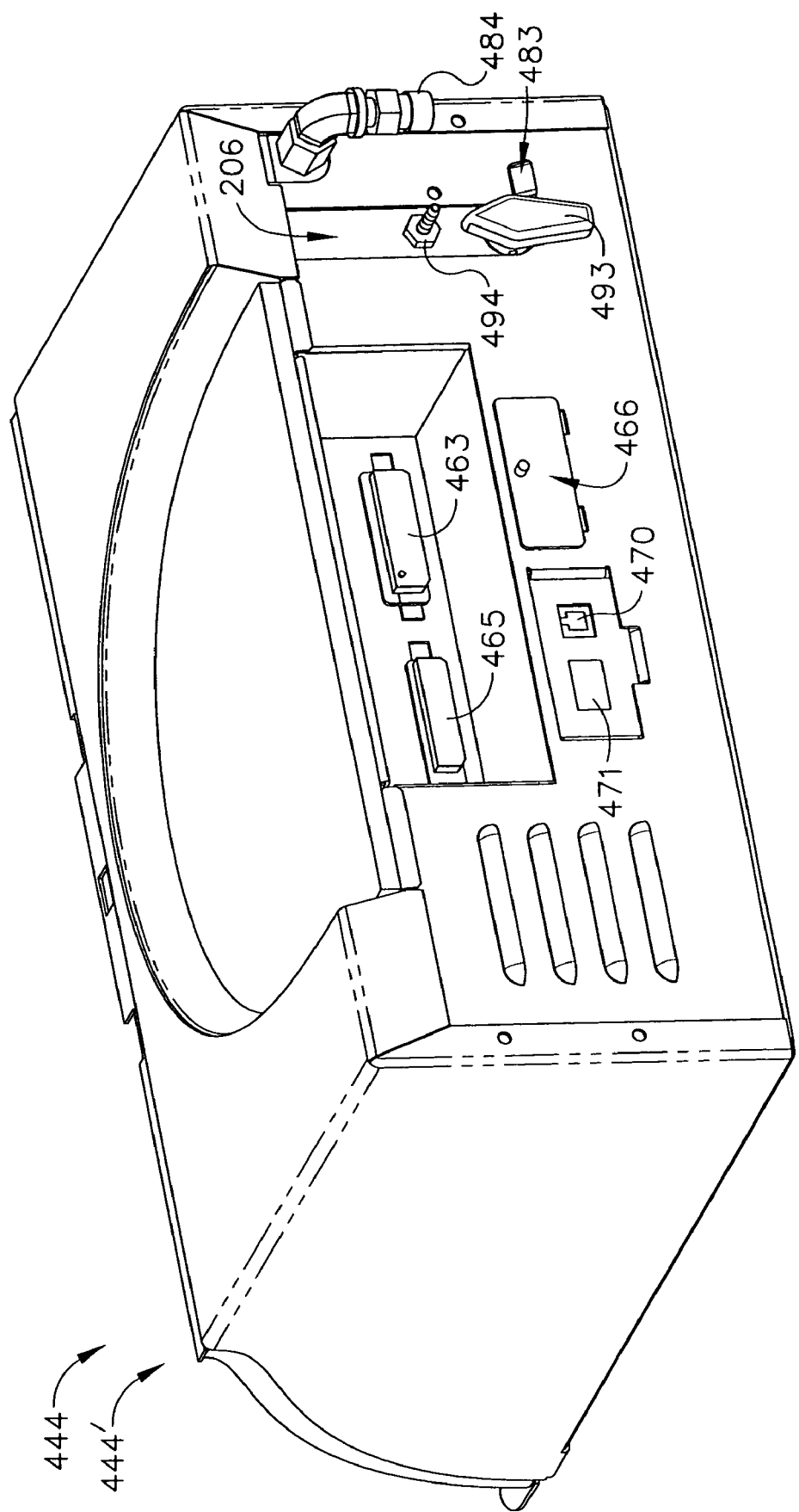
FIG. 49 is a rear perspective view of a portion of the PRU of FIG. 43.
Figure 50:
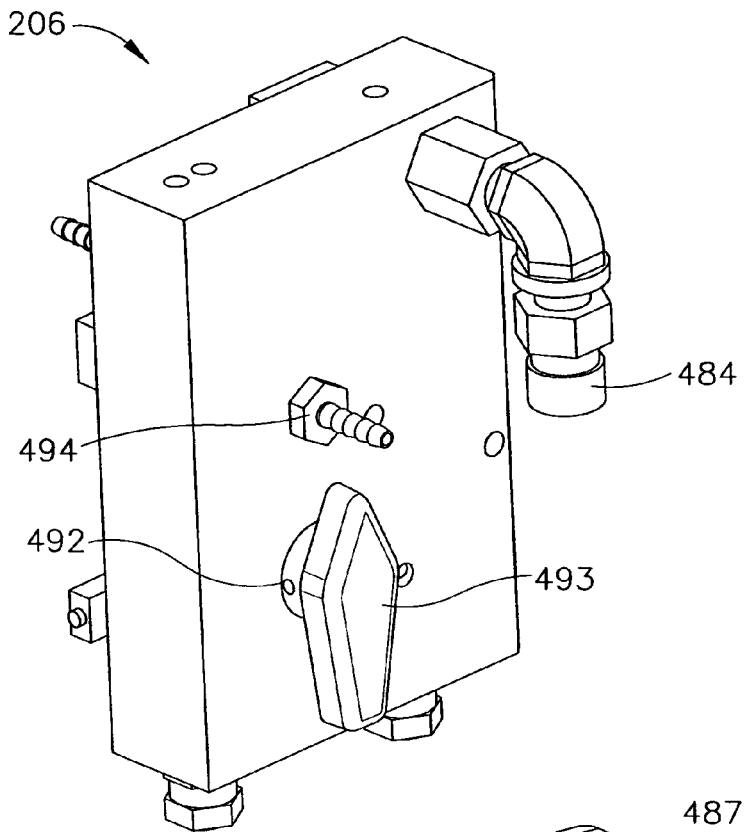
FIG. 50 is a front perspective view of the oxygen-delivery manifold seen installed in the rear of the PRU in FIG. 49.
Figure 51:
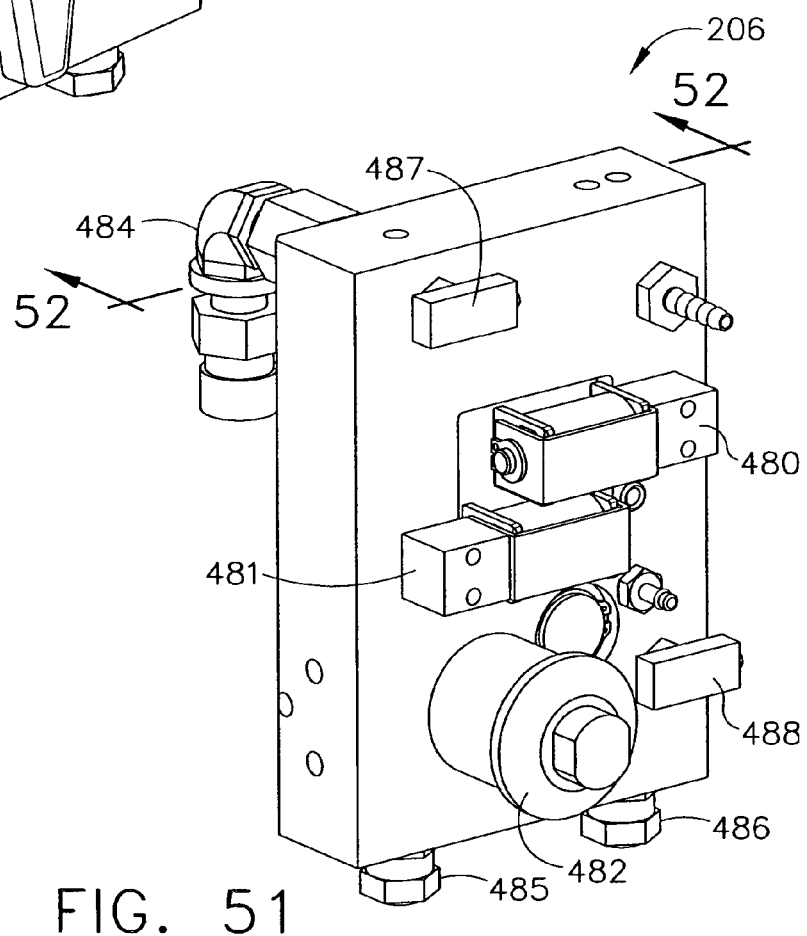
FIG. 51 is a rear perspective view of the oxygen-delivery manifold of FIG. 50.

A third expression of the embodiment of FIG. 59 is for a medical effector subsystem 306 including a drug-delivery tube 308, a pressure sensor 324, and an occlusion alarm unit 380. The drug-delivery tube 308 is adapted to contain therein a drug 328 having a variable commanded flow rate and is disposable to deliver the drug 328 to a patient 336. The pressure sensor 324 has an output signal 338 and is adapted to sense internal pressure of the drug-delivery tube 308. The occlusion alarm unit 380 is operatively connected to the output signal 338 of the pressure sensor 324 and has a variable pressure alarm setting to alert a user of an occluded drug-delivery tube 308 when the output signal 338 of the pressure sensor 324 exceeds the variable pressure alarm setting. The occlusion alarm unit 380 changes the variable pressure alarm setting based at least in part, and directly or indirectly, on the variable commanded flow rate of the drug 328. In one example, the occlusion alarm unit 380 includes the previously-described memory 326 and processor 344 of a procedure-room-unit host controller (such as previously-described host controller 204) and alerts the user through a popup window on a monitor (such as procedure-room-unit monitor 441, as shown in FIG. 48). In another example, not shown, the occlusion alarm unit does not involve a processor of a procedure-room-unit host controller.

A fourth expression of the embodiment of FIG. 59 is for a drug-delivery infusion pump subassembly 382 including a drug-delivery tube 308, peristaltic pump fingers 372, a pressure sensor 324, and an occlusion alarm unit 380. The drug-delivery tube 308 is adapted to contain therein a drug 328 and is disposable to deliver the drug 328 to a patient 336. The peristaltic pump fingers 372 are disposed to interact with the drug-delivery tube 308 and are controllable to pump the drug 328 at a commanded flow rate. The pressure sensor 324 has an output signal 338 and is adapted to sense internal pressure of the drug-delivery tube 308 downstream of the peristaltic pump fingers 372. The occlusion alarm unit 380 is operatively connected to the output signal 338 of the pressure sensor 324 and has a variable pressure alarm setting to alert a user of an occluded drug-delivery tube 308 when the output signal 338 of the pressure sensor 324 exceeds the variable pressure alarm setting. The occlusion alarm unit 380 changes the variable pressure alarm setting based entirely, and directly, on the variable commanded flow rate of the drug.

In one implementation of the fourth expression of the embodiment of FIG. 59, the drug-delivery tube 308, the peristaltic pump fingers 372, the pressure sensor 324, and the occlusion alarm unit 380 are components of a procedure room unit of a medical effector system (such as the procedure room unit 200 of the previously-described medical effector system 100'). In one example of the fourth expression of the embodiment of FIG. 59, the occlusion alarm unit 380 includes the previously-described memory 326 and processor 344 and alerts the user through a popup window and/or a flashing visual alarm displayed on a monitor (such as procedure-room-unit monitor 441, as shown in FIG. 48) and/or through a noise alarm. In another example, not shown, the occlusion alarm unit does not involve a processor of a procedure-room-unit host controller and operates independently of, and in the absence of, the previously-described procedure room unit 200.

It is noted that implementations, employments, constructions, etc. of the first expression of the embodiment of FIG. 59 are equally applicable to any one or more or all of the second through fourth expressions of the embodiment of FIG. 59. In one example of one or more or all of the expressions of the embodiment of FIG. 59, the patient 336 receiving the drug 328 is better controlled by having the occlusion pressure alarm setting change based on the variable commanded flow rate of the drug 328. Better control is achieved because the response time to an occlusion, and any bolus buildup, will be minimized compared to using a conventional fixed very-high occlusion pressure alarm setting for all commanded flow rates of the drug. It is also noted that such conventional alarm setting had to be higher than that corresponding to the highest actual flow rate of the drug (which is least used) because the internal pressure of a non-occluded drug-delivery tube increases with increasing actual flow rate of the drug, as can be appreciated by those skilled in the art. It is further noted that with such high conventional fixed alarm setting it would take much longer for a low commanded flow rate to generate enough internal pressure in an occluded drug-delivery tube to cause an occlusion alarm, and once such high internal pressure were released, a large bolus of drug would be sent to the patient as well.

The following paragraphs present a detailed description of one particular enablement of the embodiment of FIGS. 41-57. It is noted that any feature(s) of this particular enablement can be added to any of the previously-described expressions (including examples, etc. thereof) of the embodiment of FIGS. 41-57. In this enablement, the PRU 200 is the main interface between the SDS 100 and the care team member responsible for administering drug(s). The PRU 200 is designed for use in the procedure room. The PRU 200 connects to the BMU 300 by means of an Umbilical Cable 160. The PRU 200 accepts input from all physiologic signals provided by means of the BMU 300 as well as from the Nasal Capnometer Module 140 and Oral Capnometer Module 202 located within the PRU 200. The PRU 200 accepts user-input parameters such as patient data, drug dose rate targets, and alarm trigger settings. The PRU 200 processes these physiologic signals and user-input parameters; displays the physiologic signals, derivations of these signals, and related alarm status for user observation; and performs drug delivery and oxygen metering in accordance with algorithms driven by these signals.

Dosage Controller (DC) is a drug delivery algorithm utilized by the PRU 200 and is an enhancement of Dose Rate Control (DRC). The enhancement includes the algorithm's ability to calculate the appropriate loading dose, which is based upon drug labeling guidelines. For a given maintenance rate, the DC calculates an appropriate loading dose that permits the rapid achievement of the sedation effect at the initiation of the medical procedure.

The PRU 200 incorporates interactive software called the monitoring shell, which monitors and displays the patient condition and makes decisions about the patient status and resultant drug delivery schedule. The monitoring shell utilizes algorithms to quantify patient status, control drug delivery rate and oxygen delivery rate, and presents alarms to the user. The monitoring shell utilizes a broad array of input parameters including DC data, patient physiologic monitoring data, patient physical data, and alarm trigger settings. The monitoring shell reduces or stops drug delivery, along with alerting the user, if it detects certain undesired patient sedation condition(s). It will resume drug delivery if such undesired patient sedation conditions are subsequently corrected. The drug dose rate is based on user-input parameters, such as the recommended dose rate and patient weight, and software-based decisions in accordance with applied pharmacologic principles. The oxygen delivery rate is based on user-input parameters along with patient physiologic monitoring data such as oxygen saturation level.

The PRU 200 incorporates an intuitive display screen presentation that is called the PRU Graphical User Interface (PRU GUI) 210. The PRU GUI 210 displays the status of the patient in terms of physiologic parameters and alarms/alerts; it also presents the functionality status of internal sensors and operational data. The PRU GUI 210 also provides a simple intuitive means for the user to input parameters such as patient data, drug dose rate, and alarm trigger levels. One feature of the PRU GUI 210 is the PRU intelligent alarm box 249 which allows the user to rapidly ascertain the patient's general condition by means of the colors Green, Yellow, and Red. The PRU intelligent alarm box 249 utilizes algorithms to calculate and present a robust broadly defined status of the patient.

Besides the DC, the monitoring shell, and PRU GUI 210, the PRU 200 incorporates other software-driven operations. These operations include monitoring functions and convenience functions. The convenience functions include an auto-prime that provides automatic infusion line 224 priming when the cassette 251 and drug vial 250 have been installed into PRU 200. The monitoring functions include an infusion line priming interlock that allows infusion line 224 priming when the T-site luer 269 is attached to the T-site base 271 of the cassette 251. The monitoring functions also include oxygen delivery when connected to the patient and drug delivery when a cassette 251 is not recognized by the PRU as previously utilized in the PRU.

The PRU 200 includes an uninterruptible power supply (UPS) 214, a PRU console 444, and a PRU monitor 441. These items are stacked in the order described and typically reside upon an SDS cart 101 or upon the user's own platform.

The UPS 214 converts AC wall-outlet power to a low voltage power that provides all of the electrical energy utilized by the PRU console 444. The primary portion of the UPS 214 power that is fed to the PRU console 444 is utilized by the PRU console 444, while the remainder of the power is fed, via the PRU console 444, to the PRU monitor 441 and to the BMU 300. The UPS 214 also has a rechargeable battery backup subsystem, which is utilized, as a temporary power source that is automatically invoked by the UPS 214 when there is an outage of AC wall-outlet power otherwise provided via an AC power cord. The UPS 214 also provides the PRU console 444 with an earth connection for electrical grounding. There is communications means between the UPS 214 and the PRU console 444 that conveys information regarding power status and battery status related features. The power, communications, and the earth connection are conveyed to the PRU console 444 by means of a low voltage power cord, called the UPS output cable 490, that is integral to the UPS 214 whereby the UPS output cable connector 491, located on the end of this UPS output cable 490, is plugged into the PRU console 444.

The UPS 214 includes an external AC power cord, universal AC/DC power module 501, UPS power management circuit board 502, and UPS rechargeable battery pack 503. The UPS 214 has an externally located UPS on/off switch 504, an UPS power status indicator 505 to display power status, and an UPS battery status indicator 506 to indicate battery charge status.

UPS 214 further includes cooling fans 507 which are located to the rear of UPS chassis 508. A decorative front bezel 509 attaches to UPS chassis 508 and UPS top cover 473. UPS top E-PAC™ 474 and bottom E-PAC™ 475 are foam structures that function to secure all UPS internal components.

The UPS 214 incorporates electrical circuitry that permits the UPS output cable connector 491 to be detached from the PRU console 444 while power is flowing while helping to prevent electrical contact sparking or undue electrical stress to the connector. The UPS output cable connector 491 also incorporates means to assure that the earth connection contacts are the first contacts to be made during the UPS-to-PRU connection and these are the last contacts to open during disconnection.

The PRU monitor 441 provides the user with an interface to the PRU 200 that combines a color PRU monitor display 442, PRU monitor touchscreen 443 user interface, and PRU monitor speakers 458 and 459. The PRU monitor 441 is seated upon the top of the PRU console 444. The PRU monitor 441 is provided power and earth connection by the PRU console 444. Video and audio signals are also provided by the PRU console 444. The PRU monitor 441 sends PRU monitor touchscreen 443 signals to the PRU console 444.

The PRU monitor 441 is electrically attached to the PRU console 444 by means of a PRU monitor cable that is plugged into the rear of the PRU console 444. This cable provides the conveyance means for power, earth connection, video, audio, and PRU monitor touchscreen 443 signals. The PRU monitor cable connector 463 also incorporates means to assure that the earth connection contacts are the first contacts to be made during connection and the last contacts to open during disconnection.

The PRU console 444 is the central computational and process control resource of the SDS 100. The PRU console 444 also contains specific functions including the drug infusion; patient CO2 gas analysis by means of capnometry; supplemental oxygen flow control; barcode reading of cassette 251, oral/nasal cannula 145, and drug vial 250 barcode label(s) that is located upon the item or its packaging; patient data hardcopy printing; communications within the SDS 100; communications to external resources; and power control/management.

The PRU console 444 includes a PRU power management board 453, PRU processor board 452, system I/O board 451, barcode reader module assembly 455, PRU printer 454, IV (intravenous) pump module 220, oxygen manifold 206, control buttons and lighted indicators, external user connectors, and PRU console fan 456. All of these items are enclosed within a single cabinet shroud. The PRU processor board 452 and the system I/O board 451, which are linked together with a flexible circuit wire harness, are together referred to as the PRU host controller 204.

The PRU power management board 453 accepts the UPS 214 power entering the PRU console 444 and converts it to several lower voltage regulated outputs for use by the PRU 200 and the BMU 300. In one example these regulated outputs include 5V (volts), 12V, and 15V.

The PRU processor board 452 provides the primary computation resource for the SDS 100 and is one of the primary resources for signal input/output. The majority of the SDS 100 software, including the DC and the monitoring shell, reside in non-volatile memory located on the PRU processor board 452. The PRU processor board 452 includes a central processing unit (CPU), RAM Memory, disc-on-chip memory, and an assortment of digital I/O, analog I/O, video, and audio circuitry.

A flexible circuit wire harness provides interconnection between about one hundred signal input/output lines of the PRU processor board 452 and the system I/O board 451. It includes a multi-dimensional flex print circuit board incorporating about ten connectors.

The system I/O board 451 is a multi-functional circuit board that integrates and processes signals from most circuits located within the PRU console 444 including the PRU processor board 452, IV pump module 220, PRU printer 454, barcode reader module 455, and a diversity of operational circuits on the system I/O board 451 itself. It also processes signals involving other sources outside the PRU console 444 such as signals from the UPS 214, BMU 300, and PRU Monitor 441.

The system I/O board 451 has circuitry resident upon the board itself. The system I/O board 451 also contains modules that are mounted upon the board such as the nasal capnometer module 140 and oral capnometer module 202 and a flash memory module 466.

Numerous system I/O board 451 functional circuits are described in the following paragraphs.

The flash memory module 466 is detachable, user accessible, and provides for upgrades to the SDS 100 internal memory in order to revise software for system operation.

There is a nasal capnometer module 140 and an oral capnometer module 202, which are mounted to and are a part of the system I/O board 451. The nasal capnometer module 140 monitors the patient's combined nasal exhale. The oral capnometer module 202 monitors the patient's oral exhale. Each capnometer module 140 and 202 includes a suction pump control circuit that controls a suction pump, located independent from the system I/O board 451, that draws in the patient sample in a controlled sample flow rate. Each capnometer module 140 and 202 includes sample line pressure sensors that monitor sample line pressure to detect sample line occlusions and to compensate CO2 measurements in accordance with sample line barometric pressure. Both capnometer modules 140 and 202 have their own software, which provides for automatic calibrations as needed, communications with the PRU host controller 204, and other functions. There are a first and second capnometer I/O circuit that reside on the system I/O board 451 and serve as the interface between the respective capnometer module 140 and 202 and the PRU processor board 452. One function of this circuitry is to control power to the capnometer module 140 and 202 electronics and the motors of capnometer pumps 141 and 142 in accordance with PRU processor board 452 commands.

The fast switch circuit resides on the system I/O board 451 and provides for control of power that is applied to the PRU umbilical cable electrical receptacle 461. This circuit helps prevent sparking due to connect/disconnect of otherwise electrified receptacles and disconnects power to umbilical cable 160 connector pins that may be exposed during disconnection.

The PRU state circuit 510 works in conjunction with a similar state circuit, the BMU state circuit 600 in the BMU 300, whereby both state circuits 510 and 600 interact via the umbilical cable 160 communication means. The PRU state circuit 510 in the PRU console 444 provides the means for the PRU console 444 to be aware of whether the umbilical cable 160 is plugged into the BMU 300 and whether the BMU 300 is energized or off. This state status information is utilized by the PRU console 444. For example, if the PRU 200 is off and if the BMU 300 is on, then the BMU 300 is attached via the umbilical cable 160 to the PRU 200 and the PRU 200 will automatically turn itself on. Another use for the state status is to prevent umbilical cable 160 communications alarms related to intentional disconnection of the umbilical cable 160. Yet another role of the state status in the PRU 200 is to help control when power is applied to the PRU umbilical cable electrical receptacle 461 in order to help avoid application of power to the exposed pins of an unplugged umbilical cable 160.

An IV pump power control circuit controls power to the IV pump module 220 in accordance with various commands from the PRU processor board 452 and from interlocks such as the controller-monitoring module 467 circuit. Also included in this circuit is a stop drug button 497 which forces shutdown of power to the IV pump module 220 and also communicates the status of this button to the PRU processor board 452. Also included in this circuit is a pump door button 496, which communicates the status of this button to the PRU processor board 452 and also assists with the control of the door latch solenoid 222 that unlocks the pump door 201. Yet another function of this circuit is to convey the signal status of the IV pump motor encoder to the PRU processor board 452.

A PRU power button circuit monitors the power button 495, which communicates the status of this button to the PRU processor board 452. The PRU power button circuit also includes an LED indicator driver circuitry that provides a ramping current to the LED indicator of the PRU power status indicator 498 while in the standby mode which produces a variable luminous indication during standby. When in the On mode, this circuit drives the LED indicator of the PRU power status indicator 498 with a continuous current.

A PRU printer circuit provides electrically isolated controlled power for the PRU printer 454 and also provides electrically isolated communications between the PRU processor board 452 and the PRU printer 454. A barcode reader circuit provides controlled power for the barcode reader module 455 and also provides a communications interface for the barcode reader module 455 to the PRU processor board 452. A PRU fan control circuit controls power to the PRU console fan 456. This circuit is able to detect a slow running or stalled PRU console fan 456 and then issue an alert to the PRU processor board 452.

A PRU temperature sensor circuit incorporates a thermal sensor and signal processing that monitors the internal temperature of the PRU console 444 and presents that temperature data to the PRU processor board 452. This thermal sensor, along with associated support circuitry, is located on the system I/O board 451 where it can effectively monitor the thermal status inside the PRU Console 444.

The controller-monitoring module 467 is a monitor circuit that monitors the viability of the PRU host controller 204 and associated software programs it is running. If the controller-monitoring module 467 detects undesired PRU host controller 204 function (including in terms of too frequent or infrequent processor activity), the controller-monitoring module 467 will notify the PRU processor board of this condition and the controller-monitoring module 467 will take direct action to disable the IV pump module 220 and shut down most functions within a short period of time. In the event of a controller-monitoring module 467 detectable event, the controller-monitoring module 467 will also temporarily sound a buzzer that is located on the PRU system I/O board 451, as a means to notify the user of the undesired condition.

A PRU monitor control circuit controls power to the PRU monitor 441. It is controlled by the PRU processor board 452 and the circuit includes a current limiting function. A PRU audio amplifier circuit includes two audio amplifier circuits that accept low level audio from the PRU processor board 452 and amplify these signals. These amplified signals are utilized to drive the two PRU monitor speakers 458 and 459 in the PRU monitor 441. The monitor control circuit includes conveyance of a PRU monitor speaker interlock signal to the PRU processor board 452 which helps assure that the SDS 100 only operates if the PRU monitor speakers 458 and 459 are connected to the PRU console 444.

A modem circuit provides a means for the SDS 100 to communicate with non-SDS devices via a telephone line. This circuit implements isolated circuitry. An Ethernet circuit provides a means for the SDS 100 to communicate with non-SDS devices via an Ethernet line. This circuit also implements isolated circuitry;

PRU UPS communications interface is a circuit that provides the interface between the UPS communications lines and the PRU processor board 452.

A supplemental oxygen control circuit provides the basic signal processing interface between the PRU processor board 452 and supplemental oxygen related sensors. The sensors include the oxygen sensor 482, the high side oxygen pressure sensor, the low side oxygen pressure sensor, and the differential pressure sensor. One of these sensors, the differential pressure sensor, is physically located on the system I/O board 451 in the vicinity of this circuit, while the other listed sensors are located on the oxygen manifold 206. The supplemental oxygen control circuit also provides power signals that drive the variable-size-orifice (VSO) flow restrictor 480 (such as a VSO solenoid), which regulates supplemental oxygen flow. Included features are electrical control of the VSO flow restrictor 480 and the signal processing interface between the PRU processor board 452 and the VSO flow restrictor 480. Yet another role of the supplemental oxygen control circuit is to control the oxygen sampling solenoid in accordance with commands received from the PRU processor board 452.

The last-to-be-discussed system I/O board 451 functional circuit is the voltage monitoring circuit. The voltage monitoring circuit provides an interface between the PRU processor board 452 and the various power supply voltages resident on the system I/O board 451 in order to monitor those voltages and determine if they are in desired ranges.

There is a nasal capnometer pump 141, located within the PRU console 444, which is plumbed, but not physically affixed, to the nasal capnometry module 140. There is an oral capnometer pump 142, located within the PRU console 444 which is plumbed, but not physically affixed, to the oral capnometry module 202.

The barcode reader assembly 455 incorporates a self-contained barcode reader module 464 that is mounted on a metal frame that includes a mirror. The metal frame is mounted inside the housing of PRU console 444 in an orientation that allows the projection of the barcode laser beam through an open window of the housing of the PRU console 444 to shine upon an area external to the PRU console 444. The user places the barcode of the packaging containing the oral/nasal cannula 145 or cassette 251 or drug vial 250 within reading range of the active barcode reader module 464 laser beam. The barcode reader module 464 then reads the barcode.

The PRU printer 454 includes a thermal print head, a paper feed mechanism, a printer driver board, and a PRU printer door 460. This assembly is mounted to the housing of the PRU console 444 utilizing electrically isolated means that helps provide for an electrically isolated access to the printer paper roll.

The IV pump module 220 provides the drug pumping function of the PRU console 444. The IV pump module 220 accepts the disposable cassette 251. The IV pump module 220 propels metered drug(s) through the cassette 251 via peristaltic massage of the flexible tube 277. The IV pump module 220 detects the presence of the T-site commercial luer 269 placement into the respective receptacle of cassette 251 and also detects drug vial 250 seating upon the respective receptacle of the cassette 251. The IV pump module 220 incorporates several features such as detection of air-in-line and occlusion of the downstream fluid path. Another function of the IV pump module 220 is the pump door 201 and the controlled opening of the pump door 201.

The IV pump module 220 includes an IV pump housing 239 that has attached to it the pump door 201, the pump door latch 205 and the pump door lifting mechanism 207, IV pump assembly 232, IV pump control board 233, an optical sensor board, and air-in-line sensor 225. The IV pump assembly 232 includes an IV pump motor, a pump finger mechanism, an IV pump motor encoder, downstream IV pressure sensor 223, and an IV pump sensor board. The optical sensor board 227 has the T-site sensor 226 and the vial sensor 228. These two sensors protrude through the IV pump housing 239 in the vicinity of the pump cassette deck 221 where they interact with the associated mechanisms of the seated disposable cassette 251. The optical sensor board also has a door latch solenoid 222 that, when activated, presses upon the pump door latch 205 to release the pump door 201, whereby the pump door 210 is lifted by pump door lifting mechanism 207 and proceeds to the open position to expose the cassette deck 221 and permit the user access for installation or removal of the cassette 251.

The oxygen manifold 206 is the primary component of the supplemental oxygen delivery subsystem of the PRU console 444. The oxygen manifold 206 provides a path for oxygen flow, oxygen flow control, oxygen purity evaluation, and oxygen overpressure relief. It is mounted at the rear section of the PRU console 444.

The oxygen manifold 206 includes a manifold that is equipped with the following items that are encountered by incoming oxygen gas in the order listed: externally located oxygen input coupler 484, high side pressure relief valve 485 and associated exhaust port, high side pressure sensor 487, oxygen diverter 492, fixed restrictor 489, VSO flow restrictor 480, low side pressure sensor 488, low side pressure relief valve 486, and oxygen main output outlet. Ancillary gas paths include an oxygen sample solenoid 481, oxygen sensor 482, and oxygen sensor exhaust port 483. There are also outlets for plumbing gas pressure from each side of the fixed restrictor 489 to the differential pressure sensor 479 which is located on the system I/O board 451. The oxygen manifold 206 has an oxygen input coupler 484 that protrudes from the rear of the PRU console 444 for user connection to an external supply of supplemental oxygen.

The oxygen manifold 206 has a flow path that intercepts an oxygen sample. The oxygen sample is gated by an oxygen sample solenoid 481 to temporarily allow flow of supplemental oxygen past the attached oxygen sensor 482. The oxygen manifold 206 has an oxygen sensor exhaust port 483 that permits the sampled gas to be expelled from the oxygen manifold 206.

The oxygen manifold 206 utilizes a high side pressure relief valve 485 that protects the oxygen high pressure path from excessive high supply pressure by relieving that pressure via the exhaust port of the high side pressure relief valve 485. The oxygen manifold 206 utilizes a low side pressure relief valve 486 that protects the oxygen low pressure path from excessive output pressure by relieving any excessive pressure via the exhaust port of the low side pressure relief valve 486.

The oxygen diverter 492 is a manually operated valve and is operated via an externally accessible oxygen diverter knob 493. This oxygen diverter 492 can be set to the normal position whereby the supplemental oxygen flow is only directed through the regulated flow path of the SDS 100 system. The oxygen diverter 492 can alternately be set to the SDS-system-bypass position, whereby the supplemental oxygen flow no longer flows through the regulated flow path of the SDS 100 system. Instead, it flows exclusively directly to an externally accessible barbed oxygen outlet 494 that provides the user with a convenient means to connect a user-provided SDS-system-bypass oxygen delivery device.

The PRU console 444 provides a direct means for user input via the PRU power button 495, the stop drug button 497, and the pump door button 496. The PRU power button 495 allows the PRU 200 to be placed into standby or ready mode. The stop drug button 497 allows the user to halt drug(s) delivery by cutting off power to the IV pump module 220. The pump door button 496 allows the user to open the pump door 201 when there is no cassette 251 installed in the IV pump module 220 or when the cassette 251 is present and the T-Site commercial luer 269 is installed into the cassette 251.

The PRU console 444 provides the user with status indications by means of two illuminated indicators. One of these indicators is the PRU power status indicator 498, which is integral to the PRU power button 495. This indicator has a periodic fluctuating brilliance when in standby mode and a continuous brilliance in the ready mode. The other indicator is the pump door locked indicator 499 which is integral to the pump door button 496, which is lit when the pump door 201 is locked, and which is not lit when the pump door 201 is not locked.

The PRU console 444 has several externally user accessible connectors. The PRU umbilical cable electrical receptacle 461, located on the front panel of the PRU console 444, is a connector for providing convenient electrical connections to umbilical cable 160. It utilizes various pin heights to provide hot switching without degradation of pins. The PRU umbilical cable pneumatic receptacle 462, located on the front panel of the PRU console 444, is a connector for providing convenient simultaneous multiple pneumatic connections to umbilical cable 160 including pneumatic paths for oxygen delivery and patient exhale samples. The modem connector 470, located on the rear panel of the PRU console 444, is a type RJ11 connector for providing user connection to an external telephone line. The Ethernet connector 471, located on the rear panel of the PRU console 444, is a type RJ45 connector for providing user connection to an external Ethernet line. The PRU power connector 465, located on the rear panel of the PRU console 444, is a connector for providing user connection of PRU console 444 to UPS output cable connector 491.

The PRU console 444 has a fan referred to as the PRU console fan 456. The PRU console fan 456 provides thermal cooling of the components located inside the PRU console 444. The PRU console fan 456 also provides for robust ventilation of the PRU console 444 as a means to dilute any potentially present supplemental oxygen entering the PRU console 444 thereby helping keep the oxygen concentration within a desired range.

The internal components of PRU 200 are sandwiched between top PRU foam support 447 and bottom PRU foam support 448. In one example, PRU foam supports 447 and 448 are constructed of rigid foam well known in the electronics industry as an E-PAC™ chassis. Strategically located recesses and cavities in the E-PAC™ chassis efficiently capture and securely hold pc boards, pumps, LCD, speaker and other components. The outer housing of PRU 200 is constructed of rigid molded thermoplastic (e.g. ABS) and includes top chassis 445, top bezel 446 and front bezel 450. Bottom chassis 449 is constructed of sheet metal and forms part of the outer housing of PRU 200. The housing components are held together with molded-in snap features and screws. Top chassis 445 is designed to be readily removable for access to the PRU 200.

PRU/BMU Interface

A fourth aspect of the invention is directed to a procedure room unit (PRU) 200 and bedside monitoring unit (BMU) 300 interface of a sedation delivery system 100 (or other type of medical-effector system 100'), an embodiment of which is shown in FIGS. 41-57 and 60-62. An expression of the embodiment of FIGS. 41-57 and 60-62 is for a sedation delivery system 100 (or other type of medical-effector system 100') including a microprocessor-based bedside monitoring unit 300 (an embodiment of which is shown in FIGS. 41 and 60-62), a microprocessor-based procedure room unit 200 (an embodiment of which is shown in FIGS. 41-57), and an umbilical cable 160 (an embodiment of which is shown in FIGS. 41, 42, 60 and 61). The bedside monitoring unit 300 has a bedside-monitoring-unit host controller 301, has a first series of connection points for receiving patient inputs from patient monitoring connections, has a second series of connection points for outputting patient outputs based on the received inputs, and has a display screen for displaying at least some of the patient outputs. The procedure room unit 200 has a drug-delivery flow control assembly 220' (or other type of medical effector 220") and has a procedure-room-unit host controller 204. The procedure-room-unit host controller 204 has a memory containing a patient-monitoring and drug-delivery-scheduling program (or other patient-monitoring and medical-effector-scheduling program). The program is operatively connected to program inputs based at least in part on at least some of the patient outputs and controls, and/or advises a user to control, the drug-delivery flow control assembly 220' (or other medical effector 220") based at least in part on the program inputs. The umbilical cable 160 has a first end attached or attachable to the second series of connection points of the bedside monitoring unit 300 and has a second end attached or attachable to the procedure room unit 200. At least one of the first and second ends is detachable from the corresponding bedside monitoring unit 300 or the procedure room unit 200. The procedure-room-unit host controller 204 and the bedside-monitoring-unit host controller 301 are operatively connected together when the umbilical cable 160 is attached to the procedure room unit 200 and the bedside monitoring unit 300.

In one arrangement of the expression of the embodiment of FIGS. 41-57 and 60-62, the drug-delivery flow control assembly 220' includes a drug-delivery infusion pump assembly 220 such as a peristaltic pump assembly. In one variation of this arrangement, the drug(s) is delivered to the patient through an IV. In another arrangement, not shown, the drug-delivery flow control assembly includes a gaseous-drug gas flow controller. In one variation of this arrangement, the gaseous drug(s) is oxygen and/or a non-oxygen gas and is delivered to the patient through a cannula assembly.

In one example of the expression of the embodiment of FIGS. 41-57 and 60-62, the procedure room unit 200 has an individual procedure-room-unit (PRU) identifier and the bedside monitoring unit 300 has an individual bedside-monitoring-unit (BMU) identifier. The procedure-room-unit host controller 204 of the procedure-room unit 200 compiles an electronic history of the bedside monitoring unit 300 when attached to the procedure room unit 200 based on the individual BMU identifier. In one variation, the identifiers reside in the host controllers of the PRU and BMU, and the electronic history is automatically compiled when the BMU is attached to the PRU. In one extension, the sedation delivery system 100 also includes a single-patient-use drug-delivery cassette assembly 251 and a single-patient-use cannula assembly 145 and a single-patient-use drug vial 250. The drug-delivery cassette assembly 251 has an individual cassette identifier and is operatively connectable to the drug-delivery flow control assembly 220' of the procedure room unit 200. The cannula assembly 145 has an individual cannula identifier and is attachable to the bedside monitoring unit 300. The drug vial has an individual vial identifier and is operatively connectable to the drug-delivery cassette assembly 251. The procedure-room-unit host controller 204 of the procedure-room unit 200 compiles an electronic history of the drug-delivery cassette assembly 251 and the cannula assembly 145 and drug vial 250 based on the individual cassette and cannula and vial identifiers (the SPU identifiers).

In a further expression of the embodiment of FIGS. 41-57 and 60-62, the procedure room unit 200 downloads has an individual procedure-room-unit (PRU) identifier and the bedside monitoring unit 300 has an individual bedside-monitoring-unit (BMU) identifier. The procedure-room-unit host controller 204 of the procedure-room unit 200 compiles an electronic history of the bedside monitoring unit 300 when attached to the procedure room unit 200 based on the individual BMU identifier.

In a further expression of the embodiment of FIGS. 1-57 and 60-62, the drug cassette assembly 251 individual cassette identifier is a unique barcode of a sterile package containing the drug cassette assembly 251 and/or a barcode on the drug cassette assembly 251. The cannula assembly 145 individual cannula assembly identifier is a unique barcode of a sterile package containing the cannula assembly 145 and/or a barcode on the cannula assembly 145. The drug vial 250 individual vial identifier is a unique barcode of a sterile package containing the drug vial 250 and/or a barcode on the drug vial 250. The unique identifiers are read at PRU 200 using barcode reader 455.

In one enablement of the expression of the embodiment of FIGS. 41-57 and 60-62, when the bedside monitoring unit 300 is attached to the procedure room unit 200, the electronic history of the cassette, cannula and vial identifiers is passed on to BMU 300. The BMU 300 updates its electronic history of SPU identifiers so previously used SPUs cannot be used again with that particular BMU. In a further enablement, the BMU 300 also copies its history of SPU identifiers to PRU 200. This is particularly useful in surgical procedure suites that have multiple BMUs and fewer PRUs. The cross copy of SPU identifiers between BMUs and PRUs further prevents multiple use of SPUs on different PRUs within a surgical suite.

In one enablement of the expression of the embodiment of FIGS. 41-57 and 60-62, when the bedside monitoring unit 300 is attached to the procedure room unit 200, the bedside-monitoring-unit host controller 301 of a turned-on bedside monitoring unit 300 turns on a turned-off procedure room unit 200. In the same or a different enablement, when the bedside monitoring unit 300 is attached to the procedure room unit 200, the procedure-room-unit host controller 204 of a turned-on procedure room unit 200 turns on a turned-off bedside monitoring unit 300. In one variation, when a PRU 200 or a BMU 300 is turned on, its host controller 204 and 301 boots up.

In one illustration of the expression of the embodiment of FIGS. 41-57 and 60-62, the bedside monitoring unit 300 displays patient monitoring while not attached to the procedure room unit 200 and displays patient monitoring while attached to the procedure room unit 200 when the procedure-room-unit host controller 204 detects certain faults in the procedure room unit 200. In the same or a different illustration, the procedure-room-unit host controller 204 shuts off the drug-delivery infusion pump assembly 220 when certain faults are detected in an attached bedside monitoring unit 300 and/or in the procedure room unit 200.

In one implementation of the expression of the embodiment of FIGS. 41-57 and 60-62, the umbilical cable 160 includes a power feed line, and the procedure-room-unit host controller 204 shuts off power to the power feed line of the umbilical cable 160 when the umbilical cable 160 is disconnected from the bedside monitoring unit 300 and/or the umbilical cable 160 is disconnected from the procedure room unit 200. In one variation, the bedside monitoring unit 300 includes a bedside-monitoring-unit battery 303, and power from the procedure room unit 200 charges the bedside-monitoring-unit battery 303 via the power feed line of the umbilical cable 160.

Bedside Monitoring Unit

A fifth aspect of the invention is directed to, or a component of, or can be used by, a bedside monitoring unit (BMU) 300, an embodiment of which is shown in FIGS. 6, 41 and 60-62. A first expression of the embodiment of FIGS. 6, 41 and 60-62 is for a stand-alone patient monitoring device including a oral/nasal cannula 145, a first series of connection points from receiving input signals from patient monitoring connections and a connector 151 for receiving a supplemental $O_2$ supply 152.

A second expression of the embodiment of FIGS. 6, 41, 60-62 is for a BMU 300 that accepts user inputs of patient and procedure data including a graphic user interface 212. In this application, BMU 300 may be used for inputting and displaying patient parameters (such as physiological parameters) during a pre-procedure set-up, a surgical procedure or during post-procedure recovery.

A third expression of the embodiment of FIGS. 6, 41, 60-62 is for a BMU 300 that provides for the delivery of audible commands to patient 10 including a ARM module 340, an audible output through oral/nasal cannula 145 and earpiece 135 vibratory handset 342 and input cable 150.

In one implementation of the third expression, during a pre-procedure set-up BMU 300 provides an audible command to patient 10 via ear piece 135, such as "squeeze left hand" and monitors the response time to establish a baseline response rate. In one illustration of the implementation cannula 145 provides for the delivery of audible commands to a patient 10 requesting a response for an Automated Responsiveness Monitor (ARM) 340.

A fourth expression of the embodiment of FIGS. 6, 41, 60-62 is for a BMU 300 in combination with a procedure room unit including a oral/nasal cannula 145, a first series of connection points from receiving input signals from patient monitoring connections and a second series of connection points for outputting patient parameters and a display screen for displaying patient parameters. In one implementation of the fourth expression umbilical cable 160 connects to BMU umbilical cable connector 151 (in lieu of connection to supplemental $O_2$ supply 152) and communicates patient parameters from BMU 300 to PRU 200. In one illustration BMU 300 travels with patient 10 to a procedure area. Umbilical cable 160 connects BMU to PRU 210 and BMU 300 downloads all patient input data and parameters (inclusive of physiological parameters and $CO_2$ readings) to PRU 210. PRU 210 initiates $O_2$ delivery to the patient (as required) via cable 160.

In a fifth expression of the embodiment of FIGS. 6, 41, and 60-62, BMU 300 monitors user inputs of patient parameters and includes patient information on graphic user interface 212 during post-procedure recovery. In this application, BMU 300 may be used for displaying patient parameters (such as physiological parameters) during a post-procedure recovery, providing an $O_2$ supply, if required and allowing medical personnel to assess the condition of patient 10 prior to release. In one implementation of the fifth expression, BMU 300 includes a light bar 208 of multiple LEDs for easy viewing by medical personnel. Light bar 208 is able to convey patient condition in different formats, such as green lighting, red lighting and yellow lighting, blinking lights and steady state lights.

In a second implementation of the fifth expression, BMU 300 utilizes ARM module 340 and ARM handset 342 to automatically query the patient and record time-based responsiveness replies and combine the responses with other monitored parameters to conduct patient assessment.

The following paragraphs present a detailed description of one particular enablement of the embodiment of FIGS. 6, 41 and 60-62. It is noted that any feature(s) of this particular enablement can be added to any of the previously-described expressions (including examples, etc. thereof) of the embodiment of FIGS. 6, 41 and 60-62. In this enablement BMU 300 provides for monitoring of patient physiologic parameters during all phases of a procedure. When BMU 300 is connected to PRU 200 via umbilical cable 160 in the procedure room, the physiologic parameters monitored by BMU 300 are displayed on PRU 200. BMU 300 contains BMU host controller 301, which is the computer for the unit. BMU host controller 301 includes both hardware and software components. The hardware contains interface components for communicating with the patient monitors. This communication includes receiving patient data, monitoring operating status, and sending routine commands to the modules. The software processes the data received from the patient monitors for display on the visual display monitor. The software contains drivers for the visual display monitor, touch screen, speakers, ARM functions, internal memory, and printer. BMU 300 is designed to stay with the patient throughout the procedure flow from the pre-procedure room to the procedure room and finally to the recovery room.

BMU 300 contains electrocardiogram (ECG) module 330, which contains electronics, and software used to process patient signals as supplied through ECG pads 332 and ECG leads 334. ECG pads 332 and ECG leads 334 are well known in the medical. One example of ECG module 330 is available from Mortara Instrument, Inc., Milwaukee, Wis., Model M12A. The resultant data from this module are then sent to BMU host controller 301 for display of patient physiologic parameters (heart rate and wave form).

BMU 300 also contains non-invasive blood pressure (NIBP) module 320. NIBP module 320 includes NIBP pump 322. One example of NIBP module 320 is available from SunTech Medical Instruments, Inc., Morrisville, N.C., Model MC2619045. Non-invasive blood pressure (NIBP) module 320 contains the electronic components, software, pump, and valves used to inflate non-invasive blood pressure (NIBP) cuff 321. NIBP cuffs are well known in the medical arts. The electronic components process the information received through NIBP cuff 321 with software. The resultant blood pressure data (systolic, diastolic pressures) are then sent to BMU host controller 301.

Pulse oximeter ($SpO_2$) module 310 is also contained within BMU 300. One example of pulse oximeter module 310 is available from Dolphin Medical, Inc., Hawthorne, Calif., Model OEM701. Pulse oximeter module 310 contains the electronic components and software used to process patient information received through reusable pulse oximeter probe 311. One example of pulse oximeter probe 311 is available from Dolphin Medical, Inc., Hawthorne, Calif., Model 210. The resultant data (pulse rate, $SpO_2$, and wave form) are sent to BMU host controller 301.

Also located within BMU 300 is automated responsiveness monitor (ARM) module 340. Arm module 340 includes ARM speaker assembly 341. During a procedure, ARM module 340, which includes hardware and software, provides simultaneous audible and tactile stimuli via earpiece 135 and a vibratory ARM handset 342 to the patient. Arm handset 342 is ergonomically designed to fit comfortably in the hand of the patient and held in the palm by a retaining strap. The stimuli continue for up to a fixed period of time, or until the patient responds by squeezing ARM handset 342 which activates a mechanical switch within the handset and sends a signal to ARM module 340. The ARM audible stimulus is a request ("please squeeze your hand") and a mild vibration of ARM handset 342. If the patient fails to respond a more urgent audible request is repeated ("squeeze your hand") and the vibration intensity is increased, which may include an increase in audible volume. If the patient again fails to respond an even more urgent audible request is repeated ("squeeze your hand now!") and ARM handset 342 vibration intensity is increased a third and final time. If the patient fails to squeeze ARM handset 342 during this sequence the patient is deemed non-responsive. If the patient does not respond within the fixed period of time, the monitoring shell takes action and alerts the care team.

Oral/nasal cannula 145 attaches to the patient at one end that includes three gas sampling ports, one for the left nostril, one for the right nostril, and one for the mouth. The patient end also includes nasal and oral outlets for oxygen delivery. The other end of oral/nasal cannula 145 connects to BMU 300 via cannula connector plate 304. Cannula connector plate 304 fluidly connects outputs from oral/nasal cannula 145 with BMU 300. Cannula connector plate 304 also connects outputs from BMU 300 with oral/nasal cannula 145. Within BMU 300 is located a pressure transducer (which, in one example, is a nasal pressure transducer 47) which functions to detect when the patient is inhaling or exhaling and communicates to PRU 200 to control oxygen flow. Oral/nasal cannula 145 also includes earpiece 135, which delivers audible respond commands to the patient from ARM module 340.

A power button 318 is located on the face of BMU 300, illuminates green when BMU 300 power is on, and pulses green when BMU 300 is in standby mode. BMU 300 includes a user interface that relays information gathered from the physiologic monitors and sensors to the user and allows the user to enter information and commands to the control system. BMU Graphic User Interface (GUI) 212 includes a backlit LCD visual display monitor with a touch screen for user input and an alarm system with audio and video components. Speaker 216, for providing audible indicators to the user, is located on the face of BMU 300. A light bar 208 is located on the top portion of BMU 300, is molded from a semi-transparent thermoplastic (e.g., polycarbonate), and is illuminated by LED's 203 to provide visual indication of alarm conditions. The light bar 208 is particularly useful to convey information to medical personnel in the post-procedure room where numerous patients may be recovering from surgical procedures and numerous BMUs are present. When patient physiology crosses alert and alarm thresholds, the digital display indicates the alarm condition. In addition to the visual indicators, the BMU incorporates distinct audible tones for alarms. Light bar 208 may, for example, display or flash green when the BMU 300 does not detect any abnormalities or display or flash yellow when an alert occurs or display or flash red when an alarm occurs. Further, light bar 208 may change color, intensity and flashing cycle to portray ventilation magnitude and/or status. Light bar 208 may also include alpha, numeric or alphanumeric displays. Such displays may provide additional detailed information such as heartbeats per minute, respiration rate or alarm details.

A separate thermal printer may be used to create a hard copy record of sedation information. Printer port 218 is provided on the side of BMU 300 for connection of a remote printer. BMU 300 can operate on either internal battery power by utilizing BMU batteries 303 or through an external a/c power adaptor. Further, BMU 300 receives power from PRU 200 when they are connected in the procedure room. An oxygen adaptor 152 and tubing set can be connected between BMU 300 and a standard oxygen wall outlet or oxygen tank to allow oxygen to be conveniently provided to a patient through BMU 300 when BMU 300 is not connected through umbilical 160 to PRU 200 (typically pre-procedure and recovery).

Figure 62:
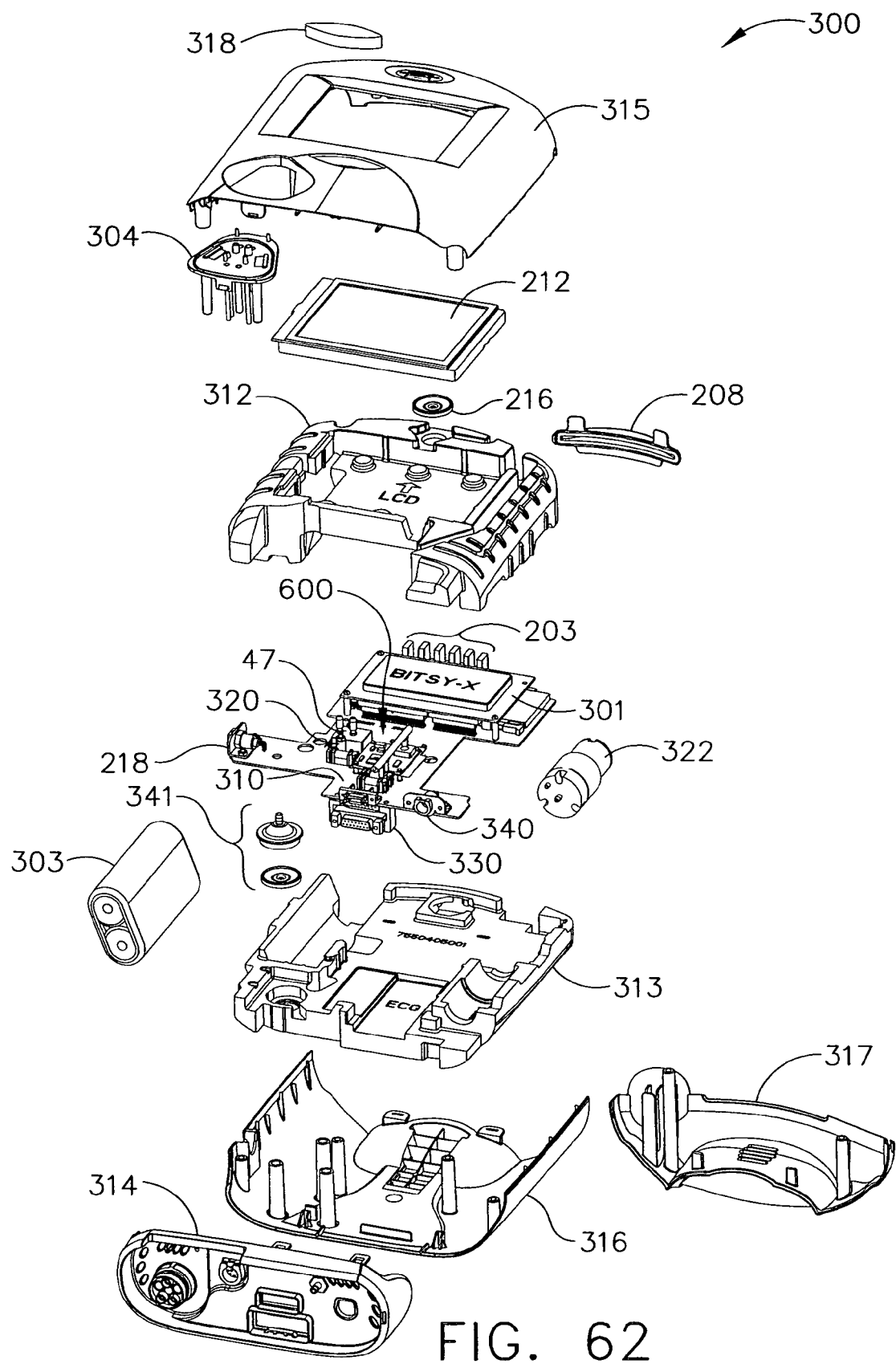
FIG. 62 is an exploded view of the BMU of FIG. 41.
Figure 63:
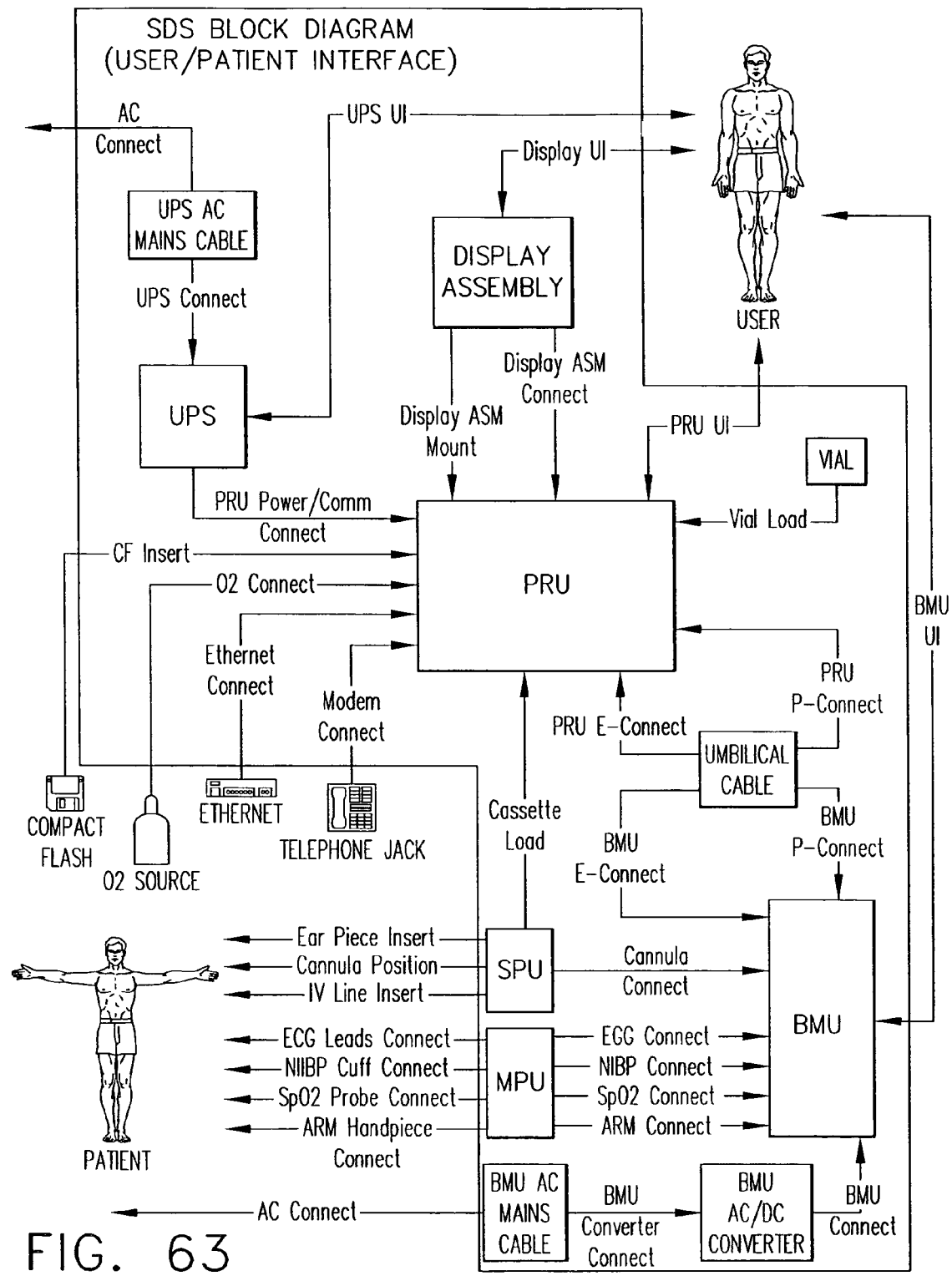
FIG. 63 is a block diagram identifying elements of an embodiment of a sedation delivery system (SDS)
Figure 64:
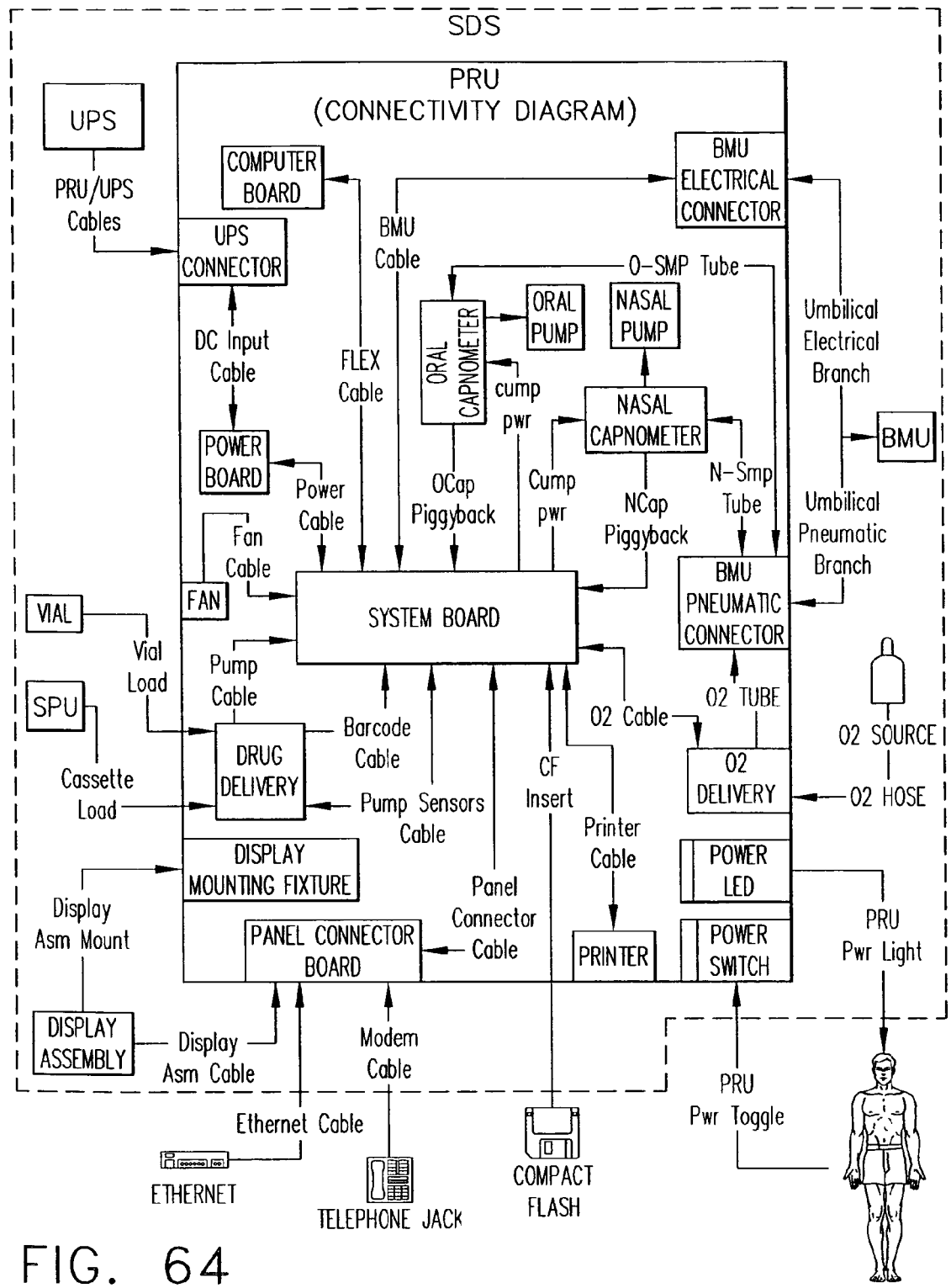
FIG. 64 is a block diagram identifying elements of an embodiment of a procedure room unit (PRU) for use in an SDS of FIG. 63.
Figure 65:
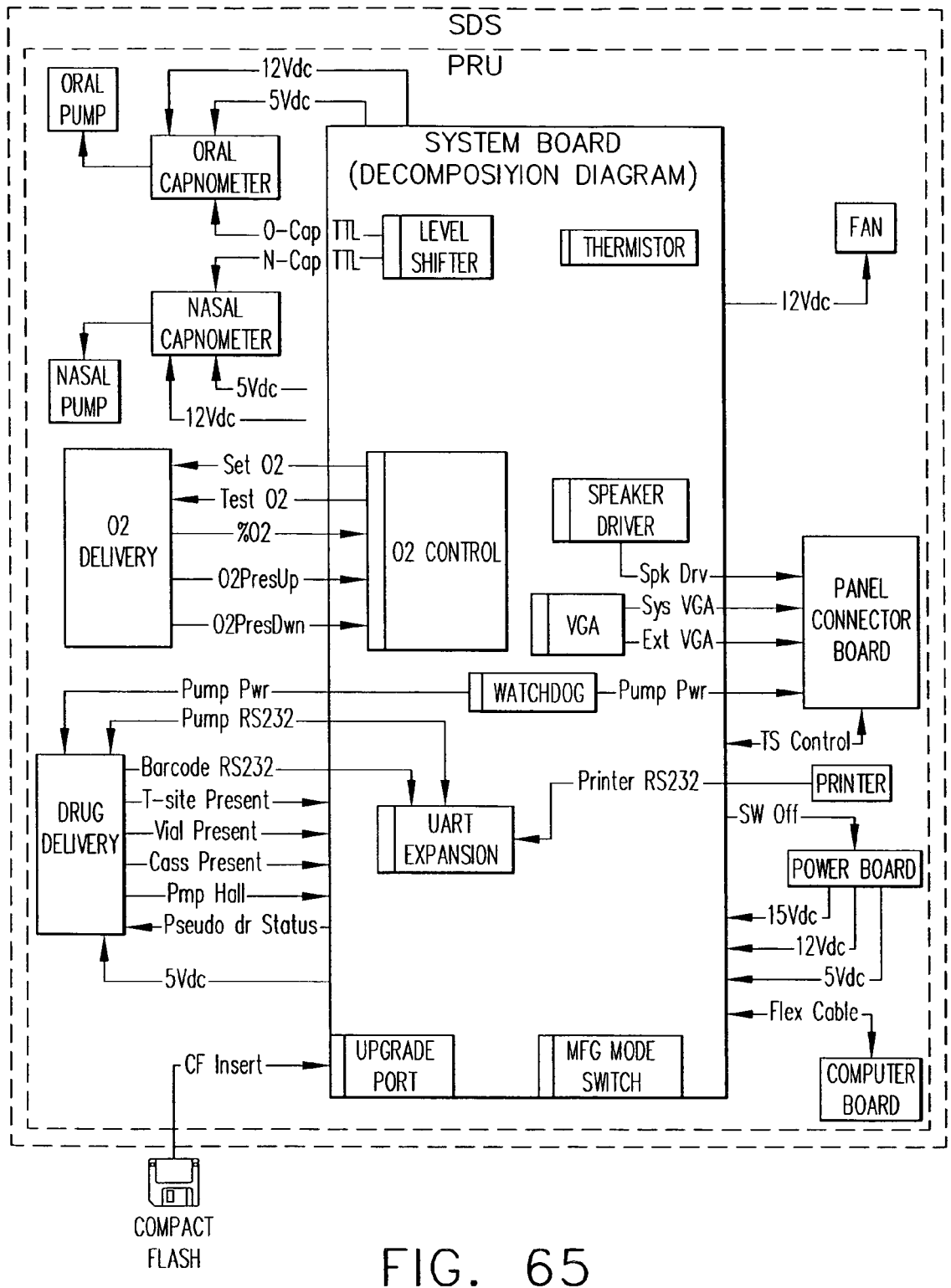
FIG. 65 is a block diagram identifying elements of a system board for use with a PRU of FIG. 64.
Figure 66:
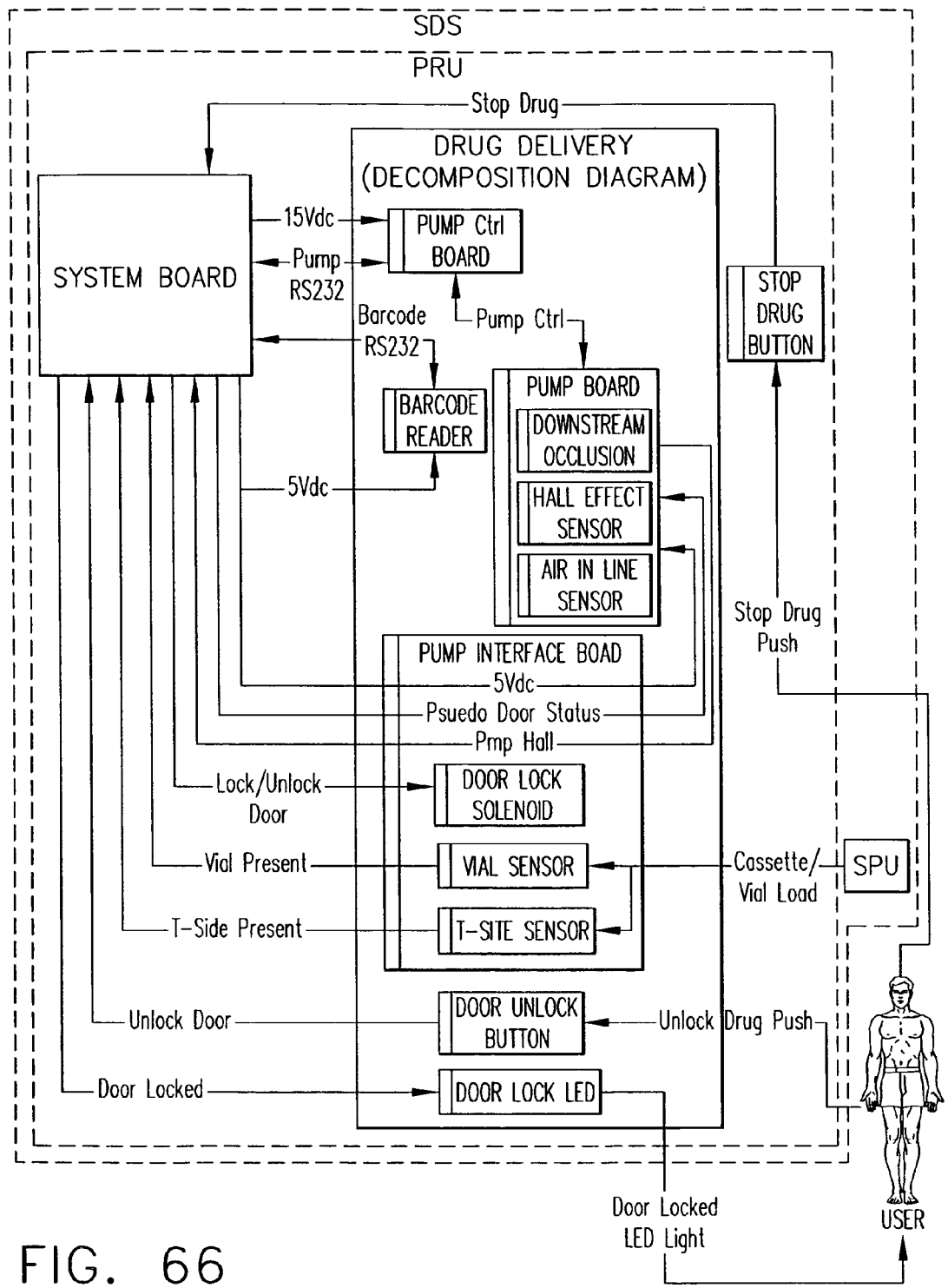
FIG. 66 is a block diagram of a drug delivery module for use with a PRU of FIG. 64.
Figure 67:
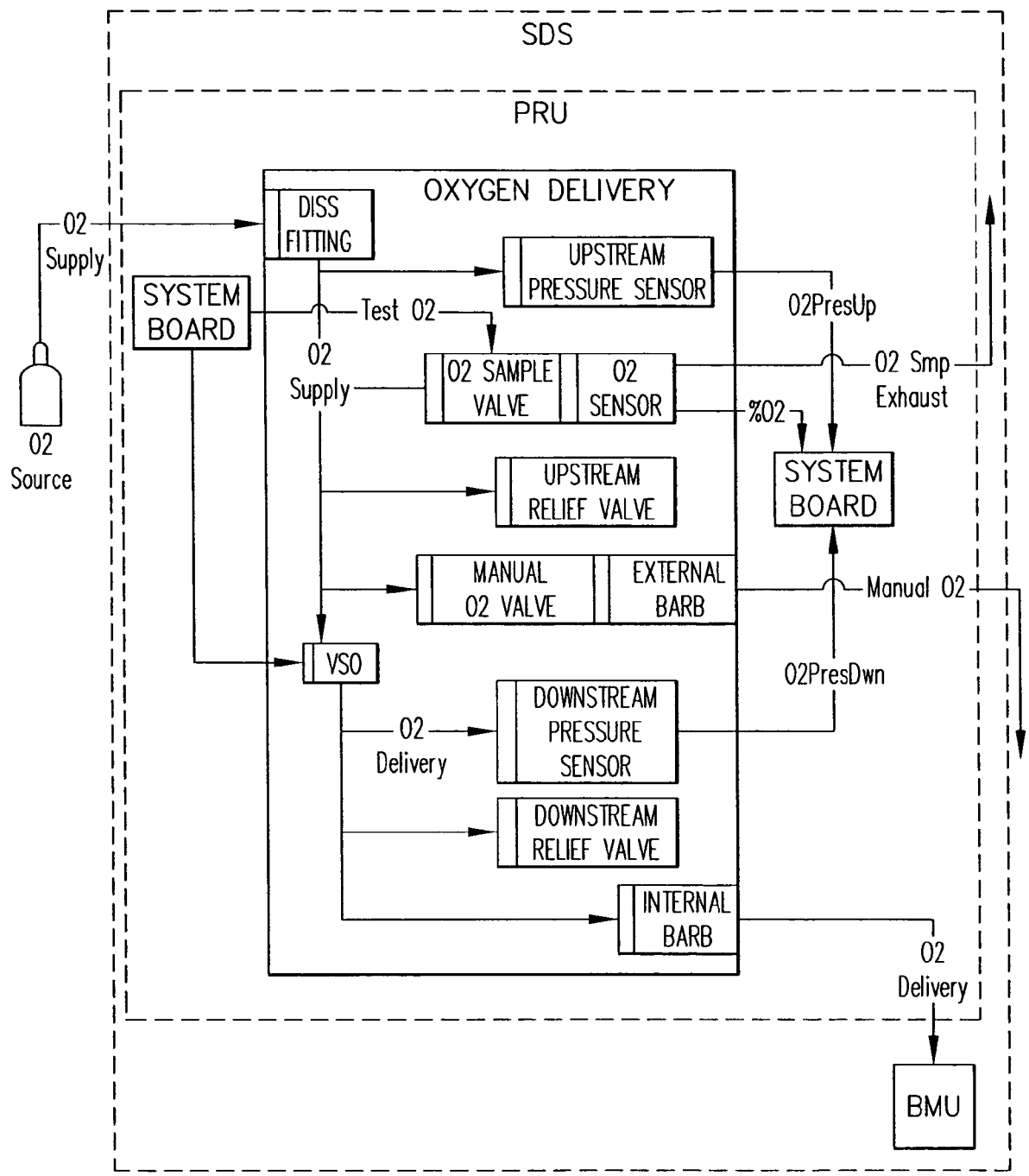
FIG. 67 is a block diagram of an oxygen delivery module for use with a PRU of FIG. 64.
Figure 68:
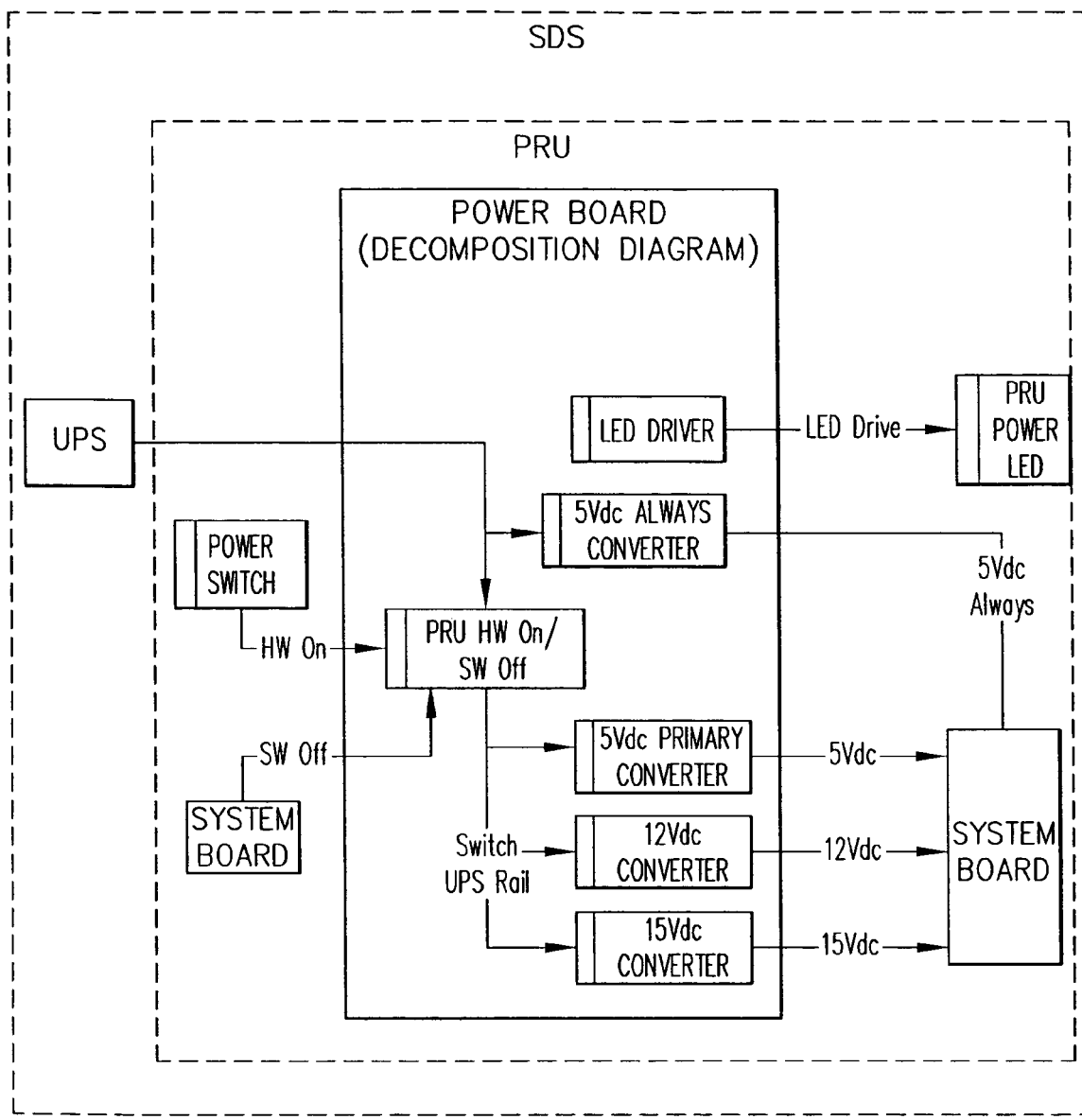
FIG. 68 is a block diagram of a power board module for use with a PRU of FIG. 64.
Figure 69:
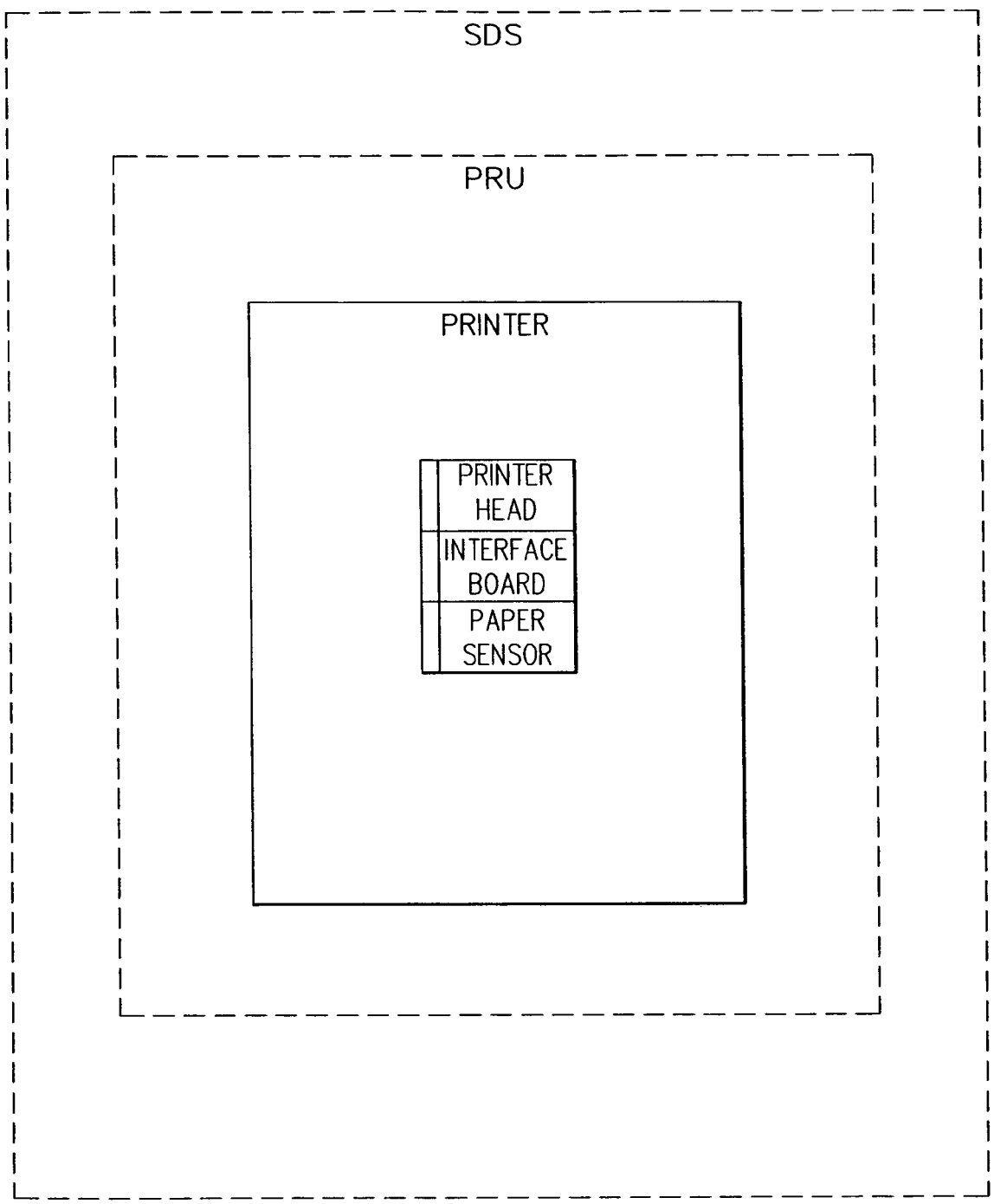
FIG. 69 is a block diagram of a printer module for use with a PRU of FIG. 64.
Figure 70:
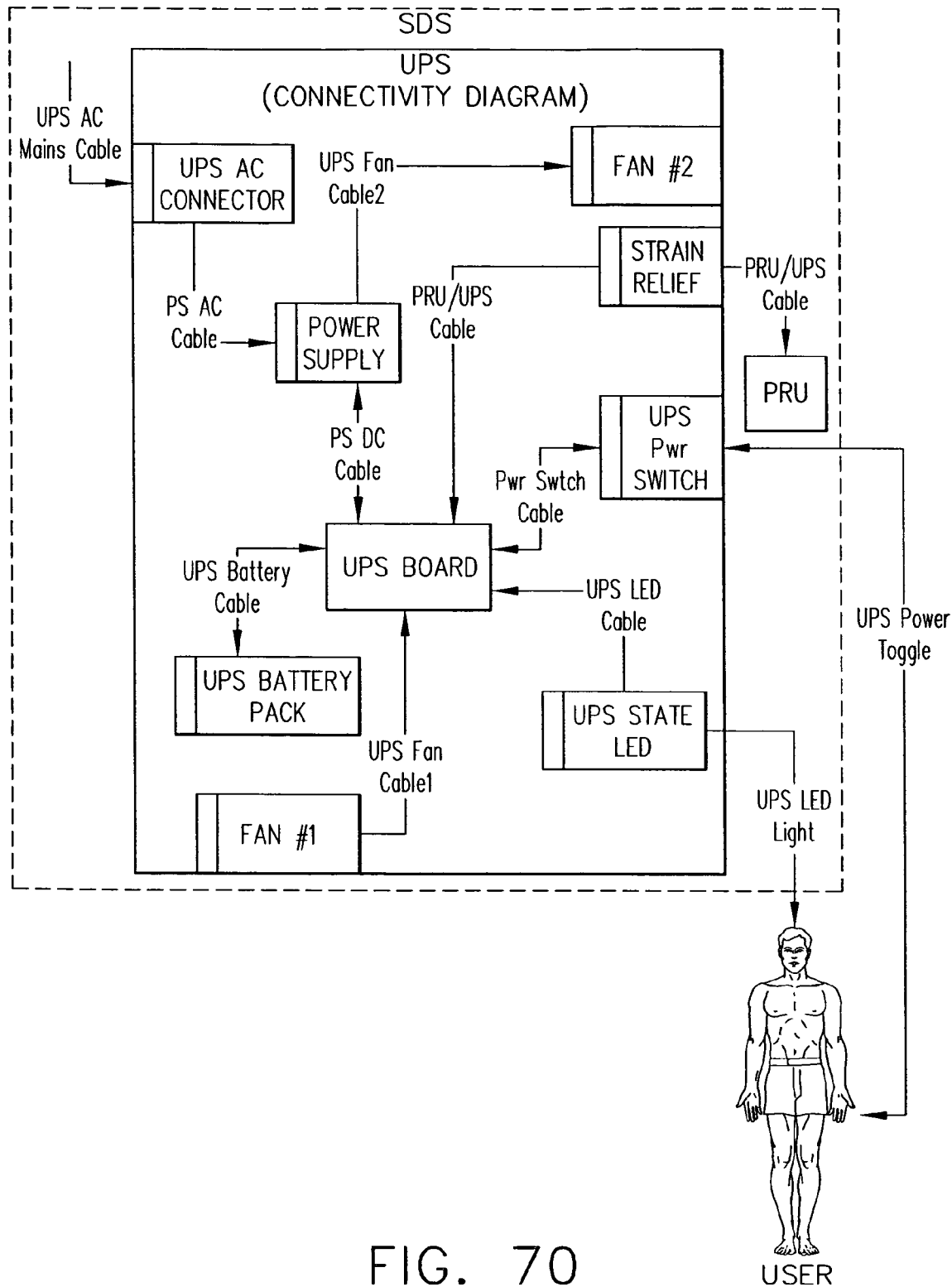
FIG. 70 is a block diagram of an uninterruptible power supply (UPS) for use with a PRU of FIG. 64.
Figure 71:
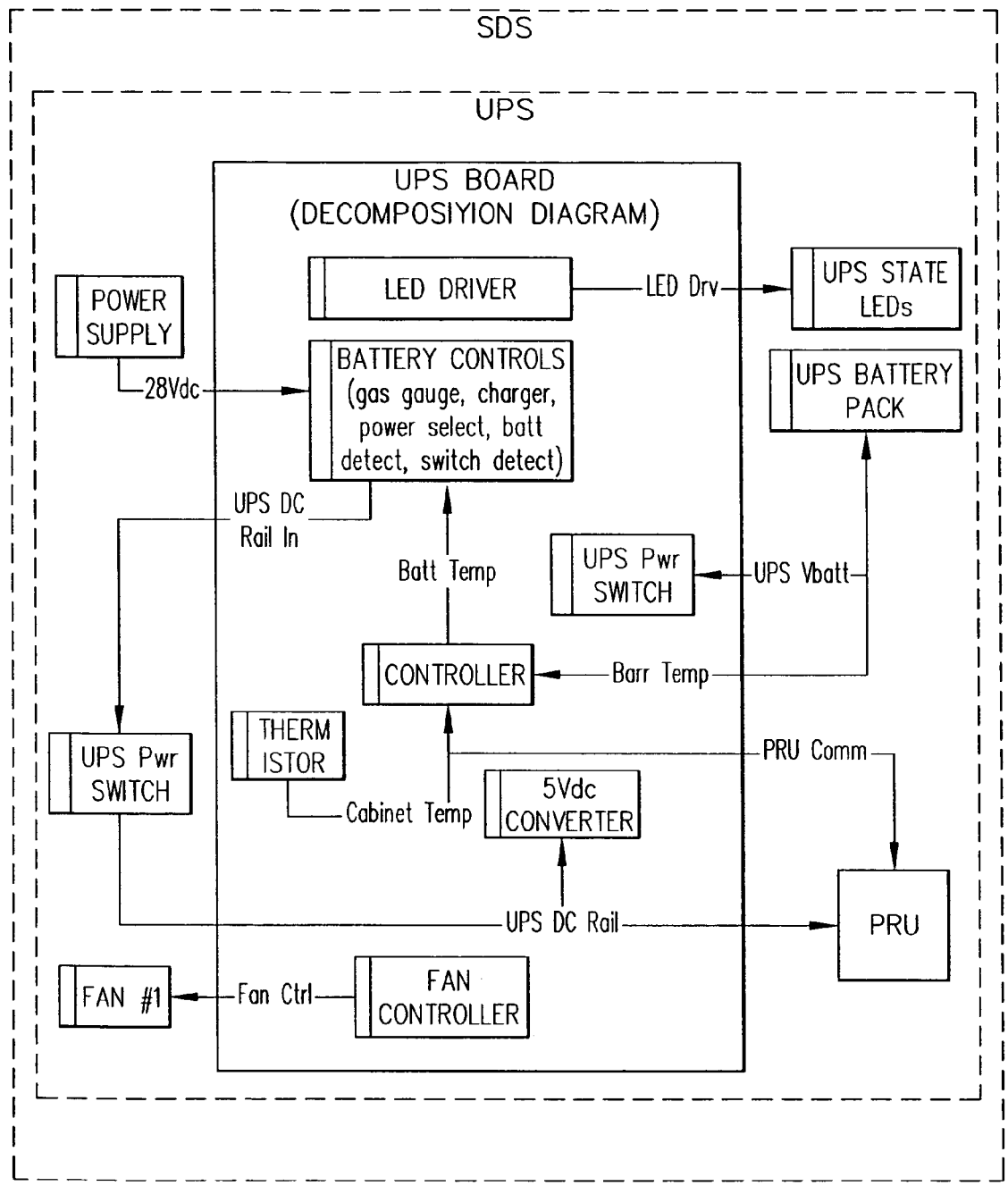
FIG. 71 is a block diagram of a UPS module for use with a UPS of FIG. 70.
Figure 72:
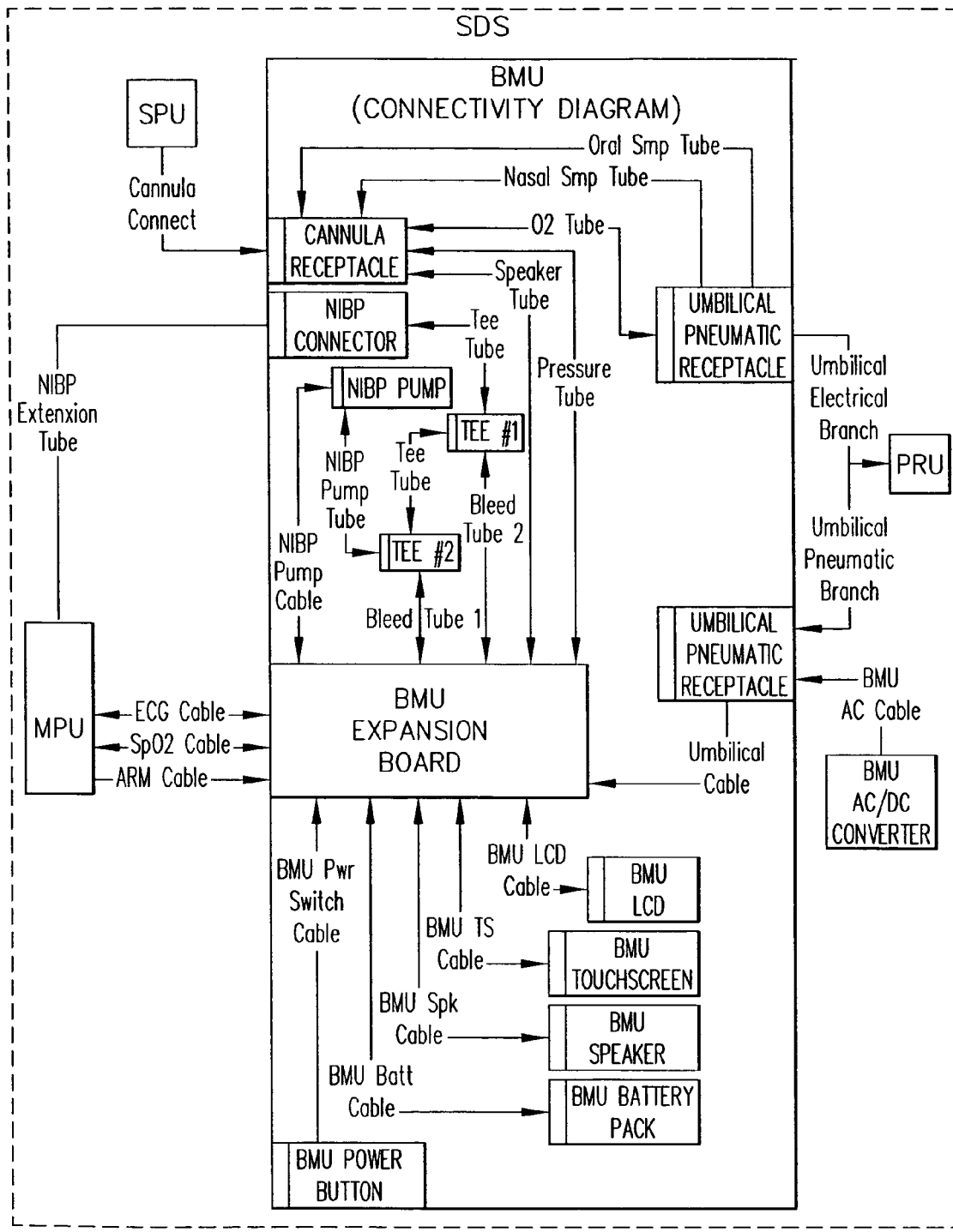
FIG. 72 is a block diagram of a bedside monitoring unit (BMU) for use with an SDS of FIG. 63.
Figure 73:
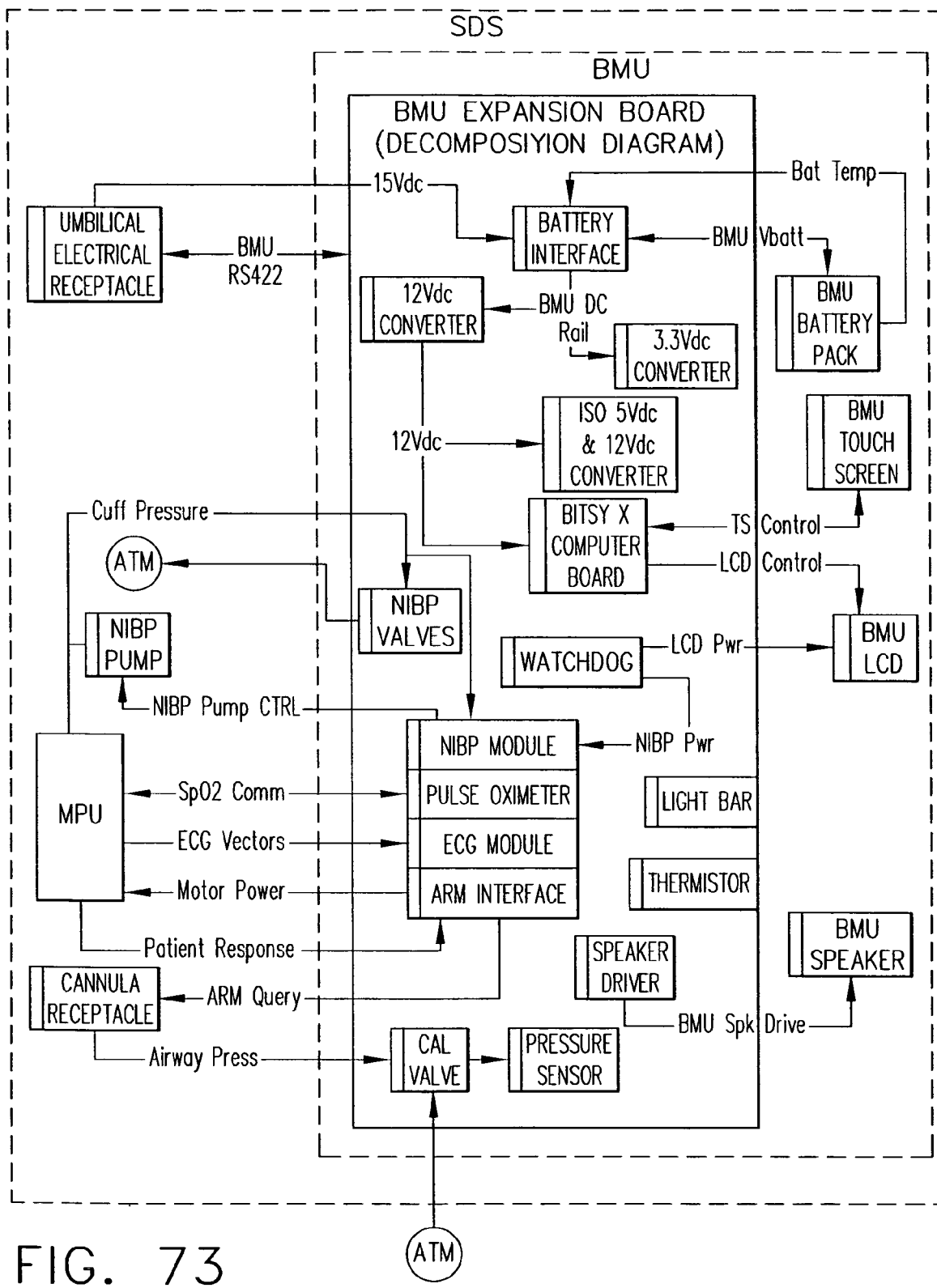
FIG. 73 is a block diagram of a BMU expansion board for use with a BMU of FIG. 72.
Figure 74:
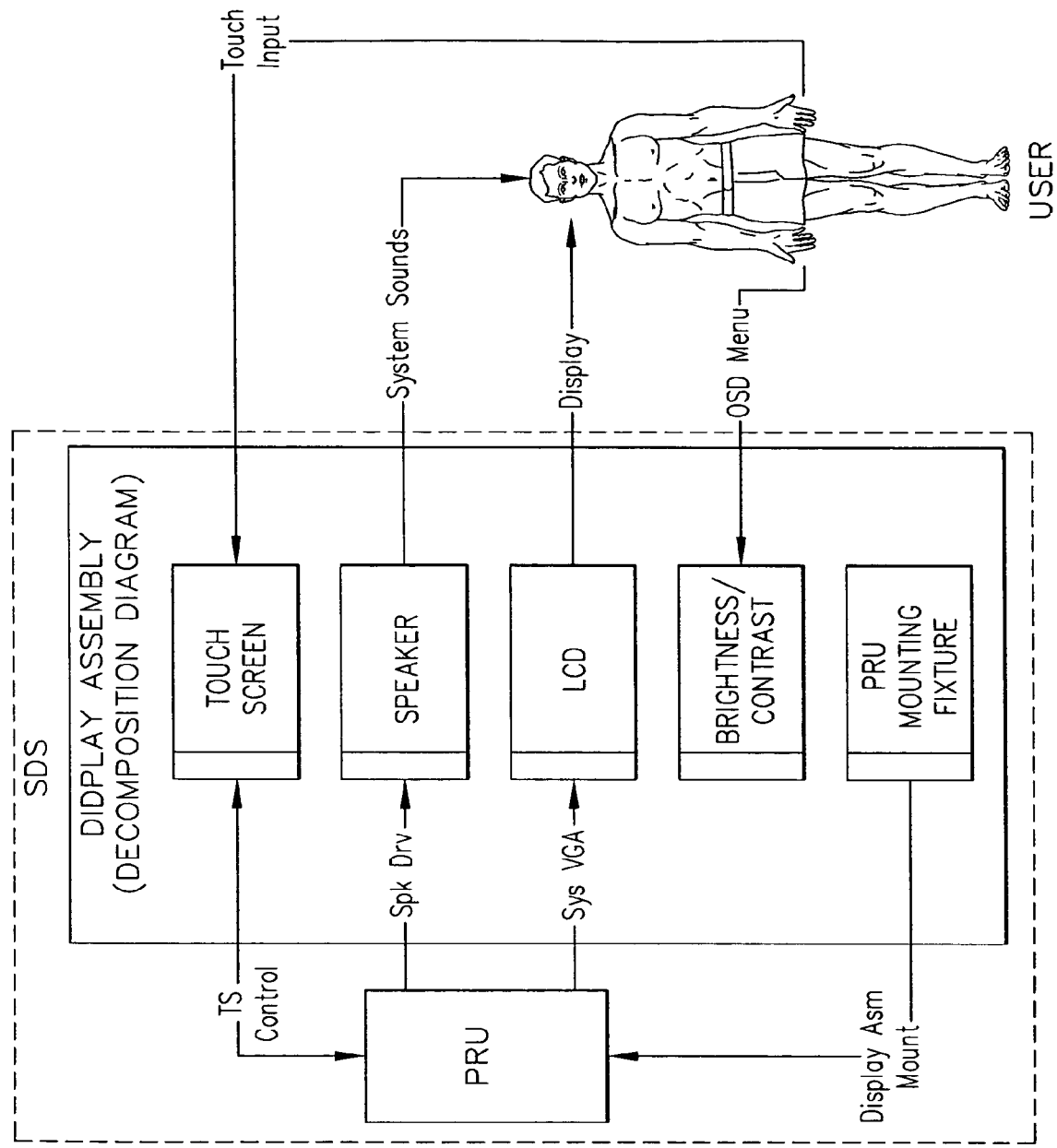
FIG. 74 is a block diagram of a display assembly for use with an SDS of FIG. 63.
Figure 75:
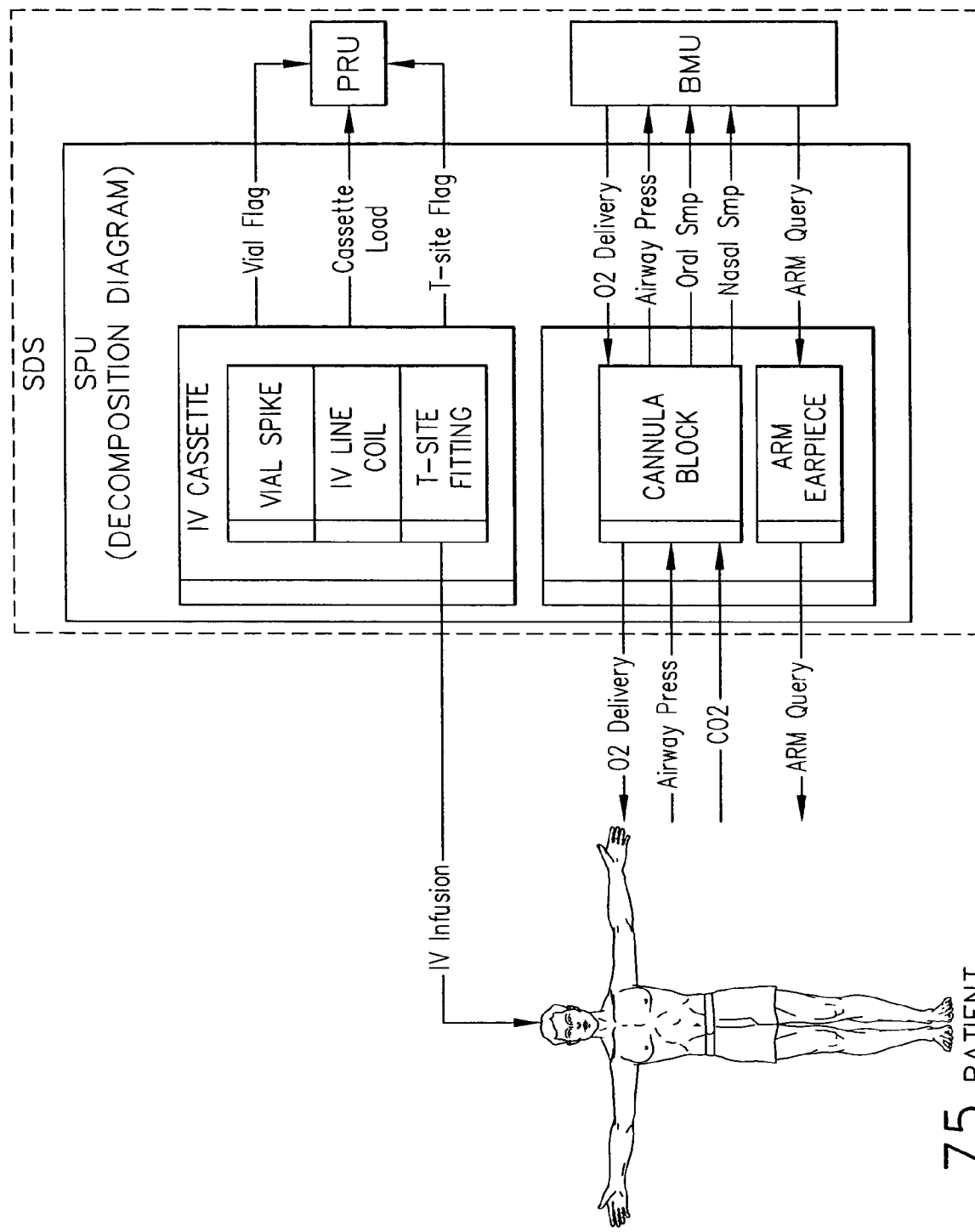
FIG. 75 is a block diagram of single-patient-use (SPU) items for use with an SDS of FIG. 63.
Figure 76:
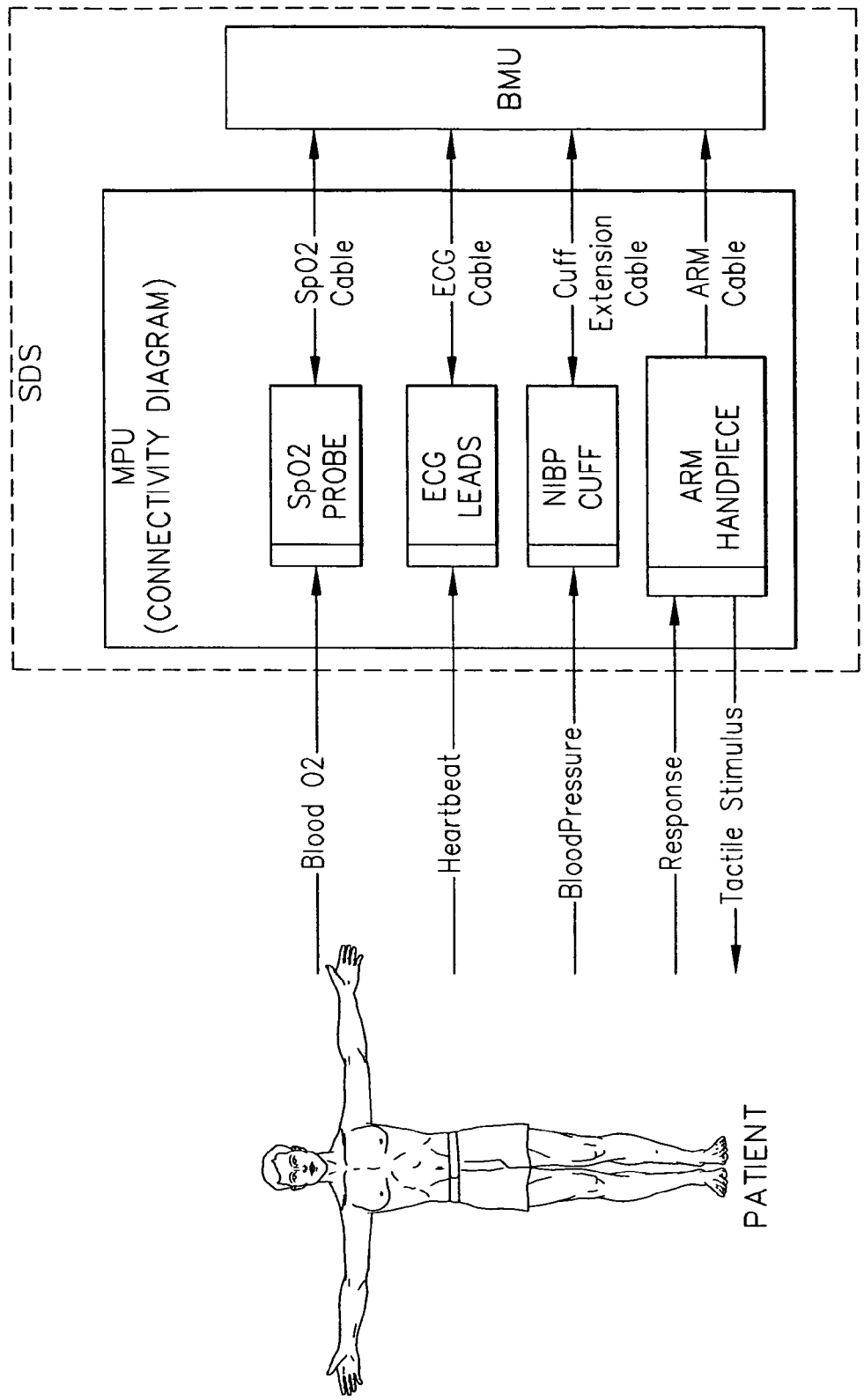
FIG. 76 is a block diagram of multiple-patient-use (MPU) items for use with an SDS of FIG. 63.
Figure 77:
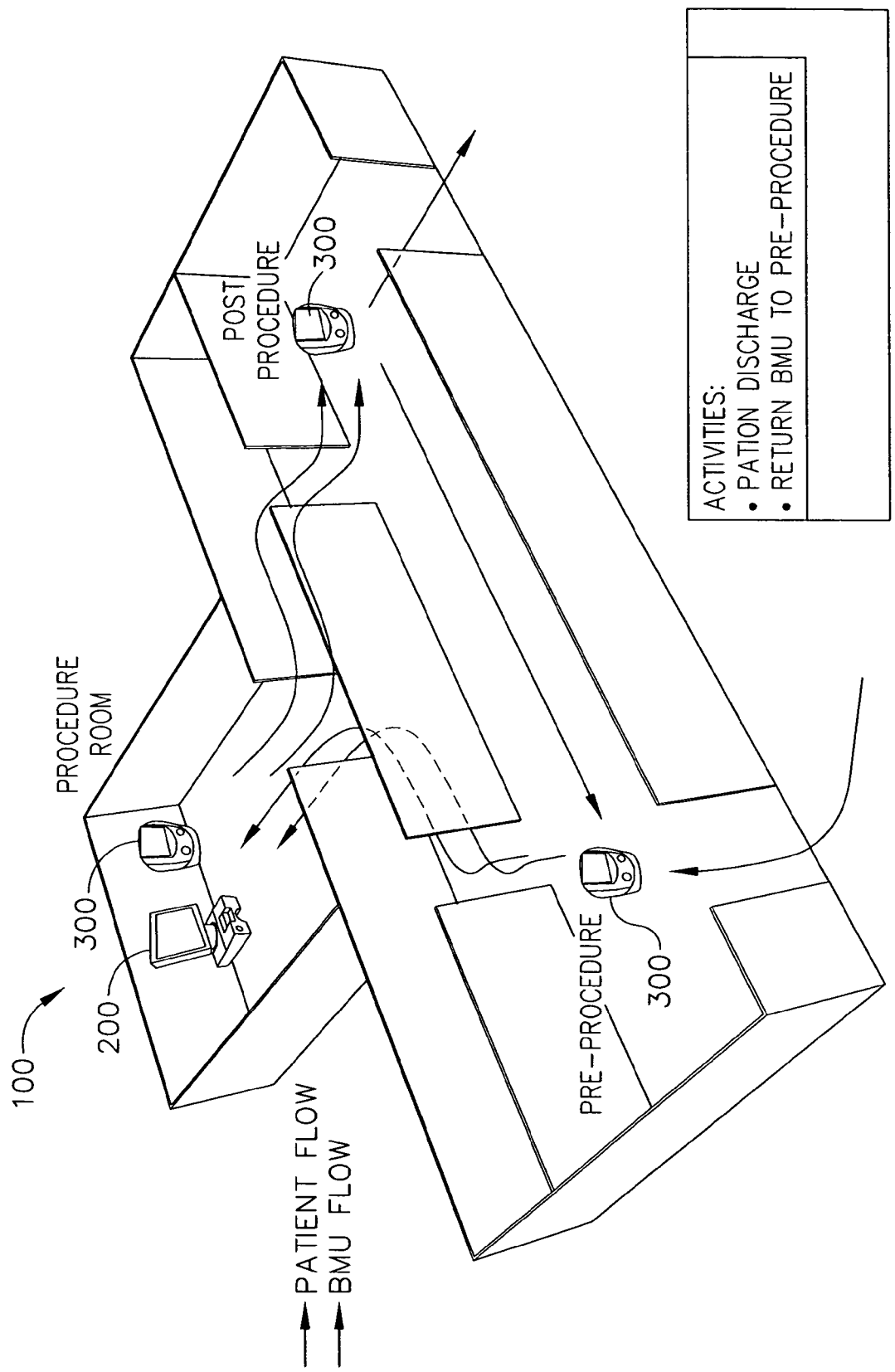
FIG. 77 is diagrammatical process flow of the BMU and PRU of an SDS of FIG. 63 during one example of a surgical procedure.
Figure 78:
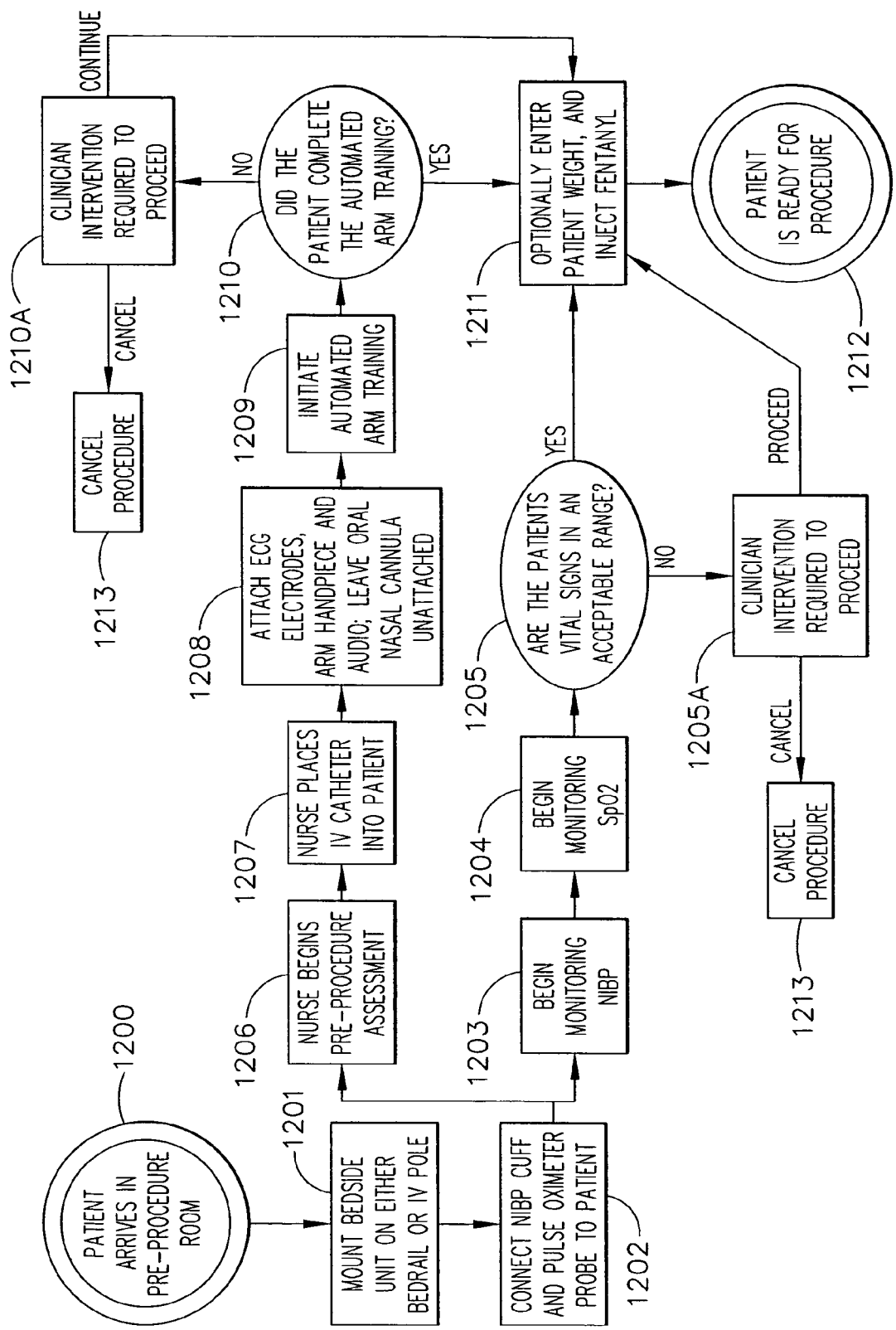
FIG. 78 is an overview data-flow diagram depicting the pre-medical procedure aspect of an SDS of FIG. 63.
Figure 79:
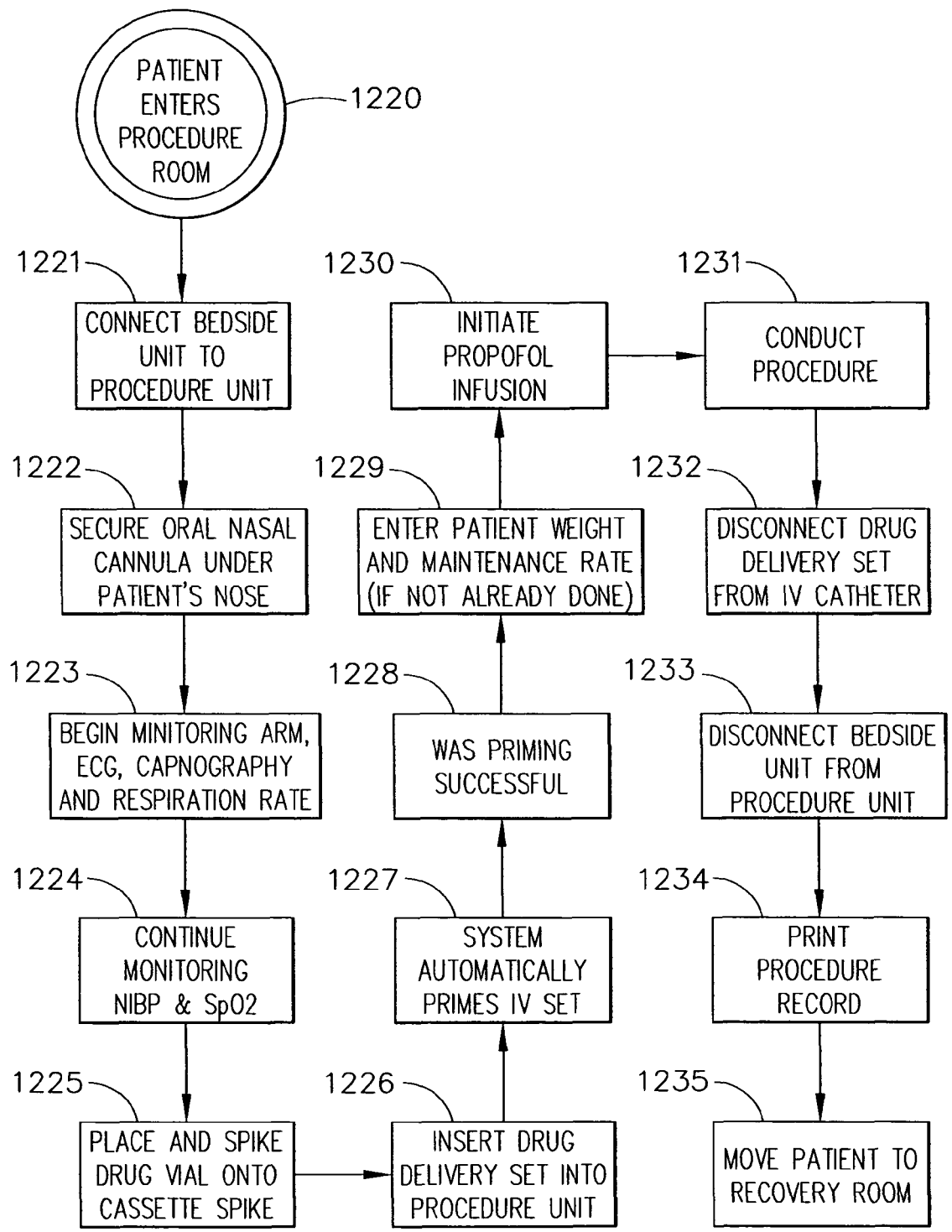
FIG. 79 is an overview data-flow diagram depicting the medical procedure aspect of an SDS of FIG. 63.
Figure 80:
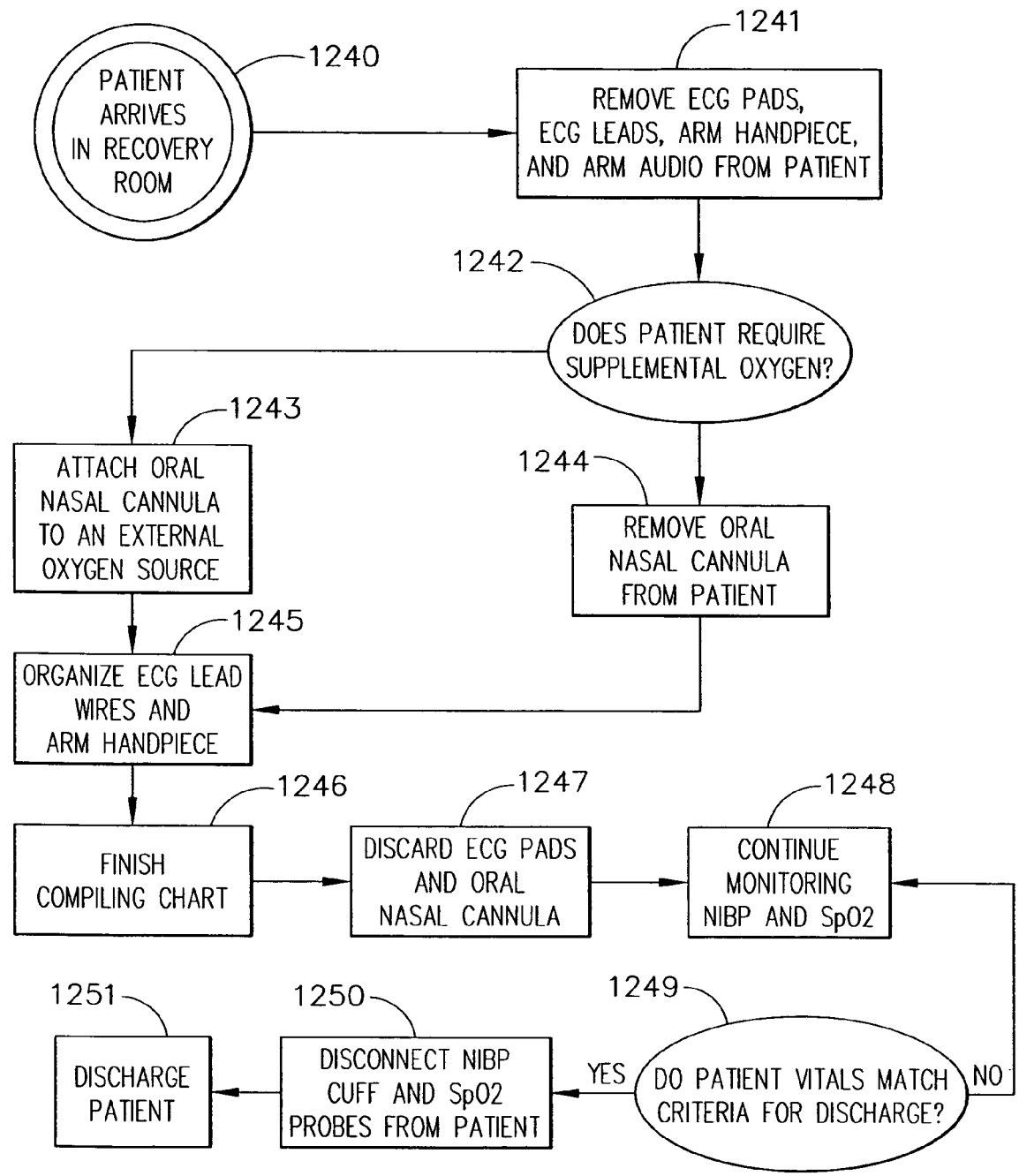
FIG. 80 is an overview data-flow diagram depicting the post-medical procedure aspect of an SDS of FIG. 63.

As best illustrated in FIG. 62, the internal components of BMU 300 are sandwiched between top foam support 312 and bottom foam support 313. In one example, foam supports 312 and 313 are constructed of rigid foam well known in the electronics industry as an E-PAC™ chassis. Strategically located recesses and cavities in the E-PAC™ chassis efficiently capture and securely hold pc boards, pump, LCD, speaker, and other components. The outer housing of BMU 300 is constructed of rigid molded thermoplastic (e.g., ABS) and includes bottom 314, front 315, back 316, and top 317. The housing components are held together with molded-in snap features and screws. Housing top 317 is designed to be readily removable for access to batteries 303.

Sedation Delivery System

Referring to FIGS. 63-76, the following paragraphs present one combination of particular examples of the previously-described aspects of the invention and is for a sedation delivery system (SDS) 100, which is an integrated monitoring, and drug delivery system and which is intended to provide a means of sedating a patient during medical procedures. SDS 100 uses a drug delivery algorithm called Dosage Controller (DC) and an intravenous infusion pump 220 to deliver drug(s) with a variable rate infusion that rapidly achieves and maintains a desired sedation effect. It enables the physician/ nurse (non-anesthesiologist) care team to adjust the patient's sedation level by simply entering the dose rate that they believe will maintain the desired sedation effect. DC calculates the appropriate loading dose, based on the guidelines in the drug labeling, that will rapidly achieve the sedation effect for the given maintenance rate.

SDS 100 includes four routine physiologic monitors. These are a pulse oximeter 110 for monitoring the patient's arterial oxygenation, non-invasive blood pressure (NIBP) 120 and electrocardiogram pads (ECG) 332 for monitoring the patient's cardiodynamics, and a capnometer 140 and 202 for measuring the patient's respiratory activity. In addition, SDS 100 has an automated responsiveness monitor (ARM) 150 to aid the care team in assessing the patient's level of sedation. All five monitors and DC are integrated together through a software module referred to as the monitoring shell. The monitoring shell is intended to keep the patient at the desired level of sedation. It monitors the patient's condition, keeps the care team informed of the patient's status, and immediately stops the delivery of drug(s) if it detects an undesired sedation condition. Under certain circumstances, the monitoring shell will re-initiate drug delivery, but at a reduced maintenance rate, once the patient's condition returns to a desired sedation condition. The monitoring shell will not re-initiate infusion if such inaction is warranted by the undesired sedation condition. Instead, it requires intervention by a care team member to re-initiate drug delivery following such a condition. An integral part of the monitoring shell is procedure room unit (PRU) Graphical User Interface (GUI) 210 and bedside monitoring unit (BMU) graphic user interface 212; each displays the monitored physiologic values in a fashion that enables the care team to readily determine the status of the patient. The GUI has also been designed to give the care team an efficient means of adjusting the patient's level of sedation through changes in the maintenance rate.

SDS 100 is designed to provide continuous hemodynamic monitoring of the patient in the pre-procedure room, the procedure room, and the recovery (post-procedure) room. It includes two main units, which are the bedside monitoring unit (BMU) 300 and the procedure room unit (PRU) 200. BMU 300 is connected to the patient in the pre-procedure room and stays with the patient through recovery. BMU 300 contains pulse oximeter module 310, NIBP module 320, ECG module 330, and ARM module 340. Once connected to the patient, it monitors and displays the patient's arterial saturation, arterial pressure, and heart rate. Supplemental oxygen (which includes air having an enriched oxygen content) can be delivered at this time through BMU 300 and oral/nasal cannula 145. When the patient is wheeled into the procedure room, BMU 300 is attached to PRU 200 by umbilical cable 160, which contains both pneumatic and electrical lines. During the procedure, umbilical cable 160 allows PRU 200 to receive patient physiologic data from BMU 300 as well as the patient's respiratory gases. In addition, umbilical cable 160 allows for delivery of oxygen to the patient from PRU 200.

PRU 200 adds capnography to the system, monitoring and displaying the patient's respiration rate and end-tidal $CO_2$. ARM monitoring is activated and the patient's responsiveness is displayed to the care team. As soon as PRU 200 detects respiration activity (from the capnometer), mandatory oxygen delivery is initiated. All drug delivery is performed by PRU 200 as it contains intravenous infusion pump 220, DC and the monitoring shell. Drug infusion cannot be initiated until all monitors are connected and providing valid values and oxygen is being delivered to the patient. PRU 200 is the main interface between the care team member responsible for administering sedation and SDS 100. It contains GUI 210 that displays the status of the patient and facilitates adjustment of the patient's level of sedation.

Figure 42:
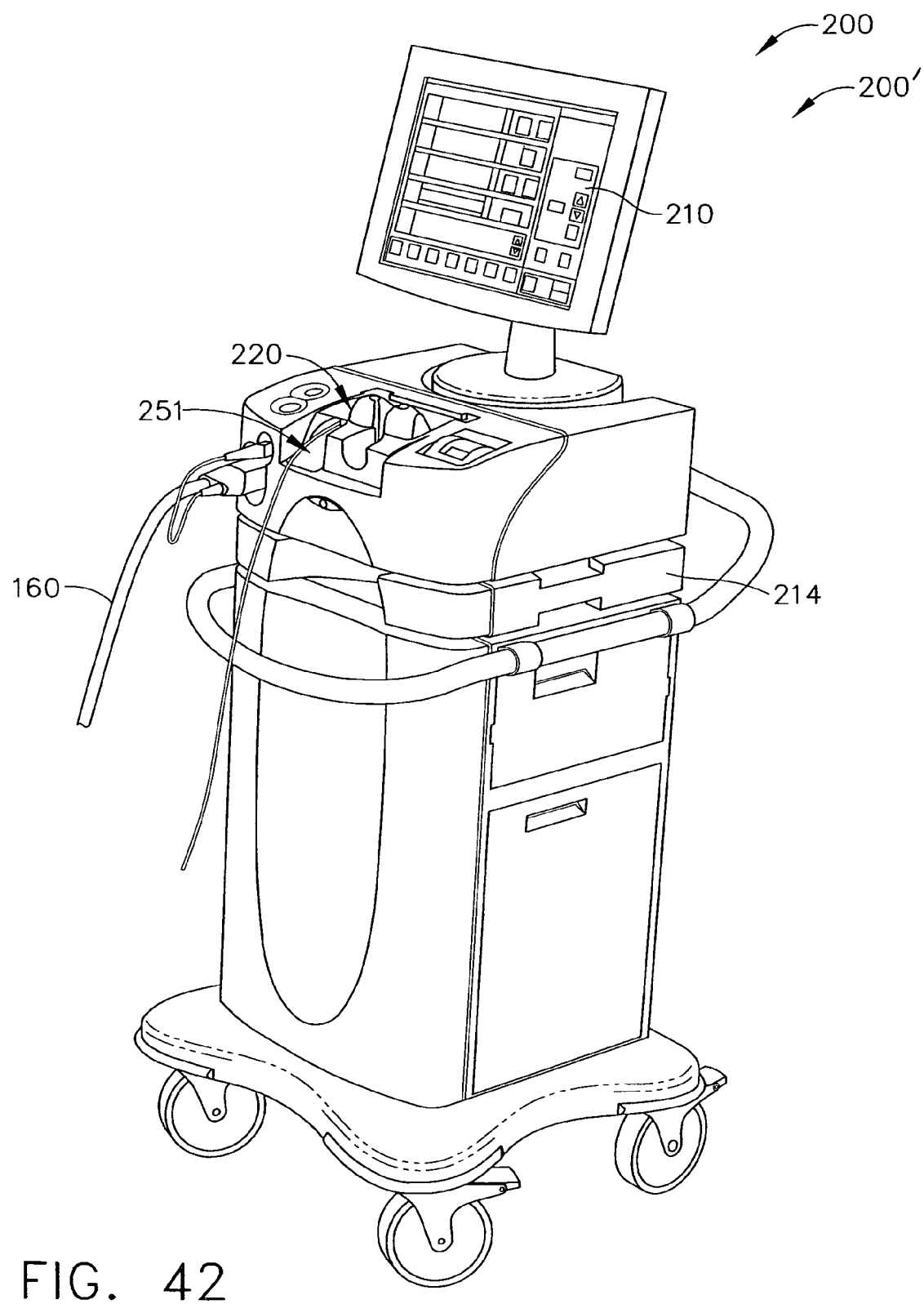
FIG. 42 is a front perspective view of the SDS cart and the PRU of FIG. 41 including the universal power supply (UPS) of the PRU.
Figure 43:
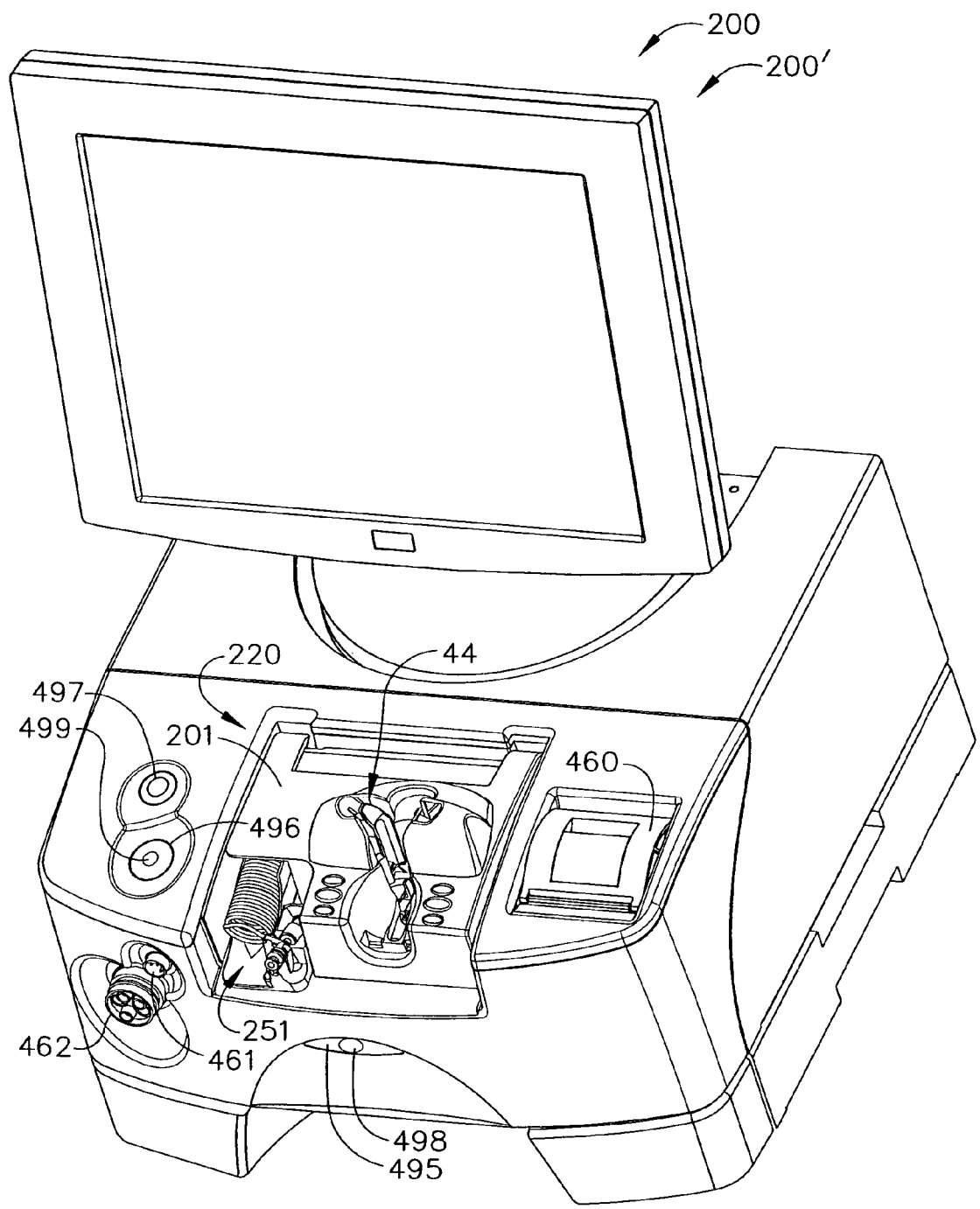
FIG. 43 is a top perspective view of the PRU of FIG. 41 with an installed drug-delivery cassette assembly and with the pump-housing door closed.
Figure 44:
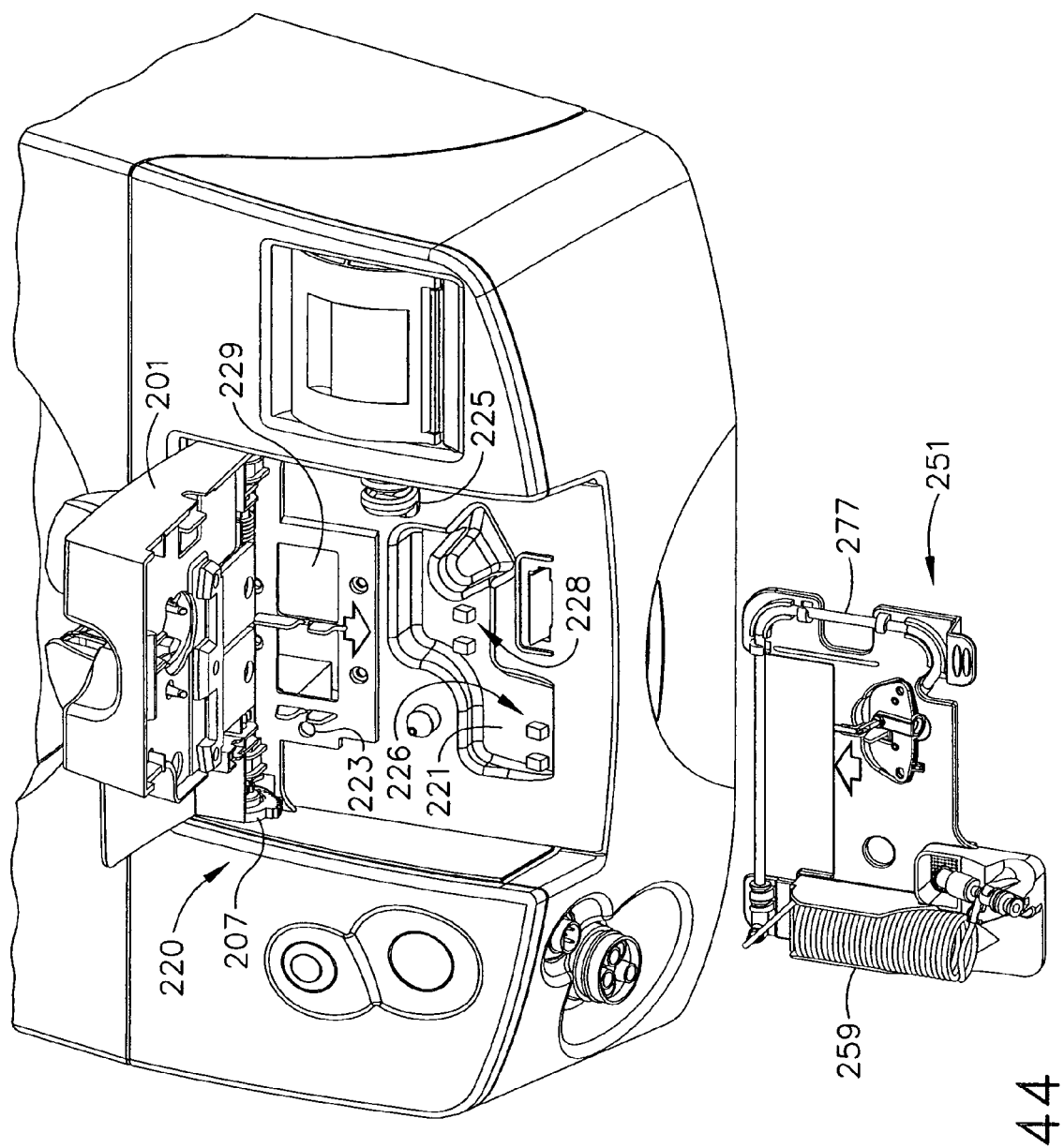
FIG. 44 is a top perspective view of a portion of the PRU of FIG. 43 with the pump-housing door open and with an uninstalled drug-delivery cassette assembly.

Referring now to FIGS. 42 and 43, PRU 200 is a component of the system that provides for: monitoring and display of patient physiologic parameters; user input of patient data; user input of dose rate; and hardware and software for delivery of drug(s) during the procedure. PRU 200 is designed to stay in the procedure room and is the mechanism for drug delivery.

Within PRU 200 are located two capnometers 140 and 202 used for sampling $CO_2$ from the areas in front of the patient's mouth and nostrils. Software monitors respiratory activity and the site with the greater respiratory activity is displayed to the user. Sensors analyze the samples, and the resultant data (respiratory rate, $EtCO_2$, and respiration wave form) are sent to PRU host controller 204.

Sedation Delivery System 100 is an apparatus for delivering a sedative drug to a patient during a medical procedure. The amount of sedative drug delivered to the patient is determined by the level of patient responsiveness as measured by ARM system 340. In an alternate embodiment, the level of pain a patient is enduring determines the amount of sedative drug delivered to the patient. Patient pain level can be indicated by physiological parameters, such as, increased heart rate and/or blood pressure and/or brain activity. Sedation Delivery System 100 includes the capability to monitor heart rate through the ECG monitor and blood pressure by way of the NIBP monitor. An EEG (brainwave) monitor is optionally supplied with Sedation Delivery System 100 to monitor a patient's brain activity. Sedation Delivery System 100 therefore interprets an elevated output from the ECG, NIBP, and/or EEG as an indication that the patient is experience pain or stress and adjusts the drug delivery to better manage the patient. For example, Sedation Delivery System 100 will increase drug flow to the patient or notify the clinician to increase drug if any of ECG, NIBP, and/or EEG monitors increase by a predetermined threshold, for example, 20% in a predetermined time period. Other monitored physiological parameters are within the scope of this embodiment as is well appreciated by those skilled in the art.

Referring to FIGS. 42 through 47, Infusion pump 220 is located in the front portion of PRU 200 and provides for the delivery of drug(s). Disposable cassette 251 interfaces with pump 220. Cassette 251 holds a drug vial 250 from which drug(s) is delivered to the patient. Cassette 251 includes a base plate holding vial spike 261, infusion tubing 277 & 259, and t-site luer connector 269 located at the patient end of the infusion tubing. As illustrated in FIG. 44, pump door 201 on PRU 200 opens to accept cassette 251 and secures cassette 251 into proper position with pump 220 when closed. T-site sensor 226 is an optical type sensor located in Pump 220 that is used to signal PRU host controller 204 of the presence of T-site 269 when cassette 251 is installed. Another optical type sensor located in pump 220 is vial sensor 228. It is used to signal PRU host controller 204 of the presence of a drug vial 250. Air-in-line sensor 225 is an ultrasonic device that straddles a short segment of tubing 277 and detects the presence of air or air bubbles being pumped through tubing 277 from the drug vial. Occlusion detector 223, located in pump 220, is a small pressure transducer that rests against tubing 277 to detect an increase in the tubing internal pressure indicating a possible occlusion in infusion tubing 259. Pump fingers 229 interface with a segment of tube 277 located across the top of cassette 251 and their peristaltic pumping action pumps drug(s) from the drug vial 250 through tubes 277 & 259 and to the patient. Pump 220 is driven by software on electronic circuit boards that interface with PRU host controller 204.

Figure 45:
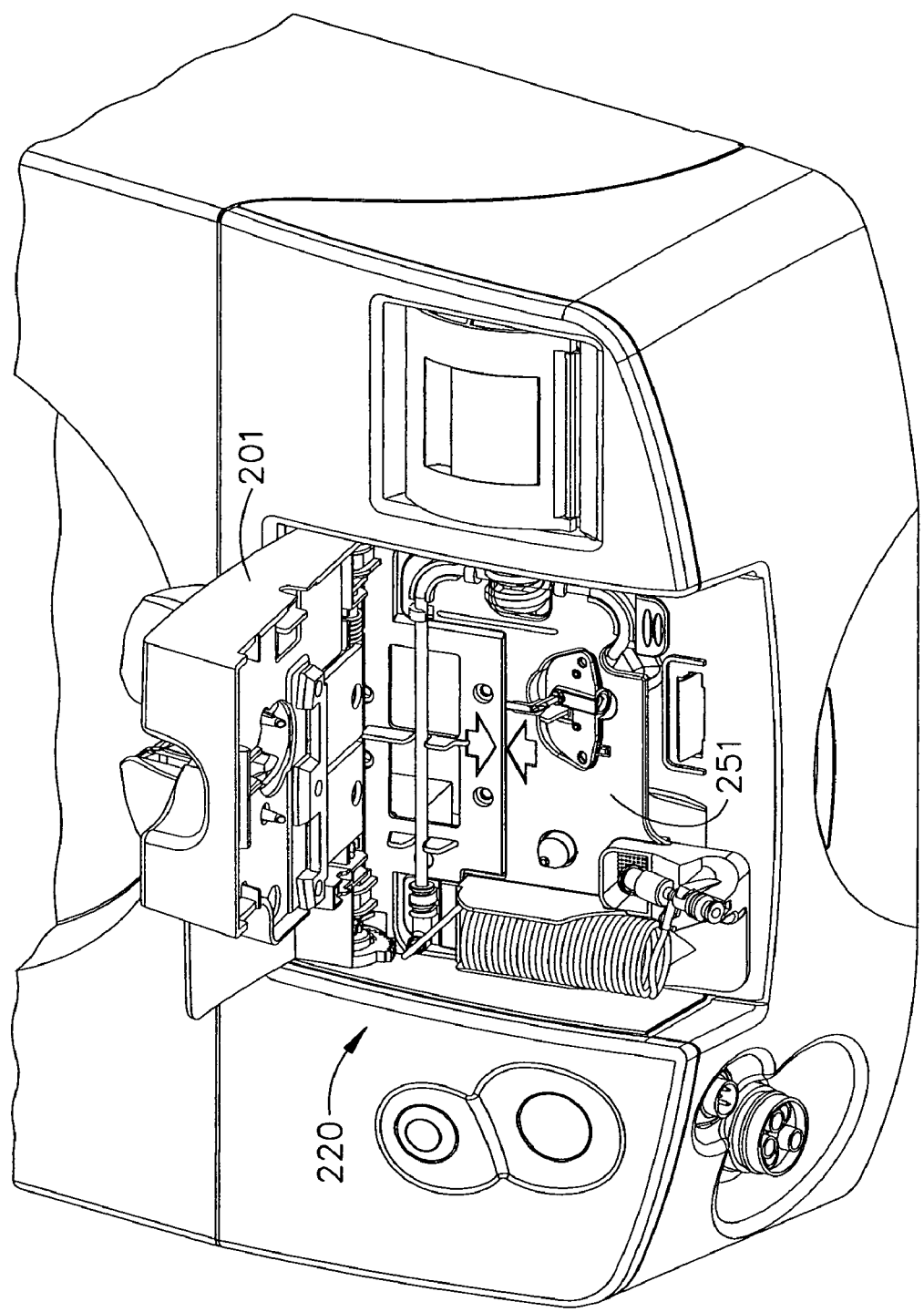
FIG. 45 is a top perspective view of a portion of the PRU of FIG. 43 with an installed drug-delivery cassette assembly and with the pump-housing door open.
Figure 46:
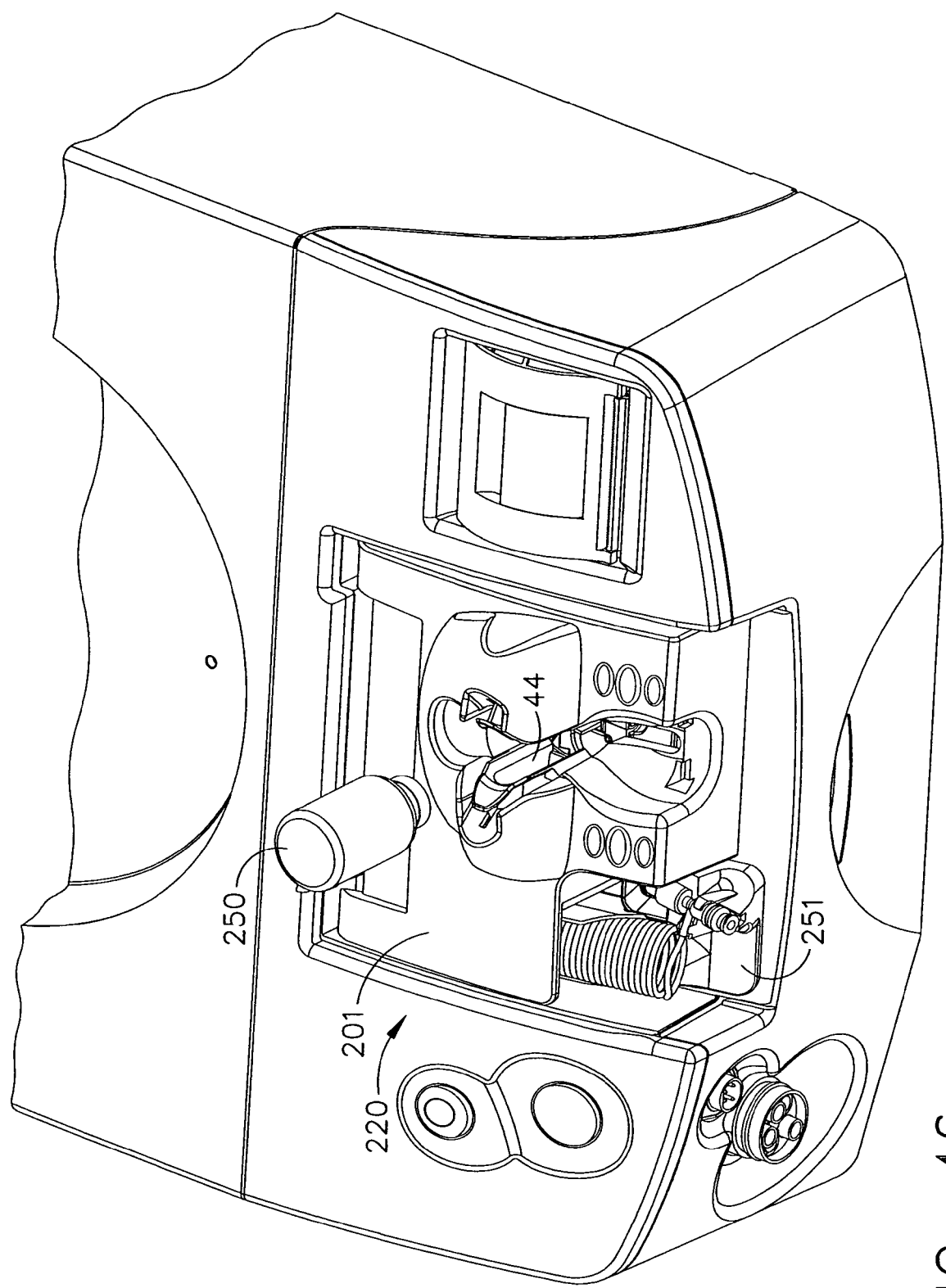
FIG. 46 is a top perspective view of a portion of the PRU of FIG. 43 with an installed drug-delivery cassette assembly, with the pump-housing door closed, and with an about-to-be-installed drug vial.
Figure 47:
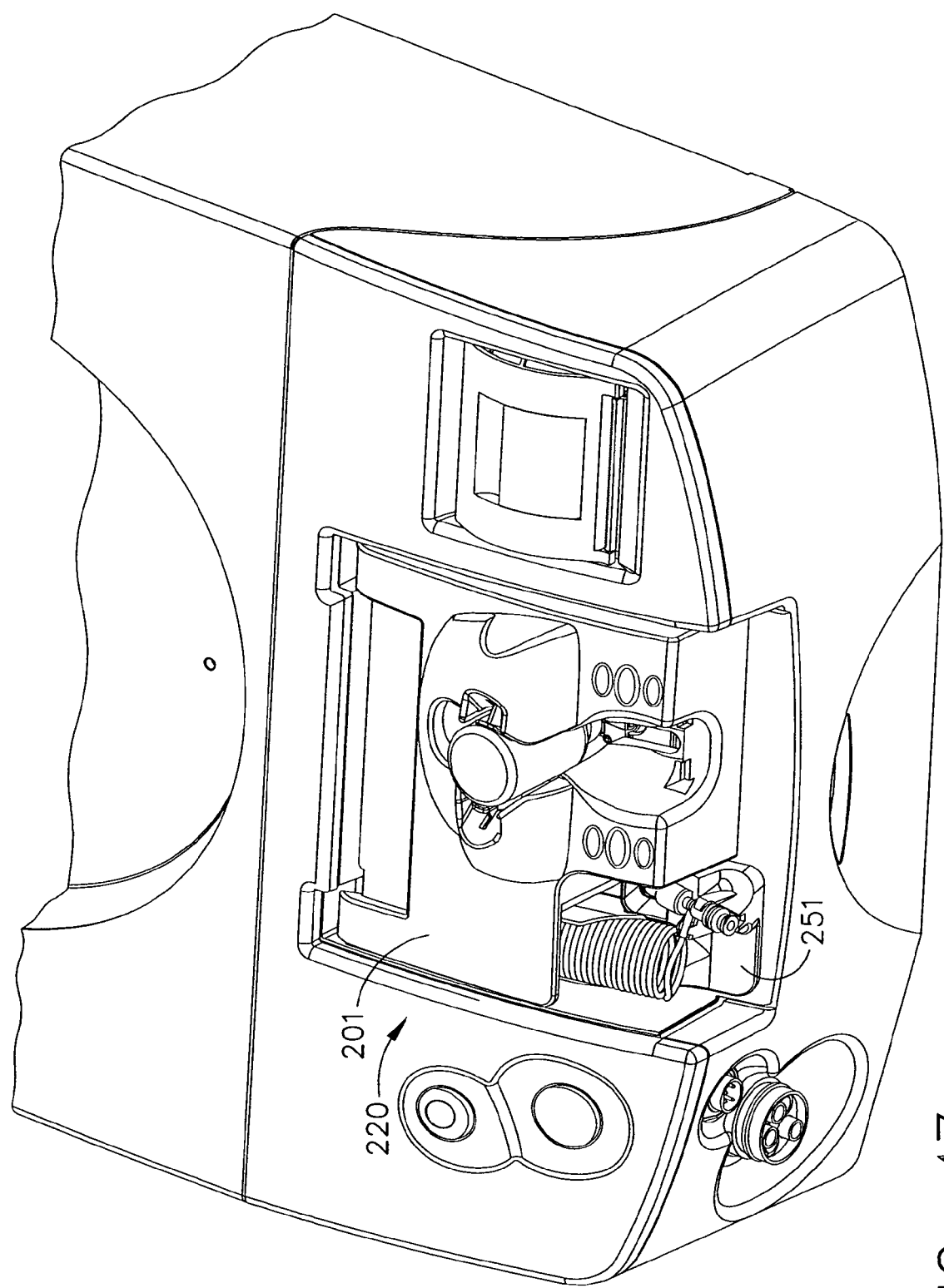
FIG. 47 is a top perspective view of a portion of the PRU of FIG. 43 with an installed drug-delivery cassette assembly, with the pump-housing door closed, and with an installed drug vial.

FIG. 45 further illustrates the proper location of cassette 251 in pump 220 and shows pump door 201 open. FIG. 46 illustrates cassette 251 in pump 220, door 201 closed, and a drug vial 250 in position to be placed on vial spike 261. FIG.

47 illustrates cassette 251 inserted into pump 220, door 201 closed, and a drug vial 250 placed on vial spike 261.

Referring again to FIGS. 42 and 43, located within PRU 200 is oxygen delivery module 206, which controls the delivery of oxygen to the patient during the procedure. Oxygen delivery module 206 contains sensors, flow control devices, and tubing that provide for oxygen delivery. One of the sensors measures the concentration of oxygen in the line coming into PRU 200, and, if the concentration of oxygen is below a predetermined level, oxygen delivery is not permitted and a message is displayed to the user. This feature is intended to help prevent delivery of a gas other than oxygen to the patient.

PRU graphic user interface (GUI) 210 allows PRU 200 to relay information gathered from the physiologic monitors and sensors to the user and allows the user to enter information and commands. PRU graphic user interface 210 includes a visual display monitor with a touchscreen for user input and an alarm system with audio and video components. In addition, a printer is used to create a hard copy record of sedation information. When the monitored patient physiologic measurements are within desired parameters, an alarm box area of the monitor displays green. When the respiratory rate or oxygen saturation ($SpO_2$) is outside a desired state by a first amount, their respective status bar indicates a first alarm condition by displaying it in the color yellow. When these same physiologic parameters are outside the desired state by a larger second amount, the respective status bar indicates a second alarm condition by displaying red. In addition to the visual indicators, SDS 100 incorporates distinct audible tones for different alarm levels (i.e., yellow or red).

PRU 200 is powered by universal power supply (UPS) 214, which converts available a/c voltage to constant DC voltage. This voltage is provided to all modules within SDS 100. UPS 214 also includes a battery powered back-up system that allows the user several minutes of system use time in the event of a power failure.

PRU 200 includes PRU host controller 204 which has both hardware and software modules. The hardware contains interface components for communicating with all of the patient monitors. This communication includes receiving patient data, monitoring operating status, and sending routine commands to the modules. The software also processes data received from the patient monitors for display on the video display monitor. The software contains drivers for the display, touchscreen, speakers, internal memory, printer, ARM functions, Ethernet port, external video display, internal sensors, and infusion pump 220.

Operating software controls the interaction and function of SDS 100. Through the monitoring shell, the software makes pertinent decisions based on information it receives from user input, various internal sensors, and patient monitors. If the patient status reaches a level outside of desired limits for conditions associated with deeper than desired sedation (e.g., low respiratory rate or low oxygen saturation), the software takes appropriate action alerting the user and decreasing or stopping the administration of drug(s). The software also executes delivery of drug(s) based on the dose rate prescribed by the user. The infusion model is based on pharmacologic principles and uses patient weight along with desired dosage to calculate the infusion rate of drug(s).

As a user convenience, SDS 100 contains software to automatically prime the patient infusion line 224 when a valid drug delivery cassette and drug vial is loaded into infusion pump 220. As a monitoring feature, with cassette 251 installed into infusion pump 220, a sensor detects the presence of the t-site connector installed on drug delivery cassette 251. The SDS primes the infusion line 224 when the t-site is detected as being attached to the drug delivery cassette.

The following paragraphs present particular examples of several SDS 100 functional subsystems comprising components of one or more of the previously-described aspects, and the one previously-described combination of particular examples of aspects, of the invention.

The oxygen delivery functional subsystem accepts supplemental oxygen from a standard user-provided external source and dispenses it to the patient in a controlled flow pattern that is influenced by the patient's breathing pattern. When the patient is breathing primarily from a nasal aspect, the oxygen is at a higher flow rate during inhale and at a lower flow rate during exhale. When the patient is breathing primarily orally, the oxygen is turned on continuously. The flow rate is adjustable by the user input to the PRU GUI 210. The oxygen is delivered to the patient by means of the oral/nasal cannula 145, which includes a specialized mask-like portion that is affixed to the oral/nasal zone of the patient's face.

The oxygen flow is controlled within the PRU console 444 in accordance with algorithms that are influenced by the patient's nasal pressure. The metered oxygen flow produced by PRU console 444 is presented to and fed through the umbilical cable 160 to the BMU 300. The BMU 300 presents the oxygen to a single-use disposable called the oral/nasal cannula 145 that is attached to the BMU 300. The oral/nasal cannula 145 conveys the oxygen to the patient, via its oxygen tube 353, and dispenses the oxygen to the patient's nasal and oral zones via two nasal oxygen prongs 422 and one oral prong 369.

The oxygen delivery functional subsystem has several ancillary oxygen related functions, which are primarily resident within the PRU console 444. These functions include a means to verify that the supplemental oxygen supply is not hypoxic and is not at an oxygen content lower than ambient air. In the event of detection of hypoxic gas, the PRU console 444 will shut off gas delivery to the patient and alert the user. Another ancillary oxygen function is protection against inadvertently high pressure supplemental oxygen acquired from the user's supplemental oxygen source, which is mitigated via pressure release blow-off of the excessive pressure. Another ancillary oxygen function is protection against inadvertently high oxygen pressure in the relatively low pressure oxygen flow path, which is mitigated via pressure release blow-off of the excessive pressure. Another ancillary oxygen function is the detection of a disconnected umbilical pneumatic cable connector end A 161 or umbilical pneumatic cable connector end B 162 at either the PRU console 444 or at the BMU 300 or the disconnection of the oral/nasal cannula 145 from the BMU 300. When the oral/nasal cannula 145 is disconnected from the BMU 300, the oxygen is not delivered to the intended patient site. This disconnection is detected by PRU console 444's observation of the unexpected pressure level measured in the oxygen delivery path. When detachment is discerned, the oxygen delivery is automatically ceased by the PRU console 444 until the detachment is resolved by the user. Another ancillary oxygen function is the hand-operated oxygen gas valve called the oxygen diverter 492 at the rear of the PRU console 444. The oxygen diverter 492 permits the user to conveniently manually divert the incoming supplemental oxygen away from the PRU Console 444 interior and instead present that oxygen supply to an SDS-system-bypass oxygen source fitting referred to as the barbed oxygen outlet 494. The barbed oxygen outlet 494 permits the user to access oxygen via the SDS 100 for use with alternate oxygen care equipment, such as would be utilized to bypass the SDS system.

The oxygen manifold 206, located in the PRU console 444, is a metallic structure containing internal hollow pathways that provides an efficient means for routing the supplemental oxygen to or through oxygen-related measurement and control devices that are mounted to the oxygen manifold 206 or are not mounted to the oxygen manifold 206 but are plumbed to the oxygen manifold 206. The supplemental oxygen is attached by the user to a coupling on the oxygen manifold 206 referred to as the oxygen input coupler 484, which is located at the rear of the PRU console 444. This incoming oxygen has its pressure measured by a high side pressure sensor 487, located on the oxygen manifold 206 that monitors the high side pressure and presents that data to the PRU host controller 204. This incoming oxygen is also presented to a high side pressure relief valve 485, located on the oxygen manifold 206, which will exhaust excessive pressure to the ambient atmosphere. This incoming oxygen is also presented to an oxygen sample solenoid 481 that is normally closed except during sampling. Whenever the PRU console 444 checks the incoming oxygen for possible hypoxic content, the oxygen sample solenoid 481 is momentarily opened. This presents a stream of incoming oxygen that is blown down an ancillary gas path past the oxygen sensor 482 and subsequently exhausted out of the oxygen manifold 206 to the ambient atmosphere. The PRU host controller 204 compares this sample to the oxygen content of the ambient air, having measured ambient air oxygen concentration prior to or after incoming oxygen sampling. If the incoming oxygen sample has a higher content of oxygen, then the supplemental oxygen connected to the PRU console 444 is deemed non-hypoxic and is permitted to be utilized by the SDS 100.

The incoming oxygen primary gas path continues into the oxygen diverter 492. The oxygen diverter 492 normally allows the oxygen to pass through along the primary gas path. However, if the oxygen diverter knob 493 is in the SDS-system-bypass position, the oxygen is instead directed away from the primary gas path and rather is directed into an oxygen external output orifice 478 that serves as a flow restrictor. Then the oxygen goes to an external nozzle referred to as the barbed oxygen outlet 494. The primary oxygen path proceeds to the fixed restrictor 489, which is a single size orifice that provides a controlled restriction of oxygen flow and produces a resulting differential pressure across the orifice that is proportional to flow rate through the fixed restrictor 489. The differential pressure, as seen on each side of the fixed restrictor 489, portrays the oxygen flow rate in the primary gas path; whereby the flow is implicitly measured via a pair of tubes that convey these two pressures to a differential pressure sensor 479 that is located on the system input/output (I/O) board. The differential pressure transducer 479 provides the oxygen pressure data to the PRU host controller 204. The PRU host controller 204 determines the implied oxygen flow rate through the fixed restrictor by means of mathematical formulae and tabulated correlation data.

The oxygen proceeds past the fixed restrictor 489 and proceeds into a voltage sensitive orifice (VSO) solenoid, referred to as VSO Solenoid 480, which has an orifice size that is proportional to the voltage applied to its actuator coil. The VSO variable gas flow restriction provides for the PRU console 444 control of the oxygen gas flow rate, including the complete shut-off of oxygen flow when appropriate. The VSO solenoid 480 is operated by the PRU host controller 204 in accordance with the oxygen control algorithm, utilizing a hardware/software feedback loop that includes the differential pressure sensor 479. The output of the VSO solenoid 480 is presented to a low side pressure sensor 488 that monitors the low side pressure and presents that data to the PRU host controller 204.

The primary gas path continues past a low side pressure relief valve 486 which will exhaust excessive pressure to the ambient atmosphere. The oxygen exits the oxygen manifold 206 at a fitting, which has flexible tubing, connected to it. This flexible tubing conveys the flow-controlled oxygen over to the PRU umbilical cable pneumatic receptacle 462 located at the front of the PRU console 444. One of the channels of the PRU umbilical pneumatic receptacle 462 is dedicated for oxygen delivery. The umbilical cable 160 is attached by the user to the PRU umbilical pneumatic receptacle 462. The controlled flow oxygen is transported along the umbilical cable 160 via a dedicated oxygen tubing line within the umbilical cable 160 where it is delivered at the other end of the umbilical cable 160 into the BMU 300.

The capnometry functional subsystem (CFS) provides the means to measure and display the patient's exhaled CO2 levels, end tidal CO2 (EtCO2), and respiration rate (RR). This CO2 related data is presented on the PRU screen in the form of a CO2 graph, EtCO2 value, and RR value that is updated on a breath-to-breath basis. The CFS collects patient exhale samples of the nasal and oral site, monitors patient nasal exhale velocity, analyzes the exhale samples for CO2 content, selects the most robust CO2 data, whether it be nasal or oral, in accordance with algorithms that then display the most robust data and derivatives of that data on the PRU Monitor.

Ancillary functions of the CFS include detection of occluded or partially occluded exhale sample air line, filtration to guard against intrusion of air-borne particulate that could effect the measurement sensor, extended capacity trapping of water condensate precipitating from the sampled air, and reduction of sampled air humidity to avoid precipitation of fluid in the measurement sensor.

The cannula has two nasal exhale sample ports, left and right nostril that are inserted into the patient's nostrils. Each sample port has its own dedicated sample line tube that extends to the cannula SPU (single-patient-use) connector. The cannula SPU connector body joins the sample paths of these two tubes into a singular sample path where mixing of the two samples occurs. At this point, a singular nasal-dedicated water trap is employed to separate out precipitate that is present. The combined nasal sample is presented at the nasal exhale sample output of the SPU cannula connector. There are also two additional tubes emanating from the left and right nasal sample ports, which convey the pressure of these two ports over to the cannula SPU connector. These two pressure signals are conveyed discretely to the output of the cannula SPU connector without combining with each other.

The cannula has one oral exhale sample port that is positioned in front of the mouth. This sample port has its own dedicated sample line tube that extends to the cannula SPU connector. At this point, an oral-dedicated water trap is employed to separate out precipitate that is present. The oral sample is presented at the oral exhale sample output of the cannula SPU connector.

The BMU cannula connector accepts the cannula SPU connector and associated nasal/oral exhale samples and nasal pressure signal. The nasal exhale sample is conveyed, via tubing, through the BMU and is presented at the BMU umbilical pneumatic receptacle as a single pneumatic line in that connector. The oral exhale sample is conveyed through the BMU and is presented at the BMU umbilical pneumatic receptacle as a single pneumatic line in that connector. The nasal pressure sample is terminated within the BMU at the nasal pressure sensor. The nasal pressure sensor signal is measured by the BMU expansion board, which conveys the nasal pressure signal data to the PRU console 444 via the BMU umbilical electrical connector and associated umbilical cable.

The oral and nasal exhale samples are transported through oral and nasal transport tubing lines in the umbilical cable. Those samples are delivered to the PRU umbilical pneumatic receptacle, which conveys these exhale samples to the inside of the PRU console 444.

The nasal exhale sample is then directed into a hydrophobic filter that prevents airborne particulate and water droplets from proceeding further into the system. The filtered exhale sample is fed, via tubing, to the nasal capnometer module. The nasal capnometer module performs CO2 measurements upon the exhale sample as it passes through the capnometer CO2 sensor. The nasal capnometer is an OEM (original equipment manufacture) device, made by Cardio Pulmonary Technology Inc, part number CO2WFA. It contains an infrared (IR) sensor, control electronics, pressure sensor, and pneumatic reservoir. The exhale sample exits the nasal capnometer module and travels via tubing to the nasal capnometer pump 141 which is located in the E-PAC™ chassis within the PRU console 444. The nasal capnometer pump 141 provides the vacuum that is propelling the sample from the cannula into the PRU console 444. The nasal capnometer pump 141 is controlled by the nasal capnometer module control electronics, which controls and regulates the air flow to a target flow rate. The nasal exhale sample passes through the nasal capnometer pump 141 and then passes through tubing to an exit port located within the PRU console 444 where that gas is diluted with the PRU console 444 enclosure air that is being circulated by the PRU console fan.

The oral exhale sample is directed into a filter that prevents airborne particulates from proceeding further into the system. The filtered exhale sample is fed, via tubing, to the oral capnometer module. The oral capnometer module performs CO2 measurements upon the exhale sample as it passes through the capnometer CO2 sensor. The oral capnometer is an OEM device, made by Cardio Pulmonary Technology Inc, part number CO2WFA. It contains an infrared (IR) sensor, control electronics, pressure sensor, and pneumatic reservoir. The exhale sample exits the oral capnometer module and travels via tubing to the oral capnometer pump 142 which is located in the E-PAC™ chassis within the PRU console 444. The oral capnometer pump 142 provides the vacuum that is propelling the sample from the cannula into the PRU console 444. The oral capnometer pump 142 is controlled by the oral capnometer module control electronics, which controls and regulates the air flow to a target flow rate. The oral exhale sample passes through the oral capnometer pump 142 and then passes through tubing to an exit port located within the PRU console 444 where that gas is diluted with the PRU console 444 enclosure air that is being circulated by the PRU console fan.

The nasal pressure subsystem monitors the patient nasal exhale pressure and the corresponding pressure data is employed in a nasal pressure algorithm to determine when the patient is deemed to be in a nasal breathing mode or an oral breathing mode.

The cannula body has two nasal pressure measurement channels, one for each nostril. The pressure encountered by each nasal channel by the cannula body is conveyed by two independent pneumatic lines to the cannula connector that is attached by the user to the respective BMU receptacle. These two pneumatic lines are combined together as a singular pneumatic pressure signal at the cannula connector. The singular nasal pressure signal is conveyed into the BMU. This nasal pressure is conveyed by a single tube to a BMU pressure sensor located inside the BMU. The BMU pressure sensor measures the relative nasal pressures presented to the cannula body and converts this analogous pressure to an electrical signal that is processed by the BMU expansion board and communicated via the umbilical cable to the host controller in the PRU.

The PRU host controller utilizes algorithms to analyze the pressure signal and thereby produces synchronization signals that provide timing cues relating to specific events, namely, when the nasal inhale has begun and when the nasal inhale has ceased and when the nasal exhale has begun and when the nasal exhale has ceased. Also, in the event that the patient is in an oral breathing mode, the nasal pressure signal is sufficiently weak to be recognized by these algorithms and produces a cue for the PRU host controller that indicates the oral breathing mode.

These nasal inhale/exhale timing cues and oral inhale/exhale timing cues are utilized by the respiratory functional subsystem to coordinate timed delivery of variable flow rate oxygen and also coordinate selection of oral or nasal capnometer data for use in displayed CO2 waveform, EtCO2 calculation and display, and respiration rate calculation and display.

The respiratory functional subsystem includes the supplemental oxygen subsystem, the capnometry functional subsystem, and the nasal pressure subsystem. These subsystems operate in a coordinated fashion by means of system level algorithms and control programs.

When the patient is in an oral breathing mode, the oxygen delivery subsystem is directed to set the oxygen flow to a present continuous flow rate. When the patient is in a nasal breathing mode, the oxygen delivery subsystem is directed to gate the oxygen flow between a fast and a slow flow rate in synchrony with the patient inhale/exhale timing. This synchrony is performed by means of the nasal pressure subsystem function to determine when the nasal inhale has begun and when the nasal inhale has ceased and when the nasal exhale has begun and when the nasal exhale has ceased. These inhale/exhale begin/cease detection means serve as cues for the control of step changes in oxygen flow rates. Thus, the oxygen delivery is a varying flow rate in synchrony with the patient's respiratory cycle.

The drug delivery functional subsystem provides a means for controlled delivery of drug(s) from the drug vial 250 installed in the PRU console. The drug pumping means includes an IV pump module that operates in conjunction with an installed cassette. The drug pumping rate is controlled by commands issued to the IV pump module from the PRU host controller.

Ancillary functions of the drug delivery functional subsystem include pump door lock/unlock, detection of the T-site commercial luer position within the designated home location of the cassette, detection of the presence of the drug vial seated within the cassette, air-in-line detection for detecting air in the IV line, detection of occlusion of the IV line, and an undesired-pumping detection monitor.

The pump is enabled when the T-site commercial luer is seated within the cassette. The pump door can be opened when the T-site commercial luer is seated within the cassette.

The umbilical cable power control subsystem (fast switch and state circuit) includes the umbilical cable in conjunction with PRU console fast switch, PRU state circuit, BMU fast switch, BMU state circuit, and the PRU host controller.

The umbilical cable conveys power from the PRU to the BMU. The power provided to the BMU is for powering the BMU related circuitry including the recharging of the BMU battery. The umbilical cable utilizes a power management control subsystem that permits the "hot swap" of the umbilical cable while the equipment is energized. The umbilical cable power management disconnects power when the umbilical cable connector has become slightly disengaged from full connection. This helps prevent any spark during detachment of the umbilical cable and also helps prevent the umbilical cable connector contacts from being overly stressed due to insufficient connector engagement. These power-ceasing mitigations are implemented regardless of which end of the umbilical cable is detached. These functions are provided by means of a jumper located at each end of the umbilical cable, which straps between the shortest pin, called the fast pin, in the connector, and the power return pin of the connector. The strap located at the first end of the umbilical cable is detected by the PRU console fast switch. The strap located at the second end of the umbilical cable is detected by the BMU fast switch.

Upon disconnection of the umbilical, the fast pin is the first pin to break contact with the respective receptacle. This triggers the respective fast switch to interrupt power flow through the umbilical cable power pins.

Another function of one example of the umbilical cable power control subsystem is to help shut off power to umbilical cable connector pins at either end of the umbilical cable when the umbilical cable is disconnected from the PRU or the BMU. This function is accomplished by means of the PRU console fast switch, the PRU state circuit, the BMU state circuit, and the PRU host controller. In this example, when the umbilical is disconnected from the BMU under nominal conditions, the BMU state circuit in conjunction with the PRU state circuit detects the disconnection and the PRU state circuit turns off the PRU fast switch, which disconnects power and communications to the umbilical resulting in no power at the pins of the Umbilical Cable. In this example, in the event of a non-nominal condition of some aspects of the state circuit, the absence of communications via the umbilical cable is detected and tagged by the PRU host controller as a possible disconnection of the umbilical cable, which evokes a turn-off signal to the fast switch. The fast switch disconnects both the power and communications lines signals that are applied to the umbilical cable.

The following paragraphs present a description of one particular exemplary use of SDS 100 without limiting the scope of the invention. As shown in FIGS. 77-80, components of SDS 100 are employed throughout a surgical procedure, including pre-procedure set-up and post-procedure recovery. The patient arrives in the pre-procedure room, step 1200. A nurse or technician mounts BMU 300 to either the bedrail or IV pole, step 1201. BMU 300 is equipped with an IV pole clamp or a quick connect to quickly and easily mount the unit on either the bedrail or IV pole. Once BMU 300 is in place, the nurse or clinician may connect NIBP cuff 120 and pulse oximeter probe 110 to the patient, step 1202. These connections are made between the patient and BMU 300. BMU 300 will automatically begin monitoring parameters such as, for example, diastolic and systolic blood pressure, mean arterial pressure, pulse rate, oxygenation plethysmogram, and oximetry value, steps 1203 and 1204. The readings taken by BMU300 will be displayed for the nurse or technician on BMU GUI 212. While patient parameters are being monitored, the nurse or technician is free to perform other tasks. As is customary with current practice, the nurse or technician may need to complete a pre-procedure assessment, step 1206. The pre-procedure assessment may include recording patient vital signs, determining any known allergies, and determining patient's previous medical history. Once the nurse or technician has completed the pre-procedure assessment, step 1206, the nurse or technician may start the peripheral IV by placing a catheter in the patient's arm, step 1207. The IV catheter is connected to the primary IV drip device such as, for example, a 500 mL bag of saline fluid. Upon completion of the above activities, the nurse or technician begins to attach ECG pads 130, ARM handset 342, ARM earpiece 362 and oral nasal cannula 351 to the patient, step 1208.

Once the patient is connected to the above-mentioned items, the nurse or technician may explain ARM system 340 to the patient. This explanation may involve the nurse or technician instructing the patient to respond to auditory stimulation from earpiece 362 and/or tactile stimulation from ARM handset 342 by squeezing ARM handset 342. If the patient fails to respond to either auditory or tactile stimulation, the intensity of the stimulation will increase until the patient responds successfully. At this point, the nurse may initiate an automated ARM training, step 1209. Automated ARM training is a program run by BMU 300 that teaches the patient how to detect an ARM stimulus and how to respond to that stimulus and sets a baseline patient response to the stimulus as disclosed in the previously referenced U.S. patent application, Ser. No. 10/674,160. The nurse or technician is free to perform other patient related tasks while the patient is participating in the automated ARM training. BMU 300 will display the automated ARM training status so the nurse or technician can quickly determine if the patient is participating in the automated training. The patient must successfully complete the automated ARM training to proceed, step 1210; if the patient fails to complete the training a nurse or other clinician must intervene and determine if the patient may continue, step 1210-A. If the clinician decides the user may proceed, then the patient will proceed to step 1211; if the clinician decides the patient is unable to continue, then the procedure will be canceled, step 1213. The user may customize the automated ARM training to automatically repeat at specified intervals (i.e. 10 minutes) if the patient is required to wait to enter the procedure room. This will help to instill the newly learned response.

In addition to successfully completing automated ARM training, the patients parameters must be in an acceptable range, step 1205. The clinician may decide upon what an acceptable range is by inputting this information into BMU 300 by means of BMU GUI 212. If any one of the parameters being monitored falls outside a given range, the patient will not be permitted to undergo a procedure until a nurse or other clinician examines the patient to determine whether or not the patient may continue, step 1205-A. If the clinician decides the patient is able to continue, the patient will proceed to step 1211, if the clinician decides the patient is unable to continue, then the procedure will be cancelled, step 1213. Just prior to leaving the pre-procedure room for the procedure room, the nurse administers a predetermined low dose of an analgesic drug, step 1211 such as, for example, a 1.5 mcg/kg of Fentanyl. After the injection of the analgesic drug, the patient is ready to be moved to the procedure room, step 1212.

The patient and BMU 300 relocate to the procedure room, step 1220 and are received by the physician (non-anesthesiologist) and procedure nurse. BMU 300 may be connected to PRU 200 via umbilical cable 160 upon the patient entering the procedure room, step 1221. Upon connection, the NIBP, pulse and oximetry history from the patient will automatically up-load to PRU 200 displaying patient history for the last period of monitoring. In addition to NIBP and pulse oximeter history, a record verifying the patient has completed ARM training will also be uploaded. Upon connection of BMU 300 to PRU 200, the BMU GUI 212 changes from a monitoring screen to a remote entry screen for PRU 200. Display information from BMU 300 is automatically transferred to PRU 200.

At this point, the procedure nurse may secure oral nasal cannula 145 to the patient's face, step 1222, if not already done so in the pre-procedure room. PRU 200 may begin monitoring patient parameters such as, for example, ARM, ECG, and capnography now that all connections between the patient and PRU 200 (via BMU 300) are complete, step 1223. PRU 200 will continue monitoring patient parameters such as, for example, NIBP, pulse, and oximetry, step 1224. Next the procedure nurse may scan the bar code label on the packaging of a drug cassette 251 and place the drug cassette within PRU 200 and spike a standard drug vial, step 1225 onto vial spike 261. Once the fluid vial and drug cassette 64 are loaded correctly, the nurse may autoprime IV tubing 259. In one embodiment, the procedure nurse would press a button located upon PRU 200 to initiate the autopriming, step 1227, or the autopriming may be an automatic procedure initiated by PRU 200 when all safety conditions are met. Autopriming is the automatic purging of air from IV tubing 259. PRU 200 continuously monitors the autopriming process to determine the overall success of the autopriming. If PRU 200 fails to properly purge IV tubing 259, a warning notification is made to the user so that the procedure nurse may repeat the autopriming sequence until IV tubing 259 is successfully purged, step 1227.

Upon successful completion of the autopriming sequence, the procedure nurse may enter the patient weight in pounds while the physician (non-anesthesiologist) may enter the initial drug maintenance dose rate as well as dose method; normal or rapid infusion, step 1229. After the patient weight and dose rate have been inputted, the physician or procedure nurse may initiate drug infusion, step 1230. While the drug is taking effect upon the patient, the physician may perform standard procedure related activities such as, for example, test the scope, and apply any topical anesthetic. Once the drug has taken the desired effect upon the patient, the physician and procedure nurse are free to conduct the procedure, step 1231. Upon completion of the procedure, the clinician may disconnect the drug delivery cassette from the catheter, step 1232 and disconnect the BMU 300 from the PRU 200, step 1233. If the clinician so desires, PRU 200 may print a record of the patient's physiological parameters from printer 454 at this time, step 1234. Included on the print out of the procedure record are patient monitoring data such as, for example, NIPB, pulse oximetry, capnography, respiration rate, and heart rate. Other system events included in the print out are, ARM competency, ARM responsiveness during the procedure, oxygen delivery history, drug dose, monitoring intervals, drug bolus amount and time, and total drug volume delivered during the procedure. The printout includes a section where the procedure nurse may enter notes, such as, for example, additional narcotic delivered, topical spray used, Ramsey Sedation Scale, procedure start and finish time, cautery unit and settings used, cautery grounding site, dilation equipment type and size, and Aldrete Score. After printing the patient record, the patient may then be moved to the recovery room, step 1235.

The patient arrives in the recovery room 1240 still attached to BMU 300 after leaving the procedure room. At this point, BMU 300 may be operating on either battery or AC power. Upon entering the room, the attending clinician may remove the ECG pads, ECG lead wires, ARM handset, and earpiece from the patient 1241. Depending upon clinician preference and status of the patient, the patient may require supplemental oxygen while in the recovery room 1242. If the patient does require supplemental oxygen, oral nasal cannula 145 is left on the patients face and oxygen is accessed from an external source such as, for example, a headwall or tank via connector 152 and BMU connector 151, step 1243. If no supplemental oxygen is required in the recovery room, the nurse or technician may remove oral nasal cannula 145 from the patient 1244.

The nurse or technician may now organize ECG leads 334 and ARM handset 342 and place near BMU 300 to be used on the next patient 1245. Alternatively, ARM handset 342 may be used for patient for time-based responsiveness to queries from ARM. The nurse or technician may need to fill out additional information on the patient record 1246. The nurse or technician will most likely write notes describing the patient's condition during recovery and record NIBP, pulse rate and oximetry values of the patient during recovery. ECG pads 332 and oral nasal cannula 145 may be discarded at this point into a standard waste container located in the recovery room 1247. It is important to note that BMU 300 is still collecting data related to NIBP, pulse rate, and pulse oximetry 1248. The nurse or technician must determine if the patient is ready to be discharged 1249. Criteria for discharge vary among patient care facilities, however an Alderate score of 10 is common for discharge. Other measures of discharge criteria include responsiveness to queries through ARM, skin color, pain assessment, IV site intact, NIBP, pulse, respiration rate, and oximetry values all must be close to the measurement taken in pre-procedure. If the patient does not meet any of these criteria, it is recommended that the patient receive additional monitoring 1248. Once a patient is cleared for discharge, the nurse or technician disconnects NIBP cuff 58, pulse oximeter probe, and if not done so already, oral nasal cannula 145 and ARM handset 342 from the patient 1250. Once all the above is completed, the patient may be discharged from the care facility 1251.

Figure 81:
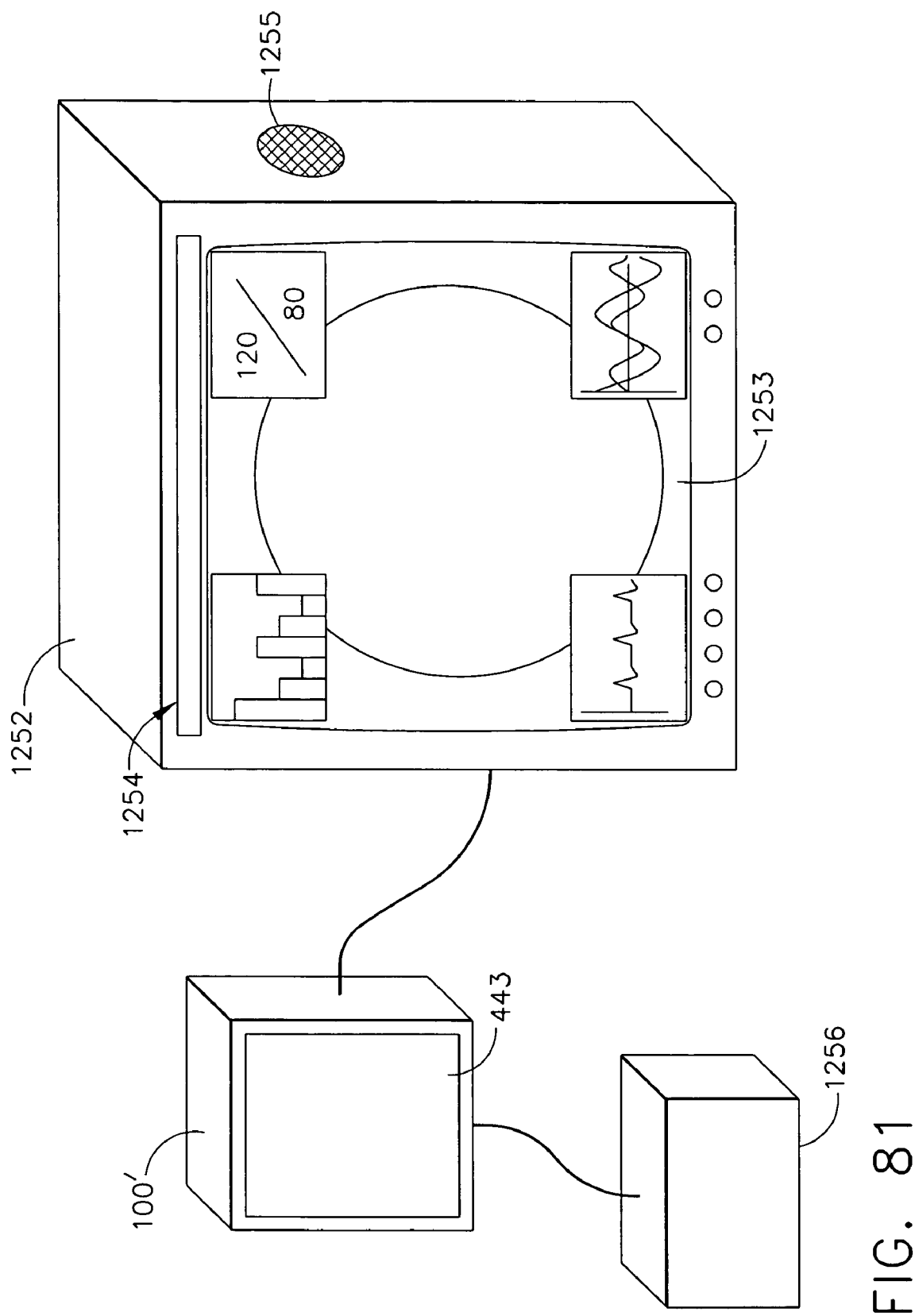
FIG. 81 is a front perspective of the peripheral monitor used in conjunction with the PRU.

Now referring to FIG. 81, peripheral medical display 1252 receives processed patient data from medical effector system 100' and then displays the processed patient data on peripheral LCD screen 1253. Information that may be displayed includes heart rate, blood pressure, pulse oximetry, capnography, electrocardiogram, and other medical parameters that are processed by medical effector system 100'. In addition to patient data, the peripheral medical display 1252 may display procedural parameters related to the function of medical effector system 100'. The functional parameters may include; battery charge level, duration of the current procedure, patient name, and other descriptive patient data, information related to IV pump module 220, the pharmaceutical drug being supplied to the patient and other parameters. Peripheral medical display 1252 further includes the ability to allow a medical practitioner set predetermined parameter limits, which if exceeded result in an alarm action by peripheral medical display 1252 which may be in addition to any alarm generated by medical effector system 100'. The alarm action may be in the form of a flashing light from peripheral light bar 1254, an auditory signal from peripheral speaker 1255, or a pop-up alarm on peripheral LCD touchscreen 1253.

Peripheral medical display 1252 may also display the output of another medical device such as endoscopic camera 1256. Peripheral medical display 1252 has the capability to simultaneously display the output of endoscopic camera 1256 as well as patient and procedural data on peripheral LCD touchscreen 1253. This functionality allows a medical practitioner to view relevant patient and procedural data without diverting his or her attention from the output of the endoscopic camera.

Peripheral medical display 1252 may also contain a user interface to allow a medical practitioner to alter display settings on the peripheral medical display 1252. A user interface may be in the form of PRU monitor touchscreen 443 or peripheral monitor LCD touchscreen 1253 located on peripheral medical display 1252. From the user interface, the medical practitioner may alter various visualization parameters including; selecting which medical and procedural parameters if any to overlay on the output of the endoscopic camera. Furthermore, the medical practitioner may modify the size and location of the parameter displays relative to one another. Additional options available through the user interface include, selecting the display format or medical parameters (bar graph, gauge, histogram, pictorial, or numeric), color adjustment, establishing a schedule to automatically change visualization parameters, establishing a priority of displays in the event of an alarm action, magnification of the output of the endoscopic camera, and selection of an alternate video source, as well as other visualization options. The patient and procedural parameters may be located apart from the output of endoscopic camera 1256 or may be overlaid on the output of endoscopic camera 1256. This is accomplished by a video mixing apparatus located in either peripheral medical display 1252 or medical effector system 100'. Similarly peripheral medical display 1252 may utilize a picture-in-picture display incorporating the output from endoscopic camera 1256 or other video source.

While aspects, embodiments and examples, etc. thereof, it is not the intention of the applicants to restrict or limit the spirit and scope of the appended claims to such detail. Numerous other variations, changes, and substitutions will occur to those skilled in the art without departing from the scope of the invention. For instance, the medical effector system and components thereof of the invention have application in robotic assisted surgery taking into account the obvious modifications of such systems and components to be compatible with such a robotic system. It will be understood that the foregoing description is provided by way of example, and that other modifications may occur to those skilled in the art without departing from the scope and spirit of the appended Claims.

What is claimed is:

1. A drug-delivery infusion pump assembly comprising:
a) a drug-delivery infusion pump housing;
b) a drug-delivery cassette assembly attachable to the infusion pump housing, the drug delivery cassette comprising:
   i) a tubing assembly for conveying a drug;
   ii) a drug-vial spike attached to a base portion, wherein the base portion is adapted to attach to the drug delivery cassette and to connect to and disconnect from the tubing;
   wherein the drug-delivery cassette assembly defines a co-planar area having a recessed portion for accepting the base portion; and
c) a pump-housing door attached to the infusion pump housing, having door-open and door-closed positions, and having drug-vial-aligning fingers which center and align different diameter drug vials when the cassette assembly is attached to the infusion pump housing; the pump-housing door is in the door-closed position; and a drug vial is inserted between the drug-vial-aligning fingers for engagement with the spike.

2. The drug-delivery infusion pump assembly of claim 1, wherein the cassette assembly is attachable to, and removable from, the infusion pump housing when the pump-housing door is in the door-open position.

3. The drug-delivery infusion pump assembly of claim 1, also including a drug-delivery peristaltic pump disposed in the infusion pump housing and having pump fingers, wherein the cassette assembly is operatively connectable to the pump fingers when the cassette assembly is attached to the infusion pump housing and the pump-housing door is in the door-open position.

4. The drug-delivery infusion pump assembly of claim 1, wherein the base portion threadedly attaches to and disconnects from the tubing.

5. The drug-delivery infusion pump assembly of claim 1, wherein the recessed portion comprises alignment pins for interfacing with corresponding alignment apertures positioned on the base portion.

6. The drug-delivery infusion pump assembly of claim 1 further comprising a removable cap element adapted for removably enclosing at least a portion of the drug-vial spike.

7. The drug-delivery infusion pump assembly of claim 1 further comprising a sensor for sensing when the drug vial is placed on the drug-vial spike.

* * * * *